United States Patent

Ando et al.

[11] Patent Number: 5,639,783
[45] Date of Patent: Jun. 17, 1997

[54] KETONE DERIVATIVES

[75] Inventors: Ryoichi Ando; Naoko Ando, both of Machida; Hirokazu Masuda, Yokohama; Yasuhiro Morinaka, Tsuchiura; Chizuko Takahashi, Yokohama; Yoshikuni Tamao, Machida; Akihiro Tobe, Yokohama, all of Japan

[73] Assignee: Mitsubishi Chemical Corporation, Tokyo, Japan

[21] Appl. No.: 451,720

[22] Filed: May 26, 1995

Related U.S. Application Data

[63] Continuation of Ser. No. 252,397, Jun. 1, 1994, abandoned, which is a continuation of Ser. No. 907,228, Jul. 1, 1992, abandoned.

[30] Foreign Application Priority Data

| Jul. 1, 1991 | [JP] | Japan | 3-160674 |
| Oct. 24, 1991 | [JP] | Japan | 3-277905 |
| Dec. 25, 1991 | [JP] | Japan | 3-343668 |

[51] Int. Cl.$^6$ .................... A61K 31/35; C07D 311/24
[52] U.S. Cl. ............................. 514/456; 549/402
[58] Field of Search ........................ 514/456; 549/402

[56] References Cited

U.S. PATENT DOCUMENTS 5,055,451  10/1991  Krantz et al. ........................ 514/19

FOREIGN PATENT DOCUMENTS 294176   9/1991  German Dem. Rep. .
253061  10/1988  Japan .

OTHER PUBLICATIONS

E. Shaw, The Journal of Biological Chemistry, 263(6) 2768–2772 (1988).
Robinson et al., Chemical Abstracts, 117:22302m (1992).
Krantz et al., Biochemistry, 30(19), 4678–4687 (1991).
Smith et al., J. Am. Chem. Soc., 110(13), 4429–4431 (1988).
Zumbrunn et al., Biochem. J., 256, 989–994 (1988).
Shaw et al., The Journal of Biological Chemistry, 263(6), 2768–2772 (1988).
Rauber et al., Biochem. J., 250, 871–876 (1988).
WPI Acc. No. 92–034226/05 (EP 468469) (Jul. 27, 1990).
WPI Acc. No. 92–065587/09 (DD 294176) (May 11, 1990).

Primary Examiner—Nicky Chan
Attorney, Agent, or Firm—Wenderoth, Lind & Ponack

[57] ABSTRACT

A novel ketone derivative (I) which possesses a potent inhibitory activity against thiol protease such as papain, cathepsin B, cathepsin H, cathepsin L, calpain or the like with excellent properties regarding oral absorbance, tissue transference and cell membrane permeability, and are clinically useful in the treatment of various diseases such as muscular dystrophy, amyotrophy. Also provided are a process for producing the compound (I) and a pharmaceutical composition containing the same.

5 Claims, 2 Drawing Sheets

KETONE DERIVATIVES

This application is a continuation of now abandoned application Ser. No. 08/252,397, filed Jun. 1, 1994; which is a continuation of now abandoned application Ser. No. 07/907,228, filed Jul. 1, 1992.

FIELD OF THE INVENTION

The present invention relates to novel ketone derivatives. More particularly, this invention relates to novel ketone derivatives having a potent inhibitory activity against thiol protease such as papain, cathepsin B, cathepsin H, cathepsin L, calpain or the like.

BACKGROUND OF THE INVENTION

In accordance with the elucidation of the in vivo activity of thiol protease such as papain, cathepsin B, cathepsin H, cathepsin L, calpain or the like, it has been found that their extraordinary hypersthenia causes various diseases. Further, there is increasing the report which shows thiol protease inhibitors are effective on such disease in animal models.

It is considered that thiol protease such as calpain, cathepsin B or the like takes part in the initial process such as disappearance of the Z line through the decomposition of muscular fiber protein in the collapse of skeletal muscle as seen in muscular disease such as muscular Dystrophy, amyotrophy or the like [Taisha (Metabolism), 25, 183 (1988)]. Furthermore, E-64-d, namely a thiol protease inhibitor, has been reported to have life-prolonging effect in an experimental muscular dystrophy hamster [Journal of Pharmacobio dynamics, 10, 678 (1987)]. Accordingly, such thiol protease inhibitors are expected to be useful as therapeutic agents for the treatment of muscular dystrophy, amyotrophy or the like.

The main cause of the post-ischemic cellular disorder occurs during ischemic diseases such as cardiac infarction, stroke and the like is active oxygen produced by xanthine oxidase. It has been reported that, during the ischemia, the increase in $Ca^{2+}$ concentration results in the activation of calpain which restrictively degrade xanthine dehydrogenase, a precursor of xanthine oxidase, to give xanthine oxidase [New England Journal of Medicine, 312, p. 159, (1985)]. It has also been reported that the activation of calpain may directly cause the necrosis of myocardial cells or neurocytes [Saishin Igaku, 43, p. 783, (1988)]. It has been reported that NCO-700, a calpain inhibitor, is effective on cardiac infarction when tested on animal models [Arzneimittel Forschung/Drug Research, 36, p. 190, p. 671, (1986)], and that E-64-C inhibits the degradation of microtubule-associated protein after the brain ischemia [Brain Research, 526, p. 177, (1990)]. These reports indicate that a calpain inhibitor can be useful for the treatment of ischemic diseases such as cardiac infarction, stroke and the like.

The cause of senile plaque which is found specifically in the brain of patients suffering from Alzheimer's disease is known to be the precipitated amyloid, a protein produced by the decomposition of an amyloid precursor protein (APP). Although APP does not give amyloid as a normal metabolite, it may be converted into amyloid under an abnormal metabolism where protease is extremely activated, and precipitated as senile plaque [Scientific American, (11), p. 40, (1991)]. Therefore, protease inhibitor is expected to be useful for the treatment of Alzheimer's disease.

The activation of calpain has been observed in a brain trauma model of rabbit [Neurochemical Research, 16, p. 483, (1991)]. It has also been observed, the administration of leupeptin, a calpain inhibitor, can protect axon in brain trauma models of rat [Journal of Neurosurgery, 65, p. 92, (1986)]. Thus, calpain inhibitors are considered to be useful for improving the consciousness disturbance or motor disturbance caused by brain trauma.

It has also been reported that myelin-associated protein exists in dendrite of neurocytes is decomposed by calpain [Journal of Neurochemistry, 47, p. 1007, (1986)], indicating that calpain inhibitors may be effective on diseases caused by the demyelination of neurocytes such as multiple sclerosis, peripheral nervous neuropathy and the like.

The main cause of the turbidity during cataract is hydrolytic products of a water-soluble protein crystallin by protease in lens. It has been observed the increase in calcium concentration in lens of cataractous animal models and some of human cataract [Investigative Ophthalmology & Visual Science, 28, p. 1702, (1987); Experimental Eye Research, 34, p. 413, (1982)]. The dominant protease contained in lens is calpain [Lens and Eye Toxicity Research, 6, p. 725, (1989)]. These facts indicate that the abnormal sthenia of calpain can be one of the causes of cataract. There is a report that E-64, an inhibitor of calpain, is effective on cataract in animal models [Investigative Ophthalmology & Visual Science, 32, p. 533, (1991)], indicating that calpain inhibitors can be useful in the treatment of cataract.

Neutrophils, which is deeply associated with inflammation, show the degranulation or production of superoxides in response to the stimulations by a chemotactic factor or phorbol ester through a mechanism appeared to be mediated by protein kinase C (PKC). Calpain participates in the activation of PKC in the manner where it promotes the degranulation and inhibits the production of superoxides [Journal of Biological Chemistry, 263, p. 1915, (1988)]. In another report, the concentration of cathepsin B in macrophage in rat is 30 to 40 times that of leukocytes and neutrophils, and the concentration of enzyme in inflammatory macrophage is 6 times that of normal macrophages [Journal of Biochemistry, 98, p. 87, (1985)]. These facts indicate that thiol protease inhibitors are useful as anti-inflammatory drugs.

The type I allergy reaction is mediated by immunoglobulin E (IgE) produced in the subject immunized with an antigen. Estatin A, a thiol protease inhibitor, has been reported to specifically inhibit the production of IgE without affecting on the production of IgG [The Journal of Antibiotics, 42, p. 1362, (1989)]. Accordingly, thiol protease inhibitors are considered to be useful as antiallergic drugs.

In case of necrosis of hepatic cells, it is believed that impairment of the cell membrane leads to an increase in the permeability of $Ca^{2+}$, an increase in intracellular $Ca^{2+}$ concentration, an activation of calpain, and, as the result, the decomposition of its substrate such as skeletal protein takes place, which results in the death of cells. Accordingly, a calpain inhibitor can be used as a therapeutic agent for fulminant hepatitis.

Cathepsins such as cathepsin B and cathepsin L are involved in decomposition of bone collagen in osteoclast. It has been reported that administration of an inhibitor of cathepsins, E-64 or estatin A, to a rat which has an enhanced bone destruction by administration of parathyroid hormone leads to a decrease of calcium concentration and hydroxyproline concentration in blood [Biochemical and Biophysical Research Communication, 125, p. 441, (1984): Japanese Patent Publication (kokai) No. 218610/1990]. Accordingly, it is believed that an inhibitor of cathepsins can be a therapeutic agent for osteoporosis, hypercalcemia and the like.

There exist, as a substrate for calpain, sex hormone receptors such as estrogen receptor and androgen receptor, and it is known that calpain activates these receptors. Accordingly, it is considered that an abnormal sthenia of calpain causes a disease which is suspected to be caused by an abnormal activation of the sex hormone receptors, for example, breast carcinoma, prostatic carcinoma or prostatomegaly. It is believed that an inhibitor for calpain can be a therapeutic agent for the above disease.

Receptors for epidermal growth factor (EGF) are also considered to be activated in association with the canceration of cells. It is known that calpain activates the EGF receptors as its substrate. Furthermore, it has been reported that calpain is activated in cells which have been infected with adult T cell human leukocyte virus (ATLV/HTLV-1) [Seikagaku, 57, p. 1202, (1985)]. On the other hand, it is said that cathepsin B is greatly involved in a process of cancer metastasis because it accelerates decomposition of collagen which is a important step for the cancer metastasis or directly decomposes collagen, and because it has a profound correlation with plasma membrane of neoplastic cells [Tumor Progression and Markers, p. 47, (1982); Journal of Biological Chemistry, 256, p. 8536, (1984)]. These facts suggest that a thiol protease inhibitor has an ability to suppress the growth of cancer cells and prevent the metastasis of cancer.

Activation of platelets causes the aggregation thereof which is a cause of thrombus. It has been reported that an inhibitor of calpain, E-64-d, suppressed aggregation of platelet caused by thrombin [Thrombosis Research, 57, p. 847, (1990)]. Accordingly, the inhibitor of calpain can be used as an inhibitor against aggregation of platelets.

As described above, an abnormal sthenia of thiol protease causes various diseases and a validity of several thiol protease inhibitors in animal models has been reported. However, most known inhibitors, for example, epoxy succinate derivatives such as E-64 [Agricultural and Biological Chemistry, 42, p. 529, (1978)], E-64-d [Journal of Biochemistry, 93, p. 1305, (1983)], NCO-700 [Japanese Patent Publication (kokai) No. 126879/1983], and estatins A and B [The Journal of Antibiotics, 42, p. 1362, (1989)], or s-substituted ketone of a peptide such as chloromethyl ketone [Journal of Biochemistry, 99, p. 173, (1986)] and acyloxymethyl ketone [Biochemistry, 30, p. 4678, (1991)] are irreversible inhibitors. It is generally said that the irreversible inhibitors are highly toxic because they are liable to react with non-specifically to components consisting living body, other than target enzymes. Therefore, there have been few compounds applicable to clinical use so far. Although peptidyl aldehydes such as leupeptin [The Journal of Antibiotics, 22, p. 183, (1969)] or calpeptin [Journal of Enzyme Inhibition, 3, p. 195, (1990)] are known as reversible inhibitors, they also have problems in chemical and in vivo stabilities, cell membrane permeabilities and the like.

SUMMARY OF THE INVENTION

The present inventors investigated various compounds with aim of developing reversible inhibitors against thiol protease, which have excellent properties concerning absorbance on oral administration, tissue distribution and cell membrane permeability, and have found that certain ketone derivatives have such desired properties.

Thus, the present invention provides ketone derivatives of the general formula (I):

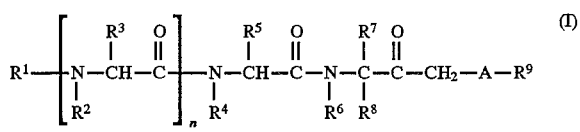

wherein $R^1$ is hydrogen atom, $R^{10}$—CO—, $R^{10}$—O—CO—, $R^{10}$—SO$_2$— or $R^{10}$—NH—CO— (in which $R^{10}$ is $C_1$–$C_{20}$ alkyl group optionally substituted by one or more substituents selected from the group consisting of $C_3$–$C_{15}$ cycloalkyl group, $C_3$–$C_{15}$ cycloalkenyl group, optionally substituted $C_6$–$C_{14}$ aryl group, optionally substituted and partially hydrogenated $C_{10}$–$C_{14}$ aryl group, fluorenyl group, optionally substituted heterocyclic group, $C_3$–$C_{15}$ cycloalkyloxy group, optionally substituted $C_6$–$C_{14}$ aryloxy group, optionally substituted and partially hydrogenated $C_6$–$C_{14}$ aryloxy group, optionally substituted heterocyclic oxy group, optionally substituted $C_7$–$C_{20}$ aralkyloxy group and optionally substituted $C_6$–$C_4$ arylthio group; $C_3$–$C_{15}$ cycloalkyl group; optionally substituted $C_6$–$C_{14}$ aryl group; optionally substituted and partially hydrogenated $C_6$–$C_{14}$ aryl group; optionally substituted $C_2$–$C_{10}$ alkenyl group; or optionally substituted heterocyclic group);

$R^2$, $R^4$ and $R^6$ each are independently hydrogen atom or $C_1$–$C_5$ alkyl group;

$R^3$ and $R^5$ each are independently hydrogen atom, $C_7$–$C_{20}$ aralkyloxy group, optionally substituted $C_6$–$C_{14}$ aryl group, $C_1$–$C_{10}$ alkoxy group or optionally substituted $C_1$–$C_{20}$ alkyl group; or $R^2$ and $R^3$ and/or $R^4$ and $R^5$ taken together may form an optionally substituted nitrogen-containing heterocyclic ring;

$R^7$ is $C_1$–$C_{20}$ alkyl group optionally substituted by one or more substituents selected from the group consisting of $C_3$–$C_{15}$ cycloalkyl group, hydroxyl group, $C_1$–$C_5$ alkoxy group optionally substituted by heterocyclic group, $C_6$–$C_{14}$ aryloxy group, $C_7$–$C_{20}$ aralkyloxy group, $C_1$–$C_5$ alkylthio group optionally substituted by heterocyclic group, $C_6$–$C_{14}$ arylthio group, $C_7$–$C_{20}$ aralkylthio group, carboxyl group, carbamoyl group, $C_2$–$C_6$ alkoxycarbonyl group, heterocyclic group and optionally substituted $C_6$–$C_{14}$ aryl group; hydrogen atom; $C_7$–$C_{20}$ aralkyloxy group; optionally substituted $C_6$–$C_{14}$ aryl group or $C_1$–$C_{10}$ alkoxy group;

$R^8$ is hydrogen atom, $C_1$–$C_5$ alkyl group or optionally substituted $C_7$–$C_{20}$ aralkyl group; or $R^7$ and $R^8$ taken together may form optionally substituted benzylidene group or $C_3$–$C_{15}$ cycloalkyl group;

A is —S—, —SO—, —SO$_2$—, —O— or —N($R^{11}$)— (in which $R^{11}$ is hydrogen atom or optionally substituted $C_1$–$C_{20}$ alkyl group), and (1) when A is —S—, —SO— or —SO$_2$—, then $R^9$ is optionally substituted $C_6$–$C_{14}$ aryl group or —(CH$_2$)$_m$—X (in which X is hydrogen atom, hydroxyl group, $C_1$–$C_5$ alkylthio group, $C_2$–$C_6$ alkoxycarbonylamino group, optionally substituted heterocyclic group, amino group, $C_1$–$C_5$ monoalkylamino group, $C_2$–$C_{10}$ dialkylamino group, $C_2$–$C_6$ acylamino group, halogen atom, $C_1$–$C_5$ alkoxy group, optionally substituted $C_6$–$C_{14}$ aryl group or optionally substituted $C_6$–$C_{14}$ aryloxy group; and m is 0 or an integer of 1 to 15); provided that if $R^1$ is benzyloxycarbonyl group, $R^{4}$, $R^6$ and $R^8$ all are hydrogen atom, $R^5$ is benzyl group, $R^7$ is methyl group and n is 0, then —A—$R^9$ is not methylthio group;

(2) when A is —O—, then $R^9$ is hydrogen atom or —(CH$_2$)$_l$—X (in which l is an integer of 1 to 15; and X is as defined above); or (3) when A is —N($R^{11}$)—, then $R^9$ is optionally substituted $C_6$–$C_{14}$ aryl group or —$(CH_2)_m$—X (in which X and m are as defined above); or $R^9$ and $R^{11}$ taken together may form an optionally substituted nitrogen-containing heterocyclic ring; and n is 0 or 1, or pharmaceutically acceptable salts thereof.

The present invention also provides a pharmaceutical composition containing, as an active ingredient, a ketone derivative of the above formula (I) or a salt thereof.

The present invention also provides a process for the preparation of ketone derivatives of the above formula (I) or salts thereof.

DETAILED DESCRIPTION OF THE INVENTION

Definition

Figure 1:
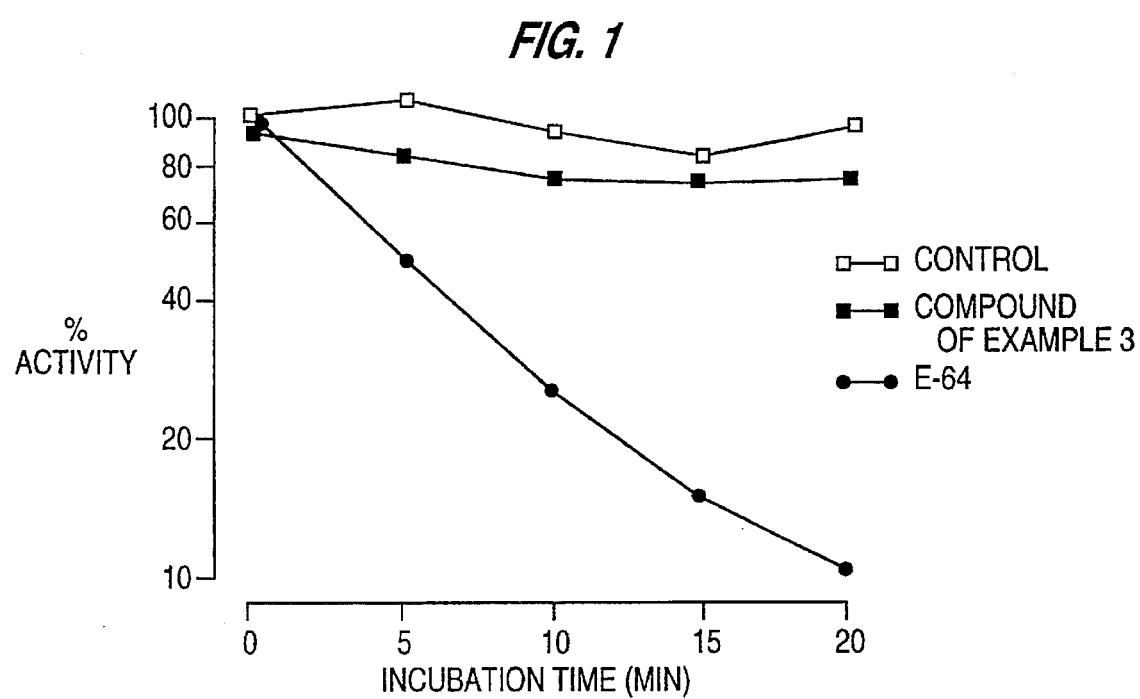
FIGS. 1, 2 and 3 show abilities of the compounds according to the present invention (compounds of Examples 3, 113 and 190, respectively) to reversibly inhibit calpain.

For the purpose of the invention the following terms used herein are defined as follows:

In the above formula (I), $C_1$–$C_{20}$ alkyl group in the definition of $R^{10}$ includes methyl group, ethyl group, propyl group, isopropyl group, butyl group, isobutyl group, sec-butyl group, tert-butyl group, pentyl group, isopentyl group, neopentyl group, tert-pentyl group, hexyl group, isohexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, icosyl group and the like. Such alkyl group may be optionally substituted by one or more substituents selected from the group consisting of $C_3$–$C_{15}$ cycloalkyl group such as cyclopropyl group, cyclobutyl group, cyclopentyl group, cyclohexyl group, cycloheptyl group, cyclooctyl group, cyclononyl group, cyclodecyl group, cycloundecyl group, cyclododecyl group, cyclotridecyl group, cyclotetradecyl group, cyclopentadecyl group or the like; $C_3$–$C_{15}$ cycloalkenyl group such as cyclopropenyl group, cyclobutenyl group, cyclopentenyl group, cyclohexenyl group, 1,4-cyclohexadienyl group, cycloheptenyl group, cyclooctenyl group, cyclodecenyl group, cyclododecenyl group, cyclopentadecenyl group or the like; $C_6$–$C_{14}$ aryl group such as phenyl group, 1-naphthyl group, 2-naphthyl group, anthryl or the like; partially hydrogenated $C_{10}$–$C_{14}$ aryl group such as 1,2-dihydronaphthyl group, 1,2,3,4-tetrahydronaphthyl group or the like; fluorenyl group; heterocyclic group having 5 to 10 of total ring atom number and containing 1 to 4 hetero atoms selected from oxygen atom, sulfur atom and nitrogen atom to form a ring such as furan ring, dihydrofuran ring, tetrahydrofuran ring, pyran ring, dihydropyran ring, tetrahydropyran ring, benzofuran ring, isobenzofuran ring, chromene ring, chroman ring, isochroman ring, thiophene ring, benzothiophene ring, pyrrole ring, pyrroline ring, pyrrolidine ring, imidazole ring, imidazoline ring, imidazolidine ring, pyrazole ring, pyrazoline ring, pyrazolidine ring, triazole ring, tetrazole ring, pyridine ring, pyridine oxide ring, piperidine ring, pyrazine ring, piperazine ring, pyrimidine ring, pyridazine ring, indolidine ring, indole ring, indoline ring, isoindole ring, isoindoline ring, indazole ring, benzoimidazole ring, purine ring, quinolidine ring, quinoline ring, phthalazine ring, naphthylidine ring, quinoxaline ring, quinazoline ring, cinnoline ring, pteridine ring, oxazole ring, oxazolidine ring, isoxazole ring, isoxazolidine ring, thiazole ring, thiazolidine ring, isothiazole ring, isothiazolidine ring, dioxane ring, dithian ring, morpholine ring, thiomorpholine ring or the like; $C_3$–$C_{15}$ cycloalkyloxy group such as cyclopropyloxy group, cyclobutyloxy group, cyclopentyloxy group, cyclohexyloxy group, cycloheptyloxy group, cyclooctyloxy group, cyclodecyloxy group, cyclododecyloxy group, cyclopentadecyloxy group or the like; $C_6$–$C_{14}$ aryloxy group such as phenoxy group, 1-naphthyloxy group, 2-naphthyloxy group or the like; partially hydrogenated $C_6$–$C_{14}$ aryloxy group such as 1,2,3,4-tetrahydro-1-naphthyloxy group, 1,2,3,4-tetrahydro-2-naphthyloxy group, 5,6,7,8-tetrahydro-1-naphthyloxy group, 5,6,7,8-tetrahydro-2-naphthyloxy group or the like; heterocyclic oxy group having 5 to 10 of total ring atom number and containing 1 to 4 hetero atoms selected from oxygen atom, sulfur atom and nitrogen atom to form a ring such as 2-tetrahydrofuryloxy group, 3-tetrahydrofuryloxy group, 2-tetrahydropyranyloxy group, 3-tetrahydropyranyloxy group, 3-pyrrolyloxy group, 1-piperazinyloxy group, 3-morpholinyloxy group, 4-morpholinyloxy group, 2-pyridyloxy group, 3-pyridyloxy group, 4-pyridyloxy group or the like; $C_7$–$C_{20}$ aralkyloxy group such as benzyloxy group, 1-phenylethoxy group, 2-phenylethoxy group, 1-phenylpropoxy group, 2-phenylpropoxy group, 3-phenylpropoxy group, 4-phenylbutoxy group, 5-phenylpentyloxy group, 1-naphthylmethoxy group, 2-naphthylmethoxy group, 1-(1-naphthyl)ethoxy group, 2-(1-naphthyl)ethoxy group, 1-(2-naphthyl)ethoxy group, 2-(2-naphthyl)ethoxy group or the like; and $C_6$–$C_{14}$ arylthio group such as phenylthio group, 1-naphthylthio group, 2-naphthylthio group or the like. Examples of $C_3$–$C_{15}$ cycloalkyl group, $C_6$–$C_{14}$ aryl group, partially hydrogenated $C_{10}$–$C_{14}$ aryl group and heterocyclic group in the definition of $R^{10}$ are the same as illustrated above for the substituents of $C_1$–$C_{20}$ alkyl group. $C_2$–$C_{10}$ alkenyl group includes vinyl group, 1-propenyl group, allyl group, isopropenyl group, 1-butenyl group, 2-butenyl group, 2-pentenyl group, 2-hexenyl group, 2-heptenyl group, 2-octenyl group, 2-nonenyl group, 2-decenyl group and the like. Such alkenyl group may be optionally substituted by one or more substituents selected from the group consisting of the above-mentioned $C_3$–$C_{15}$ cycloalkyl group, optionally substituted $C_6$–$C_{14}$ aryl group, optionally substituted heterocyclic group, $C_3$–$C_{15}$ cycloalkyloxy group, optionally substituted $C_6$–$C_{14}$ aryloxy group, optionally substituted heterocyclic oxy group, optionally substituted $C_7$–$C_{20}$ aralkyloxy group and optionally substituted $C_6$–$C_{14}$ arylthio group.

Examples of $C_1$–$C_5$ alkyl group in the definition of $R^2$, $R^4$ and $R^6$ are methyl group, ethyl group, propyl group, isopropyl group, butyl group, isobutyl group, sec-butyl group, tert-butyl group, pentyl group, isopentyl group, neopentyl group, tert-pentyl group and the like.

Examples of optionally substituted $C_1$–$C_{20}$ alkyl group in the definition of $R^3$ and $R^5$ are the same as illustrated above for $C_1$–$C_{20}$ alkyl group of $R^{10}$. Such alkyl group may be optionally substituted by one or more substituents selected from the group consisting of halogen atom such as fluorine atom, chlorine atom, bromine atom or the like; $C_3$–$C_{15}$ cycloalkyl group as defined in $R^{10}$; hydroxyl group; $C_1$–$C_5$ alkoxy group such as methoxy group, ethoxy group, propoxy group, isopropoxy group, butoxy group, isobutoxy group, sec-butoxy group, tert-butoxy group, pentyloxy group, isopentyloxy group, neopentyloxy group, tert-pentyloxy group or the like, which may be optionally substituted by heterocyclic group as defined in $R^{10}$; $C_6$–$C_{14}$ aryloxy group as defined in $R^{10}$; $C_7$–$C_{20}$ aralkyloxy group as defined in $R^{10}$; mercapto group; $C_1$–$C_5$ alkylthio group such as methylthio group, ethylthio group, propylthio group, isopropylthio group, butylthio group, isobutylthio group, tert-butylthio group, pentylthio group, isopentylthio group or the like, which may be optionally substituted by heterocyclic group as defined in $R^{10}$; $C_6$–$C_{14}$ arylthio group as defined in $R^{10}$; $C_7$–$C_{20}$ aralkylthio group such as benzylthio group, 1-phenylethylthio group, 2-phenylethylthio group, 1-naphthylmethylthio group, 2-naphthylmethylthio group and the like; carboxyl group; carbamoyl group; $C_2$–$C_6$ alkoxycarbonyl group such as methoxycarbonyl group, ethoxycarbonyl group, propoxycarbonyl group, isopropoxycarbonyl group, butoxycarbonyl group, isobutoxycarbonyl group, tert-butoxycarbonyl group, pentyloxycarbonyl group, isopentyloxycarbonyl group or the like; heterocyclic group as defined in $R^{10}$; amino group; $C_1$–$C_5$ monoalkylamino group such as methylamino group, ethylamino group, propylamino group, isopropylamino group or the like; $C_2$–$C_{10}$ dialkylamino group such as dimethylamino group, ethylmethylamino group, diethylamino group or the like; $C_2$–$C_6$ alkoxycarbonylamino group such as methoxycarbonylamino group, ethoxycarbonylamino group, propoxycarbonylamino group, isopropoxycarbonylamino group, butoxycarbonylamino group, isobutoxycarbonylamino group, tert-butoxycarbonylamino group, pentyloxycarbonylamino group, isopentyloxycarbonylamino group or the like; $C_2$–$C_6$ acylamino group such as acetylamino group, propionylamino group, butyrylamino group, isobutyrylamino group, valerylamino group, isovalerylamino group or the like; guanidino group; oxo group; and $C_6$–$C_{14}$ aryl group such as phenyl group, 1-naphthyl group, 2-naphthyl group, anthryl or the like. Examples of $C_7$–$C_{20}$ aralkyloxy group and $C_6$–$C_{14}$ aryl group are the same as defined in $R^{10}$, and examples of $C_1$–$C_{10}$ alkoxy group are methoxy group, ethoxy group, propoxy group, isopropoxy group, butoxy group, isobutoxy group, sec-butoxy group, tert-butoxy group, pentyloxy group, isopentyloxy group, neopentyloxy group, tert-pentyloxy group, hexyloxy group, isohexyloxy group, heptyloxy group, octyloxy group, decyloxy group and the like.

Examples of nitrogen-containing heterocyclic ring formed together with $R^2$ and $R^3$ as well as $R^4$ and $R^5$ are heterocyclic ring having 5 to 10 of total ring atom number and containing 1 to 4 hetero atoms to form a ring such as pyrrolidine ring, piperidine ring, 1,2,3,4-tetrahydroquinoline ring, 1,2,3,4-tetrahydroisoquinoline ring, perhydroquinoline ring, perhydroisoquinoline ring or the like. Such heterocyclic ring may be optionally substituted.

Examples of $C_7$–$C_{20}$ aralkyloxy group and $C_6$–$C_{14}$ aryl group as defined in $R^7$ are the same as defined in $R^{10}$, and examples of $C_1$–$C_{10}$ alkoxy group as defined there are the same as defined in $R^3$ and $R^5$. Examples of optionally substituted $C_1$–$C_{20}$ alkyl group as defined in $R^7$ are the same as defined in $R^{10}$. Such alkyl group may be optionally substituted by one or more substituents selected from the group consisting of $C_3$–$C_{15}$ cycloalkyl group as defined in $R^{10}$; hydroxyl group; $C_1$–$C_5$ alkoxy group such as methoxy group, ethoxy group, propoxy group, isopropoxy group, butoxy group, isobutoxy group, sec-butoxy group, tert-butoxy group, pentyloxy group, isopentyloxy group, neopentyloxy group, tert-pentyloxy group or the like, which may be optionally substituted by heterocyclic group as defined in $R^{10}$; $C_6$–$C_{14}$ aryloxy group as defined in $R^{10}$; $C_7$–$C_{20}$ aralkyloxy group as defined in $R^{10}$; $C_1$–$C_5$ alkylthio group such as methylthio group, ethylthio group, propylthio group, isopropylthio group, butylthio group, isobutylthio group, tert-butylthio group, pentylthio group, isopentylthio group or the like, which may be optionally substituted by heterocyclic group as defined in $R^{10}$; $C_6$–$C_{14}$ arylthio group as defined in $R^{10}$; $C_7$–$C_{20}$ aralkylthio group such as benzylthio group, 1-phenylethylthio group, 2-phenylethylthio group, 1-naphthylmethylthio group, 2-naphthylmethylthio group and the like; carboxyl group; carbamoyl group; $C_2$–$C_6$ alkoxycarbonyl group such as methoxycarbonyl group, ethoxycarbonyl group, propoxycarbonyl group, isopropoxycarbonyl group, butoxycarbonyl group, isobutoxycarbonyl group, tert-butoxycarbonyl group, pentyloxycarbonyl group, isopentyloxycarbonyl group or the like; heterocyclic group as defined in $R^{10}$; and $C_6$–$C_{14}$ aryl group such as phenyl group, 1-naphthyl group, 2-naphthyl group, anthryl or the like.

Examples of $C_1$–$C_5$ alkyl group as defined in $R^8$ are the same as defined in $R^2$, $R_4$ and $R_6$. Examples of $C_7$–$C_{20}$ aralkyl group are benzyl group, 1-phenethyl group, 2-phenethyl group, 1-phenylpropyl group, 2-phenylpropyl group, 3-phenylpropyl group, 4-phenylbutyl group, 5-phenylpentyl group, 1-naphthylmethyl group, 2-naphthylmethyl group, 1-(1-naphthyl)ethyl group, 1-(2-naphthyl)ethyl group, 2-(1-naphthyl)ethyl group, 2-(2-naphthyl)ethyl group and the like.

Examples of $C_3$–$C_{15}$ cycloalkyl group formed together with $R^7$ and $R^8$ are the same as defined in $R^{10}$.

Examples of $C_6$–$C_{14}$ aryl group as defined in $R^9$ are the same as defined in $R^{10}$.

Examples of $C_1$–$C_5$ alkylthio group, $C_2$–$C_6$ alkoxycarbonylamino group, $C_1$–$C_5$ monoalkylamino group, $C_2$–$C_{10}$ dialkylamino group, $C_2$–$C_6$ acylamino group and $C_1$–$C_5$ alkoxy group in the definition of X are the same as defined in $R^3$ and $R^5$ as the substituents for $C_1$–$C_{20}$ alkyl group, and examples of heterocyclic group, $C_6$–$C_{14}$ aryl group and $C_6$–$C_{14}$ aryloxy group are the same as defined in $R^{10}$.

Examples of $C_1$–$C_{20}$ alkyl group in the definition of $R^{11}$ are the same as defined in $R^{10}$, and such alkyl group may be optionally substituted by one or more substituents selected from the group consisting of hydroxyl group; mercapto group; amino group; $C_7$–$C_{20}$ aralkylthio group such as benzylthio group, 1-phenylethylthio group, 2-phenylethylthio group, 1-naphthylmethylthio group, 2-naphthylmethylthio group and the like; $C_1$–$C_5$ alkoxy group, $C_1$–$C_5$ alkylthio group, $C_1$–$C_5$ monoalkylamino group and $C_2$–$C_{10}$ dialkylamino group each of which is the same as defined in $R^3$ or $R^5$ as the substituents for $C_1$–$C_{20}$ alkyl group; $C_6$–$C_{14}$ aryloxy group, $C_7$–$C_{20}$ aralkyloxy group, $C_6$–$C_{14}$ arylthio group and heterocyclic group each of which is the same as defined in $R^{10}$.

Examples of nitrogen-containing heterocyclic ring formed together with $R^9$ and $R^{11}$ are heterocyclic ring having 5 to 10 of total ring atom number and containing 1 to 4 hetero atoms to form a ring such as pyrrolidine ring, piperidine ring, piperazine ring, 1,2,3,4-tetrahydroquinoline ring, 1,2,3,4-tetrahydroisoquinoline ring, perhydroquinoline ring, perhydroisoquinoline ring or the like. Such heterocyclic ring may be optionally substituted.

In the above definition, aryl group, partially hydrogenated aryl group and heterocyclic group positioned at the terminal of each substituent may be optionally substituted by one or more substituents selected from the group consisting of halogen atom such as fluorine atom, chlorine atom, bromine atom or the like; $C_1$–$C_5$ alkyl group such as methyl group, ethyl group, propyl group, isopropyl group, butyl group, isobutyl group, sec-butyl group, tert-butyl group, pentyl group, isopentyl group, neopentyl group or the like; trifluoromethyl group; $C_1$–$C_5$ alkoxy group such as methoxy group, ethoxy group, propoxy group, isopropoxy group, butoxy group, isobutoxy group, tert-butoxy group, pentyloxy group, isopentyloxy group or the like; $C_1$–$C_5$ cyclic acetal group such as methylenedioxy group, ethylenedioxy group, propylenedioxy group, butylenedioxy group or the like; hydroxyl group; $C_2$–$C_6$ acyloxy group such as acetoxy group, propionyloxy group, butyryloxy group, valeryloxy group or the like; carboxyl group; $C_2$–$C_6$ alkoxycarbonyl group such as methoxycarbonyl group, ethoxycarbonyl group, propoxycarbonyl group, isopropoxycarbonyl group, butoxycarbonyl group, isobutoxycarbonyl group, tert-butoxycarbonyl group, pentyloxycarbonyl group or the like; oxo group; $C_2$–$C_6$ acyl group such as acetyl group, propionyl group, butyryl group, valeryl group or the like; amino group; $C_1$–$C_5$ monoalkylamino group such as methylamino group, ethylamino group, propylamino group, isopropylamino group, butylamino group, isobutylamino group, tert-butylamino group, pentylamino group, isopentylamino group or the like; $C_2$–$C_{10}$ dialkylamino group such as dimethylamino group, ethylmethylamino group, diethylamino group, methylpropylamino group, diisopropylamino group or the like; $C_2$–$C_6$ acylamino group such as acetylamino group, propionylamino group, isopropionylamino group, butyrylamino group, isobutyrylamino group, valerylamino group or the like; carbamoyl group; $C_2$–$C_6$ alkylcarbamoyl group such as methylcarbamoyl group, ethylcarbamoyl group, propylcarbamoyl group, isopropylcarbamoyl group, butylcarbamoyl group, tert-butylcarbamoyl group, pentylcarbamoyl group or the like; and $C_6$–$C_{14}$ aryl group such as phenyl group, 1-naphthyl group, 2-naphthyl group, anthryl or the like.

The compounds of the above formula (I) wherein A is —S—, —SO—, —$SO_2$— or —$N(R^{11})$— (in which $R^{11}$ is optionally substituted $C_1$–$C_{15}$ alkyl group) are preferred in the present invention.

More preferred are the compounds wherein $R^9$ is —$(CH_2)_m$—X (in which X is hydroxyl group, $C_1$–$C_5$ alkylthio group, $C_2$–$C_6$ alkoxycarbonylamino group, optionally substituted heterocyclic group, amino group, $C_1$–$C_5$ monoalkylamino group, $C_2$–$C_{10}$ dialkylamino group, $C_2$–$C_6$ acylamino group, halogen atom, $C_1$–$C_5$ alkoxy group, optionally substituted $C_6$–$C_{14}$ aryl group or optionally substituted $C_6$–$C_{14}$ aryloxy group; and m is an integer of 1 to 10).

Particularly preferred are the compounds wherein $R^1$ is hydrogen atom, $R^{10}$—CO—, $R^{10}$—O—CO—, $R^{10}$—$SO_2$— or $R^{10}$—NH—CO— (in which $R^{10}$ is $C_1$–$C_{15}$ alkyl group optionally substituted by one or more substituents selected from the group consisting of $C_3$–$C_{15}$ cycloalkyl group, $C_3$–$C_{15}$ cycloalkenyl group, optionally substituted $C_6$–$C_{14}$ aryl group, optionally substituted and partially hydrogenated $C_{10}$–$C_{14}$ aryl group, optionally substituted heterocyclic group, $C_3$–$C_{15}$ cycloalkyloxy group, optionally substituted $C_6$–$C_{14}$ aryloxy group, optionally substituted and partially hydrogenated $C_6$–$C_{14}$ aryloxy group, optionally substituted heterocyclic oxy group, optionally substituted $C_7$–$C_{20}$ aralkyloxy group and optionally substituted $C_6$–$C_{14}$ arylthio group; $C_3$–$C_{15}$ cycloalkyl group; optionally substituted $C_6$–$C_{14}$ aryl group; optionally substituted and partially hydrogenated $C_6$–$C_{14}$ aryl group; optionally substituted $C_2$–$C_{10}$ alkenyl group; or optionally substituted heterocyclic group); $R^4$ and $R^6$ each is independently hydrogen atom or $C_1$–$C_5$ alkyl group; $R^5$ is hydrogen atom, optionally substituted $C_6$–$C_{14}$ aryl group, $C_1$–$C_{10}$ alkoxy group or optionally substituted $C_1$–$C_{15}$ alkyl group; $R^7$ is $C_1$–$C_{15}$ alkyl group optionally substituted by one or more substituents selected from the group consisting of $C_3$–$C_{15}$ cycloalkyl group, hydroxyl group, $C_1$–$C_5$ alkoxy group optionally substituted by heterocyclic group, $C_6$–$C_{14}$ aryloxy group, $C_7$–$C_{20}$ aralkyloxy group, $C_1$–$C_5$ alkylthio group optionally substituted by heterocyclic group, $C_6$–$C_{14}$ arylthio group, $C_7$–$C_{20}$ aralkylthio group, carboxyl group, carbamoyl group, $C_2$–$C_6$ alkoxycarbonyl group and heterocyclic group; hydrogen atom; optionally substituted $C_6$–$C_{14}$ aryl group or $C_1$–$C_{10}$ alkoxy group; $R^8$ is hydrogen atom.

The ketone derivatives of the general formula (I) above in the present invention can form pharmaceutically acceptable salts thereof. Examples of such salts include, if an acidic group is present, metal salts such as lithium salt, sodium salt, potassium salt, magnesium salt, calcium salt or the like and ammonium salts such as ammonium salt, methylammonium salt, dimethylammonium salt, trimethylammonium salt, dicyclohexylammonium salt or the like and, if a basic group is present, mineral acid salts such as hydrochloride, hydrobromide, sulfate, nitrate or the like and organic acid salts such as methanesulfonate, benzenesulfonate, p-toluenesulfonate, acetate, propionate, tartrate, fumarate, maleate, malate, oxalate, succinate, citrate, benzoate, mandelate, cinnamate, lactate or the like.

Regarding the stereochemistry of double bond regions existing on the ketone derivatives of the general formula (I) above, (E) form, (Z) form and (EZ) form can be provided. As for the stereochemistry of asymmetric carbon, (R) form, (S) form and (RS) form can be given.

Illustrative examples of the ketone derivatives of the general formula (I) above include the compounds as shown in the following Table 1 (in case of n=0) and the compounds as shown in the following Table 2 (in case of n=1).

TABLE 1

| Compd. No. | R¹ | R⁴ | R⁵ | R⁶ | R⁷ | R⁸ | –A–R⁹ |
|---|---|---|---|---|---|---|---|
| 1 | benzyl ester (PhCH₂-O-C(=O)-) | H | –CH₂CH(CH₃)₂ | H | H | H | –S–CH₃ |
| 2 | benzyl ester | H | –CH₂CH(CH₃)₂ | H | H | H | furan-2-yl-CH₂-S– |
| 3 | benzyl ester | H | –CH₂–Ph | H | H | H | furan-2-yl-CH₂-S– |
| 4 | benzyl ester | H | –CH₂CH(CH₃)₂ | H | H | H | pyridin-2-yl-CH₂-S– |
| 5 | benzyl ester | H | –CH₂CH(CH₃)₂ | H | H | H | pyridin-4-yl-CH₂-S– |
| 6 | benzyl ester | H | –CH₂CH(CH₃)₂ | H | H | H | pyridin-3-yl-CH₂-S– |
| 7 | benzyl ester | H | –CH₂CH(CH₃)₂ | H | –CH₃ | H | –S–CH₃ |

TABLE 1-continued

| Compd. No. | R¹ | R⁴ | R⁵ | R⁶ | R⁷ | R⁸ | —A—R⁹ |
|---|---|---|---|---|---|---|---|
| 8 | benzyl ester (–C(=O)O–CH₂–C₆H₅) | H | –CH₂CH(CH₃)₂ | H | –CH₃ | H | –S–CH₂–(2-furyl) |
| 9 | benzyl ester (–C(=O)O–CH₂–C₆H₅) | H | –CH₂–C₆H₅ | H | –CH₃ | H | –S–CH₂–(2-furyl) |
| 10 | (CH₃)₃COC(=O)– | H | –CH₂–C₆H₅ | H | –CH₃ | H | –S–CH₂–(2-furyl) |
| 11 | H | H | –CH₂–C₆H₅ | H | –CH₃ | H | –S–CH₂–(2-furyl) |
| 12 | –C(=O)CH₂–O–C₆H₅ | H | –CH₂–C₆H₅ | H | –CH₃ | H | –S–CH₂–(2-furyl) |
| 13 | –S(=O)₂–C₆H₅ | H | –CH₂–C₆H₅ | H | –CH₃ | H | –S–CH₂–(2-furyl) |
| 14 | benzyl ester (–C(=O)O–CH₂–C₆H₅) | H | –CH₂CH(CH₃)₂ | H | –CH₃ | –CH₃ | –S–CH₃ |

TABLE 1-continued

| Compd. No. | R¹ | R⁴ | R⁵ | R⁶ | R⁷ | R⁸ | —A—R⁹ |
|---|---|---|---|---|---|---|---|
| 15 | benzyl ester | H | —CH₂CH(CH₃)₂ | H | —CH₃ | —CH₃ | CH₂-S-furan |
| 16 | benzyl ester | H | —CH₂CH(CH₃)₂ | H | —CH₃ | —CH₃ | CH₂-S-(2-pyridyl) |
| 17 | benzyl ester | H | —CH₂CH(CH₃)₂ | H | —CH₃ | —CH₃ | CH₂-S-(3-pyridyl) |
| 18 | benzyl ester | H | —CH₂CH(CH₃)₂ | H | —CH₃ | —CH₃ | CH₂-S-(4-pyridyl) |
| 19 | benzyl ester | H | —CH(CH₃)₂ | H | —CH(CH₃)₂ | H | —S—CH₃ |
| 20 | benzyl ester | H | —CH₂CH(CH₃)₂ | H | —CH(CH₃)₂ | H | CH₂-S-furan |
| 21 | (CH₃)₃COCO— | H | —CH₂CH(CH₃)₂ | H | —CH(CH₃)₂ | H | CH₂-S-furan |

TABLE 1-continued

| Compd. No. | R¹ | R⁴ | R⁵ | R⁶ | R⁷ | R⁸ | —A—R⁹ |
|---|---|---|---|---|---|---|---|
| 22 | PhCH₂—O—C(=O)— | H | —CH₂CH(CH₃)₂ | H | —CH(CH₃)₂ | H | —CH₂—S—CH₂-(2-furyl) |
| 23 | H | H | —CH₂CH(CH₃)₂ | H | —CH(CH₃)₂ | H | —CH₂—S—CH₂-(2-furyl) |
| 24 | PhO—CH₂—C(=O)— | H | —CH₂CH(CH₃)₂ | H | —CH(CH₃)₂ | H | —CH₂—S—CH₂-(2-furyl) |
| 25 | 2,6-difluorobenzoyl | H | —CH₂CH(CH₃)₂ | H | —CH(CH₃)₂ | H | —CH₂—S—CH₂-(2-furyl) |
| 26 | PhCH₂—O—C(=O)— | H | —CH₂CH(CH₃)₂ | H | —CH₂CH₂CH₃ | H | —CH₂—S—CH₂-(2-furyl) |
| 27 | (CH₃)₃COC(=O)— | H | —CH₂CH(CH₃)₂ | H | —CH₂CH₂CH₃ | H | —CH₂—S—CH₂-(2-furyl) |
| 28 | PhCH₂—O—C(=O)— | H | —CH₂CH(CH₃)₂ | H | —CH₂CH₂CH₃ | H | —CH₂—S—CH₂-(2-furyl) |
| 29 | H | H | —CH₂CH(CH₃)₂ | H | —CH₂CH₂CH₃ | H | —CH₂—S—CH₂-(2-furyl) |

TABLE 1-continued
| Compd. No. | R¹ | R⁴ | R⁵ | R⁶ | R⁷ | R⁸ | −A−R⁹ |
|---|---|---|---|---|---|---|---|
| 30 | 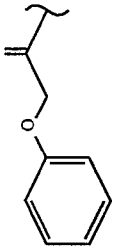 | H | −CH₂CH(CH₃)₂ | H | −CH₂CH₂CH₃ | H | 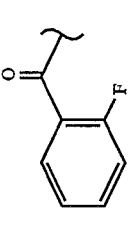 |
| 31 | 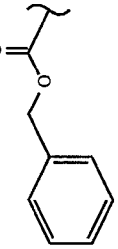 | H | −CH₂CH(CH₃)₂ | H | −CH₂CH₂CH₃ | H | 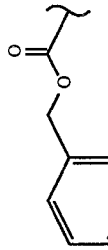 |
| 32 | 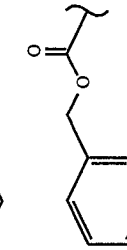 | H | −CH₂CH(CH₃)₂ | H | −CH₂CH(CH₃)₂ | H | −S−CH₃ |
| 33 | 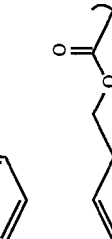 | H |  | H | −CH₂CH(CH₃)₂ | H | −S−CH₃ |
| 34 | 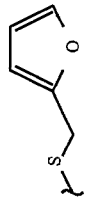 | H | −CH₃ | H | −CH₂CH(CH₃)₂ | H | 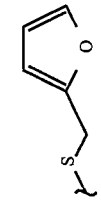 |
| 35 | 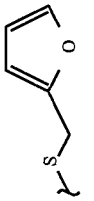 | H | −CH₂CH(CH₃)₂ | H | −CH₂CH(CH₃)₂ | H |  |
| 36 |  | H |  | H | −CH₂CH(CH₃)₂ | H |  |

TABLE 1-continued

| Compd. No. | R¹ | R⁴ | R⁵ | R⁶ | R⁷ | R⁸ | −A−R⁹ |
|---|---|---|---|---|---|---|---|
| 37 | benzyl−O−C(=O)− | H | −CH$_2$CH(CH$_3$)$_2$ | H | −CH$_2$CH$_2$CH$_2$CH$_3$ | H | −S−CH$_3$ |
| 38 | benzyl−O−C(=O)− | H | H | H | −CH$_2$CH$_2$CH$_2$CH$_3$ | H | −CH$_2$−S−(2-furyl) |
| 39 | benzyl−O−C(=O)− | H | −CH$_3$ | H | −CH$_2$CH$_2$CH$_2$CH$_3$ | H | −CH$_2$−S−(2-furyl) |
| 40 | benzyl−O−C(=O)− | H | −CH(CH$_3$)$_2$ | H | −CH$_2$CH$_2$CH$_2$CH$_3$ | H | −CH$_2$−S−(2-furyl) |
| 41 | benzyl−O−C(=O)− | H | −CH$_2$CH$_2$CH$_3$ | H | −CH$_2$CH$_2$CH$_2$CH$_3$ | H | −CH$_2$−S−(2-furyl) |
| 42 | CH$_3$CH$_2$OC(=O)− | H | −CH$_2$CH(CH$_3$)$_2$ | H | −CH$_2$CH$_2$CH$_2$CH$_3$ | H | −CH$_2$−S−(2-furyl) |
| 43 | (CH$_3$)$_3$COC(=O)− | H | −CH$_2$CH(CH$_3$)$_2$ | H | −CH$_2$CH$_2$CH$_2$CH$_3$ | H | −CH$_2$−S−(2-furyl) |
| 44 | isobutyl−O−C(=O)− | H | −CH$_2$CH(CH$_3$)$_2$ | H | −CH$_2$CH$_2$CH$_2$CH$_3$ | H | −CH$_2$−S−(2-furyl) |

TABLE 1-continued

| Compd. No. | R¹ | R⁴ | R⁵ | R⁶ | R⁷ | R⁸ | —A—R⁹ |
|---|---|---|---|---|---|---|---|
| 45 | cyclohexyl-O-C(=O)— | H | —CH₂CH(CH₃)₂ | H | —CH₂CH₂CH₂CH₃ | H | furan-2-yl-CH₂—S— |
| 46 | cyclohexyl-CH₂-O-C(=O)— | H | —CH₂CH(CH₃)₂ | H | —CH₂CH₂CH₂CH₃ | H | furan-2-yl-CH₂—S— |
| 47 | cyclohexyl-CH₂CH₂-O-C(=O)— | H | —CH₂CH(CH₃)₂ | H | —CH₂CH₂CH₂CH₃ | H | furan-2-yl-CH₂—S— |
| 48 | phenyl-CH₂-O-C(=O)— | H | —CH₂CH(CH₃)₂ | H | —CH₂CH₂CH₂CH₃ | H | furan-2-yl-CH₂—S— |
| 49 | (2-F-phenyl)-CH₂-O-C(=O)— | H | —CH₂CH(CH₃)₂ | H | —CH₂CH₂CH₂CH₃ | H | furan-2-yl-CH₂—S— |
| 50 | (3-F-phenyl)-CH₂-O-C(=O)— | H | —CH₂CH(CH₃)₂ | H | —CH₂CH₂CH₂CH₃ | H | furan-2-yl-CH₂—S— |
| 51 | (4-F-phenyl)-CH₂-O-C(=O)— | H | —CH₂CH(CH₃)₂ | H | —CH₂CH₂CH₂CH₃ | H | furan-2-yl-CH₂—S— |

TABLE 1-continued

| Compd. No. | R¹ | R⁴ | R⁵ | R⁶ | R⁷ | R⁸ | —A—R⁹ |
|---|---|---|---|---|---|---|---|
| 52 | 2-Cl-C₆H₄-CH₂-O-C(O)- | H | —CH₂CH(CH₃)₂ | H | —CH₂CH₂CH₂CH₃ | H | furfuryl-CH₂-S- |
| 53 | 3-Cl-C₆H₄-CH₂-O-C(O)- | H | —CH₂CH(CH₃)₂ | H | —CH₂CH₂CH₂CH₃ | H | furfuryl-CH₂-S- |
| 54 | 4-Cl-C₆H₄-CH₂-O-C(O)- | H | —CH₂CH(CH₃)₂ | H | —CH₂CH₂CH₂CH₃ | H | furfuryl-CH₂-S- |
| 55 | 4-CH₃O-C₆H₄-CH₂-O-C(O)- | H | —CH₂CH(CH₃)₂ | H | —CH₂CH₂CH₂CH₃ | H | furfuryl-CH₂-S- |
| 56 | 2-CN-C₆H₄-CH₂-O-C(O)- | H | —CH₂CH(CH₃)₂ | H | —CH₂CH₂CH₂CH₃ | H | furfuryl-CH₂-S- |
| 57 | 3-CN-C₆H₄-CH₂-O-C(O)- | H | —CH₂CH(CH₃)₂ | H | —CH₂CH₂CH₂CH₃ | H | furfuryl-CH₂-S- |
| 58 | 4-CN-C₆H₄-CH₂-O-C(O)- | H | —CH₂CH(CH₃)₂ | H | —CH₂CH₂CH₂CH₃ | H | furfuryl-CH₂-S- |

TABLE 1-continued

| Compd. No. | R¹ | R⁴ | R⁵ | R⁶ | R⁷ | R⁸ | -A-R⁹ |
|---|---|---|---|---|---|---|---|
| 59 | 2-pyridyl-CH₂-O-C(=O)- | H | -CH₂CH(CH₃)₂ | H | -CH₂CH₂CH₂CH₃ | H | -S-CH₂-(2-furyl) |
| 60 | 3-pyridyl-CH₂-O-C(=O)- | H | -CH₂CH(CH₃)₂ | H | -CH₂CH₂CH₂CH₃ | H | -S-CH₂-(2-furyl) |
| 61 | 4-pyridyl-CH₂-O-C(=O)- | H | -CH₂CH(CH₃)₂ | H | -CH₂CH₂CH₂CH₃ | H | -S-CH₂-(2-furyl) |
| 62 | H | H | -CH₂CH(CH₃)₂ | H | -CH₂CH₂CH₂CH₃ | H | -S-CH₂-(2-furyl) |
| 63 | CH₃C(=O)- | H | -CH₂CH(CH₃)₂ | H | -CH₂CH₂CH₂CH₃ | H | -S-CH₂-(2-furyl) |
| 64 | (CH₃)₂CHCH₂CH₂-C(=O)- | H | -CH₂CH(CH₃)₂ | H | -CH₂CH₂CH₂CH₃ | H | -S-CH₂-(2-furyl) |
| 65 | cyclohexyl-C(=O)- | H | -CH₂CH(CH₃)₂ | H | -CH₂CH₂CH₂CH₃ | H | -S-CH₂-(2-furyl) |
| 66 | PhCH₂-C(=O)- | H | -CH₂CH(CH₃)₂ | H | -CH₂CH₂CH₂CH₃ | H | -S-CH₂-(2-furyl) |

5,639,783

TABLE 1-continued

| Compd. No. | R¹ | R⁴ | R⁵ | R⁶ | R⁷ | R⁸ | —A—R⁹ |
|---|---|---|---|---|---|---|---|
| 67 | 2-F-C₆H₄-CH₂-C(=O)- | H | -CH₂CH(CH₃)₂ | H | -CH₂CH₂CH₂CH₃ | H | -S-CH₂-(2-furyl) |
| 68 | 3-F-C₆H₄-CH₂-C(=O)- | H | -CH₂CH(CH₃)₂ | H | -CH₂CH₂CH₂CH₃ | H | -S-CH₂-(2-furyl) |
| 69 | 4-F-C₆H₄-CH₂-C(=O)- | H | -CH₂CH(CH₃)₂ | H | -CH₂CH₂CH₂CH₃ | H | -S-CH₂-(2-furyl) |
| 70 | 2-OCH₃-C₆H₄-CH₂-C(=O)- | H | -CH₂CH(CH₃)₂ | H | -CH₂CH₂CH₂CH₃ | H | -S-CH₂-(2-furyl) |
| 71 | 3-OCH₃-C₆H₄-CH₂-C(=O)- | H | -CH₂CH(CH₃)₂ | H | -CH₂CH₂CH₂CH₃ | H | -S-CH₂-(2-furyl) |
| 72 | 4-OCH₃-C₆H₄-CH₂-C(=O)- | H | -CH₂CH(CH₃)₂ | H | -CH₂CH₂CH₂CH₃ | H | -S-CH₂-(2-furyl) |
| 73 | benzoxazol-4-yl-CH₂-C(=O)- | H | -CH₂CH(CH₃)₂ | H | -CH₂CH₂CH₂CH₃ | H | -S-CH₂-(2-furyl) |

TABLE 1-continued

| Compd. No. | R¹ | R⁴ | R⁵ | R⁶ | R⁷ | R⁸ | —A—R⁹ |
|---|---|---|---|---|---|---|---|
| 74 | phenethyl-C(=O)— | H | —CH$_2$CH(CH$_3$)$_2$ | H | —CH$_2$CH$_2$CH$_2$CH$_3$ | H | —S—CH$_2$-(2-furyl) |
| 75 | 3-phenylpropyl-C(=O)— | H | —CH$_2$CH(CH$_3$)$_2$ | H | —CH$_2$CH$_2$CH$_2$CH$_3$ | H | —S—CH$_2$-(2-furyl) |
| 76 | (naphthalen-1-yl)methyl-C(=O)— | H | —CH$_2$CH(CH$_3$)$_2$ | H | —CH$_2$CH$_2$CH$_2$CH$_3$ | H | —S—CH$_2$-(2-furyl) |
| 77 | (naphthalen-2-yl)methyl-C(=O)— | H | —CH$_2$CH(CH$_3$)$_2$ | H | —CH$_2$CH$_2$CH$_2$CH$_3$ | H | —S—CH$_2$-(2-furyl) |
| 78 | (benzothiophen-2-yl)methyl-C(=O)— | H | —CH$_2$CH(CH$_3$)$_2$ | H | —CH$_2$CH$_2$CH$_2$CH$_3$ | H | —S—CH$_2$-(2-furyl) |
| 79 | (benzofuran-2-yl)methyl-C(=O)— | H | —CH$_2$CH(CH$_3$)$_2$ | H | —CH$_2$CH$_2$CH$_2$CH$_3$ | H | —S—CH$_2$-(2-furyl) |
| 80 | cyclopropyl-O—CH$_2$—C(=O)— | H | —CH$_2$CH(CH$_3$)$_2$ | H | —CH$_2$CH$_2$CH$_2$CH$_3$ | H | —S—CH$_2$-(2-furyl) |

TABLE 1-continued

| Compd. No. | R¹ | R⁴ | R⁵ | R⁶ | R⁷ | R⁸ | –A–R⁹ |
|---|---|---|---|---|---|---|---|
| 81 | cyclohexyl-O-CH₂-C(=O)- | H | –CH₂CH(CH₃)₂ | H | –CH₂CH₂CH₂CH₃ | H | furan-2-yl-CH₂-S- |
| 82 | phenyl-O-CH₂-C(=O)- | H | –CH₂CH(CH₃)₂ | H | –CH₂CH₂CH₂CH₃ | H | furan-2-yl-CH₂-S- |
| 83 | phenyl-O-CH₂-C(=O)- | H | –CH₂CH(CH₃)₂ | H | –CH₂CH₂CH₂CH₃ | H | furan-2-yl-CH₂-S(=O)- |
| 84 | phenyl-O-CH₂-C(=O)- | H | –CH₂CH(CH₃)₂ | H | –CH₂CH₂CH₂CH₃ | H | furan-2-yl-CH₂-S(=O)₂- |
| 85 | 2-fluorophenyl-O-CH₂-C(=O)- | H | –CH₂CH(CH₃)₂ | H | –CH₂CH₂CH₂CH₃ | H | furan-2-yl-CH₂-S- |
| 86 | 3-fluorophenyl-O-CH₂-C(=O)- | H | –CH₂CH(CH₃)₂ | H | –CH₂CH₂CH₂CH₃ | H | furan-2-yl-CH₂-S- |
| 87 | 4-fluorophenyl-O-CH₂-C(=O)- | H | –CH₂CH(CH₃)₂ | H | –CH₂CH₂CH₂CH₃ | H | furan-2-yl-CH₂-S- |

TABLE 1-continued

| Compd. No. | R¹ | R⁴ | R⁵ | R⁶ | R⁷ | R⁸ | –A–R⁹ |
|---|---|---|---|---|---|---|---|
| 88 | 2-Cl-phenyl-OCH₂C(O)– | H | –CH₂CH(CH₃)₂ | H | –CH₂CH₂CH₂CH₃ | H | –SCH₂-(2-furyl) |
| 89 | 3-Cl-phenyl-OCH₂C(O)– | H | –CH₂CH(CH₃)₂ | H | –CH₂CH₂CH₂CH₃ | H | –SCH₂-(2-furyl) |
| 90 | 4-Cl-phenyl-OCH₂C(O)– | H | –CH₂CH(CH₃)₂ | H | –CH₂CH₂CH₂CH₃ | H | –SCH₂-(2-furyl) |
| 91 | 2,3-diCl-phenyl-OCH₂C(O)– | H | –CH₂CH(CH₃)₂ | H | –CH₂CH₂CH₂CH₃ | H | –SCH₂-(2-furyl) |
| 92 | 2,4-diCl-phenyl-OCH₂C(O)– | H | –CH₂CH(CH₃)₂ | H | –CH₂CH₂CH₂CH₃ | H | –SCH₂-(2-furyl) |
| 93 | 3,4-diCl-phenyl-OCH₂C(O)– | H | –CH₂CH(CH₃)₂ | H | –CH₂CH₂CH₂CH₃ | H | –SCH₂-(2-furyl) |
| 94 | 2,6-diCl-phenyl-OCH₂C(O)– | H | –CH₂CH(CH₃)₂ | H | –CH₂CH₂CH₂CH₃ | H | –SCH₂-(2-furyl) |

TABLE 1-continued

| Compd. No. | R¹ | R⁴ | R⁵ | R⁶ | R⁷ | R⁸ | −A−R⁹ |
|---|---|---|---|---|---|---|---|
| 95 | 2,3,4-trichlorophenoxy-CH₂-C(=O)- | H | −CH₂CH(CH₃)₂ | H | −CH₂CH₂CH₂CH₃ | H | furan-2-yl-CH₂-S- |
| 96 | 2-methylphenoxy-CH₂-C(=O)- | H | −CH₂CH(CH₃)₂ | H | −CH₂CH₂CH₂CH₃ | H | furan-2-yl-CH₂-S- |
| 97 | 3-methylphenoxy-CH₂-C(=O)- | H | −CH₂CH(CH₃)₂ | H | −CH₂CH₂CH₂CH₃ | H | furan-2-yl-CH₂-S- |
| 98 | 4-methylphenoxy-CH₂-C(=O)- | H | −CH₂CH(CH₃)₂ | H | −CH₂CH₂CH₂CH₃ | H | furan-2-yl-CH₂-S- |
| 99 | 2-chloro-4-methylphenoxy-CH₂-C(=O)- | H | −CH₂CH(CH₃)₂ | H | −CH₂CH₂CH₂CH₃ | H | furan-2-yl-CH₂-S- |
| 100 | 2-methyl-4-chlorophenoxy-CH₂-C(=O)- | H | −CH₂CH(CH₃)₂ | H | −CH₂CH₂CH₂CH₃ | H | furan-2-yl-CH₂-S- |

TABLE 1-continued
| Compd. No. | R¹ | R⁴ | R⁵ | R⁶ | R⁷ | R⁸ | −A−R⁹ |
|---|---|---|---|---|---|---|---|
| 101 |  | H | −CH$_2$CH(CH$_3$)$_2$ | H | −CH$_2$CH$_2$CH$_2$CH$_3$ | H | 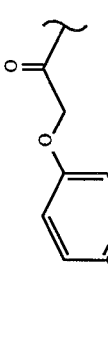 |
| 102 | 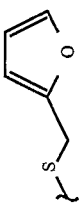 | H | −CH$_2$CH(CH$_3$)$_2$ | H | −CH$_2$CH$_2$CH$_2$CH$_3$ | H | 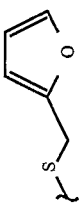 |
| 103 | 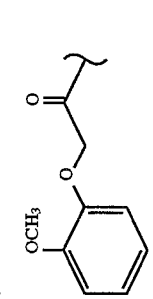 | H | −CH$_2$CH(CH$_3$)$_2$ | H | −CH$_2$CH$_2$CH$_2$CH$_3$ | H | 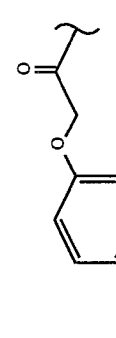 |
| 104 | 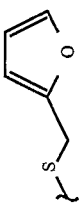 | H | −CH$_2$CH(CH$_3$)$_2$ | H | −CH$_2$CH$_2$CH$_2$CH$_3$ | H | 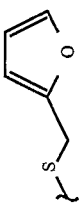 |
| 105 | 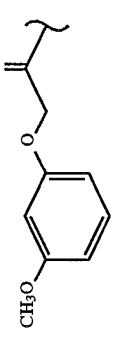 | H | −CH$_2$CH(CH$_3$)$_2$ | H | −CH$_2$CH$_2$CH$_2$CH$_3$ | H | 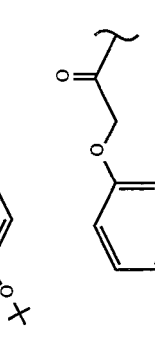 |
| 106 | 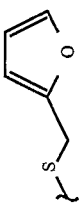 | H | −CH$_2$CH(CH$_3$)$_2$ | H | −CH$_2$CH$_2$CH$_2$CH$_3$ | H | 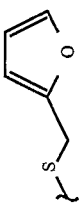 |

TABLE 1-continued

| Compd. No. | R¹ | R⁴ | R⁵ | R⁶ | R⁷ | R⁸ | —A—R⁹ |
|---|---|---|---|---|---|---|---|
| 107 | phenylthiomethyl-C(O)— | H | —CH$_2$CH(CH$_3$)$_2$ | H | —CH$_2$CH$_2$CH$_2$CH$_3$ | H | furan-2-ylmethylthio |
| 108 | benzyloxymethyl-C(O)— | H | —CH$_2$CH(CH$_3$)$_2$ | H | —CH$_2$CH$_2$CH$_2$CH$_3$ | H | furan-2-ylmethylthio |
| 109 | phenoxyethyl-C(O)— | H | —CH$_2$CH(CH$_3$)$_2$ | H | —CH$_2$CH$_2$CH$_2$CH$_3$ | H | furan-2-ylmethylthio |
| 110 | (tetrahydronaphth-1-yloxy)methyl-C(O)— | H | —CH$_2$CH(CH$_3$)$_2$ | H | —CH$_2$CH$_2$CH$_2$CH$_3$ | H | furan-2-ylmethylthio |
| 111 | (tetrahydronaphth-1-yloxy)methyl-C(O)— | H | —CH$_2$CH(CH$_3$)$_2$ | H | —CH$_2$CH$_2$CH$_2$CH$_3$ | H | furan-2-ylmethylthio |
| 112 | (tetrahydronaphth-2-yloxy)methyl-C(O)— | H | —CH$_2$CH(CH$_3$)$_2$ | H | —CH$_2$CH$_2$CH$_2$CH$_3$ | H | furan-2-ylmethylthio |
| 113 | (tetrahydronaphth-2-yloxy)methyl-C(O)— | H | —CH$_2$CH(CH$_3$)$_2$ | H | —CH$_2$CH$_2$CH$_2$CH$_3$ | H | furan-2-ylmethylthio |

TABLE 1-continued

| Compd. No. | R¹ | R⁴ | R⁵ | R⁶ | R⁷ | R⁸ | —A—R⁹ |
|---|---|---|---|---|---|---|---|
| 114 | 1-naphthyl-O-CH₂-C(=O)- | H | —CH₂CH(CH₃)₂ | H | —CH₂CH₂CH₂CH₃ | H | —S—CH₂-(2-furyl) |
| 115 | 2-naphthyl-O-CH₂-C(=O)- | H | —CH₂CH(CH₃)₂ | H | —CH₂CH₂CH₂CH₃ | H | —S—CH₂-(2-furyl) |
| 116 | C₆H₅-C(=O)- | H | —CH₂CH(CH₃)₂ | H | —CH₂CH₂CH₂CH₃ | H | —S—CH₂-(2-furyl) |
| 117 | 2-F-C₆H₄-C(=O)- | H | —CH₂CH(CH₃)₂ | H | —CH₂CH₂CH₂CH₃ | H | —S—CH₂-(2-furyl) |
| 118 | 3-F-C₆H₄-C(=O)- | H | —CH₂CH(CH₃)₂ | H | —CH₂CH₂CH₂CH₃ | H | —S—CH₂-(2-furyl) |
| 119 | 4-F-C₆H₄-C(=O)- | H | —CH₂CH(CH₃)₂ | H | —CH₂CH₂CH₂CH₃ | H | —S—CH₂-(2-furyl) |
| 120 | 2,3-diF-C₆H₃-C(=O)- | H | —CH₂CH(CH₃)₂ | H | —CH₂CH₂CH₂CH₃ | H | —S—CH₂-(2-furyl) |

TABLE 1-continued
| Compd. No. | R¹ | R⁴ | R⁵ | R⁶ | R⁷ | R⁸ | –A–R⁹ |
|---|---|---|---|---|---|---|---|
| 121 | 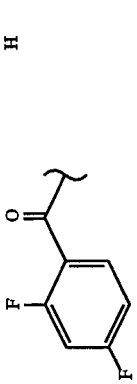 | H | –CH₂CH(CH₃)₂ | H | –CH₂CH₂CH₂CH₃ | H | 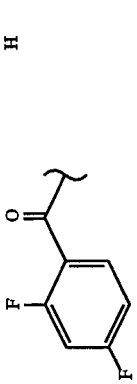 |
| 122 | 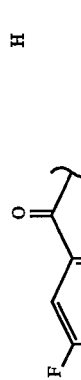 | H | –CH₂CH(CH₃)₂ | H | –CH₂CH₂CH₂CH₃ | H | 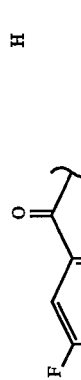 |
| 123 | 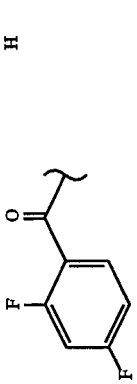 | H | –CH₂CH(CH₃)₂ | H | –CH₂CH₂CH₂CH₃ | H | 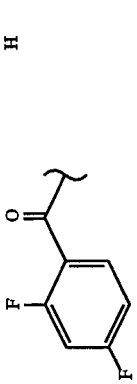 |
| 124 | 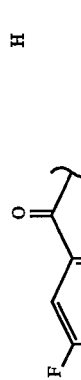 | H | –CH₂CH(CH₃)₂ | H | –CH₂CH₂CH₂CH₃ | H | 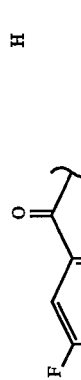 |
| 125 | 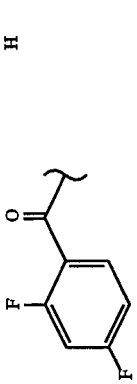 | H | –CH₂CH(CH₃)₂ | H | –CH₂CH₂CH₂CH₃ | H | 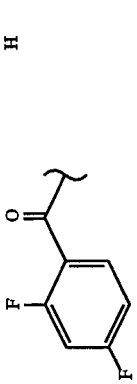 |
| 126 | 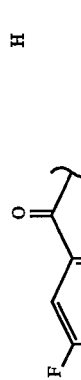 | H | –CH₂CH(CH₃)₂ | H | –CH₂CH₂CH₂CH₃ | H | 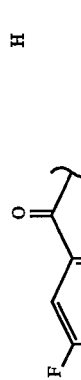 |

TABLE 1-continued
| Compd. No. | R¹ | R⁴ | R⁵ | R⁶ | R⁷ | R⁸ | –A–R⁹ |
|---|---|---|---|---|---|---|---|
| 127 | 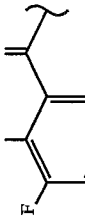 | H | –CH₂CH(CH₃)₂ | H | –CH₂CH₂CH₂CH₃ | H | 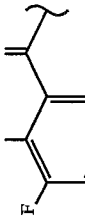 |
| 128 | 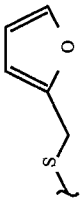 | H | –CH₂CH(CH₃)₂ | H | –CH₂CH₂CH₂CH₃ | H | 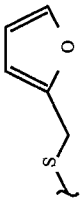 |
| 129 | 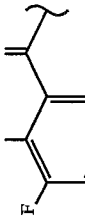 | H | –CH₂CH(CH₃)₂ | H | –CH₂CH₂CH₂CH₃ | H | 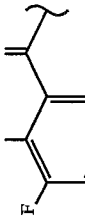 |
| 130 | 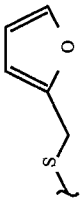 | H | –CH₂CH(CH₃)₂ | H | –CH₂CH₂CH₂CH₃ | H | 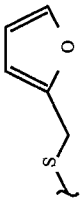 |
| 131 | 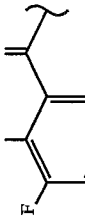 | H | –CH₂CH(CH₃)₂ | H | –CH₂CH₂CH₂CH₃ | H | 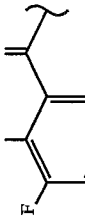 |
| 132 | 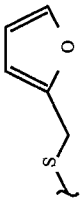 | H | –CH₂CH(CH₃)₂ | H | –CH₂CH₂CH₂CH₃ | H | 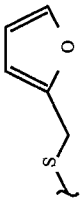 |

TABLE 1-continued
| Compd. No. | R¹ | R⁴ | R⁵ | R⁶ | R⁷ | R⁸ | —A—R⁹ |
|---|---|---|---|---|---|---|---|
| 133 | 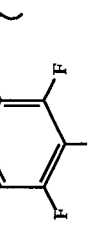 | H | —CH$_2$CH(CH$_3$)$_2$ | H | —CH$_2$CH$_2$CH$_2$CH$_3$ | H | 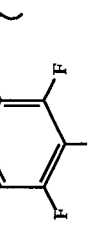 |
| 134 | 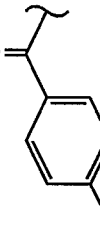 | H | —CH$_2$CH(CH$_3$)$_2$ | H | —CH$_2$CH$_2$CH$_2$CH$_3$ | H | 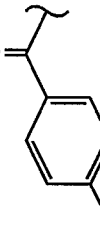 |
| 135 |  | H | —CH$_2$CH(CH$_3$)$_2$ | H | —CH$_2$CH$_2$CH$_2$CH$_3$ | H | 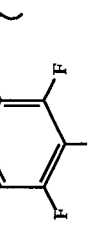 |
| 136 |  | H | —CH$_2$CH(CH$_3$)$_2$ | H | —CH$_2$CH$_2$CH$_2$CH$_3$ | H | 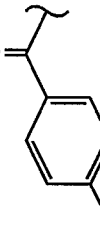 |
| 137 | 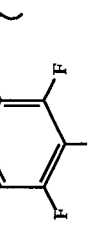 | H | —CH$_2$CH(CH$_3$)$_2$ | H | —CH$_2$CH$_2$CH$_2$CH$_3$ | H | 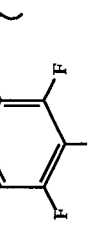 |
| 138 | 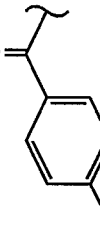 | H | —CH$_2$CH(CH$_3$)$_2$ | H | —CH$_2$CH$_2$CH$_2$CH$_3$ | H | 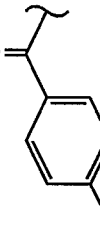 |

TABLE 1-continued
| Compd. No. | R¹ | R⁴ | R⁵ | R⁶ | R⁷ | R⁸ | —A—R⁹ |
|---|---|---|---|---|---|---|---|
| 139 | 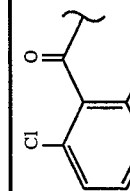 | H | —CH$_2$CH(CH$_3$)$_2$ | H | —CH$_2$CH$_2$CH$_2$CH$_3$ | H | 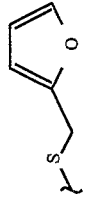 |
| 140 | 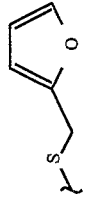 | H | —CH$_2$CH(CH$_3$)$_2$ | H | —CH$_2$CH$_2$CH$_2$CH$_3$ | H | 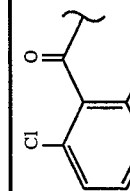 |
| 141 | 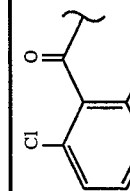 | H | —CH$_2$CH(CH$_3$)$_2$ | H | —CH$_2$CH$_2$CH$_2$CH$_3$ | H | 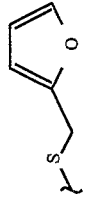 |
| 142 | 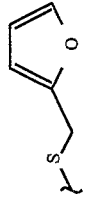 | H | —CH$_2$CH(CH$_3$)$_2$ | H | —CH$_2$CH$_2$CH$_2$CH$_3$ | H | 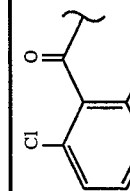 |
| 143 | 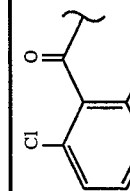 | H | —CH$_2$CH(CH$_3$)$_2$ | H | —CH$_2$CH$_2$CH$_2$CH$_3$ | H | 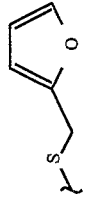 |
| 144 | 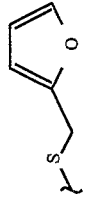 | H | —CH$_2$CH(CH$_3$)$_2$ | H | —CH$_2$CH$_2$CH$_2$CH$_3$ | H | 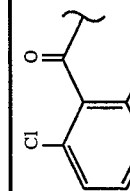 |
| 145 | 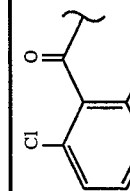 | H | —CH$_2$CH(CH$_3$)$_2$ | H | —CH$_2$CH$_2$CH$_2$CH$_3$ | H | 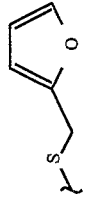 |

TABLE 1-continued

| Compd. No. | R¹ | R⁴ | R⁵ | R⁶ | R⁷ | R⁸ | —A—R⁹ |
|---|---|---|---|---|---|---|---|
| 146 | 2-CF₃, 6-F benzoyl | H | —CH₂CH(CH₃)₂ | H | —CH₂CH₂CH₂CH₃ | H | furfuryl-S- |
| 147 | 2-CF₃, 4-F benzoyl | H | —CH₂CH(CH₃)₂ | H | —CH₂CH₂CH₂CH₃ | H | furfuryl-S- |
| 148 | 2-F, 4-CF₃ benzoyl | H | —CH₂CH(CH₃)₂ | H | —CH₂CH₂CH₂CH₃ | H | furfuryl-S- |
| 149 | 3-CF₃, 4-F benzoyl | H | —CH₂CH(CH₃)₂ | H | —CH₂CH₂CH₂CH₃ | H | furfuryl-S- |
| 150 | 3-F, 4-CF₃ benzoyl | H | —CH₂CH(CH₃)₂ | H | —CH₂CH₂CH₂CH₃ | H | furfuryl-S- |
| 151 | 2-CH₃O benzoyl | H | —CH₂CH(CH₃)₂ | H | —CH₂CH₂CH₂CH₃ | H | furfuryl-S- |
| 152 | 3-CH₃O benzoyl | H | —CH₂CH(CH₃)₂ | H | —CH₂CH₂CH₂CH₃ | H | furfuryl-S- |

TABLE 1-continued

| Compd. No. | R¹ | R⁴ | R⁵ | R⁶ | R⁷ | R⁸ | —A—R⁹ |
|---|---|---|---|---|---|---|---|
| 153 | 4-methoxybenzoyl | H | —CH₂CH(CH₃)₂ | H | —CH₂CH₂CH₂CH₃ | H | —S—CH₂-(2-furyl) |
| 154 | 2,4-dimethoxybenzoyl | H | —CH₂CH(CH₃)₂ | H | —CH₂CH₂CH₂CH₃ | H | —S—CH₂-(2-furyl) |
| 155 | 3,5-dimethoxybenzoyl | H | —CH₂CH(CH₃)₂ | H | —CH₂CH₂CH₂CH₃ | H | —S—CH₂-(2-furyl) |
| 156 | 4-isopropoxybenzoyl | H | —CH₂CH(CH₃)₂ | H | —CH₂CH₂CH₂CH₃ | H | —S—CH₂-(2-furyl) |
| 157 | 4-(ethoxycarbonyl)benzoyl | H | —CH₂CH(CH₃)₂ | H | —CH₂CH₂CH₂CH₃ | H | —S—CH₂-(2-furyl) |
| 158 | 4-carboxybenzoyl | H | —CH₂CH(CH₃)₂ | H | —CH₂CH₂CH₂CH₃ | H | —S—CH₂-(2-furyl) |

TABLE 1-continued

| Compd. No. | R¹ | R⁴ | R⁵ | R⁶ | R⁷ | R⁸ | –A–R⁹ |
|---|---|---|---|---|---|---|---|
| 159 | 4-acetylbenzoyl | H | –CH$_2$CH(CH$_3$)$_2$ | H | –CH$_2$CH$_2$CH$_2$CH$_3$ | H | furan-2-yl-CH$_2$–S– |
| 160 | 4-acetamidobenzoyl | H | –CH$_2$CH(CH$_3$)$_2$ | H | –CH$_2$CH$_2$CH$_2$CH$_3$ | H | furan-2-yl-CH$_2$–S– |
| 161 | naphthalen-1-ylcarbonyl | H | –CH$_2$CH(CH$_3$)$_2$ | H | –CH$_2$CH$_2$CH$_2$CH$_3$ | H | furan-2-yl-CH$_2$–S– |
| 162 | naphthalen-2-ylcarbonyl | H | –CH$_2$CH(CH$_3$)$_2$ | H | –CH$_2$CH$_2$CH$_2$CH$_3$ | H | furan-2-yl-CH$_2$–S– |
| 163 | cinnamoyl | H | –CH$_2$CH(CH$_3$)$_2$ | H | –CH$_2$CH$_2$CH$_2$CH$_3$ | H | furan-2-yl-CH$_2$–S– |
| 164 | 2-methoxycinnamoyl | H | –CH$_2$CH(CH$_3$)$_2$ | H | –CH$_2$CH$_2$CH$_2$CH$_3$ | H | furan-2-yl-CH$_2$–S– |

TABLE 1-continued

| Compd. No. | R¹ | R⁴ | R⁵ | R⁶ | R⁷ | R⁸ | –A–R⁹ |
|---|---|---|---|---|---|---|---|
| 165 | 4-methoxy-3-methoxyphenyl vinyl ketone (trans-cinnamoyl with 4-OCH₃, 3-? see image) — *R¹ = trans-CH=CH–C(=O)– attached to 4-methoxyphenyl with CH₃O at 3-position* | H | –CH₂CH(CH₃)₂ | H | –CH₂CH₂CH₂CH₃ | H | furfuryl-S–CH₂– |
| 166 | trans-CH=CH–C(=O)– attached to 2-OCH₃, 4-CH₃O phenyl | H | –CH₂CH(CH₃)₂ | H | –CH₂CH₂CH₂CH₃ | H | furfuryl-S–CH₂– |
| 167 | trans-CH=CH–C(=O)– attached to 3,4-dimethoxyphenyl | H | –CH₂CH(CH₃)₂ | H | –CH₂CH₂CH₂CH₃ | H | furfuryl-S–CH₂– |
| 168 | 1-acetyl-piperidin-4-yl–C(=O)– | H | –CH₂CH(CH₃)₂ | H | –CH₂CH₂CH₂CH₃ | H | furfuryl-S–CH₂– |
| 169 | 1-butanoyl-piperidin-4-yl–C(=O)– | H | –CH₂CH(CH₃)₂ | H | –CH₂CH₂CH₂CH₃ | H | furfuryl-S–CH₂– |
| 170 | 1-ethoxycarbonyl-piperidin-4-yl–C(=O)– | H | –CH₂CH(CH₃)₂ | H | –CH₂CH₂CH₂CH₃ | H | furfuryl-S–CH₂– |

TABLE 1-continued
| Compd. No. | R¹ | R⁴ | R⁵ | R⁶ | R⁷ | R⁸ | —A—R⁹ |
|---|---|---|---|---|---|---|---|
| 171 |  | H | —CH$_2$CH(CH$_3$)$_2$ | H | —CH$_2$CH$_2$CH$_2$CH$_3$ | H | 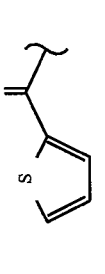 |
| 172 |  | H | —CH$_2$CH(CH$_3$)$_2$ | H | —CH$_2$CH$_2$CH$_2$CH$_3$ | H |  |
| 173 |  | H | —CH$_2$CH(CH$_3$)$_2$ | H | —CH$_2$CH$_2$CH$_2$CH$_3$ | H | 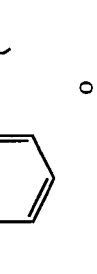 |
| 174 | 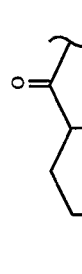 | H | —CH$_2$CH(CH$_3$)$_2$ | H | —CH$_2$CH$_2$CH$_2$CH$_3$ | H | 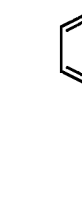 |
| 175 | 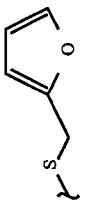 | H | —CH$_2$CH(CH$_3$)$_2$ | H | —CH$_2$CH$_2$CH$_2$CH$_3$ | H | 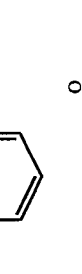 |
| 176 | 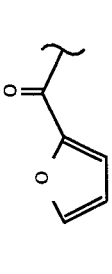 | H | —CH$_2$CH(CH$_3$)$_2$ | H | —CH$_2$CH$_2$CH$_2$CH$_3$ | H |  |
| 177 | 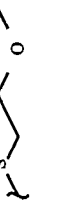 | H | —CH$_2$CH(CH$_3$)$_2$ | H | —CH$_2$CH$_2$CH$_2$CH$_3$ | H | 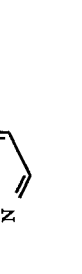 |

TABLE 1-continued
| Compd. No. | R¹ | R⁴ | R⁵ | R⁶ | R⁷ | R⁸ | —A—R⁹ |
|---|---|---|---|---|---|---|---|
| 178 |  | H | —CH$_2$CH(CH$_3$)$_2$ | H | —CH$_2$CH$_2$CH$_2$CH$_3$ | H |  |
| 179 |  | H | —CH$_2$CH(CH$_3$)$_2$ | H | —CH$_2$CH$_2$CH$_2$CH$_3$ | H |  |
| 180 |  | H | —CH$_2$CH(CH$_3$)$_2$ | H | —CH$_2$CH$_2$CH$_2$CH$_3$ | H |  |
| 181 |  | H | —CH$_2$CH(CH$_3$)$_2$ | H | —CH$_2$CH$_2$CH$_2$CH$_3$ | H |  |
| 182 |  | H | —CH$_2$CH(CH$_3$)$_2$ | H | —CH$_2$CH$_2$CH$_2$CH$_3$ | H |  |
| 183 |  | H | —CH$_2$CH(CH$_3$)$_2$ | H | —CH$_2$CH$_2$CH$_2$CH$_3$ | H |  |
| 184 |  | H | —CH$_2$CH(CH$_3$)$_2$ | H | —CH$_2$CH$_2$CH$_2$CH$_3$ | H |  |

TABLE 1-continued

| Compd. No. | R¹ | R⁴ | R⁵ | R⁶ | R⁷ | R⁸ | —A—R⁹ |
|---|---|---|---|---|---|---|---|
| 185 | 7-fluorobenzofuran-2-yl carbonyl | H | —CH$_2$CH(CH$_3$)$_2$ | H | —CH$_2$CH$_2$CH$_2$CH$_3$ | H | furan-2-ylmethylthio |
| 186 | benzothiophen-2-yl carbonyl | H | —CH$_2$CH(CH$_3$)$_2$ | H | —CH$_2$CH$_2$CH$_2$CH$_3$ | H | furan-2-ylmethylthio |
| 187 | benzothiophen-3-yl carbonyl | H | —CH$_2$CH(CH$_3$)$_2$ | H | —CH$_2$CH$_2$CH$_2$CH$_3$ | H | furan-2-ylmethylthio |
| 188 | 4-oxo-4H-chromen-3-yl carbonyl | H | —CH$_2$CH(CH$_3$)$_2$ | H | —CH$_2$CH$_2$CH$_2$CH$_3$ | H | furan-2-ylmethylthio |
| 189 | benzylaminocarbonyl | H | —CH$_2$CH(CH$_3$)$_2$ | H | —CH$_2$CH$_2$CH$_2$CH$_3$ | H | furan-2-ylmethylthio |
| 190 | phenylaminocarbonyl | H | —CH$_2$CH(CH$_3$)$_2$ | H | —CH$_2$CH$_2$CH$_2$CH$_3$ | H | furan-2-ylmethylthio |
| 191 | CH$_3$SO$_2$— | H | —CH$_2$CH(CH$_3$)$_2$ | H | —CH$_2$CH$_2$CH$_2$CH$_3$ | H | furan-2-ylmethylthio |

TABLE 1-continued

| Compd. No. | R¹ | R⁴ | R⁵ | R⁶ | R⁷ | R⁸ | —A—R⁹ |
|---|---|---|---|---|---|---|---|
| 192 | phenylsulfonyl | H | —CH$_2$CH(CH$_3$)$_2$ | H | —CH$_2$CH$_2$CH$_2$CH$_3$ | H | furfurylthio |
| 193 | 4-fluorophenylsulfonyl | H | —CH$_2$CH(CH$_3$)$_2$ | H | —CH$_2$CH$_2$CH$_2$CH$_3$ | H | furfurylthio |
| 194 | 4-methylphenylsulfonyl | H | —CH$_2$CH(CH$_3$)$_2$ | H | —CH$_2$CH$_2$CH$_2$CH$_3$ | H | furfurylthio |
| 195 | benzyloxycarbonyl | H | —CH$_2$CH(CH$_3$)$_2$ | H | —CH$_2$CH$_2$CH$_2$CH$_3$ | H | —O—CH$_3$ |
| 196 | benzyloxycarbonyl | H | —CH$_2$CH(CH$_3$)$_2$ | H | —CH$_2$CH$_2$CH$_2$CH$_3$ | H | furfurylthio |
| 197 | benzyloxycarbonyl | H | —CH$_2$CH(CH$_3$)$_2$ | H | —CH$_2$CH$_2$CH$_2$CH$_3$ | H | —N(CH$_3$)$_2$ |
| 198 | benzyloxycarbonyl | H | —CH$_2$CH(CH$_3$)$_2$ | H | —CH$_2$CH$_2$CH$_2$CH$_3$ | H | —N(CH$_2$CH$_3$)$_2$ |

TABLE 1-continued
| Compd. No. | R¹ | R⁴ | R⁵ | R⁶ | R⁷ | R⁸ | —A—R⁹ |
|---|---|---|---|---|---|---|---|
| 199 | 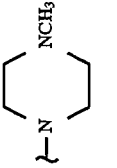 | H | —CH$_2$CH(CH$_3$)$_2$ | H | —CH$_2$CH$_2$CH$_3$ | H |  |
| 200 | 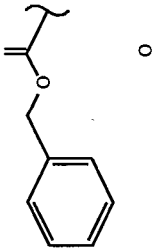 | H | —CH$_2$CH(CH$_3$)$_2$ | H | —CH$_2$CH$_2$CH$_3$ | H | 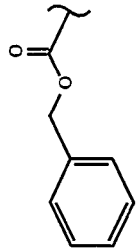 |
| 201 | 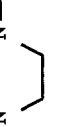 | H | —CH$_2$CH(CH$_3$)$_2$ | H | —CH$_2$CH$_2$CH$_3$ | H | 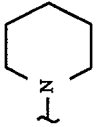 |
| 202 | 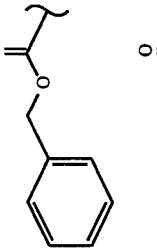 | H | —CH$_2$CH(CH$_3$)$_2$ | H | —CH$_2$CH$_2$CH$_3$ | H | 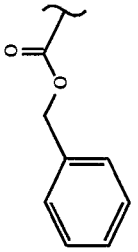 |
| 203 | 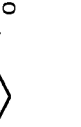 | H | —CH$_2$CH(CH$_3$)$_2$ | H | —CH$_2$CH$_2$CH$_3$ | H | 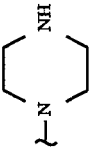 |
| 204 | 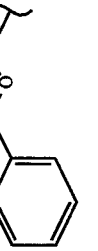 | H | —CH$_2$CH(CH$_3$)$_2$ | H | —CH$_2$CH$_2$CH$_3$ | H | 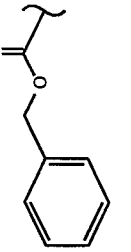 |
| 205 |  | H | —CHCH$_2$CH$_3$<br>    |<br>   CH$_3$ | H | —CH$_2$CH$_2$CH$_3$ | H | |

TABLE 1-continued

| Compd. No. | R¹ | R⁴ | R⁵ | R⁶ | R⁷ | R⁸ | —A—R⁹ |
|---|---|---|---|---|---|---|---|
| 206 | benzyl ester | H | —CH$_2$CH$_2$CH$_2$CH$_3$ | H | —CH$_2$CH$_2$CH$_2$CH$_3$ | H | furfuryl thio |
| 207 | benzyl ester | H | —CH$_2$-cyclohexyl | H | —CH$_2$CH$_2$CH$_2$CH$_3$ | H | furfuryl thio |
| 208 | benzyl ester | H | —CH$_2$-phenyl | H | —CH$_2$CH$_2$CH$_2$CH$_3$ | H | furfuryl thio |
| 209 | benzyl ester | H | —CH$_2$OCH$_3$ | H | —CH$_2$CH$_2$CH$_2$CH$_3$ | H | furfuryl thio |
| 210 | benzyl ester | H | —CH$_2$OC(CH$_3$)$_3$ | H | —CH$_2$CH$_2$CH$_2$CH$_3$ | H | furfuryl thio |
| 211 | benzyl ester | H | —CH$_2$OH | H | —CH$_2$CH$_2$CH$_2$CH$_3$ | H | furfuryl thio |
| 212 | benzyl ester | H | —CH$_2$COOCH$_3$ | H | —CH$_2$CH$_2$CH$_2$CH$_3$ | H | furfuryl thio |

TABLE 1-continued

| Compd. No. | R¹ | R⁴ | R⁵ | R⁶ | R⁷ | R⁸ | —A—R⁹ |
|---|---|---|---|---|---|---|---|
| 213 | benzyl ester (PhCH₂—O—C(O)—) | H | —CH₂COOC(CH₃)₃ | H | —CH₂CH₂CH₂CH₃ | H | —CH₂—S—CH₂—(2-furyl) |
| 214 | benzyl ester | H | —CH₂COOH | H | —CH₂CH₂CH₂CH₃ | H | —CH₂—S—CH₂—(2-furyl) |
| 215 | benzyl ester | H | —CH₂CH₂COOCH₃ | H | —CH₂CH₂CH₂CH₃ | H | —CH₂—S—CH₂—(2-furyl) |
| 216 | benzyl ester | H | —CH₂CH₂COOC(CH₃)₃ | H | —CH₂CH₂CH₂CH₃ | H | —CH₂—S—CH₂—(2-furyl) |
| 217 | benzyl ester | H | —CH₂CH₂COOH | H | —CH₂CH₂CH₂CH₃ | H | —CH₂—S—CH₂—(2-furyl) |
| 218 | benzyl ester | H | —CH₂C(O)NH₂ | H | —CH₂CH₂CH₂CH₃ | H | —CH₂—S—CH₂—(2-furyl) |
| 219 | benzyl ester | H | —CH₂CH₂C(O)NH₂ | H | —CH₂CH₂CH₂CH₃ | H | —CH₂—S—CH₂—(2-furyl) |

TABLE 1-continued
| Compd. No. | R¹ | R⁴ | R⁵ | R⁶ | R⁷ | R⁸ | -A-R⁹ |
|---|---|---|---|---|---|---|---|
| 220 | 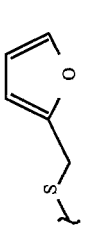 | H | -(CH$_2$)$_4$NCOC(CH$_3$)$_3$ with H and C=O | H | -CH$_2$CH$_2$CH$_2$CH$_3$ | H |  |
| 221 | 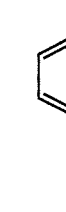 | H | -(CH$_2$)$_4$NH$_2$ | H | -CH$_2$CH$_2$CH$_2$CH$_3$ | H | 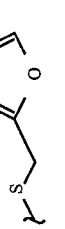 |
| 222 |  | H | -(CH$_2$)$_4$NCCH$_3$ with H and C=O | H | -CH$_2$CH$_2$CH$_2$CH$_3$ | H |  |
| 223 | 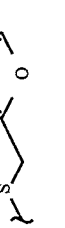 | H | -CH$_2$CH$_2$SCH$_3$ | H | -CH$_2$CH$_2$CH$_2$CH$_3$ | H | 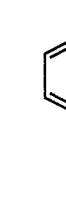 |
| 224 | 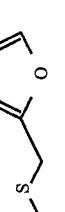 | H |  | H | -CH$_2$CH$_2$CH$_2$CH$_3$ | H | 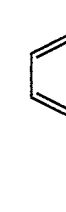 |
| 225 | 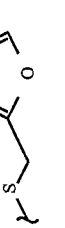 | H | -CH$_2$CH(CH$_3$)$_2$ | H | -CH$_2$CH$_2$CH$_2$CH$_3$ | H | 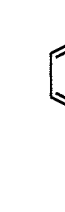 |
| 226 | 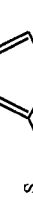 | H | -CH$_2$CH(CH$_3$)$_2$ | H | -CH$_2$CH$_2$CH$_2$CH$_3$ | H | 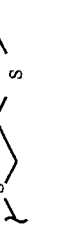 |

TABLE 1-continued
| Compd. No. | R¹ | R⁴ | R⁵ | R⁶ | R⁷ | R⁸ | —A—R⁹ |
|---|---|---|---|---|---|---|---|
| 227 | 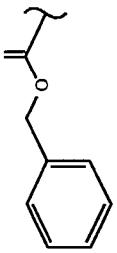 | H | —CH$_2$CH(CH$_3$)$_2$ | H | —CH$_2$CH$_2$CH$_2$CH$_3$ | H |  |
| 228 | 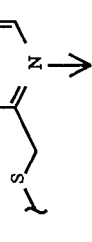 | H | —CH$_2$CH(CH$_3$)$_2$ | H | —CH$_2$CH$_2$CH$_2$CH$_3$ | H | 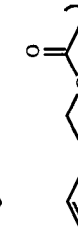 |
| 229 | 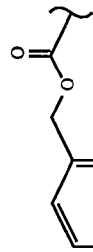 | H | —CH$_2$CH(CH$_3$)$_2$ | H | —CH$_2$CH$_2$CH$_2$CH$_3$ | H | 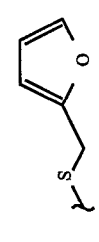 |
| 230 | 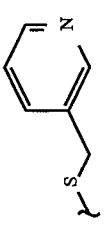 | H | —CH$_2$CH(CH$_3$)$_2$ | H | —CH$_2$CH$_2$CH$_2$CH$_3$ | H | 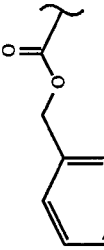 |
| 231 |  | H | —CH$_2$CH(CH$_3$)$_2$ | H | —CH$_2$CH$_2$CH$_2$CH$_3$ | H |  |
| 232 | 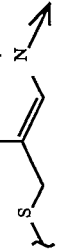 | H | —CH$_2$CH(CH$_3$)$_2$ | H | —CH$_2$CH$_2$CH$_2$CH$_3$ | H |  |
| 233 |  | —CH$_3$ | —CH$_2$CH(CH$_3$)$_2$ | H | —CH$_2$CH$_2$CH$_2$CH$_3$ | H |  |

TABLE 1-continued

| Compd. No. | R¹ | R⁴ | R⁵ | R⁶ | R⁷ | R⁸ | —A—R⁹ |
|---|---|---|---|---|---|---|---|
| 234 | benzyl ester (–OC(O)CH₂–C₆H₅) | —CH₃ | —CH₂CH(CH₃)₂ | —CH₃ | —CH₂CH₂CH₂CH₃ | H | —CH₂—S—(furan-2-yl) |
| 235 | benzyl ester | H | —CH(CH₃)₂ | H | —CH₂—cyclohexyl | H | —CH₂—S—(furan-2-yl) |
| 236 | benzyl ester | H | —CH₂CH(CH₃)₂ | H | —CH₂—cyclohexyl | H | —S—CH₃ |
| 237 | (CH₃)₃COC(O)— | H | —CH₂CH(CH₃)₂ | H | —CH₂—cyclohexyl | H | —CH₂—S—(furan-2-yl) |
| 238 | benzyl ester | H | —CH₂CH(CH₃)₂ | H | —CH₂—cyclohexyl | H | —CH₂—S—(furan-2-yl) |
| 239 | H | H | —CH₂CH(CH₃)₂ | H | —CH₂—cyclohexyl | H | —CH₂—S—(furan-2-yl) |
| 240 | benzyl ester | H | —CH₂CH(CH₃)₂ | H | —CH₂—cyclohexyl | H | —CH₂—S—(furan-2-yl) |

TABLE 1-continued

| Compd. No. | R¹ | R⁴ | R⁵ | R⁶ | R⁷ | R⁸ | —A—R⁹ |
|---|---|---|---|---|---|---|---|
| 241 | 2,6-difluorobenzoyl | H | —CH₂CH(CH₃)₂ | H | —CH₂-cyclohexyl | H | —CH₂-S-(2-furyl) |
| 242 | benzyloxycarbonyl | H | —CH₂CH(CH₃)₂ | H | —CH₂-phenyl | H | —S—H |
| 243 | (CH₃)₃COC(O)— | H | —CH₂CH(CH₃)₂ | H | —CH₂-phenyl | H | —S—CH₃ |
| 244 | benzyloxycarbonyl | H | —CH₂CH(CH₃)₂ | H | —CH₂-phenyl | H | —S—CH₃ |
| 245 | benzyloxycarbonyl | H | —CH₂CH(CH₃)₂ | H | —CH₂-phenyl | H | —S—CH₃ |
| 246 | benzyloxycarbonyl | —CH₃ | —CH₂CH(CH₃)₂ | H | —CH₂-phenyl | H | —S—CH₃ |
| 247 | benzyloxycarbonyl | —CH₃ | —CH₂CH(CH₃)₂ | H | —CH₂-phenyl | H | —S—CH₃ |

TABLE 1-continued

| Compd. No. | R¹ | R⁴ | R⁵ | R⁶ | R⁷ | R⁸ | −A−R⁹ |
|---|---|---|---|---|---|---|---|
| 248 | benzyl ester C(=O)O-CH₂-C₆H₅ | H | −CH₂CH(CH₃)₂ | H | −CH₂−C₆H₅ | H | −S(=O)−CH₃ |
| 249 | benzyl ester C(=O)O-CH₂-C₆H₅ | H | −CH₂CH(CH₃)₂ | H | −CH₂−C₆H₅ | H | −S(=O)₂−CH₃ |
| 250 | H | H | −CH₂CH(CH₃)₂ | H | −CH₂−C₆H₅ | H | −S−CH₃ |
| 251 | CH₃C(=O)− | H | −CH₂CH(CH₃)₂ | H | −CH₂−C₆H₅ | H | −S−CH₃ |
| 252 | (CH₃)₂CHCH₂CH₂C(=O)− | H | −CH₂CH(CH₃)₂ | H | −CH₂−C₆H₅ | H | −S−CH₃ |
| 253 | C₆H₅CH₂C(=O)− | H | −CH₂CH(CH₃)₂ | H | −CH₂−C₆H₅ | H | −S−CH₃ |
| 254 | C₆H₅CH₂CH₂C(=O)− | H | −CH₂CH(CH₃)₂ | H | −CH₂−C₆H₅ | H | −S−CH₃ |
| 255 | C₆H₅CH₂CH₂CH₂C(=O)− | H | −CH₂CH(CH₃)₂ | H | −CH₂−C₆H₅ | H | −S−CH₃ |

TABLE 1-continued

| Compd. No. | R¹ | R⁴ | R⁵ | R⁶ | R⁷ | R⁸ | —A—R⁹ |
|---|---|---|---|---|---|---|---|
| 256 | 1-naphthyl-CH₂-C(=O)- | H | —CH₂CH(CH₃)₂ | H | —CH₂—C₆H₅ | H | —S—CH₃ |
| 257 | 2-naphthyl-CH₂-C(=O)- | H | —CH₂CH(CH₃)₂ | H | —CH₂—C₆H₅ | H | —S—CH₃ |
| 258 | phenyl-O-CH₂-C(=O)- | H | —CH₂CH(CH₃)₂ | H | —CH₂—C₆H₅ | H | —S—CH₃ |
| 259 | 2-fluorophenyl-C(=O)- | H | —CH₂CH(CH₃)₂ | H | —CH₂—C₆H₅ | H | —S—CH₃ |
| 260 | 2,6-difluorophenyl-C(=O)- | H | —CH₂CH(CH₃)₂ | H | —CH₂—C₆H₅ | H | —S—CH₃ |
| 261 | CH₃—S(=O)₂— | H | —CH₂CH(CH₃)₂ | H | —CH₂—C₆H₅ | H | —S—CH₃ |
| 262 | C₆H₅—S(=O)₂— | H | —CH₂CH(CH₃)₂ | H | —CH₂—C₆H₅ | H | —S—CH₃ |

TABLE 1-continued

| Compd. No. | R$^1$ | R$^4$ | R$^5$ | R$^6$ | R$^7$ | R$^8$ | —A—R$^9$ |
|---|---|---|---|---|---|---|---|
| 263 | 4-Cl-C$_6$H$_4$-SO$_2$- | H | —CH$_2$CH(CH$_3$)$_2$ | H | —CH$_2$-C$_6$H$_5$ | H | —S—CH$_3$ |
| 264 | 4-CH$_3$-C$_6$H$_4$-SO$_2$- | H | —CH$_2$CH(CH$_3$)$_2$ | H | —CH$_2$-C$_6$H$_5$ | H | —S—CH$_3$ |
| 265 | PhCH$_2$O-C(O)- | H | —CH$_2$CH(CH$_3$)$_2$ | H | —CH$_2$-C$_6$H$_5$ | H | —S—CH$_2$CH$_3$ |
| 266 | PhCH$_2$O-C(O)- | H | —CH$_2$CH(CH$_3$)$_2$ | H | —CH$_2$-C$_6$H$_5$ | H | —S—(CH$_2$)$_3$CH$_3$ |
| 267 | PhCH$_2$O-C(O)- | H | —CH$_2$CH(CH$_3$)$_2$ | H | —CH$_2$-C$_6$H$_5$ | H | —S—(CH$_2$)$_5$CH$_3$ |
| 268 | PhCH$_2$O-C(O)- | H | —CH$_2$CH(CH$_3$)$_2$ | H | —CH$_2$-C$_6$H$_5$ | H | —S—(CH$_2$)$_7$CH$_3$ |
| 269 | PhCH$_2$O-C(O)- | H | —CH$_2$CH(CH$_3$)$_2$ | H | —CH$_2$-C$_6$H$_5$ | H | —S—(CH$_2$)$_{11}$CH$_3$ |

TABLE 1-continued

| Compd. No. | R¹ | R⁴ | R⁵ | R⁶ | R⁷ | R⁸ | —A—R⁹ |
|---|---|---|---|---|---|---|---|
| 270 | benzyl-O-C(O)- | H | —CH₂CH(CH₃)₂ | H | —CH₂-Ph | H | —S—(CH₂)₁₃CH₃ |
| 271 | benzyl-O-C(O)- | H | —CH₂CH(CH₃)₂ | H | —CH₂-Ph | H | —S—CH₂CH₂Cl |
| 272 | benzyl-O-C(O)- | H | —CH₂CH(CH₃)₂ | H | —CH₂-Ph | H | —S—CH₂CH₂OCH₃ |
| 273 | benzyl-O-C(O)- | H | —CH₂CH(CH₃)₂ | H | —CH₂-Ph | H | —S—CH₂CH₂OH |
| 274 | benzyl-O-C(O)- | H | —CH₂CH(CH₃)₂ | H | —CH₂-Ph | H | —S—CH₂CH₂SCH₃ |
| 275 | benzyl-O-C(O)- | H | —CH₂CH(CH₃)₂ | H | —CH₂-Ph | H | —S—CH₂CH₂N(CH₃)₂ |
| 276 | benzyl-O-C(O)- | H | —CH₂CH(CH₃)₂ | H | —CH₂-Ph | H | —S—CH₂CH₂N(H)C(O)CH₃ |

TABLE 1-continued

| Compd. No. | R¹ | R⁴ | R⁵ | R⁶ | R⁷ | R⁸ | —A—R⁹ |
|---|---|---|---|---|---|---|---|
| 277 | PhCH₂-O-C(O)- | H | —CH₂CH(CH₃)₂ | H | —CH₂-Ph | H | —S—CH₂-Ph |
| 278 | PhCH₂-O-C(O)- | H | —CH₂CH(CH₃)₂ | H | —CH₂-Ph | H | —S—CH₂—CH₂-Ph |
| 279 | PhCH₂-O-C(O)- | H | —CH₂CH(CH₃)₂ | H | —CH₂-Ph | H | —S-Ph |
| 280 | PhCH₂-O-C(O)- | H | H | H | —CH₂-Ph | H | —S—CH₂-(2-furyl) |
| 281 | PhCH₂-O-C(O)- | H | —CH₃ | H | —CH₂-Ph | H | —S—CH₂-(2-furyl) |
| 282 | PhCH₂-O-C(O)- | H | —CH(CH₃)₂ | H | —CH₂-Ph | H | —S—CH₂-(2-furyl) |
| 283 | CH₃CH₂OC(O)- | H | —CH₂CH(CH₃)₂ | H | —CH₂-Ph | H | —S—CH₂-(2-furyl) |

TABLE 1-continued

| Compd. No. | R¹ | R⁴ | R⁵ | R⁶ | R⁷ | R⁸ | —A—R⁹ |
|---|---|---|---|---|---|---|---|
| 284 |  | H | —CH₂CH(CH₃)₂ | H | —CH₂—(phenyl) | H | 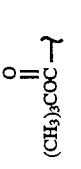 |
| 285 | (CH₃)₃COC(O)— | H | —CH₂CH(CH₃)₂ | H | —CH₂—(phenyl) | H | (furan-CH₂-S—) |
| 286 | cyclopropyl-CH₂-O-C(O)— | H | —CH₂CH(CH₃)₂ | H | —CH₂—(phenyl) | H | (furan-CH₂-S—) |
| 287 | cyclopentyl-CH₂-O-C(O)— | H | —CH₂CH(CH₃)₂ | H | —CH₂—(phenyl) | H | (furan-CH₂-S—) |
| 288 | cyclohexyl-CH₂-O-C(O)— | H | —CH₂CH(CH₃)₂ | H | —CH₂—(phenyl) | H | (furan-CH₂-S—) |
| 289 | cycloheptyl-CH₂-O-C(O)— | H | —CH₂CH(CH₃)₂ | H | —CH₂—(phenyl) | H | (furan-CH₂-S—) |
| 290 | cyclohexyl-CH₂CH₂-O-C(O)— | H | —CH₂CH(CH₃)₂ | H | —CH₂—(phenyl) | H | (furan-CH₂-S—) |
| 291 | cyclohexenyl-CH₂-O-C(O)— | H | —CH₂CH(CH₃)₂ | H | —CH₂—(phenyl) | H | (furan-CH₂-S—) |

TABLE 1-continued

| Compd. No. | R¹ | R⁴ | R⁵ | R⁶ | R⁷ | R⁸ | —A—R⁹ |
|---|---|---|---|---|---|---|---|
| 292 | cyclohex-2-enylmethyl ester | H | —CH$_2$CH(CH$_3$)$_2$ | H | —CH$_2$-phenyl | H | —S—CH$_2$-(furan-2-yl) |
| 293 | cyclohex-3-enylmethyl ester | H | —CH$_2$CH(CH$_3$)$_2$ | H | —CH$_2$-phenyl | H | —S—CH$_2$-(furan-2-yl) |
| 294 | cyclopropyl ester | H | —CH$_2$CH(CH$_3$)$_2$ | H | —CH$_2$-phenyl | H | —S—CH$_2$-(furan-2-yl) |
| 295 | cyclopentyl ester | H | —CH$_2$CH(CH$_3$)$_2$ | H | —CH$_2$-phenyl | H | —S—CH$_2$-(furan-2-yl) |
| 301 | (2-chlorophenoxy)methyl ketone | H | —CH$_2$CH(CH$_3$)$_2$ | H | —CH$_2$-phenyl | H | —S—CH$_2$-(furan-2-yl) |
| 302 | (3-chlorophenoxy)methyl ketone | H | —CH$_2$CH(CH$_3$)$_2$ | H | —CH$_2$-phenyl | H | —S—CH$_2$-(furan-2-yl) |
| 303 | (4-chlorophenoxy)methyl ketone | H | —CH$_2$CH(CH$_3$)$_2$ | H | —CH$_2$-phenyl | H | —S—CH$_2$-(furan-2-yl) |

TABLE 1-continued

| Compd. No. | R¹ | R⁴ | R⁵ | R⁶ | R⁷ | R⁸ | —A—R⁹ |
|---|---|---|---|---|---|---|---|
| 304 | 2,3-dichlorophenoxy-CH₂-C(=O)- | H | —CH₂CH(CH₃)₂ | H | —CH₂—C₆H₅ | H | —S—CH₂-(2-furyl) |
| 305 | 2-methoxyphenoxy-CH₂-C(=O)- | H | —CH₂CH(CH₃)₂ | H | —CH₂—C₆H₅ | H | —S—CH₂-(2-furyl) |
| 296 | cyclohexyl-O-C(=O)- | H | —CH₂CH(CH₃)₂ | H | —CH₂—C₆H₅ | H | —S—CH₂-(2-furyl) |
| 297 | benzyl-O-C(=O)- | H | —CH₂CH(CH₃)₂ | H | —CH₂—C₆H₅ | H | —S—CH₂-(2-furyl) |
| 298 | benzyl-O-C(=O)- | H | —CH₂CH(CH₃)₂ | —CH₃ | —CH₂—C₆H₅ | H | —S—CH₂-(2-furyl) |
| 299 | benzyl-O-C(=O)- | —CH₃ | —CH₂CH(CH₃)₂ | H | —CH₂—C₆H₅ | H | —S—CH₂-(2-furyl) |
| 300 | benzyl-O-C(=O)- | —CH₃ | —CH₂CH(CH₃)₂ | —CH₃ | —CH₂—C₆H₅ | H | —S—CH₂-(2-furyl) |

TABLE 1-continued

| Compd. No. | R¹ | R⁴ | R⁵ | R⁶ | R⁷ | R⁸ | –A–R⁹ |
|---|---|---|---|---|---|---|---|
| 306 | 3-methoxyphenoxyacetyl | H | –CH$_2$CH(CH$_3$)$_2$ | H | –CH$_2$–phenyl | H | furfuryl thiomethyl |
| 307 | 4-methoxyphenoxyacetyl | H | –CH$_2$CH(CH$_3$)$_2$ | H | –CH$_2$–phenyl | H | furfuryl thiomethyl |
| 308 | 1,2,3,4-tetrahydronaphthalen-1-yloxycarbonyl | H | –CH$_2$CH(CH$_3$)$_2$ | H | –CH$_2$–phenyl | H | furfuryl thiomethyl |
| 309 | 9H-fluoren-9-ylmethoxycarbonyl | H | –CH$_2$CH(CH$_3$)$_2$ | H | –CH$_2$–phenyl | H | furfuryl thiomethyl |
| 310 | (tetrahydrofuran-2-yl)methoxycarbonyl | H | –CH$_2$CH(CH$_3$)$_2$ | H | –CH$_2$–phenyl | H | furfuryl thiomethyl |
| 311 | (tetrahydropyran-2-yl)methoxycarbonyl | H | –CH$_2$CH(CH$_3$)$_2$ | H | –CH$_2$–phenyl | H | furfuryl thiomethyl |

TABLE 1-continued

| Compd. No. | R¹ | R⁴ | R⁵ | R⁶ | R⁷ | R⁸ | −A−R⁹ |
|---|---|---|---|---|---|---|---|
| 312 | furan-2-ylmethyl ester (−C(O)O−CH₂−(2-furyl)) | H | −CH₂CH(CH₃)₂ | H | −CH₂−(phenyl) | H | −S−CH₂−(2-furyl) |
| 313 | pyridin-2-ylmethyl ester (−C(O)O−CH₂−(2-pyridyl)) | H | −CH₂CH(CH₃)₂ | H | −CH₂−(phenyl) | H | −S−CH₂−(2-furyl) |
| 314 | (pyridin-2-yl N-oxide)methyl ester | H | −CH₂CH(CH₃)₂ | H | −CH₂−(phenyl) | H | −S−CH₂−(2-furyl) |
| 315 | pyridin-3-ylmethyl ester | H | −CH₂CH(CH₃)₂ | H | −CH₂−(phenyl) | H | −S−CH₂−(2-furyl) |
| 316 | (pyridin-3-yl N-oxide)methyl ester | H | −CH₂CH(CH₃)₂ | H | −CH₂−(phenyl) | H | −S−CH₂−(2-furyl) |
| 317 | pyridin-4-ylmethyl ester | H | −CH₂CH(CH₃)₂ | H | −CH₂−(phenyl) | H | −S−CH₂−(2-furyl) |
| 318 | (pyridin-4-yl N-oxide)methyl ester | H | −CH₂CH(CH₃)₂ | H | −CH₂−(phenyl) | H | −S−CH₂−(2-furyl) |

TABLE 1-continued

| Compd. No. | R¹ | R⁴ | R⁵ | R⁶ | R⁷ | R⁸ | −A−R⁹ |
|---|---|---|---|---|---|---|---|
| 319 | phenyl ester | H | −CH$_2$CH(CH$_3$)$_2$ | H | −CH$_2$−phenyl | H | −CH$_2$−(2-furyl) via S |
| 320 | tetrahydronaphthyl ester | H | −CH$_2$CH(CH$_3$)$_2$ | H | −CH$_2$−phenyl | H | −CH$_2$−(2-furyl) via S |
| 321 | 1-naphthyl ester | H | −CH$_2$CH(CH$_3$)$_2$ | H | −CH$_2$−phenyl | H | −CH$_2$−(2-furyl) via S |
| 322 | 2-naphthyl ester | H | −CH$_2$CH(CH$_3$)$_2$ | H | −CH$_2$−phenyl | H | −CH$_2$−(2-furyl) via S |
| 323 | H | H | −CH$_2$CH(CH$_3$)$_2$ | H | −CH$_2$−phenyl | H | −CH$_2$−(2-furyl) via S |
| 324 | CH$_3$C(O)− | H | −CH$_2$CH(CH$_3$)$_2$ | H | −CH$_2$−phenyl | H | −CH$_2$−(2-furyl) via S |
| 325 | isobutyl ketone | H | −CH$_2$CH(CH$_3$)$_2$ | H | −CH$_2$−phenyl | H | −CH$_2$−(2-furyl) via S |

TABLE 1-continued

| Compd. No. | R¹ | R⁴ | R⁵ | R⁶ | R⁷ | R⁸ | —A—R⁹ |
|---|---|---|---|---|---|---|---|
| 326 | isobutyl-C(=O)– | H | —CH$_2$CH(CH$_3$)$_2$ | H | —CH$_2$–(phenyl) | H | —S—CH$_2$–(2-furyl) |
| 327 | cyclohexyl-CH$_2$-C(=O)– | H | —CH$_2$CH(CH$_3$)$_2$ | H | —CH$_2$–(phenyl) | H | —S—CH$_2$–(2-furyl) |
| 328 | cyclohexyl-(CH$_2$)$_2$-C(=O)– | H | —CH$_2$CH(CH$_3$)$_2$ | H | —CH$_2$–(phenyl) | H | —S—CH$_2$–(2-furyl) |
| 329 | cyclohexyl-(CH$_2$)$_3$-C(=O)– | H | —CH$_2$CH(CH$_3$)$_2$ | H | —CH$_2$–(phenyl) | H | —S—CH$_2$–(2-furyl) |
| 330 | phenyl-CH$_2$-C(=O)– | H | —CH$_2$CH(CH$_3$)$_2$ | H | —CH$_2$–(phenyl) | H | —S—CH$_2$–(2-furyl) |
| 331 | phenyl-(CH$_2$)$_2$-C(=O)– | H | —CH$_2$CH(CH$_3$)$_2$ | H | —CH$_2$–(phenyl) | H | —S—CH$_2$–(2-furyl) |
| 332 | phenyl-(CH$_2$)$_3$-C(=O)– | H | —CH$_2$CH(CH$_3$)$_2$ | H | —CH$_2$–(phenyl) | H | —S—CH$_2$–(2-furyl) |

TABLE 1-continued

| Compd. No. | R¹ | R⁴ | R⁵ | R⁶ | R⁷ | R⁸ | —A—R⁹ |
|---|---|---|---|---|---|---|---|
| 333 | 1-naphthyl-CH₂-C(=O)- | H | —CH₂CH(CH₃)₂ | H | —CH₂-phenyl | H | —S—CH₂-(2-furyl) |
| 334 | 2-naphthyl-CH₂-C(=O)- | H | —CH₂CH(CH₃)₂ | H | —CH₂-phenyl | H | —S—CH₂-(2-furyl) |
| 335 | phenyl-CH=CH-C(=O)- | H | —CH₂CH(CH₃)₂ | H | —CH₂-phenyl | H | —S—CH₂-(2-furyl) |
| 336 | (4-CH₃O-phenyl)-CH=CH-C(=O)- | H | —CH₂CH(CH₃)₂ | H | —CH₂-phenyl | H | —S—CH₂-(2-furyl) |
| 337 | (2-OCH₃,4-CH₃O-phenyl)-CH=CH-C(=O)- | H | —CH₂CH(CH₃)₂ | H | —CH₂-phenyl | H | —S—CH₂-(2-furyl) |
| 338 | (3-furyl)-CH₂-C(=O)- | H | —CH₂CH(CH₃)₂ | H | —CH₂-phenyl | H | —S—CH₂-(2-furyl) |
| 339 | (2-furyl)-CH₂-C(=O)- | H | —CH₂CH(CH₃)₂ | H | —CH₂-phenyl | H | —S—CH₂-(2-furyl) |

TABLE 1-continued

| Compd. No. | R¹ | R⁴ | R⁵ | R⁶ | R⁷ | R⁸ | —A—R⁹ |
|---|---|---|---|---|---|---|---|
| 340 | 2-pyridyl-CH₂-C(=O)- | H | —CH₂CH(CH₃)₂ | H | —CH₂-phenyl | H | furan-2-yl-CH₂-S- |
| 341 | 3-pyridyl-CH₂-C(=O)- | H | —CH₂CH(CH₃)₂ | H | —CH₂-phenyl | H | furan-2-yl-CH₂-S- |
| 342 | 3-pyridyl-CH₂-C(=O)- | H | —CH₂CH(CH₃)₂ | H | —CH₂-phenyl | H | furan-2-yl-CH₂-S- |
| 343 | benzofuran-2-yl-CH₂-C(=O)- | H | —CH₂CH(CH₃)₂ | H | —CH₂-phenyl | H | furan-2-yl-CH₂-S- |
| 344 | benzofuran-2-yl-CH₂-C(=O)- | H | —CH₂CH(CH₃)₂ | H | —CH₂-phenyl | H | furan-2-yl-CH₂-S- |
| 345 | benzothiophen-2-yl-CH₂-C(=O)- | H | —CH₂CH(CH₃)₂ | H | —CH₂-phenyl | H | furan-2-yl-CH₂-S- |
| 346 | cyclopropyl-O-CH₂-C(=O)- | H | —CH₂CH(CH₃)₂ | H | —CH₂-phenyl | H | furan-2-yl-CH₂-S- |
| 347 | cyclohexyl-O-CH₂-C(=O)- | H | —CH₂CH(CH₃)₂ | H | —CH₂-phenyl | H | furan-2-yl-CH₂-S- |

TABLE 1-continued

| Compd. No. | R¹ | R⁴ | R⁵ | R⁶ | R⁷ | R⁸ | −A−R⁹ |
|---|---|---|---|---|---|---|---|
| 348 | phenoxy-CH₂-C(=O)- | H | −CH₂CH(CH₃)₂ | H | −CH₂−phenyl | H | −S−CH₂−furyl |
| 349 | phenoxy-CH(CH₃)-C(=O)- | H | −CH₂CH(CH₃)₂ | H | −CH₂−phenyl | H | −S−CH₂−furyl |
| 350 | phenoxy-CH(CH₂CH₃)-C(=O)- | H | −CH₂CH(CH₃)₂ | H | −CH₂−phenyl | H | −S−CH₂−furyl |
| 351 | (2-F-phenoxy)-CH₂-C(=O)- | H | −CH₂CH(CH₃)₂ | H | −CH₂−phenyl | H | −S−CH₂−furyl |
| 352 | (3-F-phenoxy)-CH₂-C(=O)- | H | −CH₂CH(CH₃)₂ | H | −CH₂−phenyl | H | −S−CH₂−furyl |
| 353 | (4-F-phenoxy)-CH₂-C(=O)- | H | −CH₂CH(CH₃)₂ | H | −CH₂−phenyl | H | −S−CH₂−furyl |
| 354 | (2-Cl-phenoxy)-CH₂-C(=O)- | H | −CH₂CH(CH₃)₂ | H | −CH₂−phenyl | H | −S−CH₂−furyl |

TABLE 1-continued
| Compd. No. | R¹ | R⁴ | R⁵ | R⁶ | R⁷ | R⁸ | -A-R⁹ |
|---|---|---|---|---|---|---|---|
| 355 | 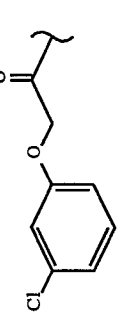 | H | -CH$_2$CH(CH$_3$)$_2$ | H | -CH$_2$- | H |  |
| 356 | 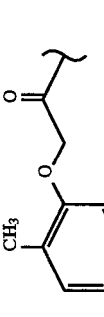 | H | -CH$_2$CH(CH$_3$)$_2$ | H | -CH$_2$- | H | 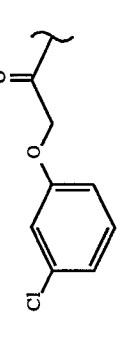 |
| 357 | 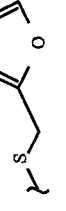 | H | -CH$_2$CH(CH$_3$)$_2$ | H | -CH$_2$- | H | 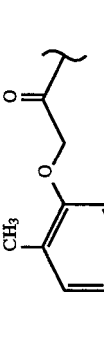 |
| 358 | 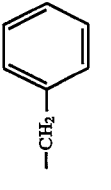 | H | -CH$_2$CH(CH$_3$)$_2$ | H | -CH$_2$- | H | 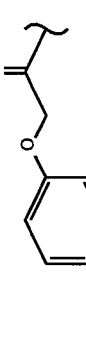 |
| 359 | 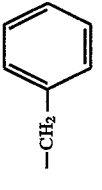 | H | -CH$_2$CH(CH$_3$)$_2$ | H | -CH$_2$- | H | 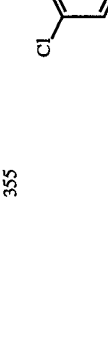 |
| 360 | 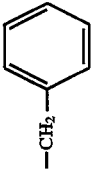 | H | -CH$_2$CH(CH$_3$)$_2$ | H | -CH$_2$- | H |  |
| 361 |  | H |  | H | -CH$_2$- | H |  |

TABLE 1-continued
| Compd. No. | R¹ | R⁴ | R⁵ | R⁶ | R⁷ | R⁸ | —A—R⁹ |
|---|---|---|---|---|---|---|---|
| 362 |  | H | —CH$_2$CH(CH$_3$)$_2$ | H | —CH$_2$— (phenyl) | H |  (furan-CH$_2$-S) |
| 363 |  | H | —CH$_2$CH(CH$_3$)$_2$ | H | —CH$_2$— (phenyl) | H | (furan-CH$_2$-S) |
| 364 |  | H | —CH$_2$CH(CH$_3$)$_2$ | H | —CH$_2$— (phenyl) | H | (furan-CH$_2$-S) |
| 365 |  | H | —CH$_2$CH(CH$_3$)$_2$ | H | —CH$_2$— (phenyl) | H | (furan-CH$_2$-S) |
| 366 | 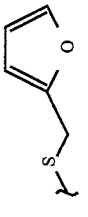 | H | —CH$_2$CH(CH$_3$)$_2$ | H | —CH$_2$— (phenyl) | H | (furan-CH$_2$-S) |
| 367 |  | H | —CH$_2$CH(CH$_3$)$_2$ | H | —CH$_2$— (phenyl) | H | (furan-CH$_2$-S) |
| 368 |  | H | —CH$_2$CH(CH$_3$)$_2$ | H | —CH$_2$— (phenyl) | H | (furan-CH$_2$-S) |

TABLE 1-continued

| Compd. No. | R¹ | R⁴ | R⁵ | R⁶ | R⁷ | R⁸ | —A—R⁹ |
|---|---|---|---|---|---|---|---|
| 369 | phenyl ester (C(=O)O-Ph) | H | —CH₂CH(CH₃)₂ | H | —CH₂-phenyl | H | —S—CH₂-furan |
| 370 | tetrahydropyranyloxy acetyl | H | —CH₂CH(CH₃)₂ | H | —CH₂-phenyl | H | —S—CH₂-furan |
| 371 | benzoyl | H | —CH₂CH(CH₃)₂ | H | —CH₂-phenyl | H | —S—CH₂-furan |
| 372 | 2-fluorobenzoyl | H | —CH₂CH(CH₃)₂ | H | —CH₂-phenyl | H | —S—CH₂-furan |
| 373 | 2,6-difluorobenzoyl | H | —CH₂CH(CH₃)₂ | H | —CH₂-phenyl | H | —S—CH₂-furan |
| 374 | 4-chlorobenzoyl | H | —CH₂CH(CH₃)₂ | H | —CH₂-phenyl | H | —S—CH₂-furan |
| 375 | 1-naphthoyl | H | —CH₂CH(CH₃)₂ | H | —CH₂-phenyl | H | —S—CH₂-furan |

TABLE 1-continued

| Compd. No. | R¹ | R⁴ | R⁵ | R⁶ | R⁷ | R⁸ | −A−R⁹ |
|---|---|---|---|---|---|---|---|
| 376 | 2-naphthyl-C(O)− | H | −CH$_2$CH(CH$_3$)$_2$ | H | −CH$_2$−phenyl | H | −CH$_2$−(2-furyl)−S− |
| 377 | 2-furyl-C(O)− | H | −CH$_2$CH(CH$_3$)$_2$ | H | −CH$_2$−phenyl | H | −CH$_2$−(2-furyl)−S− |
| 378 | 2-thienyl-C(O)− | H | −CH$_2$CH(CH$_3$)$_2$ | H | −CH$_2$−phenyl | H | −CH$_2$−(2-furyl)−S− |
| 379 | 2-pyridyl-C(O)− | H | −CH$_2$CH(CH$_3$)$_2$ | H | −CH$_2$−phenyl | H | −CH$_2$−(2-furyl)−S− |
| 380 | 3-pyridyl-C(O)− | H | −CH$_2$CH(CH$_3$)$_2$ | H | −CH$_2$−phenyl | H | −CH$_2$−(2-furyl)−S− |
| 381 | 3-pyridyl-C(O)− | H | −CH$_2$CH(CH$_3$)$_2$ | H | −CH$_2$−phenyl | H | −CH$_2$−(2-furyl)−S− |
| 382 | 2-benzofuryl-C(O)− | H | −CH$_2$CH(CH$_3$)$_2$ | H | −CH$_2$−phenyl | H | −CH$_2$−(2-furyl)−S− |

TABLE 1-continued

| Compd. No. | R¹ | R⁴ | R⁵ | R⁶ | R⁷ | R⁸ | −A−R⁹ |
|---|---|---|---|---|---|---|---|
| 383 | 2-benzofuranyl-C(=O)− | H | −CH$_2$CH(CH$_3$)$_2$ | H | −CH$_2$−phenyl | H | −CH$_2$−(2-furyl)−S− |
| 384 | 2-(2,3-dihydrobenzofuranyl)-C(=O)− | H | −CH$_2$CH(CH$_3$)$_2$ | H | −CH$_2$−phenyl | H | −CH$_2$−(2-furyl)−S− |
| 385 | 3-(2,3-dihydrobenzofuranyl)-C(=O)− | H | −CH$_2$CH(CH$_3$)$_2$ | H | −CH$_2$−phenyl | H | −CH$_2$−(2-furyl)−S− |
| 386 | 3-(4-oxo-4H-chromenyl)-C(=O)− | H | −CH$_2$CH(CH$_3$)$_2$ | H | −CH$_2$−phenyl | H | −CH$_2$−(2-furyl)−S− |
| 387 | CH$_3$NHC(=O)− | H | −CH$_2$CH(CH$_3$)$_2$ | H | −CH$_2$−phenyl | H | −CH$_2$−(2-furyl)−S− |
| 388 | PhCH$_2$NHC(=O)− | H | −CH$_2$CH(CH$_3$)$_2$ | H | −CH$_2$−phenyl | H | −CH$_2$−(2-furyl)−S− |
| 389 | cyclohexyl-NHC(=O)− | H | −CH$_2$CH(CH$_3$)$_2$ | H | −CH$_2$−phenyl | H | −CH$_2$−(2-furyl)−S− |

TABLE 1-continued

| Compd. No. | R¹ | R⁴ | R⁵ | R⁶ | R⁷ | R⁸ | —A—R⁹ |
|---|---|---|---|---|---|---|---|
| 390 | phenylaminocarbonyl | H | —CH₂CH(CH₃)₂ | H | —CH₂—phenyl | H | —S—CH₂—(furan-2-yl) |
| 391 | CH₃—S(O)₂— | H | —CH₂CH(CH₃)₂ | H | —CH₂—phenyl | H | —S—CH₂—(furan-2-yl) |
| 392 | (CH₃)₂CH—S(O)₂— | H | —CH₂CH(CH₃)₂ | H | —CH₂—phenyl | H | —S—CH₂—(furan-2-yl) |
| 393 | phenyl—S(O)₂— | H | —CH₂CH(CH₃)₂ | H | —CH₂—phenyl | H | —S—CH₂—(furan-2-yl) |
| 394 | 4-F-phenyl—S(O)₂— | H | —CH₂CH(CH₃)₂ | H | —CH₂—phenyl | H | —S—CH₂—(furan-2-yl) |
| 395 | 4-CH₃-phenyl—S(O)₂— | H | —CH₂CH(CH₃)₂ | H | —CH₂—phenyl | H | —S—CH₂—(furan-2-yl) |
| 396 | 4-CH₃O-phenyl—S(O)₂— | H | —CH₂CH(CH₃)₂ | H | —CH₂—phenyl | H | —S—CH₂—(furan-2-yl) |
| 397 | quinolin-8-yl—S(O)₂— | H | —CH₂CH(CH₃)₂ | H | —CH₂—phenyl | H | —S—CH₂—(furan-2-yl) |

TABLE 1-continued

| Compd. No. | R¹ | R⁴ | R⁵ | R⁶ | R⁷ | R⁸ | —A—R⁹ |
|---|---|---|---|---|---|---|---|
| 398 | —C(O)O—CH₂—C₆H₅ | H | —CH(CH₃)CH₂CH₃ | H | —CH₂—C₆H₅ | H | furfuryl-CH₂—S— |
| 399 | —C(O)O—CH₂—C₆H₅ | H | —CH₂CH₂CH₂CH₃ | H | —CH₂—C₆H₅ | H | furfuryl-CH₂—S— |
| 400 | —C(O)O—CH₂—C₆H₅ | H | —CH₂—cyclohexyl | H | —CH₂—C₆H₅ | H | furfuryl-CH₂—S— |
| 401 | —C(O)O—CH₂—C₆H₅ | H | —CH₂—C₆H₅ | H | —CH₂—C₆H₅ | H | furfuryl-CH₂—S— |
| 402 | —C(O)O—CH₂—C₆H₅ | H | —CH₂CH₂—C₆H₅ | H | —CH₂—C₆H₅ | H | furfuryl-CH₂—S— |
| 403 | —C(O)O—CH₂—C₆H₅ | H | —OCH₃ | H | —CH₂—C₆H₅ | H | furfuryl-CH₂—S— |
| 404 | —C(O)—C₆H₅ | H | —OCH₃ | H | —CH₂—C₆H₅ | H | furfuryl-CH₂—S— |

TABLE 1-continued

| Compd. No. | R¹ | R⁴ | R⁵ | R⁶ | R⁷ | R⁸ | —A—R⁹ |
|---|---|---|---|---|---|---|---|
| 405 | benzyl ester | H | —OCH(CH₃)₂ | H | —CH₂-phenyl | H | furan-2-yl-CH₂-S— |
| 406 | phenyl ketone | H | —OCH(CH₃)₂ | H | —CH₂-phenyl | H | furan-2-yl-CH₂-S— |
| 407 | benzyl ester | H | —CH₂CH(CH₃)₂ | H | —CH₂-phenyl | H | 5-Cl-furan-2-yl-CH₂-S— |
| 408 | benzyl ester | H | —CH₂CH(CH₃)₂ | H | —CH₂-phenyl | H | 4-Cl-furan-2-yl-CH₂-S— |
| 409 | benzyl ester | H | —CH₂CH(CH₃)₂ | H | —CH₂-phenyl | H | 3-Cl-furan-2-yl-CH₂-S— |
| 410 | benzyl ester | H | —CH₂CH(CH₃)₂ | H | —CH₂-phenyl | H | 5-CH₃-furan-2-yl-CH₂-S— |
| 411 | benzyl ester | H | —CH₂CH(CH₃)₂ | H | —CH₂-phenyl | H | 4-CH₃-furan-2-yl-CH₂-S— |

TABLE 1-continued

| Compd. No. | R¹ | R⁴ | R⁵ | R⁶ | R⁷ | R⁸ | –A–R⁹ |
|---|---|---|---|---|---|---|---|
| 412 | -C(O)O-CH₂-C₆H₅ | H | -CH₂CH(CH₃)₂ | H | -CH₂-C₆H₅ | H | 3-methyl-2-furylmethylthio |
| 413 | -C(O)O-CH₂-C₆H₅ | H | -CH₂CH(CH₃)₂ | H | -CH₂-C₆H₅ | H | 5-(methoxycarbonyl)-2-furylmethylthio |
| 414 | -C(O)O-CH₂-C₆H₅ | H | -CH₂CH(CH₃)₂ | H | -CH₂-C₆H₅ | H | 5-carboxy-2-furylmethylthio |
| 415 | -C(O)O-CH₂-C₆H₅ | H | -CH₂CH(CH₃)₂ | H | -CH₂-C₆H₅ | H | 2-furylethylthio |
| 416 | -C(O)O-CH₂-C₆H₅ | H | -CH₂CH(CH₃)₂ | H | -CH₂-C₆H₅ | H | 3-furylmethylthio |
| 417 | (CH₃)₃COC(O)- | H | -CH₂CH(CH₃)₂ | H | -CH₂-C₆H₅ | H | 2-thienylmethylthio |
| 418 | -C(O)O-CH₂-C₆H₅ | H | -CH₂CH(CH₃)₂ | H | -CH₂-C₆H₅ | H | 2-thienylmethylthio |

TABLE 1-continued

| Compd. No. | R¹ | R⁴ | R⁵ | R⁶ | R⁷ | R⁸ | -A-R⁹ |
|---|---|---|---|---|---|---|---|
| 419 | H | H | -CH₂CH(CH₃)₂ | H | -CH₂-C₆H₅ | H | -S-CH₂-(thiophene) |
| 420 | -C(O)O-CH₂-C₆H₅ | H | -CH₂CH(CH₃)₂ | H | -CH₂-C₆H₅ | H | -S-CH₂-(thiophene) |
| 421 | -C(O)-(2,6-difluorophenyl) | H | -CH₂CH(CH₃)₂ | H | -CH₂-C₆H₅ | H | -S-CH₂-(thiophene) |
| 422 | -S(O)₂-C₆H₅ | H | -CH₂CH(CH₃)₂ | H | -CH₂-C₆H₅ | H | -S-CH₂-(thiophene) |
| 423 | -C(O)O-CH₂-C₆H₅ | H | -CH₂CH(CH₃)₂ | H | -CH₂-C₆H₅ | H | -S-CH₂-(5-chlorothiophene) |
| 424 | -C(O)O-CH₂-C₆H₅ | H | -CH₂CH(CH₃)₂ | H | -CH₂-C₆H₅ | H | -S-CH₂-(4-chlorothiophene) |
| 425 | -C(O)O-CH₂-C₆H₅ | H | -CH₂CH(CH₃)₂ | H | -CH₂-C₆H₅ | H | -S-CH₂-(3-chlorothiophene) |

TABLE 1-continued

| Compd. No. | R¹ | R⁴ | R⁵ | R⁶ | R⁷ | R⁸ | —A—R⁹ |
|---|---|---|---|---|---|---|---|
| 426 | benzyl ester | H | —CH$_2$CH(CH$_3$)$_2$ | H | —CH$_2$-phenyl | H | —CH$_2$-S-(1H-pyrrol-2-yl) |
| 427 | benzyl ester | H | —CH$_2$CH(CH$_3$)$_2$ | H | —CH$_2$-phenyl | H | —CH$_2$-S-(1-methyl-pyrrol-2-yl) |
| 428 | benzyl ester | H | —CH$_2$CH(CH$_3$)$_2$ | H | —CH$_2$-phenyl | H | —CH$_2$-S-(pyridin-2-yl) |
| 429 | benzyl ester | H | —CH$_2$CH(CH$_3$)$_2$ | H | —CH$_2$-phenyl | H | —CH$_2$-S-(pyridin-2-yl N-oxide) |
| 430 | benzyl ester | H | —CH$_2$CH(CH$_3$)$_2$ | H | —CH$_2$-phenyl | H | —CH$_2$-S-(pyridin-3-yl) |
| 431 | benzyl ester | H | —CH$_2$CH(CH$_3$)$_2$ | H | —CH$_2$-phenyl | H | —CH$_2$-S-(pyridin-3-yl N-oxide) |
| 432 | benzyl ester | H | —CH$_2$CH(CH$_3$)$_2$ | H | —CH$_2$-phenyl | H | —CH$_2$-S-(pyridin-4-yl) |

TABLE 1-continued

| Compd. No. | R¹ | R⁴ | R⁵ | R⁶ | R⁷ | R⁸ | —A—R⁹ |
|---|---|---|---|---|---|---|---|
| 433 | benzyl ester | H | —CH₂CH(CH₃)₂ | H | —CH₂—phenyl | H | 4-pyridyl N-oxide-CH₂-S— |
| 434 | benzyl ester | H | —CH₂CH(CH₃)₂ | H | —CH₂—phenyl | H | benzimidazol-2-yl-CH₂-S— (NH) |
| 435 | benzyl ester | H | —CH₂CH(CH₃)₂ | H | —CH₂—phenyl | H | 1-methylbenzimidazol-2-yl-CH₂-S— |
| 436 | benzyl ester | H | —CH₂CH(CH₃)₂ | H | —CH₂—phenyl | H | isoxazol-4-yl-CH₂-S— |
| 437 | benzyl ester | H | —CH₂CH(CH₃)₂ | H | —CH₂—phenyl | H | 3-methylisoxazol-4-yl-CH₂-S— |
| 438 | benzyl ester | H | —CH₂CH(CH₃)₂ | H | —CH₂—phenyl | H | 3,5-dimethylisoxazol-4-yl-CH₂-S— |

TABLE 1-continued

| Compd. No. | R¹ | R⁴ | R⁵ | R⁶ | R⁷ | R⁸ | —A—R⁹ |
|---|---|---|---|---|---|---|---|
| 439 | benzyl-O-C(=O)- | H | —CH$_2$CH(CH$_3$)$_2$ | H | —CH$_2$-phenyl | H | —CH$_2$—S—(oxazol-4-yl) |
| 440 | benzyl-O-C(=O)- | H | —CH$_2$CH(CH$_3$)$_2$ | H | —CH$_2$-phenyl | H | —CH$_2$—S—(2-methyloxazol-4-yl) |
| 441 | benzyl-O-C(=O)- | H | —CH$_2$CH(CH$_3$)$_2$ | H | —CH$_2$-phenyl | H | —CH(CH$_3$)—S—(2-methyloxazol-4-yl) |
| 442 | benzyl-O-C(=O)- | H | —CH$_2$CH(CH$_3$)$_2$ | H | —CH$_2$-phenyl | H | —CH$_2$—S—(thiazol-4-yl) |
| 443 | benzyl-O-C(=O)- | H | —CH$_2$CH(CH$_3$)$_2$ | H | —CH$_2$-phenyl | H | —CH$_2$—S—(2-methylthiazol-4-yl) |
| 444 | benzyl-O-C(=O)- | H | —CH$_2$CH(CH$_3$)$_2$ | H | —CH$_2$-phenyl | H | —CH$_2$—S—(thiazol-2-yl) |
| 445 | benzyl-O-C(=O)- | H | —CH$_2$CH(CH$_3$)$_2$ | H | —CH$_2$-phenyl | H | —CH$_2$—(oxazolidin-2-one-4-yl) |

TABLE 1-continued

| Compd. No. | R¹ | R⁴ | R⁵ | R⁶ | R⁷ | R⁸ | –A–R⁹ |
|---|---|---|---|---|---|---|---|
| 446 | benzyl ester | H | –CH₂CH(CH₃)₂ | H | –CH₂–phenyl | H | –S–CH₂–CH(NCH₃C(O)O–) |
| 447 | benzyl ester | H | –CH₂CH(CH₃)₂ | H | –CH₂–phenyl | H | –O–CH₃ |
| 448 | benzyl ester | H | –CH₂CH(CH₃)₂ | H | –CH₂–phenyl | H | –O–CH₂CH₃ |
| 449 | benzyl ester | H | –CH₂CH(CH₃)₂ | H | –CH₂–phenyl | H | –O–CH₂CH₂CH₃ |
| 450 | (CH₃)₃COC(O)– ester | H | –CH₂CH(CH₃)₂ | H | –CH₂–phenyl | H | –O–CH₂–furyl |
| 451 | cyclohexylmethyl ester | H | –CH₂CH(CH₃)₂ | H | –CH₂–phenyl | H | –O–CH₂–furyl |
| 452 | benzyl ester | H | –CH₂CH(CH₃)₂ | H | –CH₂–phenyl | H | –O–CH₂–furyl |

TABLE 1-continued
| Compd. No. | R¹ | R⁴ | R⁵ | R⁶ | R⁷ | R⁸ | –A–R⁹ |
|---|---|---|---|---|---|---|---|
| 453 |  | H | –CH$_2$CH(CH$_3$)$_2$ | H | –CH$_2$–  | H | 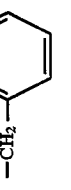 |
| 454 | H | H | –CH$_2$CH(CH$_3$)$_2$ | H | –CH$_2$–  | H | 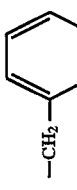 |
| 455 |  | H | –CH$_2$CH(CH$_3$)$_2$ | H | –CH$_2$– | H | 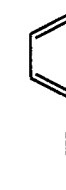 |
| 456 |  | H | –CH$_2$CH(CH$_3$)$_2$ | H | –CH$_2$– | H | 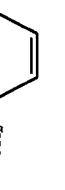 |
| 457 |  | H | –CH$_2$CH(CH$_3$)$_2$ | H | –CH$_2$– | H | 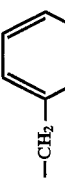 |
| 458 |  | H | –CH$_2$CH(CH$_3$)$_2$ | H | –CH$_2$– | H | |
| 459 | 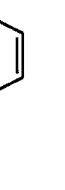 | H | –CH$_2$CH(CH$_3$)$_2$ | H | –CH$_2$– | H | |
| 460 |  | H | –CH$_2$CH(CH$_3$)$_2$ | H | –CH$_2$– | H | |

TABLE 1-continued

| Compd. No. | R¹ | R⁴ | R⁵ | R⁶ | R⁷ | R⁸ | —A—R⁹ |
|---|---|---|---|---|---|---|---|
| 461 | benzyl ester (–C(=O)O–CH₂–C₆H₅) | H | –CH₂CH(CH₃)₂ | H | –CH₂–C₆H₅ | H | –NH(CH₃) |
| 462 | isobutyl ester (–C(=O)O–CH₂CH(CH₃)₂) | H | –CH₂CH(CH₃)₂ | H | –CH₂–C₆H₅ | H | –N(CH₃)₂ |
| 463 | (CH₃)₃COC(=O)– | H | –CH₂CH(CH₃)₂ | H | –CH₂–C₆H₅ | H | –N(CH₃)₂ |
| 464 | cyclohexylmethyl ester | H | –CH₂CH(CH₃)₂ | H | –CH₂–C₆H₅ | H | –N(CH₃)₂ |
| 465 | benzyl ester | H | –CH₂CH(CH₃)₂ | H | –CH₂–C₆H₅ | H | –N(CH₃)₂ |
| 466 | 4-methoxybenzyl ester | H | –CH₂CH(CH₃)₂ | H | –CH₂–C₆H₅ | H | –N(CH₃)₂ |
| 467 | H | H | –CH₂CH(CH₃)₂ | H | –CH₂–C₆H₅ | H | –N(CH₃)₂ |

TABLE 1-continued

| Compd. No. | R¹ | R⁴ | R⁵ | R⁶ | R⁷ | R⁸ | —A—R⁹ |
|---|---|---|---|---|---|---|---|
| 468 | phenoxymethyl ketone (PhOCH₂C(O)–) | H | —CH₂CH(CH₃)₂ | H | —CH₂–C₆H₅ | H | —N(CH₃)₂ |
| 469 | 2-fluorobenzoyl | H | —CH₂CH(CH₃)₂ | H | —CH₂–C₆H₅ | H | —N(CH₃)₂ |
| 470 | 2,6-difluorobenzoyl | H | —CH₂CH(CH₃)₂ | H | —CH₂–C₆H₅ | H | —N(CH₃)₂ |
| 471 | 2-furoyl | H | —CH₂CH(CH₃)₂ | H | —CH₂–C₆H₅ | H | —N(CH₃)₂ |
| 472 | 2-thenoyl | H | —CH₂CH(CH₃)₂ | H | —CH₂–C₆H₅ | H | —N(CH₃)₂ |
| 473 | CH₃SO₂– | H | —CH₂CH(CH₃)₂ | H | —CH₂–C₆H₅ | H | —N(CH₃)₂ |
| 474 | C₆H₅SO₂– | H | —CH₂CH(CH₃)₂ | H | —CH₂–C₆H₅ | H | —N(CH₃)₂ |
| 475 | 4-Cl-C₆H₄-SO₂– | H | —CH₂CH(CH₃)₂ | H | —CH₂–C₆H₅ | H | —N(CH₃)₂ |

TABLE 1-continued

| Compd. No. | R¹ | R⁴ | R⁵ | R⁶ | R⁷ | R⁸ | —A—R⁹ |
|---|---|---|---|---|---|---|---|
| 476 | PhCH₂-O-C(=O)- | H | -CH₂CH(CH₃)₂ | H | -CH₂-Ph | H | -N(CH₃)-CH₂CH₂CH₃ |
| 477 | PhCH₂-O-C(=O)- | H | -CH₂CH(CH₃)₂ | H | -CH₂-Ph | H | -N(H)-CH₂-(2-furyl) |
| 478 | (CH₃)₃C-O-C(=O)- | H | -CH₂CH(CH₃)₂ | H | -CH₂-Ph | H | -N(CH₃)-CH₂-(2-furyl) |
| 479 | PhCH₂-O-C(=O)- | H | -CH₂CH(CH₃)₂ | H | -CH₂-Ph | H | -N(CH₃)-CH₂-(2-furyl) |
| 480 | H | H | -CH₂CH(CH₃)₂ | H | -CH₂-Ph | H | -N(CH₃)-CH₂-(2-furyl) |
| 481 | PhO-CH₂-C(=O)- | H | -CH₂CH(CH₃)₂ | H | -CH₂-Ph | H | -N(CH₃)-CH₂-(2-furyl) |
| 482 | (2,6-F₂-C₆H₃)-C(=O)- | H | -CH₂CH(CH₃)₂ | H | -CH₂-Ph | H | -N(CH₃)-CH₂-(2-furyl) |

TABLE 1-continued

| Compd. No. | R¹ | R⁴ | R⁵ | R⁶ | R⁷ | R⁸ | –A–R⁹ |
|---|---|---|---|---|---|---|---|
| 483 | CH₃SO₂– | H | –CH₂CH(CH₃)₂ | H | –CH₂–C₆H₅ | H | furan-2-yl-CH₂–N(CH₃)– |
| 484 | C₆H₅SO₂– | H | –CH₂CH(CH₃)₂ | H | –CH₂–C₆H₅ | H | furan-2-yl-CH₂–N(CH₃)– |
| 485 | C₆H₅CH₂O–C(O)– | H | –CH₂CH(CH₃)₂ | H | –CH₂–C₆H₅ | H | pyrrolidin-1-yl |
| 486 | C₆H₅CH₂O–C(O)– | H | –CH₂CH(CH₃)₂ | H | –CH₂–C₆H₅ | H | piperidin-1-yl |
| 487 | C₆H₅CH₂O–C(O)– | H | –CH₂CH(CH₃)₂ | H | –CH₂–C₆H₅ | H | piperazin-1-yl |
| 488 | C₆H₅CH₂O–C(O)– | H | –CH₂CH(CH₃)₂ | H | –CH₂–C₆H₅ | H | 4-methylpiperazin-1-yl |
| 489 | C₆H₅CH₂O–C(O)– | H | –CH₂CH(CH₃)₂ | H | –CH₂–C₆H₅ | H | 4-ethylpiperazin-1-yl |

TABLE 1-continued

| Compd. No. | R¹ | R⁴ | R⁵ | R⁶ | R⁷ | R⁸ | −A−R⁹ |
|---|---|---|---|---|---|---|---|
| 490 | −C(=O)O−CH₂−C₆H₅ | H | −CH₂CH(CH₃)₂ | H | −CH₂−(2-F-C₆H₄) | H | −S−CH₃ |
| 491 | −C(=O)O−CH₂−C₆H₅ | H | −CH₂CH(CH₃)₂ | H | −CH₂−(2-F-C₆H₄) | H | −CH₂−S−(2-furyl) |
| 492 | −C(=O)O−CH₂−C₆H₅ | H | −CH₂CH(CH₃)₂ | H | −CH₂−(3-F-C₆H₄) | H | −S−CH₃ |
| 493 | −C(=O)O−CH₂−C₆H₅ | H | −CH₂CH(CH₃)₂ | H | −CH₂−(3-F-C₆H₄) | H | −CH₂−S−(2-furyl) |
| 494 | −C(=O)O−CH₂−C₆H₅ | H | −CH₂CH(CH₃)₂ | H | −CH₂−(4-F-C₆H₄) | H | −S−CH₃ |
| 495 | (CH₃)₃COC(=O)− | H | −CH₂CH(CH₃)₂ | H | −CH₂−(4-F-C₆H₄) | H | −CH₂−S−(2-furyl) |
| 496 | −C(=O)O−CH₂−C₆H₅ | H | −CH₂CH(CH₃)₂ | H | −CH₂−(4-F-C₆H₄) | H | −CH₂−S−(2-furyl) |

TABLE 1-continued
| Compd. No. | R¹ | R⁴ | R⁵ | R⁶ | R⁷ | R⁸ | —A—R⁹ |
|---|---|---|---|---|---|---|---|
| 497 | H | H | —CH$_2$CH(CH$_3$)$_2$ | H | 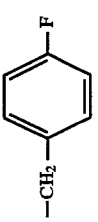 —CH$_2$— | H | 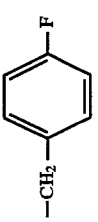 |
| 498 |  | H | —CH$_2$CH(CH$_3$)$_2$ | H | 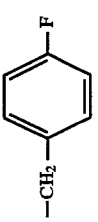 —CH$_2$— | H | 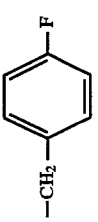 |
| 499 | 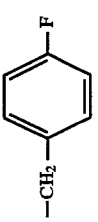 | H | —CH$_2$CH(CH$_3$)$_2$ | H | 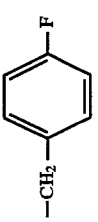 —CH$_2$— | H | 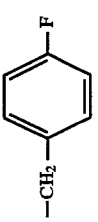 |
| 500 | 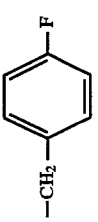 | H | —CH$_2$CH(CH$_3$)$_2$ | H | 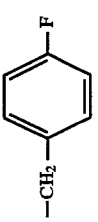 —CH$_2$— | H | 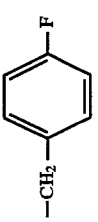 |
| 501 | 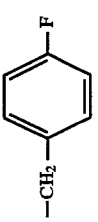 | H | —CH$_2$CH(CH$_3$)$_2$ | H | 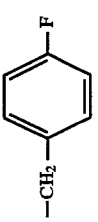 —CH$_2$— | H | 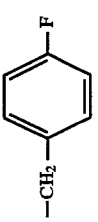 |
| 502 | 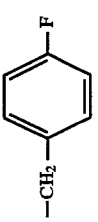 | H | —CH$_2$CH(CH$_3$)$_2$ | H |  —CH$_2$— | H | —S—CH$_3$ |
| 503 |  | H | —CH$_2$CH(CH$_3$)$_2$ | H |  —CH$_2$— | H | 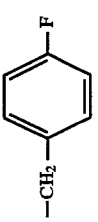 |

TABLE 1-continued

| Compd. No. | R¹ | R⁴ | R⁵ | R⁶ | R⁷ | R⁸ | —A—R⁹ |
|---|---|---|---|---|---|---|---|
| 504 | benzyl ester (–C(O)O–CH₂–C₆H₅) | H | –CH₂CH(CH₃)₂ | H | 3-Cl-C₆H₄–CH₂– | H | –S–CH₃ |
| 505 | benzyl ester | H | –CH₂CH(CH₃)₂ | H | 3-Cl-C₆H₄–CH₂– | H | –S–CH₂–(2-furyl) |
| 506 | benzyl ester | H | –CH₂CH(CH₃)₂ | H | 4-Cl-C₆H₄–CH₂– | H | –S–CH₃ |
| 507 | (CH₃)₃COC(O)– | H | –CH₂CH(CH₃)₂ | H | 4-Cl-C₆H₄–CH₂– | H | –S–CH₂–(2-furyl) |
| 508 | benzyl ester | H | –CH₂CH(CH₃)₂ | H | 4-Cl-C₆H₄–CH₂– | H | –S–CH₂–(2-furyl) |
| 509 | (2-pyridyl)-CH₂–O–C(O)– | H | –CH₂CH(CH₃)₂ | H | 4-Cl-C₆H₄–CH₂– | H | –S–CH₂–(2-furyl) |
| 510 | H | H | –CH₂CH(CH₃)₂ | H | 4-Cl-C₆H₄–CH₂– | H | –S–CH₂–(2-furyl) |

TABLE 1-continued

| Compd. No. | R¹ | R⁴ | R⁵ | R⁶ | R⁷ | R⁸ | –A–R⁹ |
|---|---|---|---|---|---|---|---|
| 511 | phenoxyacetyl | H | –CH$_2$CH(CH$_3$)$_2$ | H | 4-Cl-benzyl | H | –S–CH$_2$-(2-furyl) |
| 512 | 2-fluorobenzoyl | H | –CH$_2$CH(CH$_3$)$_2$ | H | 4-Cl-benzyl | H | –S–CH$_2$-(2-furyl) |
| 513 | 2-furoyl | H | –CH$_2$CH(CH$_3$)$_2$ | H | 4-Cl-benzyl | H | –S–CH$_2$-(2-furyl) |
| 514 | methanesulfonyl | H | –CH$_2$CH(CH$_3$)$_2$ | H | 4-Cl-benzyl | H | –S–CH$_2$-(2-furyl) |
| 515 | phenylsulfonyl | H | –CH$_2$CH(CH$_3$)$_2$ | H | 4-Cl-benzyl | H | –S–CH$_2$-(2-furyl) |
| 516 | benzyloxycarbonyl | H | –CH$_2$CH(CH$_3$)$_2$ | H | 4-OCH$_3$-benzyl | H | –S–CH$_3$ |
| 517 | benzyloxycarbonyl | H | –CH$_2$CH(CH$_3$)$_2$ | H | 4-OCH$_3$-benzyl | H | –S–CH$_2$-(2-furyl) |

TABLE 1-continued

| Compd. No. | R¹ | R⁴ | R⁵ | R⁶ | R⁷ | R⁸ | -A-R⁹ |
|---|---|---|---|---|---|---|---|
| 518 | benzyl ester | H | $-CH_2CH(CH_3)_2$ | H | $-CH_2-$C₆H₄-$OC(CH_3)_3$ | H | $-S-CH_3$ |
| 519 | benzyl ester | H | $-CH_2CH(CH_3)_2$ | H | $-CH_2-$C₆H₄-$OC(CH_3)_3$ | H | furfuryl-S- |
| 520 | benzyl ester | H | $-CH_2CH(CH_3)_2$ | H | $-CH_2-$C₆H₄-$OH$ | H | $-S-CH_3$ |
| 521 | $(CH_3)_3COC(O)-$ | H | $-CH_2CH(CH_3)_2$ | H | $-CH_2-$C₆H₄-$OH$ | H | furfuryl-S- |
| 522 | cyclohexylmethyl ester | H | $-CH_2CH(CH_3)_2$ | H | $-CH_2-$C₆H₄-$OH$ | H | furfuryl-S- |
| 523 | benzyl ester | H | $-CH_2CH(CH_3)_2$ | H | $-CH_2-$C₆H₄-$OH$ | H | furfuryl-S- |
| 524 | H | H | | H | $-CH_2-$C₆H₄-$OH$ | H | furfuryl-S- |

TABLE 1-continued

| Compd. No. | R¹ | R⁴ | R⁵ | R⁶ | R⁷ | R⁸ | —A—R⁹ |
|---|---|---|---|---|---|---|---|
| 525 | 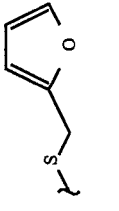 | H | —CH$_2$CH(CH$_3$)$_2$ | H | 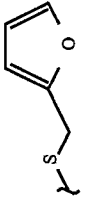 4-hydroxybenzyl | H | 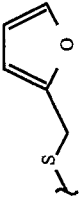 furfuryl-S- |
| 526 | phenylsulfonyl | H | —CH$_2$CH(CH$_3$)$_2$ | H | 4-hydroxybenzyl | H | furfuryl-S- |
| 527 | benzyl ester | H | —CH$_2$CH(CH$_3$)$_2$ | H | 2-thienylmethyl | H | —S—CH$_3$ |
| 528 | cyclohexylmethyl ester | H | —CH$_2$CH(CH$_3$)$_2$ | H | 2-thienylmethyl | H | furfuryl-S- |
| 529 | benzyl ester | H | —CH$_2$CH(CH$_3$)$_2$ | H | 2-thienylmethyl | H | furfuryl-S- |
| 530 | 2-pyridylmethyl ester | H | —CH$_2$CH(CH$_3$)$_2$ | H | 2-thienylmethyl | H | furfuryl-S- |
| 531 | benzyl ester | H | —CH$_2$CH(CH$_3$)$_2$ | H | 2-thienylmethyl | H | —S—CH$_3$ |

TABLE 1-continued

| Compd. No. | R¹ | R⁴ | R⁵ | R⁶ | R⁷ | R⁸ | -A-R⁹ |
|---|---|---|---|---|---|---|---|
| 532 | benzyl-O-C(=O)- | H | -CH₂CH(CH₃)₂ | H | -CH₂-(thienyl) | H | -S-CH₂-(furyl) |
| 533 | (CH₃)₃C-C(=O)-O-C(=O)- | H | -CH₂CH(CH₃)₂ | H | -CH₂-phenyl | H | -S-CH₃ |
| 534 | benzyl-O-C(=O)- | H | -CH₂CH(CH₃)₂ | H | -CH₂-phenyl | H | -S-CH₃ |
| 535 | H | H | -CH₂CH(CH₃)₂ | H | -CH₂-phenyl | H | -S-CH₃ |
| 536 | phenoxy-CH₂-C(=O)- | H | -CH₂CH(CH₃)₂ | H | -CH₂-phenyl | H | -S-CH₃ |
| 537 | 2-F-phenyl-C(=O)- | H | -CH₂CH(CH₃)₂ | H | -CH₂-phenyl | H | -S-CH₃ |
| 538 | (CH₃)₃C-C(=O)-O-C(=O)- | H | -CH₂CH(CH₃)₂ | H | -CH₂-phenyl | H | -S-CH₂-(furyl) |
| 539 | cyclohexyl-CH₂-O-C(=O)- | H | -CH₂CH(CH₃)₂ | H | -CH₂-phenyl | H | -S-CH₂-(furyl) |

TABLE 1-continued
| Compd. No. | R¹ | R⁴ | R⁵ | R⁶ | R⁷ | R⁸ | —A—R⁹ |
|---|---|---|---|---|---|---|---|
| 540 |  | H | —CH$_2$CH(CH$_3$)$_2$ | H | —CH$_2$CH$_2$— 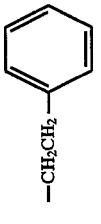 | H | 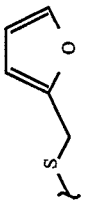 |
| 541 | 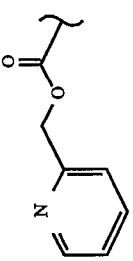 | H | —CH$_2$CH(CH$_3$)$_2$ | H | —CH$_2$CH$_2$— 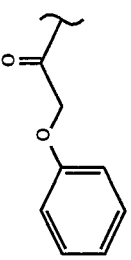 | H | 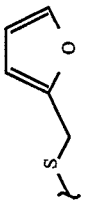 |
| 542 | H | H | —CH$_2$CH(CH$_3$)$_2$ | H | —CH$_2$CH$_2$— 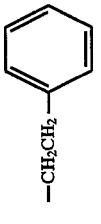 | H | 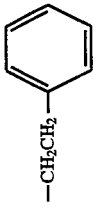 |
| 543 | 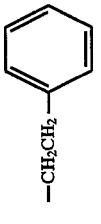 | H | —CH$_2$CH(CH$_3$)$_2$ | H | —CH$_2$CH$_2$— 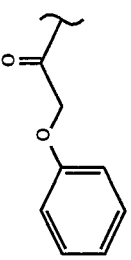 | H | 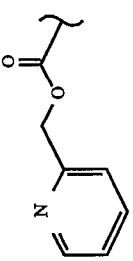 |
| 544 | 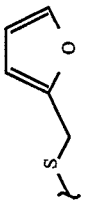 | H | —CH$_2$CH(CH$_3$)$_2$ | H | —CH$_2$CH$_2$— | H | |
| 545 | 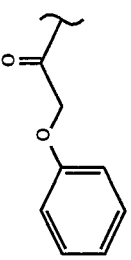 | H | —CH$_2$CH(CH$_3$)$_2$ | H | —CH$_2$CH$_2$— | H | |
| 546 | 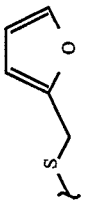 | H | —CH$_2$CH(CH$_3$)$_2$ | H | —CH$_2$CH$_2$— | H | |

TABLE 1-continued

| Compd. No. | R¹ | R⁴ | R⁵ | R⁶ | R⁷ | R⁸ | −A−R⁹ |
|---|---|---|---|---|---|---|---|
| 547 | benzyl ester (−C(O)O−CH₂−C₆H₅) | H | −CH₂CH(CH₃)₂ | H | −CH₂−(1-naphthyl) | H | −S−CH₂−(2-furyl) |
| 548 | (CH₃)₃COC(O)− | H | −CH₂CH(CH₃)₂ | H | −CH₂−(1-naphthyl) | H | −S−CH₂−(2-furyl) |
| 549 | cyclohexylmethyl ester (−C(O)O−CH₂−C₆H₁₁) | H | −CH₂CH(CH₃)₂ | H | −CH₂−(1-naphthyl) | H | −S−CH₂−(2-furyl) |
| 550 | benzyl ester (−C(O)O−CH₂−C₆H₅) | H | −CH₂CH(CH₃)₂ | H | −CH₂−(1-naphthyl) | H | −S−CH₂−(2-furyl) |
| 551 | (2-pyridyl)methyl ester (−C(O)O−CH₂−(2-pyridyl)) | H | −CH₂CH(CH₃)₂ | H | −CH₂−(1-naphthyl) | H | −S−CH₂−(2-furyl) |

TABLE 1-continued

| Compd. No. | R¹ | R⁴ | R⁵ | R⁶ | R⁷ | R⁸ | -A-R⁹ |
|---|---|---|---|---|---|---|---|
| 552 | phenylsulfonyl (PhSO₂-) | H | -CH₂CH(CH₃)₂ | H | -CH₂-(1-naphthyl) | H | -S-CH₂-(2-furyl) |
| 553 | H | H | -CH₂CH(CH₃)₂ | H | -CH₂-(1-naphthyl) | H | -S-CH₂-(2-furyl) |
| 554 | 4-methylpentanoyl (isopentyl-C(=O)-) | H | -CH₂CH(CH₃)₂ | H | -CH₂-(1-naphthyl) | H | -S-CH₂-(2-furyl) |
| 555 | phenoxyacetyl (PhO-CH₂-C(=O)-) | H | -CH₂CH(CH₃)₂ | H | -CH₂-(1-naphthyl) | H | -S-CH₂-(2-furyl) |
| 556 | 2-fluorobenzoyl (2-F-C₆H₄-C(=O)-) | H | -CH₂CH(CH₃)₂ | H | -CH₂-(1-naphthyl) | H | -S-CH₂-(2-furyl) |

TABLE 1-continued
| Compd. No. | R¹ | R⁴ | R⁵ | R⁶ | R⁷ | R⁸ | −A−R⁹ |
|---|---|---|---|---|---|---|---|
| 557 | 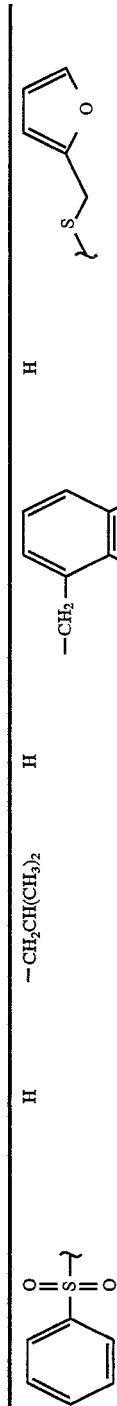 | H | −CH$_2$CH(CH$_3$)$_2$ | H |  | H |  |
| 558 |  | H | −CH$_2$CH(CH$_3$)$_2$ | H | 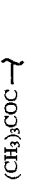 | H | $\xi$−S−CH$_3$ |
| 559 |  | H | −CH$_2$CH(CH$_3$)$_2$ | H |  | H | $\xi$−S−CH$_3$ |
| 560 | H | H | −CH$_2$CH(CH$_3$)$_2$ | H |  | H | $\xi$−S−CH$_3$ |
| 561 |  | H | −CH$_2$CH(CH$_3$)$_2$ | H |  | H | $\xi$−S−CH$_3$ |
| 562 |  | H | −CH$_2$CH(CH$_3$)$_2$ | H |  | H | $\xi$−S−CH$_3$ |

TABLE 1-continued
| Compd. No. | R¹ | R⁴ | R⁵ | R⁶ | R⁷ | R⁸ | —A—R⁹ |
|---|---|---|---|---|---|---|---|
| 563 | 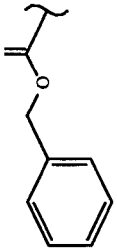 | H | —CH$_2$CH(CH$_3$)$_2$ | H | 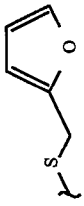 | H | 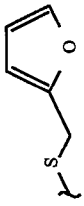 |
| 564 | 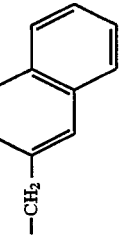 | H | —CH$_2$CH(CH$_3$)$_2$ | H |  | H | 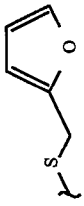 |
| 565 | 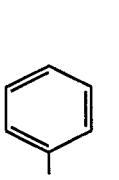 | H | —CH$_2$CH(CH$_3$)$_2$ | H | 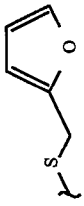 | H | $\xi$—S—CH$_3$ |
| 566 | 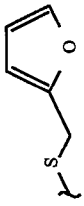 | H | —CH$_2$CH(CH$_3$)$_2$ | H |  | H | 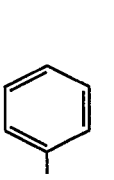 |
| 567 | 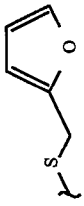 | H | —CH$_2$CH(CH$_3$)$_2$ | H | —CH$_2$OCH$_3$ | H | $\xi$—S—CH$_3$ |
| 568 |  | H | —CH$_2$CH(CH$_3$)$_2$ | H | —CH$_2$OCH$_3$ | H | 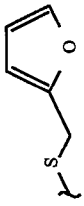 |
| 569 | (same benzyl ester) | H | —CH$_2$CH(CH$_3$)$_2$ | H | —CH$_2$OCH$_2$CH$_3$ | H | $\xi$—S—CH$_3$ |

| Compd. No. | R¹ | R⁴ | R⁵ | R⁶ | R⁷ | R⁸ | −A−R⁹ |
|---|---|---|---|---|---|---|---|
| 570 | 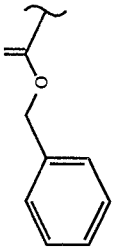 | H | −CH₂CH(CH₃)₂ | H | −CH₂OCH₂CH₃ | H | 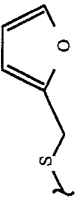 |
| 571 |  | H | −CH₂CH(CH₃)₂ | H | −CH₂OCH₂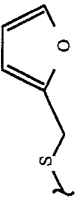 | H | ⟩−S−CH₃ |
| 572 |  | H | −CH₂CH(CH₃)₂ | H | −CH₂OCH₂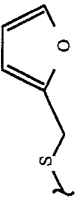 | H |  |
| 573 | (CH₃)₃COC(O)− | H | −CH₂CH(CH₃)₂ | H | −CH₂OCH₂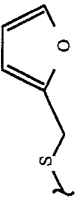 | H | ⟩−S−CH₃ |
| 574 |  | H | −CH₂CH(CH₃)₂ | H | −CH₂OCH₂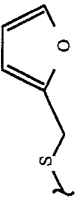 | H | ⟩−S−CH₃ |
| 575 | H | H | −CH₂CH(CH₃)₂ | H | −CH₂OCH₂ | H | ⟩−S−CH₃ |
| 576 | 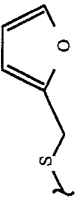 | H | −CH₂CH(CH₃)₂ | H | −CH₂OCH₂ | H | ⟩−S−CH₃ |

TABLE 1-continued

| Compd. No. | R¹ | R⁴ | R⁵ | R⁶ | R⁷ | R⁸ | –A–R⁹ |
|---|---|---|---|---|---|---|---|
| 577 | benzyl ester | H | –CH$_2$CH(CH$_3$)$_2$ | H | –CH$_2$OCH$_2$-furan | H | –S–CH$_2$-furan |
| 578 | benzyl ester | H | –CH$_2$CH(CH$_3$)$_2$ | H | –CH$_2$SCH$_3$ | H | –S–CH$_3$ |
| 579 | benzyl ester | H | –CH$_2$CH(CH$_3$)$_2$ | H | –CH$_2$SCH$_3$ | H | –S–CH$_2$-furan |
| 580 | benzyl ester | H | –CH$_2$CH(CH$_3$)$_2$ | H | –CH$_2$SCH$_2$CH$_3$ | H | –S–CH$_3$ |
| 581 | benzyl ester | H | –CH$_2$CH(CH$_3$)$_2$ | H | –CH$_2$SCH$_2$CH$_3$ | H | –S–CH$_2$-furan |
| 582 | benzyl ester | H | –CH$_2$CH(CH$_3$)$_2$ | H | –CH$_2$SCH$_2$-phenyl | H | –S–CH$_3$ |
| 583 | benzyl ester | H | –CH$_2$CH(CH$_3$)$_2$ | H | –CH$_2$SCH$_2$-phenyl | H | –S–CH$_2$-furan |

TABLE 1-continued

| Compd. No. | R¹ | R⁴ | R⁵ | R⁶ | R⁷ | R⁸ | –A–R⁹ |
|---|---|---|---|---|---|---|---|
| 584 | benzyl ester (–C(O)O–CH₂–C₆H₅) | H | –CH₂CH(CH₃)₂ | H | –CH₂CH₂SCH₃ | H | –S–CH₃ |
| 585 | benzyl ester | H | –CH₂CH(CH₃)₂ | H | –CH₂CH₂SCH₃ | H | –CH₂–S–(2-furyl) |
| 586 | (CH₃)₃COC(O)– | H | –CH₂CH(CH₃)₂ | H | –CH₂CH₂S–CH₂–(2-furyl) | H | –S–CH₃ |
| 587 | cyclohexylmethyl ester | H | –CH₂CH(CH₃)₂ | H | –CH₂CH₂S–CH₂–(2-furyl) | H | –S–CH₃ |
| 588 | benzyl ester | H | –CH₂CH(CH₃)₂ | H | –CH₂CH₂S–CH₂–(2-furyl) | H | –S–CH₃ |
| 589 | H | H | –CH₂CH(CH₃)₂ | H | –CH₂CH₂S–CH₂–(2-furyl) | H | –S–CH₃ |
| 590 | phenoxyacetyl (–C(O)CH₂–O–C₆H₅) | H | –CH₂CH(CH₃)₂ | H | –CH₂CH₂S–CH₂–(2-furyl) | H | –S–CH₃ |

TABLE 1-continued

| Compd. No. | R¹ | R⁴ | R⁵ | R⁶ | R⁷ | R⁸ | —A—R⁹ |
|---|---|---|---|---|---|---|---|
| 596 | benzyl ester | H | —CH$_2$CH(CH$_3$)$_2$ | H | —CH$_2$COOH | H | —S—CH$_2$-furan |
| 597 | benzyl ester | H | —CH$_2$CH(CH$_3$)$_2$ | H | —CH$_2$CH$_2$COOCH$_3$ | H | —S—CH$_3$ |
| 598 | benzyl ester | H | —CH$_2$CH(CH$_3$)$_2$ | H | —CH$_2$CH$_2$COOCH$_3$ | H | —S—CH$_2$-furan |
| 599 | benzyl ester | H | —CH$_2$CH(CH$_3$)$_2$ | H | —CH$_2$CH$_2$COOH | H | —S—CH$_3$ |
| 600 | benzyl ester | H | —CH$_2$CH(CH$_3$)$_2$ | H | —CH$_2$CH$_2$COOH | H | —S—CH$_2$-furan |
| 591 | 2,6-difluorophenyl ketone | H | —CH$_2$CH(CH$_3$)$_2$ | H | —CH$_2$CH$_2$S—CH$_2$-furan | H | —S—CH$_3$ |
| 592 | benzyl ester | H | —CH$_2$CH(CH$_3$)$_2$ | H | —CH$_2$CH$_2$S—CH$_2$-furan | H | —S—CH$_2$-furan |

TABLE 1-continued

| Compd. No. | R¹ | R⁴ | R⁵ | R⁶ | R⁷ | R⁸ | —A—R⁹ |
|---|---|---|---|---|---|---|---|
| 593 | benzyl ester (PhCH₂OC(O)—) | H | —CH₂CH(CH₃)₂ | H | —CH₂COOCH₃ | H | —S—CH₃ |
| 594 | benzyl ester | H | —CH₂CH(CH₃)₂ | H | —CH₂COOCH₃ | H | —CH₂—S—(2-furyl) |
| 595 | benzyl ester | H | —CH₂CH(CH₃)₂ | H | —CH₂COOH | H | —S—CH₃ |
| 601 | benzyl ester | H | —CH₂CH(CH₃)₂ | H | —OCH₂CH₂CH₃ | H | —S—CH₃ |
| 602 | (CH₃)₃COC(O)— | H | —CH₂CH(CH₃)₂ | H | —OCH₂CH₂CH₃ | H | —CH₂—S—(2-furyl) |
| 603 | cyclohexylmethyl ester | H | —CH₂CH(CH₃)₂ | H | —OCH₂CH₂CH₃ | H | —CH₂—S—(2-furyl) |
| 604 | benzyl ester | H | —CH₂CH(CH₃)₂ | H | —OCH₂CH₂CH₃ | H | —CH₂—S—(2-furyl) |

TABLE 1-continued

| Compd. No. | R¹ | R⁴ | R⁵ | R⁶ | R⁷ | R⁸ | —A—R⁹ |
|---|---|---|---|---|---|---|---|
| 605 | H | H | —CH₂CH(CH₃)₂ | H | —OCH₂CH₂CH₃ | H | furfuryl-S-CH₂ |
| 606 | phenoxyacetyl | H | —CH₂CH(CH₃)₂ | H | —OCH₂CH₂CH₃ | H | furfuryl-S-CH₂ |
| 607 | benzyloxycarbonyl | H | —CH₂CH(CH₃)₂ | H | —OCH₂-C₆H₅ | H | —S—CH₃ |
| 608 | benzyloxycarbonyl | H | —CH₂CH(CH₃)₂ | H | —OCH₂-C₆H₅ | H | furfuryl-S-CH₂ |
| 609 | benzyloxycarbonyl | H | —CH₂CH(CH₃)₂ | H | —CH₂-C₆H₅ | | —S—CH₃ |
| 610 | benzyloxycarbonyl | H | —CH₂CH(CH₃)₂ | H | —CH₂-C₆H₅ | | —S—C₆H₅ |
| 611 | (CH₃)₃COC(O)O— | H | —CH₂CH(CH₃)₂ | H | —CH₂-C₆H₅ | | furfuryl-S-CH₂ |

TABLE 1-continued

| Compd. No. | R¹ | R⁴ | R⁵ | R⁶ | R⁷ | R⁸ | —A—R⁹ |
|---|---|---|---|---|---|---|---|
| 612 | benzyl ester | H | —CH$_2$CH(CH$_3$)$_2$ | H | styryl | phenyl | furfuryl thiomethyl |
| 613 | (pyridin-2-yl)methyl ester | H | —CH$_2$CH(CH$_3$)$_2$ | H | styryl | phenyl | furfuryl thiomethyl |
| 614 | (pyridin-3-yl)methyl ester | H | —CH$_2$CH(CH$_3$)$_2$ | H | styryl | phenyl | furfuryl thiomethyl |
| 615 | H | H | —CH$_2$CH(CH$_3$)$_2$ | H | styryl | phenyl | furfuryl thiomethyl |
| 616 | phenoxyacetyl | H | —CH$_2$CH(CH$_3$)$_2$ | H | styryl | phenyl | furfuryl thiomethyl |
| 617 | 2,6-difluorobenzoyl | H | —CH$_2$CH(CH$_3$)$_2$ | H | styryl | phenyl | furfuryl thiomethyl |
| 618 | CH$_3$SO$_2$— | H | —CH$_2$CH(CH$_3$)$_2$ | H | styryl | phenyl | furfuryl thiomethyl |

TABLE 1-continued
| Compd. No. | R¹ | R⁴ | R⁵ | R⁶ | R⁷ | R⁸ | —A—R⁹ |
|---|---|---|---|---|---|---|---|
| 619 | 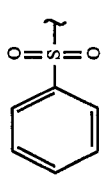 | H | —CH$_2$CH(CH$_3$)$_2$ | H | 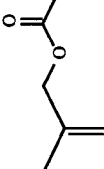 | | 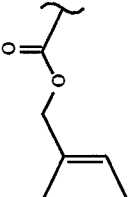 |
| 620 | 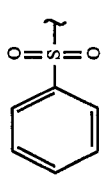 | H | —CH$_2$CH(CH$_3$)$_2$ | H | —CH$_2$CH$_2$— | | 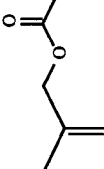 |
| 621 | 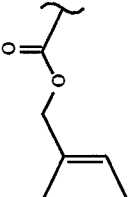 | H | —CH$_2$CH(CH$_3$)$_2$ | H | —CH$_2$CH$_2$— | | 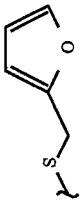 |
| 622 | 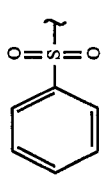 | H | —CH$_2$CH(CH$_3$)$_2$ | H | —CH$_2$CH$_2$CH$_2$— | | 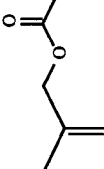 |
| 623 | 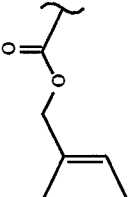 | H | —CH$_2$CH(CH$_3$)$_2$ | H | —CH$_2$CH$_2$CH$_2$— | | 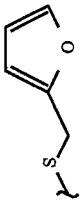 |
| 624 | 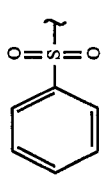 | H | —CH$_2$CH(CH$_3$)$_2$ | H | —CH$_2$CH$_2$CH$_2$CH$_2$— | | 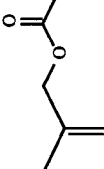 |
| 625 | 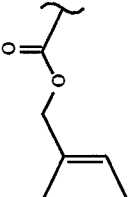 | H | —CH$_2$CH(CH$_3$)$_2$ | H | —CH$_2$CH$_2$CH$_2$CH$_2$— | | 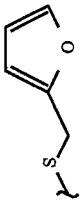 |

TABLE 1-continued

| Compd. No. | R¹ | R⁴ | R⁵ | R⁶ | R⁷ | R⁸ | —A—R⁹ |
|---|---|---|---|---|---|---|---|
| 626 | cyclohexylmethyl ester | H | —CH$_2$CH(CH$_3$)$_2$ | H | —CH$_2$CH$_2$CH$_2$CH$_2$— | —CH$_2$CH$_2$CH$_2$— | furan-2-ylmethylthio |
| 627 | benzyl ester | H | —CH$_2$CH(CH$_3$)$_2$ | H | —CH$_2$CH$_2$CH$_2$CH$_2$— | —CH$_2$CH$_2$CH$_2$— | furan-2-ylmethylthio |
| 628 | (pyridin-2-yl)methyl ester | H | —CH$_2$CH(CH$_3$)$_2$ | H | —CH$_2$CH$_2$CH$_2$CH$_2$— | —CH$_2$CH$_2$CH$_2$— | furan-2-ylmethylthio |
| 629 | (pyridin-3-yl)methyl ester | H | —CH$_2$CH(CH$_3$)$_2$ | H | —CH$_2$CH$_2$CH$_2$CH$_2$— | —CH$_2$CH$_2$CH$_2$— | furan-2-ylmethylthio |
| 630 | (pyridin-4-yl)methyl ester | H | —CH$_2$CH(CH$_3$)$_2$ | H | —CH$_2$CH$_2$CH$_2$CH$_2$— | —CH$_2$CH$_2$CH$_2$— | furan-2-ylmethylthio |
| 631 | H | H | —CH$_2$CH(CH$_3$)$_2$ | H | —CH$_2$CH$_2$CH$_2$CH$_2$— | —CH$_2$CH$_2$CH$_2$— | furan-2-ylmethylthio |
| 632 | isobutyl ketone | | | | | | furan-2-ylmethylthio |

TABLE 1-continued

| Compd. No. | R¹ | R⁴ | R⁵ | R⁶ | R⁷ | R⁸ | —A—R⁹ |
|---|---|---|---|---|---|---|---|
| 633 | phenoxymethyl ketone | H | —CH$_2$CH(CH$_3$)$_2$ | H | —CH$_2$CH$_2$CH$_2$CH$_2$CH$_2$— | — | furan-2-ylmethylthio |
| 634 | 2,6-difluorophenyl ketone | H | —CH$_2$CH(CH$_3$)$_2$ | H | —CH$_2$CH$_2$CH$_2$CH$_2$CH$_2$— | — | furan-2-ylmethylthio |
| 635 | furan-2-yl ketone | H | —CH$_2$CH(CH$_3$)$_2$ | H | —CH$_2$CH$_2$CH$_2$CH$_2$CH$_2$— | — | furan-2-ylmethylthio |
| 636 | methanesulfonyl | H | —CH$_2$CH(CH$_3$)$_2$ | H | —CH$_2$CH$_2$CH$_2$CH$_2$CH$_2$— | — | furan-2-ylmethylthio |
| 637 | phenylsulfonyl | H | —CH$_2$CH(CH$_3$)$_2$ | H | —CH$_2$CH$_2$CH$_2$CH$_2$CH$_2$— | — | furan-2-ylmethylthio |
| 638 | benzyloxycarbonyl | H | —CH$_2$CH(CH$_3$)$_2$ | H | —CH$_2$CH$_2$CH$_2$CH$_2$CH$_2$— | — | pyridin-2-ylmethylthio |
| 639 | benzyloxycarbonyl | H | —CH$_2$CH(CH$_3$)$_2$ | H | —CH$_2$CH$_2$CH$_2$CH$_2$CH$_2$— | — | pyridin-3-ylmethylthio |

TABLE 1-continued

| Compd. No. | R¹ | R⁴ | R⁵ | R⁶ | R⁷ | R⁸ | —A—R⁹ |
|---|---|---|---|---|---|---|---|
| 640 | benzyl ester | H | —CH$_2$CH(CH$_3$)$_2$ | H | —CH$_2$CH$_2$CH$_2$CH$_2$— | | pyridinyl-CH$_2$-S- |
| 641 | benzyl ester | H | —CH$_2$CH(CH$_3$)$_2$ | H | —CH$_2$CH$_2$CH$_2$CH$_2$— | | —O—CH$_3$ |
| 642 | benzyl ester | H | —CH$_2$CH(CH$_3$)$_2$ | H | —CH$_2$CH$_2$CH$_2$CH$_2$— | | furanyl-CH$_2$-S- |
| 643 | benzyl ester | H | —CH$_2$CH(CH$_3$)$_2$ | H | —CH$_2$CH$_2$CH$_2$CH$_2$— | | —N(CH$_3$)$_2$ |
| 644 | furanyl-CH=CH-C(O)- | H | —CH$_2$CH(CH$_3$)$_2$ | H | —CH$_2$CH$_2$CH$_2$CH$_3$ | H | —S—CH$_3$ |
| 645 | furanyl-CH=CH-C(O)- | H | —CH$_2$CH(CH$_3$)$_2$ | H | —CH$_2$CH$_2$CH$_2$CH$_3$ | H | furanyl-CH$_2$-S- |
| 646 | furanyl-CH=CH-C(O)- | H | —CH$_2$CH(CH$_3$)$_2$ | H | —CH$_2$-phenyl | H | —S—CH$_3$ |
| 647 | furanyl-CH=CH-C(O)- | H | —CH$_2$CH(CH$_3$)$_2$ | H | —CH$_2$-phenyl | H | furanyl-CH$_2$-S- |

TABLE 1-continued

| Compd. No. | R¹ | R⁴ | R⁵ | R⁶ | R⁷ | R⁸ | —A—R⁹ |
|---|---|---|---|---|---|---|---|
| 648 | furyl-CH=CH-C(=O)- | H | -CH₂CH(CH₃)₂ | H | -CH₂CH₂CH₂CH₃ | H | -S-CH₃ |
| 649 | furyl-CH=CH-C(=O)- | H | -CH₂CH(CH₃)₂ | H | -CH₂CH₂CH₂CH₃ | H | furfuryl-S- |
| 650 | furyl-CH=CH-C(=O)- | H | -CH₂CH(CH₃)₂ | H | -CH₂-Ph | H | -S-CH₃ |
| 651 | furyl-CH=CH-C(=O)- | H | -CH₂CH(CH₃)₂ | H | -CH₂-Ph | H | furfuryl-S- |
| 652 | thienyl-CH=CH-C(=O)- | H | -CH₂CH(CH₃)₂ | H | -CH₂CH₂CH₂CH₃ | H | -S-CH₃ |
| 653 | thienyl-CH=CH-C(=O)- | H | -CH₂CH(CH₃)₂ | H | -CH₂CH₂CH₂CH₃ | H | furfuryl-S- |
| 654 | thienyl-CH=CH-C(=O)- | H | -CH₂CH(CH₃)₂ | H | -CH₂-Ph | H | -S-CH₃ |
| 655 | thienyl-CH=CH-C(=O)- | H | -CH₂CH(CH₃)₂ | H | -CH₂-Ph | H | furfuryl-S- |
| 656 | thienyl-CH=CH-C(=O)- | H | -CH₂CH(CH₃)₂ | H | -CH₂CH₂CH₂CH₃ | H | -S-CH₃ |
| 657 | thienyl-CH=CH-C(=O)- | H | -CH₂CH(CH₃)₂ | H | -CH₂CH₂CH₂CH₃ | H | furfuryl-S- |

TABLE 1-continued

| Compd. No. | R¹ | R⁴ | R⁵ | R⁶ | R⁷ | R⁸ | —A—R⁹ |
|---|---|---|---|---|---|---|---|
| 658 | thiophene-CH=CH-C(=O)- | H | -CH₂CH(CH₃)₂ | H | -CH₂- (phenyl) | H | -S-CH₃ |
| 659 | thiophene-CH=CH-C(=O)- | H | -CH₂CH(CH₃)₂ | H | -CH₂- (phenyl) | H | furan-CH₂-S- |
| 660 | pyridin-2-yl-CH=CH-C(=O)- | H | -CH₂CH(CH₃)₂ | H | -CH₂CH₂CH₂CH₃ | H | furan-CH₂-S- |
| 661 | pyridin-3-yl-CH=CH-C(=O)- | H | -CH₂CH(CH₃)₂ | H | -CH₂CH₂CH₂CH₃ | H | furan-CH₂-S- |
| 662 | pyridin-4-yl-CH=CH-C(=O)- | H | -CH₂CH(CH₃)₂ | H | -CH₂CH₂CH₂CH₃ | H | furan-CH₂-S- |
| 663 | CH₃CH=CHC(=O)- | H | -CH₂CH(CH₃)₂ | H | -CH₂CH₂CH₂CH₃ | H | furan-CH₂-S- |
| 664 | CH₃(CH₂)₄CH=CHC(=O)- | H | -CH₂CH(CH₃)₂ | H | -CH₂CH₂CH₂CH₃ | H | furan-CH₂-S- |
| 665 | PhCH₂-O-C(=O)- | H | -CH₂CH₂CH₂- | | -CH₃ | | -S-CH₃ |

TABLE 1-continued

| Compd. No. | R¹ | R⁴ | R⁵ | R⁶ | R⁷ | R⁸ | –A–R⁹ |
|---|---|---|---|---|---|---|---|
| 666 | benzyl ester (–C(O)O–CH₂–C₆H₅) | | –CH₂CH₂CH₂– | H | –CH₃ | H | –CH₂–(2-furyl) via S |
| 667 | benzyl ester | | –CH₂CH₂CH₂– | H | –CH₂CH₂CH₃ | H | –S–CH₃ |
| 668 | (CH₃)₃COC(O)– | | –CH₂CH₂CH₂– | H | –CH₂CH₂CH₃ | H | –CH₂–(2-furyl) via S |
| 669 | benzyl ester | H | –CH₂CH₂CH₂– | H | –CH₂CH₂CH₃ | H | –CH₂–(2-furyl) via S |
| 670 | phenoxy-CH₂–C(O)– | | –CH₂CH₂CH₂– | H | –CH₂CH₂CH₃ | H | –CH₂–(2-furyl) via S |
| 671 | C₆H₅–SO₂– | | –CH₂CH₂CH₂– | H | –CH₂CH₂CH₃ | H | –CH₂–(2-furyl) via S |
| 672 | benzyl ester | | –CH₂CH₂CH₂– | H | –CH₂CH₂CH₃ | H | –CH₂–(2-furyl) via S |
| 673 | benzyl ester | | –CH₂CH₂CH₂– | H | –CH₂–C₆H₅ | H | –S–CH₃ |

TABLE 1-continued

| Compd. No. | R¹ | R⁴ | R⁵ | R⁶ | R⁷ | R⁸ | —A—R⁹ |
|---|---|---|---|---|---|---|---|
| 674 | —C(=O)O—CH₂—C₆H₅ | | —CH₂CH₂CH₂— | H | —CH₂—C₆H₅ | H | —S—CH₂-(2-furyl) |
| 675 | —C(=O)O—CH₂—C₆H₅ | | —CH₂CH(OH)CH₂— | H | —CH₂—C₆H₅ | H | —S—CH₃ |
| 676 | —C(=O)O—CH₂—C₆H₅ | | —CH₂CH(OH)CH₂— | H | —CH₂—C₆H₅ | H | —S—CH₂-(2-furyl) |
| 677 | —C(=O)O—CH₂—C₆H₅ | | —CH₂C(=O)CH₂— | H | —CH₂—C₆H₅ | H | —S—CH₃ |
| 678 | —C(=O)O—CH₂—C₆H₅ | | —CH₂C(=O)CH₂— | H | —CH₂—C₆H₅ | H | —S—CH₂-(2-furyl) |
| 679 | —C(=O)O—CH₂—C₆H₅ | | —CH₂CH₂CH₂CH₂— | H | —CH₂—C₆H₅ | H | —S—CH₃ |
| 680 | —C(=O)O—CH₂—C₆H₅ | | —CH₂CH₂CH₂CH₂— | H | —CH₂—C₆H₅ | H | —S—CH₂-(2-furyl) |

TABLE 1-continued

| Compd. No. | R¹ | R⁴ | R⁵ | R⁶ | R⁷ | R⁸ | -A-R⁹ |
|---|---|---|---|---|---|---|---|
| 681 | -C(=O)O-CH₂-C₆H₅ (benzyl ester) | | -CH₂-cyclohexyl-CH₂- (1,2-cyclohexanediyl bis-methylene) | H | -CH₂-C₆H₅ (benzyl) | H | -S-CH₃ |
| 682 | (CH₃)₃COC(=O)- | | -CH₂-cyclohexyl-CH₂- | H | -CH₂-C₆H₅ | H | -CH₂-(furan-2-yl), via S |
| 683 | -C(=O)O-CH₂-C₆H₅ | | -CH₂-cyclohexyl-CH₂- | H | -CH₂-C₆H₅ | H | -CH₂-(furan-2-yl), via S |
| 684 | H | | -CH₂-cyclohexyl-CH₂- | H | -CH₂-C₆H₅ | H | -CH₂-(furan-2-yl), via S |
| 685 | -C(=O)CH₂-O-C₆H₅ (phenoxyacetyl) | | -CH₂-cyclohexyl-CH₂- | H | -CH₂-C₆H₅ | H | -CH₂-(furan-2-yl), via S |
| 686 | -C(=O)O-CH₂-C₆H₅ | | -CH₂-C₆H₄-CH₂- (1,2-phenylene bis-methylene) | H | -CH₂CH₂CH₂CH₃ | H | -S-CH₃ |
| 687 | -C(=O)O-CH₂-C₆H₅ | | -CH₂-C₆H₄-CH₂- | H | -CH₂CH₂CH₂CH₃ | H | -CH₂-(furan-2-yl), via S |

(n = 0)

TABLE 2

| Compd. No. | R¹ | R² | R³ | R⁴ | R⁵ | R⁶ | R⁷ | R⁸ | —A—R⁹ |
|---|---|---|---|---|---|---|---|---|---|
| 688 | benzyl ester | H | —CH₂CH(CH₃)₂ | H | —CH₂CH(CH₃)₂ | H | —CH₃ | H | —S—CH₃ |
| 689 | benzyl ester | H | —CH(CH₃)₂ | H | —CH₂CH(CH₃)₂ | H | —CH₃ | H | —CH₂—S—furan |
| 690 | benzyl ester | H | —CH₂CH(CH₃)₂ | H | —CH₂—phenyl | H | —CH₃ | H | —CH₂—S—furan |
| 691 | benzyl ester | H | —CH₂—phenyl | H | —CH₂—phenyl | H | —CH₃ | H | —CH₂—S—furan |
| 692 | benzyl ester | H | —CH₂CH(CH₃)₂ | H | —CH₃ | H | —CH₂CH₂CH₂CH₃ | H | —CH₂—S—furan |
| 693 | benzyl ester | H | —CH(CH₃)₂ | H | —CH(CH₃)₂ | H | —CH₂CH₂CH₂CH₃ | H | —CH₂—S—furan |
| 694 | benzyl ester | H | —CH₂CH(CH₃)₂ | H | —CH(CH₃)₂ | H | —CH₂CH₂CH₂CH₃ | H | —CH₂—S—furan |

TABLE 2-continued

| Compd. No. | R¹ | R² | R³ | R⁴ | R⁵ | R⁶ | R⁷ | R⁸ | —A—R⁹ |
|---|---|---|---|---|---|---|---|---|---|
| 695 | benzyl ester (-C(O)O-CH₂-C₆H₅) | H | —CH₃ | H | —CH₂CH(CH₃)₂ | H | —CH₂CH₂CH₂CH₃ | H | —S—CH₂-(2-furyl) |
| 696 | benzyl ester | H | —CH(CH₃)₂ | H | —CH₂CH(CH₃)₂ | H | —CH₂CH₂CH₂CH₃ | H | —S—CH₂-(2-furyl) |
| 697 | (CH₃)₃COC(O)- | H | —CH₂CH(CH₃)₂ | H | —CH₂CH(CH₃)₂ | H | —CH₂CH₂CH₂CH₃ | H | —S—CH₃ |
| 698 | cyclohexylmethyl ester | H | —CH₂CH(CH₃)₂ | H | —CH₂CH(CH₃)₂ | H | —CH₂CH₂CH₂CH₃ | H | —S—CH₂-(2-furyl) |
| 699 | benzyl ester | H | —CH₂CH(CH₃)₂ | H | —CH₂CH(CH₃)₂ | H | —CH₂CH₂CH₂CH₃ | H | —S—CH₂-(2-furyl) |
| 700 | benzyl ester | H | —CH₂CH(CH₃)₂ | H | —CH₂CH(CH₃)₂ | H | —CH₂CH₂CH₂CH₃ | H | —S—CH₂-(2-furyl) |
| 701 | (2-pyridyl)methyl ester | H | —CH₂CH(CH₃)₂ | H | —CH₂CH(CH₃)₂ | H | —CH₂CH₂CH₂CH₃ | H | —S—CH₂-(2-furyl) |

TABLE 2-continued

| Compd. No. | R¹ | R² | R³ | R⁴ | R⁵ | R⁶ | R⁷ | R⁸ | -A-R⁹ |
|---|---|---|---|---|---|---|---|---|---|
| 702 | 3-pyridyl-CH₂-O-C(=O)- | H | -CH₂CH(CH₃)₂ | H | -CH₂CH(CH₃)₂ | H | -CH₂CH₂CH₂CH₃ | H | -S-CH₂-(2-furyl) |
| 703 | H | H | -CH₂CH(CH₃)₂ | H | -CH₂CH(CH₃)₂ | H | -CH₂CH₂CH₂CH₃ | H | -S-CH₂-(2-furyl) |
| 704 | PhO-CH₂-C(=O)- | H | -CH₂CH(CH₃)₂ | H | -CH₂CH(CH₃)₂ | H | -CH₂CH₂CH₂CH₃ | H | -S-CH₂-(2-furyl) |
| 705 | 4-CH₃O-C₆H₄-O-CH₂-C(=O)- | H | -CH₂CH(CH₃)₂ | H | -CH₂CH(CH₃)₂ | H | -CH₂CH₂CH₂CH₃ | H | -S-CH₂-(2-furyl) |
| 706 | 2-F-C₆H₄-C(=O)- | H | -CH₂CH(CH₃)₂ | H | -CH₂CH(CH₃)₂ | H | -CH₂CH₂CH₂CH₃ | H | -S-CH₂-(2-furyl) |
| 707 | 2-furyl-CH₂- | H | -CH₂CH(CH₃)₂ | H | -CH₂CH(CH₃)₂ | H | -CH₂CH₂CH₂CH₃ | H | -S-CH₂-(2-furyl) |
| 708 | PhCH₂-NH-C(=O)- | H | -CH₂CH(CH₃)₂ | H | -CH₂CH(CH₃)₂ | H | -CH₂CH₂CH₂CH₃ | H | -S-CH₂-(2-furyl) |
| 709 | CH₃-S(=O)₂- | H | -CH₂CH(CH₃)₂ | H | -CH₂CH(CH₃)₂ | H | -CH₂CH₂CH₂CH₃ | H | -S-CH₂-(2-furyl) |

TABLE 2-continued

| Compd. No. | R¹ | R² | R³ | R⁴ | R⁵ | R⁶ | R⁷ | R⁸ | −A−R⁹ |
|---|---|---|---|---|---|---|---|---|---|
| 710 | phenylsulfonyl | H | −CH₂CH(CH₃)₂ | H | −CH₂CH(CH₃)₂ | H | −CH₂CH₂CH₂CH₃ | H | furan-2-yl-CH₂-S- |
| 711 | benzyloxycarbonyl | H | −CH₂CH(CH₃)₂ | H | −CH₂CH(CH₃)₂ | H | −CH₂CH₂CH₂CH₃ | H | pyridin-2-yl-CH₂-S- |
| 712 | benzyloxycarbonyl | H | −CH₂CH(CH₃)₂ | H | −CH₂CH(CH₃)₂ | H | −CH₂CH₂CH₂CH₃ | H | pyridin-3-yl-CH₂-S- |
| 713 | benzyloxycarbonyl | H | −CH₂CH(CH₃)₂ | H | −CH₂CH(CH₃)₂ | H | −CH₂CH₂CH₂CH₃ | H | pyridin-3-yl-CH₂-S- |
| 714 | benzyloxycarbonyl | H | −CH₂CH(CH₃)₂ | H | −CH₂-phenyl | H | −CH₂CH₂CH₂CH₃ | H | furan-2-yl-CH₂-S- |
| 715 | benzyloxycarbonyl | H | −CH(CH₃)₂ | H | −CH₂CH(CH₃)₂ | H | −CH₂-cyclohexyl | H | furan-2-yl-CH₂-S- |
| 716 | benzyloxycarbonyl | H | −CH₂CH(CH₃)₂ | H | −CH₂CH(CH₃)₂ | H | −CH₂-cyclohexyl | H | furan-2-yl-CH₂-S- |

TABLE 2-continued

| Compd. No. | R¹ | R² | R³ | R⁴ | R⁵ | R⁶ | R⁷ | R⁸ | —A—R⁹ |
|---|---|---|---|---|---|---|---|---|---|
| 717 | benzyl-O-C(O)– | H | –CH₂CH(CH₃)₂ | H | –CH₂CH(CH₃)₂ | H | –CH₂–phenyl | H | –S–CH₃ |
| 718 | benzyl-O-C(O)– | H | –CH₂CH(CH₃)₂ | H | –CH₂–phenyl | H | –CH₂–phenyl | H | –S–CH₃ |
| 719 | benzyl-O-C(O)– | H | –CH(CH₃)₂ | H | –CH(CH₃)₂ | H | –CH₂–phenyl | H | –CH₂–S–furyl |
| 720 | benzyl-O-C(O)– | H | –CH₂CH(CH₃)₂ | H | –CH(CH₃)₂ | H | –CH₂–phenyl | H | –CH₂–S–furyl |
| 721 | benzyl-O-C(O)– | H | –CH(CH₃)₂ | H | –CH₂CH(CH₃)₂ | H | –CH₂–phenyl | H | –CH₂–S–furyl |
| 722 | benzyl-O-C(O)– | H | –CH₂CH(CH₃)₂ | H | –CH₂CH(CH₃)₂ | H | –CH₂–phenyl | H | –CH₂–S–furyl |
| 723 | benzyl-O-C(O)– | H | –CH₂CH(CH₃)₂ | H | –CH₂CH(CH₃)₂ | –CH₃ | –CH₂–phenyl | H | –CH₂–S–furyl |

TABLE 2-continued

| Compd. No. | R¹ | R² | R³ | R⁴ | R⁵ | R⁶ | R⁷ | R⁸ | —A—R⁹ |
|---|---|---|---|---|---|---|---|---|---|
| 724 | benzyl-O-C(=O)- | H | —CH₂CH(CH₃)₂ | —CH₃ | —CH₂CH(CH₃)₂ | H | —CH₂-phenyl | H | —S—CH₂-furan |
| 725 | benzyl-O-C(=O)- | —CH₃ | —CH₂CH(CH₃)₂ | H | —CH₂CH(CH₃)₂ | H | —CH₂-phenyl | H | —S—CH₂-furan |
| 726 | benzyl-O-C(=O)- | H | —CH₂CH(CH₃)₂ | H | —CH₂-phenyl | H | —CH₂-phenyl | H | —S—CH₂-furan |
| 727 | benzyl-O-C(=O)- | H | —CH₂CH(CH₃)₂ | H | —CH₂CH(CH₃)₂ | H | —CH₂-phenyl | H | —S—CH₂-furan |
| 728 | benzyl-O-C(=O)- | H | —CH₂CH(CH₃)₂ | H | —CH₂-phenyl | H | —CH₃ | —CH₃ | —S—CH₃ |
| 729 | benzyl-O-C(=O)- | H | —CH₂CH(CH₃)₂ | H | —CH₂CH(CH₃)₂ | H | —CH₃ | —CH₃ | —S—CH₂-furan |
| 730 | benzyl-O-C(=O)- | H | —CH₂CH(CH₃)₂ | H | —CH₂CH(CH₃)₂ | H | —CH₃ | —CH₃ | —S—CH₂-pyridine |

TABLE 2-continued

| Compd. No. | R¹ | R² | R³ | R⁴ | R⁵ | R⁶ | R⁷ | R⁸ | —A—R⁹ |
|---|---|---|---|---|---|---|---|---|---|
| 731 | benzyl ester (–C(=O)O–CH₂–C₆H₅) | H | –CH₂CH(CH₃)₂ | H | –CH₂CH(CH₃)₂ | H | –CH₃ | –CH₃ | –S–CH₂–(pyridyl) |
| 732 | benzyl ester (–C(=O)O–CH₂–C₆H₅) | H | –CH₂CH(CH₃)₂ | H | –CH₂CH(CH₃)₂ | H | –CH₃ | –CH₃ | –S–CH₂–(pyridyl) |

(n = 1)

The production of the compounds according to the present invention will be then explained. The ketone derivatives of the general formula (I) above can be, for example, prepared as shown below.

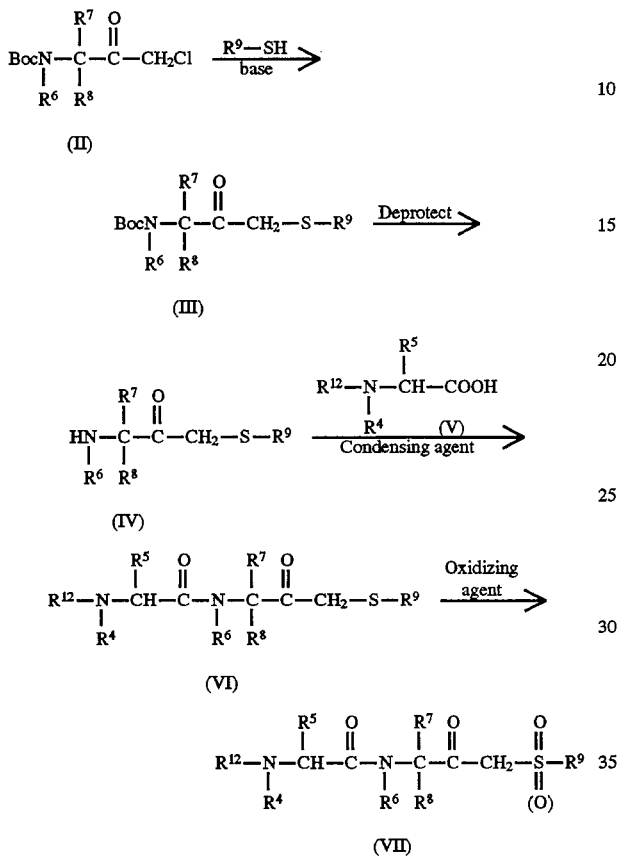

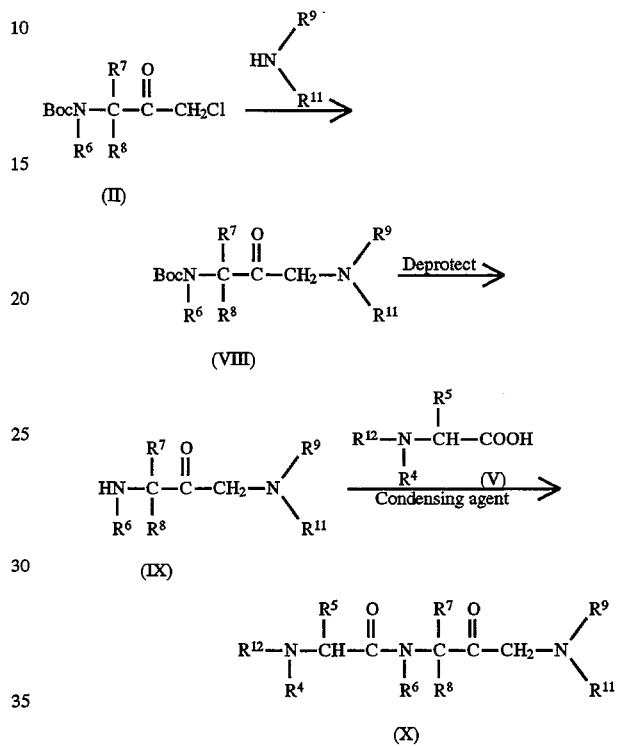

[wherein $R^4$, $R^5$, $R^6$, $R^7$, $R^8$ and $R^9$ are as defined above, $R^{12}$ is $R^1$—CO—, $R^{10}$—O—CO—, $R^{10}$—NH—CO— or $R^{10}$—$SO_2$— ($R^{10}$ is as defined above), and Boc is tert-butoxycarbonyl group].

A chloromethylketone derivative of the general formula (II) above, which can be easily prepared using a known method in a literature [Chemical and Pharmaceutical Bulletin, 37, p. 3108 (1989)], is dissolved in a solvent such as diethyl ether, tetrahydrofuran, dioxane, ethyl acetate, methylene chloride or chloroform, and reacted with a mercaptan of $R^9$—SH in the presence of a base such as sodium hydroxide, potassium hydroxide, sodium hydride, triethylamine or pyridine to obtain a thiomethylketone derivative of the general formula (III). Boc group of the compound (III) is then deprotected by a conventional reaction condition, for example, using aqueous hydrochloric acid, hydrogen chloride-ethanol, hydrogen chloride-ethyl acetate, hydrogen chloride-dioxane, hydrobromic acid, or hydrogen bromide-ethyl acetate, to obtain an amine or amine salt of the general formula (IV). Then, carboxyl group of an amino acid derivative of the general formula (V) is activated with a condensing agent such as isobutyl chloroformate, diphenylphosphorylazide, dicyclohexylcarbodiimide, or carbonyldiimidazole, and the activated amino acid derivative is reacted with the compound (IV) above obtained, if necessary, in the presence of a base such as triethylamine or pyridine, to obtain the compound of the general formula (VI). The compound (VI) is subsequently dissolved in a solvent such as chloroform, methylene chloride, methanol, ethanol, or ethyl acetate, dimethylformamide, dichloromethane, and oxidized its sulfide group to sulfoxide or sulfone group using sodium metaperiodate, hydrogen peroxide, peracetic acid, metachloroperbenzoic acid or the like to obtain the compound of the general formula (VII).

[wherein Boc, $R^4$, $R^5$, $R^6$, $R^7$, $R^8$, $R^9$, $R^{11}$ and $R^{12}$ are as defined above]

A chloromethylketone derivative of the general formula (II) above is dissolved in a solvent such as diethyl ether, tetrahydrofuran, dioxane, ethyl acetate, chloroform or methylene chloride, and reacted with an amine of $HN(R^9)(R^{11})$ to obtain a diaminoketone derivative of the general formula (VIII). In a similar procedure as described in Preparation 1, Boc group of the compound (VIII) is then deprotected to the compound of the general formula (IX), and the latter compound is condensed with the amino acid derivative of the general formula (V) to obtain the compound of the general formula (X).

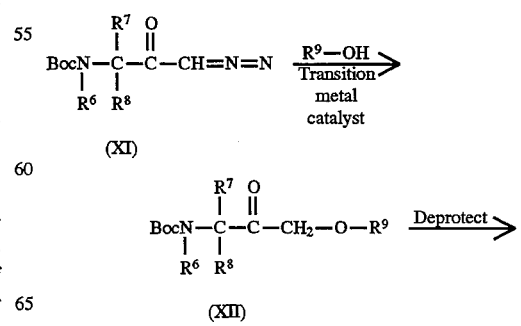

-continued
Preparation 3

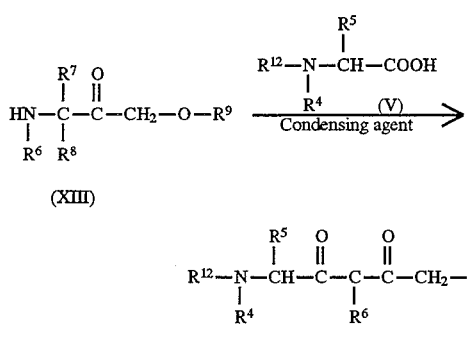

[wherein Boc, $R^4$, $R^5$, $R^6$, $R^7$, $R^8$, $R^9$ and $R^{12}$ are as defined above]

A diazomethylketone derivative of the general formula (XI) above, which can be easily prepared using a known method in a literature [Methods in Enzymology, 80, p. 820 (1981)], is dissolved in a solvent such as chloroform or methylene chloride, and reacted with an alcohol of $R^9$—OH in the presence of a transition metal catalyst such as CuO or $Rh_2(OAc)_4$ to obtain a oxymethylketone derivative of the general formula (XII). In this case, it is also possible to carry out the reaction by directly dissolving the compound of the formula (XI) in alcohol: $R^9$—OH without using the solvent such as chloroform or methylene chloride. Subsequently, in a similar procedure as described in Preparation 1, Boc group of the compound (XII) is deprotected to the compound (XIII), and the latter compound is condensed with the amino acid derivative of the general formula (V) to obtain the compound of the general formula (XIV).

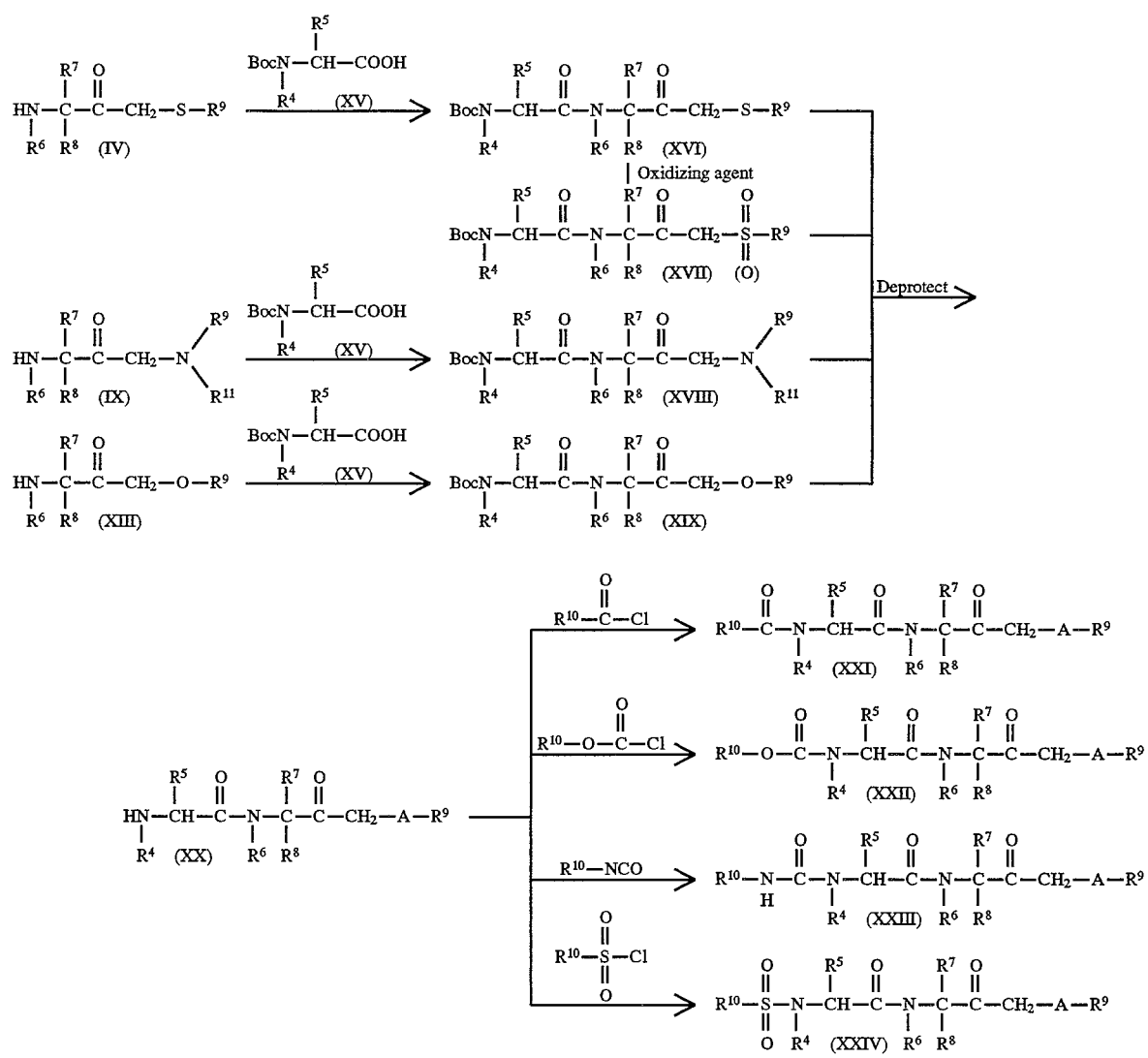

[wherein Boc, $R^4$, $R^5$, $R^6$, $R^7$, $R^8$, $R^9$, $R^{10}$, $R^{11}$ and A are as defined above]

In a similar procedure as described in Preparation 1, Boc group of the compounds of the general formulae (XVI) to (XIX), which can be prepared using the compound of the formula (XV) instead of that of the formula (V) in the Preparations 1, 2 or 3, are deprotected to obtain the compound of the general formula (XX) or a salt thereof. The compound (XX) is then dissolved in a conventional organic solvent such as chloroform, methylene chloride, ethyl acetate or dimethylformamide, and reacted with an acyl chloride of the formula: $R^{10}$—CO—Cl in the presence of an amine such as triethylamine or pyridine to obtain the compound of the general formula (XXI). In a similar manner, the compound of the general formula (XX) can be reacted with a chloroformate derivative of the formula: $R^{10}$—O—CO—Cl to obtain the compound of the general formula (XXII), reacted with an isocyanate derivative of the formula: $R^{10}$—NCO to obtain the compound of the general formula (XXIII), and reacted with a sulfonyl chloride derivative of the formula: $R^{10}$—$SO_2$—Cl to obtain the compound of the general formula (XXIV).

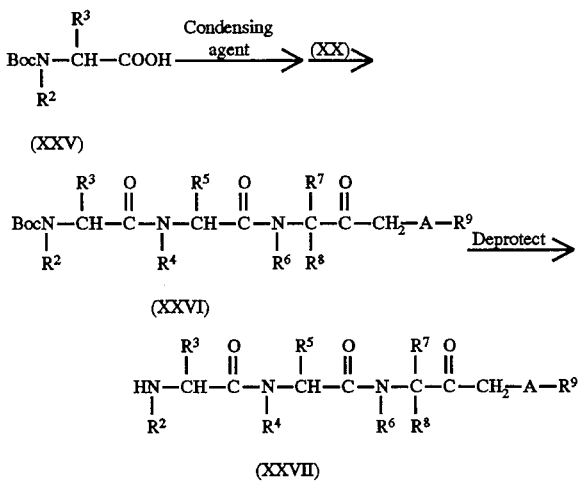

[wherein $R^2$, $R^3$, $R^4$, $R^5$, $R^6$, $R^7$, $R^8$, $R^9$ and Boc are as defined above]

In a similar procedure as described in Preparation 1, carboxyl group of an amino acid derivative of the general formula (XXV) is activated with a condensing agent, and the activated amino acid derivative is reacted with the compound (XX) obtained in the above Preparation 4, if necessary, in the presence of a base to obtain the compound of the general formula (XXVI). The compound (XXVI) can be deprotected in a similar procedure as described in Preparation 1 to obtain the compound of the general formula (XXVII) or a salt thereof. Furthermore, amino group of the compound (XXVII) may be converted according to the procedure described in Preparation 4.

Although it may be necessary to protect or deprotect any functional group present on each of the compounds in a series of the procedures in the above-described Preparations 1 to 5, these protection or deprotection can be easily carried out by applying standard methods usually employed in chemistry of organic synthesis.

As will be seen from the results of Experiments below, the compounds (I) of the invention have been proved to possess a potent inhibitory activity against thiol protease such as papain, cathepsin B, cathepsin H, cathepsin L, calpain or the like together with excellent properties regarding oral absorbance, tissue transference and cell membrane permeability, indicating that they are clinically useful in the treatment of various diseases such as muscular dystrophy, amyotrophy, cardiac infarction, stroke, Alzheimer's disease, conscious disturbance and motor disturbance caused by-brain trauma, multiple sclerosis, neuropathy of peripheral nerve, cataract, inflammation, allergy, fulminant hepatitis, osteoporosis, hypercalcemia, breast carcinoma, prostatic carcinoma, prostatomegaly or the like, and can be used as cancer growth inhibitors, cancer metastasis preventive agents or platelet-aggregation inhibitors.

When the compounds (I) of the present invention are clinically applied, they can be administered to subjects to be treated after formulating into appropriate forms containing, as an active ingredient, a therapeutically effective amount of compound (I) together with carriers therefor. The appropriate ratio of the active ingredient to the carriers may vary from about 1% by weight to about 90% by weight. For example, the compounds of the present invention may be orally administered after formulating into an appropriate form such as granules, fine granules, powders, tablets, hard capsules, soft capsules, syrups, emulsions, suspensions, solutions or the like. They can be also administered intravenously, intramuscularly or subcutaneously in the form of injections. Furthermore, they may be formulated in the form of suppositories, or powders which are prepared for injections at the time of use.

Formulations of the invention can be prepared using any of known methods in the art. Organic or inorganic, and solid or liquid pharmaceutical carriers or diluents suitable for oral, enteral or parenteral administration may be used for preparing the formulations of the present invention. Examples of excipient usable for preparing solid formulations are lactose, sucrose, starch, talc, cellulose, dextrin, kaolin, calcium carbonate and the like. Liquid formulations for oral administration such as emulsion, syrups, suspensions or solutions generally contain conventional inert diluents such as water or vegetable oils. These formulations may further contain adjuvants such as humectants, suspension aids, edulcorants, aromatics, tinctions or preservatives in addition to the inert diluents. The compound (I) can be formulated into solutions which are filled in absorbable carriers such as hard or soft gelatin capsules. Examples of solvents and suspending agents usable for preparing parenteral formulations such as injections or suppositories are water, propylene glycol, polyethylene glycol, benzyl alcohol, ethyl oleate, lecithin and the like. Examples of the base usable for suppositories are cacao butter, emulsified cacao butter, lauric acid, Wittep sol and the like.

The dose of compound (I) may vary depending on various factors such as age, conditions or symptoms of the patient to be treated. Appropriate daily dosage of the compound (I) of the present invention for oral administration to adult is generally about 0.01–1000 mg though, it is preferable to adjust appropriately for each case according to the conditions as mentioned above. The daily dosage of the compound (I) may be administered once or in two or three divisions at appropriate intervals or intermittently.

Additionally, when the compound (I) is administered in the form of injections, one dosage of 0.001–100 mg of said compound can be preferably administered to adult continuously or intermittently.

The following Examples further illustrate the present invention in more detail, but these are illustrative only and are not intended to limit the scope of the invention.

REFERENCE EXAMPLE 1

Preparation of (s)-3-tert-butoxycarbonylamino-1-furfurylthio-2-heptanone

To a solution of (s)-3-tert-butoxycarbonylamino-1-chloro-2-heptanone (6.54 g) and furfurylmercaptan (3.11 g)

in tetrahydrofuran (200 ml) was added 2N sodium hydroxide (13 ml), and the mixture was stirred at room temperature for 17 hours. Then, aqueous sodium hydrogencarbonate was added to the mixture, which was extracted with ethyl acetate. The extract was washed with saturated brine, dried over magnesium sulfate and filtered. The filtrate was concentrated and chromatographed on a silica gel column, eluting with hexane containing 10% ethyl acetate to give the titled product (7.82 g).

Yield: 92% NMR(CDCl$_3$, δ): 0.89(t, J=6.6 Hz, 3H), 1.20–1.95(m, 6H), 1.44(s, 9H), 3.28(d, J=15 Hz, 1H), 3.39 (d, J=15 Hz, 1H), 3.74(s, 2H), 4.52(m, 1H), 5.09(m, 1H), 6.22(d, J=2.9 Hz, 1H), 6.31(m, 1H), 7.36(m, 1H)

REFERENCE EXAMPLE 2

Preparation of (s)-3-amino-1-furfurylthio-2-heptanone hydrochloride

To a solution of (s)-3-tert-butoxycarbonylamino-1-furfurylthio-2-heptanone (7.8 g) obtained in Reference Example 1 dissolved in ethyl acetate (80 ml) was added 4N hydrogen chloride-containing ethyl acetate solution (80 ml), and the mixture was stirred at room temperature for 1 hour. Hexane (100 ml) was then added to the mixture. The resultant crystals were filtered, and washed with hexane to give the titled product (5.93 g).

Yield: 93% NMR(DMSO-d$_6$, δ): 0.87(t, J=6.8 Hz, 3H), 1.16–1.40(m, 4H), 1.63–1.95(m, 2H), 3.55(d, J=16 Hz, 1H), 3.70(d, J=16 Hz, 1H), 3.81(s, 2H), 4.27(m, 1H), 6.30(m, 1H), 6.41(m, 1H), 7.61(m, 1H), 8.29(m, 3H)

EXAMPLE 1

Preparation of (s)-3-((s)-2-tert-butoxycarbonylamino-4-methylvalerylamino)-1-furfurylthio-2-heptanone (Compd. No. 43 in Table 1)

(s)-3-Amino-1-furfurylthio-2-heptanone hydrochloride (5.39 g) obtained in Reference Example 2 and (s)-tert-butoxycarbonylleucine N-hydroxysuccinimido ester (6.37 g) were dissolved in methylene chloride (150 ml), and triethylamine (5.4 ml) was added to the solution. After the mixture was stirred at room temperature for 15 hours, 0.5N aqueous hydrochloric acid (100 ml) was added to the mixture and extracted with methylene chloride. The extract was washed with water, saturated aqueous sodium hydrogencarbonate and saturated brine sequentially, dried over magnesium sulfate and filtered. The filtrate was concentrated and chromatographed on a silica gel column, eluting with hexane containing 25% of ethyl acetate to give the titled product (8.49 g).

Yield: 96% IR(neat, cm$^{-1}$): 3350, 1700, 1675, 1660 NMR(CDCl$_3$, δ): 0.90–1.0(m, 9H), 1.15–1.75(m, 8H), 1.45 (s, 9H), 1.80–1.95(m, 1H), 3.26(d, J=15 Hz, 1H), 3.35(d, J=15 Hz, 1H), 3.72(s, 2H), 4.14(m, 1H), 4.75(m, 1H), 4.92(d, J=8 Hz, 1H), 6.22(d, J=3.1 Hz, 1H), 6.30(m, 1H), 6.72(d, J=7 Hz, 1H), 7.36(m, 1H)

EXAMPLE 2

Preparation of (s)-3-((s)-2-amino-4-methylvalerylamino)-1-furfurylthio-2-heptanone Hydrochloride (Compd. No. 62 in Table 1)

(s)-3-((s)-2-tert-Butoxycarbonylamino-4-methylvalerylamino)-1-furfurylthio-2-heptanone (8.47 g) obtained in Example 1 was dissolved in ethyl acetate (25 ml), and 4N hydrogen chloride-containing ethyl acetate solution (25 ml) was added to the solution. After the mixture was stirred at room temperature for 50 minutes, hexane (50 ml) was added to the mixture. Then, the resultant crystals were filtered, and washed with hexane to give the titled product (4.31 g).

Yield: 59% IR(KBr, cm$^{-1}$): 3300, 1698, 1670 NMR (CD$_3$OD, δ): 0.88–1.18(m, 9H), 1.27–2.03(m, 9H), 3.41(d, J=15 Hz, 1H), 3.50(d, J=15 Hz, 1H), 3.79(s, 2H), 3.98(m, 1H), 4.75(dd, J=4.2 Hz, 9.3 Hz, 1H), 6.28(d, J=3.4 Hz, 1H), 6.37(m, 1H), 7.46(m, 1H)

EXAMPLE 3

Preparation of (s)-1-furfurylthio-3-((s)-4-methyl-2-phenoxyacetylaminovalerylamino)-2-heptanone (Compd. No. 82 in Table 1)

(s)-3-((s)-2-Amino-4-methylvalerylamino)-1-furfurylthio-2-heptanone hydrochloride (4.31 g) obtained in Example 2 was dissolved in methylene chloride (100 ml) and chilled to 0° C. To the solution were added phenoxyacetylchloride (2.07 g) and triethylamine (3.2 ml), and the mixture was stirred at 0° C. for 30 minutes, and at room temperature for 30 minutes. Then, 0.5N aqueous hydrochloric acid (50 ml) was added to the mixture, which was extracted with methylene chloride. The extract was washed with water, saturated sodium hydrogencarbonate and saturated brine sequentially, dried over magnesium sulfate and filtered. The filtrate was concentrated, and chromatographed on a silica gel column, eluting with hexane containing 25% ethyl acetate to give the titled product (3.96 g).

Yield: 74% IR(neat, cm$^{-1}$): 3300, 1710, 1650 NMR (CDCl$_3$, δ): 0.87(t, J=6.7 Hz, 3H), 0.93(d, J=6.0 Hz, 6H), 1.14–1.40(m, 4H), 1.48–2.0(m, 5H), 3.27(d, J=15 Hz, 1H), 3.35(d, J=15 Hz, 1H), 3.73(s, 2H), 4.53(s, 2H), 4.56(m, 1H), 4.74(m, 1H), 6.23(m, 1H), 6.30(m, 1H), 6.59(d, J=7 Hz, 1H), 6.90–7.10(m, 4H), 6.25–6.40(m, 3H)

EXAMPLE 4

Preparation of (s)-1-furfurylsulfinyl-3-((s)-4-methyl-2-phenoxyacetylaminovalerylamino)-2-heptanone (Compd. No. 83 in Table 1)

(s)-1-Furfurylthio-3-((s)-4-methyl-2-phenoxyacetylaminovalerylamino)-2-heptanone (176 mg) obtained in Example 3 was dissolved in methanol (10 ml) and water (10 ml). To the solution was added sodium metaperiodate (82 mg), and the mixture was reacted at room temperature for 48 hours. Then, methanol was removed in vacuo, saturated brine was added to the residue, and the resultant mixture was extracted with chloroform. The extract was washed with saturated brine, dried over sodium sulfate, and filtered. The filtrate was concentrated and chromatographed on a silica gel column, eluting with hexane:ethyl acetate (1:1) to give the titled product (66 mg).

Yield: 37% mp: 96°–99° C. IR(KBr, cm$^{-1}$): 3320, 1720, 1690, 1650 NMR(CDCl$_3$, δ): 0.78–1.07(m, 9H), 1.15–2.05 (m, 9H), 3.34–3.70(m, 1H), 4.05–4.78(m, 7H), 6.40(m, 1H), 6.47(m, 1H), 6.80–7.18(m, 5H), 7.20–7.40(m, 2H), 7.43(m, 1H)

EXAMPLE 5

Preparation of (s)-1-furfurylsulfonyl-3-((s)-4-methyl-2-phenoxyacetylaminovalerylamino)-2-heptanone (Compd. No. 84 in Table 1)

(s)-1-Furfurylthio-3-((s)-4-methyl-2-phenoxyacetylaminovalerylamino)-2-heptanone (150 mg)

obtained in Example 3 was dissolved in methylene chloride (3 ml) and chilled to 0° C. To the mixture was added metachlorobenzoic acid (177 mg), and the mixture was reacted at 0° C. for 30 minutes, and at room temperature for 10 hours. Then, an aqueous solution of 10% potassium carbonate was added to the mixture, and extracted with methylene chloride. The extract was washed with saturated brine, dried over sodium sulfate, and filtrated. The filtrate was concentrated and chromatographed on a silica gel column, eluting with hexane:ethyl acetate (2:1) to give the titled product (130 mg).

Yield: 80% mp: 120°–121° C. IR(KBr, cm$^{-1}$): 3300, 1730, 1650 NMR(CDCl$_3$, δ): 0.80–1.0(m, 9H), 1.15–2.05 (m, 9H), 3.97(d, J=15 Hz, 1H), 4.28(d, J=15 Hz, 1H), 4.40–4.63(m, 6H), 6.42(m, 1H), 6.58(m, 1H), 6.82–6.99(m, 4H), 7.04(t, J=7, 4 Hz, 1H), 7.22–7.40(m, 2H), 7.48(m, 1H)

EXAMPLE 6

Preparation of (s)-3-((s)-2-benzyloxycarbonylamino-4-methyl-valerylamino)-1-furfuryloxy-4-phenyl-2-butanone (Compd. No. 452 in Table 1)

N-Benzyloxycarbonyl-L-leucyl-L-phenylalanine diazomethylketone (314 mg) was dissolved in furfuryl alcohol (2 ml) and methylene chloride (1 ml). To the solution was added rhodium acetate (II) dimer (10 mg). After the mixture was stirred at room temperature for 1 hour, the solvents was removed in vacuo and the residue was chromatographed on a silica gel column, eluting with hexane-ethyl acetate to give the titled product (27 mg).

Yield: 7.4% mp: 94°–95° C. IR(KBr, cm$^{-1}$): 3314, 3285, 1738, 1692, 1653 NMR(CDCl$_3$, δ): 0.89(d, J=6.0 Hz, 6H), 1.35–1.70(m, 3H), 2.94(dd, J=14 Hz, 6.2 Hz, 1H), 3.10(dd, J=14 Hz, 6.5 Hz, 1H), 3.97(d, J=17 Hz, 1H), 4.12(m, 1H), 4.15(d, J=17 Hz, 1H), 4.44(d, J=13 Hz, 1H), 4.53(d, J=13 Hz, 1H), 4.90–5.05(m, 2H), 5.09(s, 2H), 6.28–6.43(m, 2H), 6.51(d, J=7.0 Hz, 1H), 7.08(d, J=7.1 Hz, 2H), 7.17–7.30(m, 3H), 7.35(s, 5H), 7.41(m, 1H)

The compounds in the following Examples were prepared in the same manner as described in Reference Examples 1 and 2 and Examples 1 to 6. Physicochemical properties of each product are shown below.

EXAMPLE 7

Preparation of 1-((s)-2-benzyloxycarbonylamino)-4-methylvalerylamino)-3-furfurylthio-2-propanone (Compd. No. 2 in Table 1)

mp: 59°–62° C. IR(KBr, cm$^{-1}$): 3340, 1730 1692, 1648 NMR(CDCl$_3$, δ): 0.94(d, J=6.0 Hz, 6H), 1.48–1.77(m, 3H), 3.24(s, 2H), 3.72(s, 2H), 4.10–4.35(m, 3H), 4.95–5.11(m, 1H), 5.12(s, 2H), 6.21(d, J=3.1 Hz, 1H), 6.32(m, 1H), 6.63(m, 1H), 7.15–7.38(m, 6H)

EXAMPLE 8

Preparation of 1-((s)-2-benzyloxycarbonylamino-4-methylvalerylamino)-3-(3-pyridylmethylthio)-2-propanone (Compd. No. 5 in Table 1)

IR(Neat, cm$^{-1}$): 3306, 1717, 1666 NMR(CDCl$_3$, δ): 0.93 (d, J=5.8 Hz, 6H), 1.42–1.79(m, 3H), 3.10(s, 2H), 3.66(s, 2H), 4.25(d, J=4.7 Hz, 2H), 4.28(m, 1H), 5.11(s, 2H), 5.50(d, J=8.2 Hz, 1H), 6.93(m, 1H), 7.18–7.42(m, 6H), 7.65(d, J=7.8 Hz, 1H), 8.42–8.60(m, 2H)

EXAMPLE 9

Preparation of 3-((s)-2-benzyloxycarbonylamino-4-methylvalerylamino)-1-furfurylthio-3-methyl-2-butanone (Compd. No. 15 in Table 1)

mp: 80°–82° C. IR(KBr, cm$^{-1}$): 3275, 1728, 1684, 1651 NMR(CDCl$_3$, δ): 0.92(d, J=5.8 Hz, 3H), 0.93(d, J=6.2 Hz, 3H), 1.44(s, 3H), 1.46(s, 3H), 1.57–1.77(m, 3H), 3.37(s, 2H), 3.77(s, 2H), 4.13(m, 1H), 5.10(s, 2H), 6.23(d, J=3.2 Hz, 1H), 6.29(m, 1H), 6.66(s, 1H), 7.32–7.42(m, 6H)

EXAMPLE 10

Preparation of (s)-3-((s)-2-benzyloxycarbonylamino-4-methylvalerylamino)-1-furfurylthio-4-methyl-2-pentanone (Compd. No. 22 in Table 1)

IR(neat, cm$^{-1}$): 3300, 1720, 1705, 1660 NMR(CDCl$_3$, δ): 0.79(d, J=6.8 Hz, 3H), 0.92(d, J=6.8 Hz, 3H), 0.93(d, J=5.0 Hz, 6H), 1.42–1.77(m, 3H), 2.20(m, 1H), 3.24(d, J=15 Hz, 1H), 3.31(d, J=15 Hz, 1H), 3.70(s, 2H), 4.25(m, 1H), 4.78(dt, J=8.9 Hz, 4.6 Hz, 1H), 5.16(s, 2H), 5.39(d, J=7.4 Hz, 1H), 6.21(d, J=2.8 Hz, 1H), 6.28(m, 1H), 6.73(d, J=8.9 Hz, 1H), 7.32(s, 5H), 7.35(m, 1H)

EXAMPLE 11

Preparation of (s)-1-furfurylthio-4-methyl-3-((s)-4-methyl-2-phenoxyacetylaminovalerylamino)-2-pentanone (Compd. No. 24 in Table 1)

IR(neat, cm$^{-1}$): 3300, 1720, 1710, 1650 NMR(CDCl$_3$, δ): 0.82(d, J=6.9 Hz, 3H), 0.91–0.96(m, 9H), 1.49–1.82(m, 3H), 2.23(m, 1H), 3.26(d, J=15 Hz, 1H), 3.34(d, J=15 Hz, 1H), 3.72(s, 2H), 4.53(s, 2H), 4.60(m, 1H), 4.78(dt, J=8.8 Hz, 4.5 Hz, 1H), 6.23(d, J=2.7 Hz, 1H), 6.30(m, 1H), 6.75(d, J=8.7 Hz, 1H), 6.90–6.99(m, 3H), 7.03(m, 1H), 7.25–7.40(m, 3H)

EXAMPLE 12

Preparation of (s)-3-((s)-2-benzyloxycarbonylamino-4-methylvalerylamino-1-furfurylthio-2-hexanone (Compd. No. 28 in Table 1)

IR(Neat, cm$^{-1}$): 3350, 1710, 1655 NMR(CDCl$_3$, δ): 0.89 (t, J=7.2 Hz, 3H), 0.94(d, J=6.2 Hz, 6H), 1.15–1.95(m, 7H), 3.24(d, J=15 Hz, 1H), 3.31(d, J=15 Hz, 1H), 3.71(s, 2H), 4.21(m, 1H), 4.75(m, 1H), 5.11(s, 2H), 5.21(d, J=8 Hz, 1H), 6.22(d, J=2.9 Hz, 1H), 6.28(m, 1H), 6.65(m, 1H), 7.30–7.35 (m, 6H)

EXAMPLE 13

Preparation of (s)-1-furfurylthio-3-((s)-4-methyl-2-phenoxyacetylaminovalerylamino)-2-hexanone (Compd. No. 30 in Table 1)

IR(neat, cm$^{-1}$): 3300, 1720, 1650 NMR(CDCl$_3$, δ): 0.78–1.05(m, 9H), 1.17–1.95(m, 7H), 3.27(d, J=15 Hz, 1H), 3.34(d, J=15 Hz, 1H), 3.72(s, 2H), 4.53(m, 1H), 4.55(s, 2H), 4.75(m, 1H), 6.23(d, J=3.0 Hz, 1H), 6.30(m, 1H), 6.58(d, J=10 Hz, 1H), 6.85–7.15(m, 3H), 7.23–7.37(m, 4H)

EXAMPLE 14

Preparation of (s)-3-((s)-2-benzyloxycarbonylamino-4-methylvalerylamino)-5-methyl-1-methylthio-2-hexanone (Compd. No. 32 in Table 1)

mp: 96°–97° C. IR(KBr, cm$^{-1}$): 3220, 1725, 1693, 1640 NMR(CDCl$_3$, δ): 0.93–1.0(m, 12H), 1.35–1.75(m, 6H), 2.06(s, 3H), 3.20(d, J=14 Hz, 1H), 3.48(d, J=14 Hz, 1H), 4.19(m, 1H), 4.84(m, 1H), 5.11(s, 2H), 5.17(m, 1H), 6.48(d, J=7 Hz, 1H), 7.35(s, 5H)

EXAMPLE 15

Preparation of (s)-3-((s)-2-benzyloxycarbonylamino-4-methylvalerylamino)-1-furfurylthio-5-methyl-2-hexanone (Compd. No. 35 in Table 1)

IR(neat, cm$^{-1}$): 3300, 1710, 1650 NMR(CDCl$_3$, δ): 0.92 (d, J=5.0 Hz, 6H), 0.94(d, J=5.0 Hz, 6H), 1.38–1.79(m, 6H), 3.25(d, J=15 Hz, 1H), 3.33(d, J=18 Hz, 1H), 3.71(s, 2H), 4.19(m, 1H), 4.77(ddd, J=6.7 Hz, 6.7 Hz, 2.2 Hz, 1H), 5.11(s, 2H), 5.15(d, J=6.7 Hz, 1H), 6.22(d, J=2.5 Hz, 1H), 6.29(m, 1H), 6.49(d, J=6.7 Hz, 0.5H), 6.59(d, J=6.7 Hz, 0.5H), 7.27–7.40(m, 6H)

EXAMPLE 16

Preparation of (s)-3-((s)-2-benzyloxycarbonylamino-4-methylvalerylamino)-1-methylthio-2-heptanone (Compd. No. 37 in Table 1)

mp: 80°–82° C. IR(KBr, cm$^{-1}$): 3320, 1720, 1685, 1643 NMR(CDCl$_3$, δ): 0.83–1.0(m, 9H), 1.18–2.05(m, 9H), 2.07 (s, 3H), 3.20(d, J=14 Hz, 1H), 3.36(d, J=14 Hz, 1H), 4.23(m, 1H), 4.84(m, 1H), 5.12(s, 2H), 5.16(m, 1H), 6.56(d, J=8 Hz, 1H), 7.35(s, 5H)

EXAMPLE 17

Preparation of (s)-3-benzyloxycarbonylaminoacetylamino-1-furfurylthio-2-heptanone (Compd. No. 38 in Table 1)

IR(neat, cm$^{-1}$): 3350, 1720, 1715, 1670 NMR(CDCl$_3$, δ): 0.87(d, J=6.7 Hz, 3H), 1.12–1.40(m, 4H), 1.55(m, 1H), 1.85(m, 1H), 3.26(d, J=15 Hz, 1H), 3.34(d, J=15 Hz, 1H), 3.71(s, 2H), 3.90(d, J=4.3 Hz, 2H), 4.81(m, 1H), 5.13(s, 2H), 5.54(m, 1H), 6.21(d, J=3.2 Hz, 1H), 6.29(m, 1H), 6.72(d, J=7.0 Hz, 1H), 7.27–7.41(m, 6H)

EXAMPLE 18

Preparation of (s)-3-((s)-2-benzyloxycarbonylaminopropionylamino)-1-furfurylthio-2-heptanone (Compd. No. 39 in Table 1)

mp: 85°–87° C. IR(KBr, cm$^{-1}$): 3300, 1730, 1690, 1660 NMR(CDCl$_3$, δ): 0.87(d, J=6.8 Hz, 3H), 1.15–1.37(m, 3H), 1.39(d, J=7.0 Hz, 3H), 1.45–1.75(m, 2H), 1.87(m, 1H), 3.26(d, J=15 Hz, 1H), 3.33(d, J=15 Hz, 1H), 3.71(s, 2H), 4.26(m, 1H), 4.75(m, 1H), 5.12(s, 2H), 5.32(m, 1H), 6.22(d, J=3.2 Hz, 1H), 6.29(m, 1H), 6.61(m, 1H), 7.30–7.36(m, 6H)

EXAMPLE 19

Preparation of (s)-3-((s)-2-benzyloxycarbonylamino-3-methylbutyrylamino)-1-furfurylthio-2-heptanone (Compd. No. 40 in Table 1)

mp: 115°–116° C. IR(KBr, cm$^{-1}$): 3280, 1715, 1690, 1630 NMR(CDCl$_3$, δ): 0.86(t, J=7.0 Hz, 3H), 0.92(d, J=6.8 Hz, 3H), 0.97(d, J=6.8 Hz, 3H), 1.15–1.39(m, 4H), 1.53(m, 1H), 1.89(m, 1H), 2.14(m, 1H), 3.27(d, J=15 Hz, 1H), 3.35(d, J=15 Hz, 1H), 3.71(s, 2H), 4.02(dt, J=8.2 Hz, 6.1 Hz, 1H), 4.78(m, 1H), 5.11(s, 2H), 5.38(d, J=8.2 Hz, 1H), 6.21(d, J=2.6 Hz, 1H), 6.29(m, 1H), 6.56(d, J=7.7 Hz, 1H), 7.27–7.42(m, 6H)

EXAMPLE 20

Preparation of (s)-3-((s)-2-benzyloxycarbonylaminovalerylamino)-1-furfurylthio-2-heptanone (Compd. No. 41 in Table 1)

mp: 95°–96° C. IR(KBr, cm$^{-1}$): 3280, 3260, 1690, 1680, 1640 NMR(CDCl$_3$, δ): 0.86(t, J=7.0 Hz, 3H), 0.93(t, J=7.2 Hz, 3H), 1.16–1.47(m, 6H), 1.50–1.67(m, 2H), 1.75–1.97 (m, 2H), 3.27(d, J=15 Hz, 1H), 3.33(d, J=15 Hz, 1H), 3.71(s, 2H), 4.19(m, 1H), 4.77(m, 2H), 5.11(s, 2H), 5.30(d, J=7.1 Hz, 1H), 6.21(d, J=3.1 Hz, 1H), 6.30(m, 1H), 6.59(d, J=7.1 Hz, 1H), 7.37–7.43(m, 6H)

EXAMPLE 21

Preparation of (s)-3-((s)-2-cyclohexylmethoxycarbonylamino-4-methylvalerylamino)-1-furfurylthio-2-heptanone (Compd. No. 46 in Table 1)

IR(neat, cm$^{-1}$): 3330, 1715, 1660 NMR(CDCl$_3$, δ): 0.93 (t, J=6.9 Hz, 3H), 0.94(d, J=3.9 Hz, 6H), 1.10–2.0(m, 20H), 3.26(d, J=15 Hz, 1H), 3.34(d, J=15 Hz, 1H), 3.71(s, 2H), 3.87(d, J=6.4 Hz, 2H), 4.13(m, 1H), 4.74(m, 1H), 5.0(d, J=6.4 Hz, 1H), 6.21(d, J=2.6 Hz, 1H), 6.29(m, 1H), 6.60(d, J=8 Hz, 1H), 7.35(m, 1H)

EXAMPLE 22

Preparation of (s)-3-((s)-2-benzyloxycarbonylamino-4-methylvalerylamino)-1-furfurylthio-2-heptanone (Compd. No. 48 in Table 1)

IR(neat, cm$^{-1}$): 3300, 1710, 1655 NMR(CDCl$_3$, δ): 0.87 (t, J=6.8 Hz, 3H), 0.95(d, J=5.9 Hz, 6H), 1.15–2.0(m, 9H), 3.26(d, J=14 Hz, 1H), 3.33(d, J=14 Hz, 1H), 3.72(s, 2H), 4.20(m, 1H), 4.75(m, 1H), 5.12(s, 2H), 5.13(m, 1H), 6.22(m, 1H), 6.30(m, 1H), 6.55(d, J=7 Hz, 1H), 7.26–7.45(m, 6H)

EXAMPLE 23

Preparation of (s)-3-[(s)-2-(2-fluorobenzyloxycarbonylamino)-4-methylvalerylamino]-1-furfurylthio-2-heptanone (Compd. No. 49 in Table 1)

IR(neat, cm$^{-1}$): 3320, 1710, 1655 NMR(CDCl$_3$, δ): 0.87 (t, J=5.8 Hz, 3H), 0.94(d, J=5.6 Hz, 6H), 1.07–2.0(m, 9H), 3.25(d, J=14 Hz, 1H), 3.32(d, J=14 Hz, 1H), 3.71(s, 2H), 4.13(m, 1H), 4.75(m, 1H), 5.05–5.27(m, 3H), 6, 22(m, 1H), 6.29(m, 1H), 6.53(d, J=9 Hz, 1H), 6.98–7.19(m, 2H), 7.21–7.43(m, 3H)

EXAMPLE 24

Preparation of (s)-3-[(s)-2-(4-fluorobenzyloxycarbonylamino)-4-methylvalerylamino]-1-furfurylthio-2-heptanone (Compd. No. 51 in Table 1)

mp: 67°–68° C. IR(KBr, cm$^{-1}$); 3400, 3250, 1725, 1640 NMR(CDCl$_3$, δ): 0.87(t, J=7.2 Hz, 3H), 0.94(d, J=5.0 Hz, 6H), 1.10–2.0(m, 9H), 3.27(d, J=14 Hz, 1H), 3.37(d, J=14 Hz, 1H), 3.71(s, 2H), 4.17(m, 1H), 4.76(m, 1H), 5.07(s, 2H), 5.15(d, J=7 Hz, 1H), 6.22(d, J=2.9 Hz, 1H), 6, 30(m, 1H), 6, 50(d, J=7 Hz, 1H), 7.05(t, J=8.6 Hz, 2H), 7.30–7.45(m, 3H)

EXAMPLE 25

Preparation of (s)-3-[(s)-2-(2-cyanobenzyloxycarbonylamino)-4-methylvalerylamino]-1-furfurylthio-2-heptanone (Compd. No. 56 in Table 1)

IR(neat, cm$^{-1}$): 3281, 1766, 1712, 1658 NMR(CDCl$_3$, δ): 0.85–1.06(m, 9H), 1.25–1.43(m, 4H), 1.52–1.83(m, 3H), 1.83–2.02(m, 2H), 3.24(d, J=15 Hz, 1H), 3.33(d, J=15 Hz, 1H), 3.67(s, 2H), 4.56(m, 1H), 4.77(m, 1H), 5.33(s, 2H), 6.17(d, J=3.1 Hz, 1H), 6.23(m, 1H), 6, 25(d, J=8.3 Hz, 1H), 7.28(dd, J=6.4 Hz, 5.3 Hz, 1H), 7.36(m, 1H), 7.43–7.65(m, 3H), 7.90(d, J=7.3 Hz, 1H)

EXAMPLE 26

Preparation of (s)-3-[(s)-2-(3-cyanobenzyloxycarbonylamino)-4-methylvalerylamino]-1-furfurylthio-2-heptanone (Compd. No. 57 in Table 1)

IR(KBr, cm⁻¹): 3400, 3250, 2220, 1710, 1630 NMR (CDCl₃, δ): 0.87(t, J=6.6 Hz, 3H), 0.95(d, J=5.3 Hz, 6H), 1.09–1.39(m, 4H), 1.42–1.77(m, 4H), 1.89(m, 1H), 3.26(d, J=15 Hz, 1H), 3.34(d, J=15 Hz, 1H), 3.71(s, 2H), 4.19(m, 1H), 4.77(m, 1H), 5.13(s, 2H), 5.25(d, J=7.8 Hz, 1H), 6.21(d, J=3.1 Hz, 1H), 6.30(m, 1H), 6.61(d, J=7.3 Hz, 1H), 7.26(s, 1H), 7.35(m, 1H), 7.45(m, 1H), 7.51–7.63(m, 2H)

EXAMPLE 27

Preparation of (s)-3-[(s)-2-(4-cyanobenzyloxycarbonylamino)-4-methylvalerylamino]-1-furfurylthio-2-heptanone (Compd. No. 58 in Table 1)

mp: 83°–89° C. IR(KBr, cm⁻¹): 3400, 3270, 2220, 1720, 1700, 1640 NMR(CDCl₃, δ): 0.86(t, J=7.0 Hz, 3H), 0.95(d, J=6.2 Hz, 6H), 1.13–1.40(m, 3H), 1.43–1.79(m, 5H), 1.79–1.99(m, 1H), 3.26(d, J=15 Hz, 1H), 3.30(d, J=15 Hz, 1H), 3.72(s, 2H), 4.19(m, 1H), 4.77(m, 1H), 5.16(s, 2H), 5.32(d, J=8.0 Hz, 1H), 6.21(d, J=2.9 Hz, 1H), 6.30(m, 1H), 6.55(d, J=7.6 Hz, 1H), 7.36(m, 1H), 7.44(d, J=8.3 Hz, 2H), 7.65(d, J=8.3 Hz, 2H)

EXAMPLE 28

Preparation of (s)-1-furfurylthio-3-[(s)-4-methyl-2-(2-pyridylmethoxycarbonylamino)valerylamino]-2-heptanone (Compd. No. 59 in Table 1)

IR(neat, cm⁻¹) 3350, 1715, 1660 NMR(CDCl₃, δ): 0.86(t, J=6.7 Hz, 3H), 0.95(d, J=3.8 Hz, 6H), 1.07–1.99(m, 9H), 3.27(d, J=15 Hz, 1H), 3.32(d, J=15 Hz, 1H), 3.71(s, 2H), 4.22(m, 1H), 4.77(m, 1H), 5.24(s, 2H), 5.32(d, J=8 Hz, 1H), 6.21(d, J=3.2 Hz, 1H), 6.29(m, 1H), 6.63(d, J=7 Hz, 1H), 7.20–7.40(m, 3H), 7.69(m, 1H), 8.58(d, J=3.1 Hz, 1H)

EXAMPLE 29

Preparation of (s)-3-((s)-2-cyclohexylcarbonylamino-4-methylvalerylamino)-1-furfurylthio-2-heptanone (Compd. No. 65 in Table 1)

mp: 109° C.(dec.) IR(KBr, cm⁻¹): 3294, 1707, 1637 NMR(CDCl₃, δ): 0.87(t, J=7.0 Hz, 3H), 0.98(d, J=6.7 Hz, 3H), 0.99(d, J=6.7 Hz, 3H), 1.11–1.75(m, 13H), 1.75–1.99 (m, 6H), 2.10(m, 1H), 3.26(d, J=15 Hz, 1H), 3.30(d, J=15 Hz, 1H), 3.72(s, 2H), 4.47(m, 1H), 4.71(m, 1H), 5.90(d, J=8.1 Hz, 1H), 6.21(d, J=2.6 Hz, 1H), 6.30(m, 1H), 6.81(d, J=7.6 Hz, 1H), 7.36(m, 1H)

EXAMPLE 30

Preparation of (s)-1-furfurylthio-3-((s)-4-methyl-2-phenylacetylaminovalerylamino)-2-heptanone (Compd. No. 66 in Table 1)

IR(neat, cm⁻¹): 3260, 1710, 1635 NMR(CDCl₃, δ): 0.75–1.07(m, 9H), 1.13–1.99(m, 9H), 3.20–3.38(m, 2H), 3.59(s, 2H), 3.71(s, 2H), 4.43(m, 1H), 4.68(m, 1H), 5.78(d, J=8 Hz, 1H), 6.21(d, J=3.2 Hz, 1H), 6.29(m, 1H), 6.62(d, J=7.4 Hz, 1H), 7.16–7.40(m, 6H)

EXAMPLE 31

Preparation of (s)-3-[(s)-2-(4-fluorophenylacetylamino)-4-methylvalerylamino]-1-furfurylthio-2-heptanone (Compd. No. 69 in Table 1)

IR(neat, cm⁻¹) 3300, 1715, 1660, 1640 NMR(CDCl₃, δ): 0.76–0.97(m, 9H), 1.07–1.96(m, 9H), 3.20–3.35(m, 2H), 3.55(d, J=4.3 Hz, 2H), 3.71(s, 2H), 4.46(m, 1H), 4.71(m, 1H), 5.85(d, J=7 Hz, 1H), 6.20(d, J=3.0 Hz, 1H), 6.29(m, 1H), 6.59(d, J=6 Hz, 0.6H), 6.69(d, J=6 Hz, 0.4H), 7.03(t, J=8.6 Hz, 2H), 7.17–7.35(m, 3H)

EXAMPLE 32

Preparation of (s)-1-furfurylthio-3-[(s)-4-methyl-2-(2,3-methylenedioxyphenylacetylamino)valerylamino]-2-heptanone (Compd. No. 73 in Table 1)

IR(neat, cm⁻¹): 3280, 1720, 1640 NMR(CDCl₃, δ): 0.80–1.0(m, 9H), 1.13–1.98(m, 9H), 3.20–3.37(m, 2H), 3.55 (d, J=3.9 Hz, 2H), 3.71(s, 2H), 4.44(m, 1H), 4.70(m, 1H), 5.90–6.07(m, 3H), 6.21(d, J=3.1 Hz, 1H), 6.29(m, 1H), 6.65(d, J=7 Hz, 1H), 6.70–6.93(m, 3H), 7.35(m, 1H)

EXAMPLE 33

Preparation of (s)-1-furfurylthio-3-[(s)-4-methyl-2-(1-naphtylacetylamino)valerylamino]-2-heptanone (Compd. No. 76 in Table 1)

IR(neat, cm⁻¹): 3300, 1710, 1640 NMR(CDCl₃, δ): 0.70 (d, J=6.5 Hz, 3H), 0.72(d, J=6.5 Hz, 3H), 0.85(t, J=7.2 Hz, 3H), 1.05–1.91(m, 9H), 3.20–3.38(m, 2H), 3.70(s, 2H), 4.02(d, J=11 Hz, 1H), 4.10(d, J=11 Hz, 1H), 4.39(m, 1H), 4.63(m, 1H), 5.59(d, J=8 Hz, 1H), 6.21(d, J=2.9 Hz, 1H), 6.36(m, 1H), 6.55(d, J=7 Hz, 0.5H), 6.62(d, J=7 Hz, 0.5H), 7.30–7.61(m, 5H), 7.80–8.0(m, 3H)

EXAMPLE 34

Preparation of (s)-3-[(s)-2-(3-benzothienylacetylamino)-4-methylvalerylamino]-1-furfurylthio-2-heptanone (Compd. No. 79 in Table 1)

IR(neat, cm⁻¹): 3300, 1715, 1640 NMR(CDCl₃, δ): 0.71–1.0(m, 9H), 1.07–1.97(m, 9H), 3.24(d, J=3.7 Hz, 0.7H), 3.27(d, J=3.0 Hz, 1.3H), 3.70(s, 1.3H), 3.71(s, 0.7H), 3.84(s, 1.3H), 3.85(s, 0.7H), 4.40(m, 1H), 4.67(m, 1H), 5.91(m, 1H), 6.20(d, J=3.2 Hz, 1H), 6.29(m, 1H), 6.57(d, J=6 Hz, 0.7H), 6.70(d, J=6 Hz, 0.3H), 7.34–7.45(m, 4H), 7.71(m, 1H), 7.87(m, 1H)

EXAMPLE 35

Preparation of (s)-3-((s)-2-cyclohexyloxyacetylamino-4-methylvalerylamino)-1-furfurylthio-2-heptanone (Compd. No. 81 in Table 1)

IR(neat, cm⁻¹): 3400, 3300, 1715, 1665 NMR(CDCl₃, δ): 0.80–1.0(m, 11H), 1.10–1.99(m, 17H), 3.29–3.40(m, 3H), 3.71(s, 0.7H), 3.72(s, 1.3H), 3.98(d, J=1.0 Hz, 1.3H), 3.99(s, 0.7H), 4.50(m, 1H), 4.74(m, 1H), 6.22(d, J=2.7 Hz, 1H), 6.30(m, 1H), 6.70(d, J=7 Hz, 0.7H), 6.77(d, J=7 Hz, 0.3H), 6.92(d, J=8 Hz, 1H), 7.35(m, 1H)

EXAMPLE 36

Preparation of (s)-3-[(s)-2-(2-fluorophenoxyacetylamino)-4-methylvalerylamino]-1-furfurylthio-2-heptanone (Compd. No. 85 in Table 1)

mp: 60°–62° C. IR(KBr, cm$^{-1}$): 3340, 1715, 1670, 1640 NMR(CDCl$_3$, δ): 0.87(t, J=7.0 Hz, 3H), 0.95(d, J=6.1 Hz, 6H), 1.10–1.99(m, 9H), 3.26(d, J=15 Hz, 1H), 3.34(d, J=15 Hz, 1H), 3.72(s, 2H), 4.53(m, 1H), 4.57(s, 2H), 4.75(m, 1H), 6.22(d, J=2.8 Hz, 1H), 6.29(m, 1H), 6.65(d, J=8 Hz, 1H), 6.90–7.20(m, 5H), 7.36(m, 1H)

EXAMPLE 37

Preparation of (s)-3-[(s)-2-(3-fluorophenoxyacetylamino)-4-methylvalerylamino]-1-furfurylthio-2-heptanone (Compd. No. 86 in Table 1)

IR(neat, cm$^{-1}$): -3300, 1750, 1650 NMR(CDCl$_3$, δ): 0.87(t, J=7.2 Hz, 3H), 0.93(d, J=6.3 Hz, 6H), 1.15–2.0(m, 9H), 3.20–3.40(m, 2H), 3.71(d, J=6.4 Hz, 2H), 4.51(d, J=2.2 Hz, 2H), 4.61(m, 1H), 4.76(m, 1H), 6.21(d, J=3.1 Hz, 1H), 6.28(m, 1H), 6.62–6.79(m, 3H), 6.81–7.10(m, 2H), 7.18–7.39(m, 2H)

EXAMPLE 38

Preparation of (s)-3-[(s)-2-(4-fluorophenoxyacetylamino)-4-methylvalerylamino]-1-furfurylthio-2-heptanone (Compd. No. 87 in Table 1)

mp: 88°–91° C. IR(KBr, cm$^{-1}$): 3300, 1700, 1640 NMR (CDCl$_3$, δ): 0.86(t, J=7.0 Hz, 3H), 0.93(d, J=5.7 Hz, 6H), 1.10–2.0(m, 9H), 3.21–3.32(m, 2H), 3.71(d, J=5.6 Hz, 2H), 4.48(d, J=2.7 Hz, 2H), 4.59(m, 1H), 4.76(m, 1H), 6.20(d, J=3.1 Hz, 1H), 6.27(m, 1H), 6.65(m, 1H), 6.78–7.10(m, 5H), 7.30–7.42(m, 1H)

EXAMPLE 39

Preparation of (s)-3-[(s)-2-(2-chlorophenoxyacetylamino)-4-methylvalerylamino]-1-furfurylthio-2-heptanone (Compd. No. 88 in Table 1)

IR(neat, cm$^{-1}$): 3320, 1715, 1650 NMR(CDCl$_3$, δ): 0.85 (t, J=3.9 Hz, 3H), 0.92–1.05(m, 6H), 1.15–1.98(m, 9H), 3.27(d, J=15 Hz, 1H), 3.35(d, J=15 Hz, 1H), 3.71(s, 2H), 4.54(s, 2H), 4.52(m, 1H), 4.75(m, 1H), 6.22(m, 1H), 6.29(m, 1H), 6.79–7.05(m, 3H), 7.17–7.31(m, 2H), 7.33–7.45(m, 2H)

EXAMPLE 40

Preparation of (s)-3-[(s)-2-(4-chlorophenoxyacetylamino)-4-methylvalerylamino]-1-furfurylthio-2-heptanone (Compd. No. 90 in Table 1)

mp: 66°–67° C. IR(KBr, cm$^{-1}$): 3320, 1710, 1645 NMR (CDCl$_3$, δ): 0.87(t, J=6.9 Hz, 3H), 0.92(d, J=7.4 Hz, 6H), 1.07–1.99(m, 9H), 3.23–3.38(m, 2H), 3.72(d, J=5.0 Hz, 2H), 4.50(d, J=3.2 Hz, 2H), 4.53(m, 1H), 4.76(m, 1H), 6.20(m, 1H), 6.28(m, 1H), 6.57(d, J=8 Hz, 0.5H), 6.70(d, J=8 Hz, 0.5H), 6.79–6.99(m, 4H), 7.29(d, J=1.5 Hz, 1H), 7.36(m, 1H)

EXAMPLE 41

Preparation of (s)-3-[(s)-2-(2, 3-dichlorophenoxyacetylamino)-4-methylvalerylamino]-1-furfurylthio-2-heptanone (Compd. No. 91 in Table 1)

mp. 79°–80° C. IR(KBr, cm$^{-1}$): 3300, 1715, 1660, 1645 NMR(CDCl$_3$, δ): 0.87(t, J=7.0 Hz, 3H), 0.94(d, J=5.2 Hz, 3H), 0.96(d, J=5.5 Hz, 3H), 1.10–2.0(m, 9H), 3.23–3.40(m, 2H), 3.72(d, J=3.6 Hz, 2H), 4.51(m, 1H), 4.57(s, 2H), 4.75(m, 1H), 6.21(m, 1H), 6.29(m, 1H), 6.58(d, J=7 Hz, 0.7H), 6.70(d, J=7 Hz, 0.3H), 6.82(m, 1H), 7.10–7.22(m, 3H), 7.35(d, J=1.9 Hz, 1H)

EXAMPLE 42

P reparation of (s)-3-[(s)-2-(2,4-dichlorophenoxyacetylamino)-4-methylvalerylamino]-1-furfurylthio-2-heptanone (Compd. No. 92 in Table 1)

mp: 107°–108° C. IR(KBr, cm$^{-1}$): 3300, 1715, 1660, 1640 NMR(CDCl$_3$, δ): 0.87(t, J=7.1 Hz, 3H), 0.93–0.98(m, 6H), 1.05–1.99(m, 9H), 3.27(d, J=14 Hz, 1H), 3.36(d, J=14 Hz, 1H), 3.70(s, 0.4H), 3.72(s, 1.6H), 4.52(m, 1H), 4.54(s, 2H), 4.78(m, 1H), 6.21(d, J=3.1 Hz, 1H), 6.30(m, 1H), 6.58(d, J=7 Hz, 0.8H), 6.70(d, J=7 Hz, 0.2H), 6.84(d, J=9 Hz, 1H), 7.08–7.50(m, 4H)

EXAMPLE 43

Preparation of (s)-1-furfurylthio-3-[(s)-4-methyl-2-(2,4,6-trichlorophenoxyacetylamino)valerylamino]-2-heptanone (Compd. No. 94 in Table 1)

IR(neat, cm$^{-1}$); 3300, 1710, 1640 NMR(CDCl$_3$, δ): 0.82–0.89(m, 3H), 0.92–1.10(m, 6H), 1.17–2.0(m, 9H), 3.22–3.40(m, 2H), 3.70(s, 0.4H), 3.72(s, 1.6H), 4.51(d, J=1.6 Hz, 2H), 4.63(m, 1H), 4.76(m, 1H), 6.21(d, J=2.6 Hz, 1H), 6.28(m, 1H), 6.83(d, J=7 Hz, 0.8H), 6.92(d, J=7 Hz, 0.2H), 7.23–7.40(m, 4H)

EXAMPLE 44

Preparation of (s)-1-furfurylthio-3-[(s)-4-methyl-2-(2-methylphenoxyacetylamino)valerylamino]-2-heptanone (Compd. No. 96 in Table 1)

IR(neat, cm$^{-1}$): 3300, 1710, 1650 NMR(CDCl$_3$, δ): 0.87 (t, J=6.9 Hz, 3H), 0.94(d, J=6.1 Hz, 6H), 1.07–1.97(m, 9H), 2.30(s, 3H), 3.19–3.39(m, 2H), 3.71(d, J=4.6 Hz, 2H), 4.53(d, J=1.8 Hz, 2H), 4.54(m, 1H), 4.76(m, 1H), 6.22(m, 1H), 6.30(m, 1H), 6.55–6.82(m, 2H), 6.87–7.03(m, 2H), 7.11–7.21(m, 2H), 7.30–7.40(m, 1H)

EXAMPLE 45

Preparation of (s)-1-furfurylthio-3-[(s)-4-methyl-2-(3-methylphenoxyacetylamino)valerylamino]-2-heptanone (Compd. No. 97 in Table 1)

IR(neat, cm$^{-1}$): 3300, 1710, 1650 NMR(CDCl$_3$, δ): 0.78–1.01(m, 9H), 1.05–1.95(m, 9H), 2.33(s, 3H), 3.21–3.38(m, 2H), 3.70(s, 1.3H), 3.72(s, 0.7H), 4.50(s, 0.7H), 4.51(s, 1.3H), 4.56(m, 1H), 4.73(m, 1H), 6.20(m, 1H), 6.28(m, 1H), 6.58–6.80(m, 3H), 6.84(d, J=6.9 Hz, 1H), 6.92(d, J=8.3 Hz, 1H), 7.19(t, J=7.7 Hz, 1H), 7.35(m, 1H)

EXAMPLE 46

Preparation of (s)-3-[(s)-2-(4-chloro-2-methylphenoxyacetylamino)-4-methylvalerylamino]-1-furfurylthio-2-heptanone (Compd. No. 100 in Table 1)

IR(neat, cm$^{-1}$): 3300, 1715, 1650 NMR(CDCl$_3$, δ): 0.86 (t, J=7.0 Hz, 3H), 0.95(d, J=5.3 Hz, 6H), 1.19–1.99(m, 9H), 2.25(s, 3H), 3.22–3.38(m, 2H), 3.71(d, J=5.9 Hz, 2H), 4.49(s, 2H), 4.60(q, J=7.6 Hz, 1H), 4.78(m, 1H), 6.20(m, 1H), 6.27(m, 1H), 6.63–6.80(m, 1.5H), 6.82–7.20(m, 3.5H), 7.35(m, 1H)

EXAMPLE 47

Preparation of (s)-1-furfurylthio-3-[(s)-2-(2-methoxyphenoxyacetylamino)-4-methylvalerylamino]-2-heptanone (Compd. No. 102 in Table 1)

IR(neat, cm$^{-1}$): 3300, 1710, 1650 NMR(CDCl$_3$, δ): 0.85 (t, J=7.1 Hz, 3H), 0.91(d, J=6.2 Hz, 3H), 0.93(d, J=6.2 Hz, 3H), 1.07–1.37(m, 5H), 1.42–1.63(m, 2H), 1.63–1.95(m, 2H), 3.25(d, J=15 Hz, 1H), 3.33(d, J=15 Hz, 1H), 3.71(s, 2H), 3.88(s, 3H), 4.50(m, 1H), 4.56(s, 2H), 4.70(m, 1H), 6.22(d, J=2.9 Hz, 1H), 6.30(m, 1H), 6.74(d, J=7.6 Hz, 1H), 6.84–7.0(m, 3H), 7.05(m, 1H), 7.35(m, 1H), 7.47(d, J=8.0 Hz, 1H)

EXAMPLE 48

Preparation of (s)-1-furfurylthio-3-[(s)-2-(4-methoxyphenoxyacetylamino)-4-methylvalerylamino]-2-heptanone (Compd. No. 104 in Table 1)

mp: 86°–88° C. IR(KBr, cm$^{-1}$): 3302, 3261, 1712, 1668, 1637 NMR(CDCl$_3$, δ): 0.86(t, J=6.9 Hz, 3H), 0.94(d, J=6.0 Hz, 6H), 1.17–1.39(m, 4H), 1.45–1.78(m, 4H), 1.89(m, 1H), 3.27(d, J=15 Hz, 1H), 3.35(d, J=15 Hz, 1H), 3.73(s, 2H), 3.77(s, 3H), 4.43(d, J=10 Hz, 1H), 4.48(d, J=10 Hz, 1H), 4.61(m, 1H), 4.74(m, 1H), 6.22(d, J=3.1 Hz, 1H), 6.30(m, 1H), 6.80–6.91(m, 5H), 7.01(d, J=8.4 Hz, 1H), 7.36(m, 1H)

EXAMPLE 49

Preparation of (s)-1-furfurylthio-3-((s)-4-methyl-2-phenylthioacetylaminovalerylamino)-2-heptanone (Compd. No. 107 in Table 1)

IR(neat, cm$^{-1}$): 3300, 1715, 1640 NMR(CDCl$_3$, δ): 0.78–1.05(m, 9H), 1.15–2.05(m, 9H), 3.18–3.27(m, 2H), 3.57–3.75(m, 4H), 4.50(m, 1H), 4.69(m, 1H), 6.21(d, J=2.4 Hz, 1H), 6.29(m, 1H), 6.68(d, J=8 Hz, 0.4H), 6.81(d, J=8 Hz, 0.6H), 7.08–7.40(m, 7H)

EXAMPLE 50

Preparation of (s)-1-furfurylthio-3-[(s)-4-methyl-2-(3-phenoxypropionylamino)valerylamino]-2-heptanone (Compd. No. 109 in Table 1)

IR(neat, cm$^{-1}$): 3300, 1715, 1640 NMR(CDCl$_3$, δ): 0.83 (t, J=6.8 Hz, 3H), 0.90–0.94(m, 6H), 1.10–1.99(m, 9H), 2.66(t, J=5.9 Hz, 1H), 2.69(t, J=5.9 Hz, 1H), 3.20–3.38(m, 2H), 3.68(s, 1.3H), 3.70(s, 0.7H), 4.25(t, J=5.9 Hz, 2H), 4.55(m, 1H), 4.70(m, 1H), 6.20(d, J=3.3 Hz, 1H), 6.28(m, 1H), 6.52(d, J=7 Hz, 1H), 6.80–7.01(m, 4H), 7.20–7.40(m, 3H)

EXAMPLE 51

Preparation of (s)-1-furfurylthio-3-[(s)-4-methyl-2-(5,6,7,8-tetrahydro-1-naphtoxyacetylamino)valerylamino]-2-heptanone (Compd. No. 111 in Table 1)

NMR(CDCl$_3$, δ): 0.80–1.08(m, 9H), 1.15–2.0(m, 13H), 2.67–2.80(m, 4H), 3.21–3.40(m, 2H), 3.71(d, J=7.3 Hz, 2H), 4.49(s, 2H), 4.60(m, 1H), 4.76(q, J=4.6 Hz, 1H), 6.20(m, 1H), 6.27(m, 1H), 6.58(d, J=8 Hz, 1H), 6.70–6.85(m, 2H), 6.87–7.10(m, 2H), 7.35(m, 1H)

EXAMPLE 52

Preparation of (s)-1-furfurylthio-3-[-(s)-4-methyl-2-(1-naphtoxyacetylamino)valerylamino]-2-heptanone (Compd. No. 114 in Table 1)

IR(neat, cm$^{-1}$): 3300, 1710, 1650 NMR(CDCl$_3$, δ): 0.80–0.98(m, 9H), 1.10–2.0(m, 9H), 3.28(d, J=15 Hz, 1H), 3.35(d, J=15 Hz, 1H), 3.73(s, 2H), 4.58(m, 1H), 4.73(s, 2H), 4.74(m, 1H), 6.22(m, 1H), 6.29(m, 1H), 6.63(d, J=7 Hz, 1H), 6.83(d, J=7 Hz, 1H), 7.01(d, J=7.1 Hz, 1H), 7.32–7.60 (m, 5H), 7.83(m, 1H), 8.21(m, 1H)

EXAMPLE 53

Preparation of (s)-1-furfurylthio-3-[(s)-4-methyl-2-(2-naphtoxyacetylamino)valerylamino]-2-heptanone (Compd. No. 115 in Table 1)

mp: 87°–89° C. IR(KBr, cm$^{-1}$): 3260, 1700, 1665, 1640 NMR(CDCl$_3$, δ): 0.78–1.0(m, 9H), 1.05–1.98(m, 9H), 3.21–3.40(m, 2H), 3.69(s, 0.2H), 3.72(s, 1.8H), 4.50–4.70 (m, 1H), 4.62(s, 2H), 4.74(m, 1H), 6, 22(d, J=3.1 Hz, 1H), 6.29(m, 1H), 6.67(d, J=9 Hz, 0.9H), 6.80(d, J=9 Hz, 0.1H), 6.97(d, J=9 Hz, 1H), 7.12–7.93(m, 8H)

EXAMPLE 54

Preparation of (s)-3-((s)-2-benzoylamino-4-methylvalerylamino)-1-furfurylthio-2-heptanone (Compd. No. 116 in Table 1)

IR(neat, cm$^{-1}$): 3300, 1710, 1630 NMR(CDCl$_3$, δ): 0.83 (t, J=6.7 Hz, 1.5H), 0.89(t, J=6.7 Hz, 1.5H), 1.01(d, J=5.8 Hz, 6H), 1.15–2.0(m, 9H), 3.28(d, J=15 Hz, 0.5H), 3.30(d, J=15 Hz, 0.5H), 3.36(d, J=15 Hz, 0.5H), 3.38(d, J=15 Hz, 0.5H), 3.71(s, 1H), 3.75(s, 1H), 4.69–4.84(m, 2H), 6.21(d, J=2.5 Hz, 0.5H), 6.24(d, J=2.5 Hz, 0.5H), 6.29(m, 0.5H), 6.33(m, 0.5H), 6.61(d, J=7 Hz, 1H), 6.76(d, J=7 Hz, 0.5H), 6.82(d, J=7 Hz, 0.5H), 7.24–7.87(m, 6H)

EXAMPLE 55

Preparation of (s)-3-[(s)-2-(2-fluorobenzoylamino)-4-methylvalerylamino]-1-furfurylthio-2-heptanone (Compd. No. 117 in Table 1)

mp: 102°–103° C. IR(KBr, cm$^{-1}$): 3287, 1734, 1635 NMR(CDCl$_3$, δ): 0.81(t, J=6.7 Hz, 3H), 0.97(d, J=5.6 Hz, 3H), 0.99(d, J=5.7 Hz, 3H), 1.15–1.40(m, 4H), 1.51–1.65(m, 1H), 1.65–1.82(m, 3H), 1.90(m, 12), 3.27(d, J=15 Hz, 1H), 3.35(d, J=15 Hz, 12), 3.72(s, 1H), 4.63–4.82(m, 2H), 6.23(d,

J=3.2 Hz, 1H), 6.30(m, 12), 6.74(d, J=7.4 Hz, 1H), 7.04(dd, J=9.0 Hz, 7.6 Hz, 1H), 7.12(dd, J=12 Hz, 8.3 Hz, 1H), 7.27(d, J=12 Hz, 12), 7.36(m, 12), 7.48(m, 12), 8.07(ddd, J=7.8 Hz, 7.8 Hz, 1.7 Hz, 1H)

EXAMPLE 56

Preparation of (s)-3-[(s)-2-(3-fluorobenzoylamino)-4-methylvalerylamino]-1-furfurylthio-2-heptanone (Compd. No. 118 in Table 1)

IR(KBr, cm$^{-1}$): 3285, 1734, 1635 NMR(CDCl$_3$, δ): 0.79 (t, J=6.7 Hz, 3H), 0.94(d, J=5.0 Hz, 6H), 1.13–1.38(m, 4HI, 1.43–1.63(m, 1H), 1.64–1.97(m, 4H), 3.34(s, 2H), 3.72(s, 2H), 4.71(m, 1H), 4.85(m, 12), 6.22(d, J=3.1 Hz, 1H), 6.29(m, 1H), 7.16(ddd, J=8.3 Hz, 8.3 Hz, 2.4 Hz, 1H), 7.28–7.45(m, 32), 7.50–7.62(m, 3H)

EXAMPLE 57

Preparation of (s)-3-[(s)-2-(4-fluorobenzoylamino)-4-methylvalerylamino]-1-furfurylthio-2-heptanone (Compd. No. 119 in Table 1)

IR(KBr, cm$^{-1}$): 3315, 1715, 1637 NMR(CDCl$_3$, δ): 0.81 (t, J=6.6 Hz, 3H), 0.98(d, J=5.5 Hz, 6H), 1.17–1.39(m, 4H), 1.57(m, 1H), 1.62–1.82(m, 3H), 1.89(m, 1H), 3.27(d, J=15 Hz, 1H), 3.35(d, J=15 Hz, 1H), 3.73(s, 2H), 4.65–4.87(m, 2H), 6.22(d, J=3.1 Hz, 1H), 6.30(m, 1H), 6.67(d, J=7.7 Hz, 1H), 6.75(d, J=7.7 Hz, 1H), 7.11(dd, J=8.7 Hz, 8.7 Hz, 2H), 7.36(m, 1H), 7.75–7.84(m, 2H)

EXAMPLE 58

Preparation of (s)-3-[(s)-2-(2,3-difluorobenzoylamino)-4-methylvalerylamino]-1-furfurylthio-2-heptanone (Compd. No. 120 in Table 1)

mp: 120°–122° C. IR(KBr, cm$^{-1}$): 3285, 1734, 1658, 1635 NMR(CDCl$_3$, δ): 0.82(t, J=6.6 Hz, 3H), 0.98(d, J=6.0 Hz, 3H), 0.99(d, J=6.2 Hz, 3H), 1.15–1.39(m, 4H), 1.56(m, 1H), 1.63–1.82(m, 3H), 1.90(m, 1H), 3.27(d, J=15 Hz, 1H), 3.30(d, J=15 Hz, 1H), 3.72(s, 2H), 4.68(m, 1H), 4.76(m, 1H), 6.23(d, J=3.1 Hz, 1H), 6.30(m, 1H), 6.64(d, J=7.4 Hz, 1H), 6.92(d, J=11 Hz, 0.5H), 6.96(d, J=11 Hz, 0.5H), 7.17–7.40(m, 4H)

EXAMPLE 59

Preparation of (s)-3-[(s)-2-(2,4-difluorobenzoylamino)-4-methylvalerylamino]-1-furfurylthio-2-heptanone (Compd. No. 121 in Table 1)

mp: 97°–98° C. IR(KBr, cm$^{-1}$): 3283, 1730, 1658, 1633 NMR(CDCl$_3$, δ): 0.82(t, J=6.7 Hz, 3H), 0.97(d, J=6.1 Hz, 3H), 0.99(d, J=6.1 Hz, 3H), 1.17–1.39(m, 4H), 1.57(m, 1H), 1.61–1.82(m, 3H), 1.89(m, 1H), 3.27(d, J=15 Hz, 1H), 3.35(d, J=15 Hz, 1H), 3.73(s, 2H), 4.69(m, 1H), 4.77(m, 1H), 6.22(d, J=3.2 Hz, 1H), 6.30(m, 1H), 6.67(d, J=7.3 Hz, 1H), 6.82–7.05(m, 3H), 7.36(m, 1H), 8.11(m, 1H)

EXAMPLE 60

Preparation of (s)-3-[(s)-2-(2,5-difluorobenzoylamino)-4-methylvalerylamino]-1-furfurylthio-2-heptanone (Compd. No. 122 in Table 1)

mp: 102° C. IR(KBr, cm$^{-1}$): 3282, 1734, 1637 NMR (CDCl$_3$, δ): 0.83(t, J=6.8 Hz, 3H), 0.98(d, J=6.0 Hz, 3H), 0.99(d, J=5.9 Hz, 3H), 1.17–1.37(m, 4H), 1.49–1.82(m, 4H), 1.90(m, 1H), 3.27(d, J=15 Hz, 1H), 3.35(d, J=15 Hz, 1H), 3.73(s, 2H), 4.69(m, 1H), 4.77(m, 1H), 6.22(d, J=3.2 Hz, 1H), 6.30(m, 1H), 6.64(d, J=6.5 Hz, 1H), 7.02–7.23(m, 3H), 7.35(m, 1H), 7.75(m, 1H)

EXAMPLE 61

Preparation of (s)-3-[(s)-2-(2,6-difluorobenzoylamino)-4-methylvalerylamino]-1-furfurylthio-2-heptanone (Compd. No. 123 in Table 1)

mp: 116° C. IR(KBr, cm$^{-1}$): 3250, 1720, 1670, 1640, 1620 NMR(CDCl$_3$, δ): 0.87(t, J=6.7 Hz, 3H), 0.99(d, J=5.8 Hz, 6H), 1.18–1.41(m, 4H), 1.50–1.82(m, 4H), 1.89(m, 1H), 3.27(d, J=15 Hz, 1H), 3.35(d, J=15 Hz, 1H), 3.73(s, 2H), 4.65–4.86(m, 2H), 6.22(d, J=3.2 Hz, 1H), 6.30(m, 1H), 6.44(d, J=8.0 Hz, 1H), 6.73(d, J=7.6 Hz, 1H), 6.95(dd, J=8.1 Hz, 8.1 Hz, 2H), 7.31–7.43(m, 2H)

EXAMPLE 62

Preparation of (s)-3-[(s)-2-(3,4-difluorobenzoylamino)-4-methylvalerylamino]-1-furfurylthio-2-heptanone (Compd. No. 124 in Table 1)

mp: 94°–100° C. IR(KBr, cm$^{-1}$): 3315, 1720, 1639, 1602 NMR(CDCl$_3$, δ): 0.79(t, J=7.0 Hz, 3H), 0.86(d, J=5.1 Hz, 6H), 1.09–1.39(m, 4H), 1.47–1.64(m, 1H), 1.64–1.98(m, 4H), 3.34(s, 2H), 3.73(s, 2H), 4.72(m, 1H), 4.85(m, 1H), 6.22(d, J=3.2 Hz, 1H), 6.29(m, 1H), 7.12(ddd, J=8.6 Hz, 8.6 Hz, 8.6 Hz, 1H), 7.35(m, 1H), 7.45–7.63(m, 2H), 7.67(m, 1H), 7.89(m, 1H)

EXAMPLE 63

Preparation of (s)-3-[(s)-2-(3,5-difluorobenzoylamino)-4-methylvalerylamino]-1-furfurylthio-2-heptanone (Compd. No. 125 in Table 1)

mp: 125°–126° C. IR(KBr, cm$^{-1}$): 3283, 1723, 1637 NMR(CDCl$_3$, δ): 0.84(t, J=6.7 Hz, 3H), 0.97(d, J=6.1 Hz, 6H), 1.17–1.40(m, 4H), 1.54(m, 1H), 1.64–1.82(m, 3H), 1.90(m, 1H), 3.28(d, J=15 Hz), 1H), 3.35(d, J=15 Hz, 1H), 3.73(s, 2H), 4.68(m, 1H), 4.81(m, 1H), 6.22(d, J=3.0 Hz, 1H), 6.31(m, 1H), 6.66(d, J=7.6 Hz, 1H), 6.85(d, J=8.2 Hz, 1H), 6.95(m, 1H), 7.25–7.31(m, 2H), 7.37(m, 1H)

EXAMPLE 64

Preparation of (s)-1-furfurylthio-3-[(s)-4-methyl-2-(2,3,4-trifluorobenzoylamino)valerylamino]-2-heptanone (Compd. No. 126 in Table 1)

mp: 101°–102° C. IR(KBr, cm$^{-1}$): 3288 1732, 1660, 1637 NMR(CDCl$_3$, δ): 0.83(t, J=6.8 Hz, 3H), 0.98(d, J=6.1 Hz, 3H), 0.99(d, J=6.1 Hz, 3H), 1.17–1.40(m, 4H), 1.47–1.82(m, 4H), 1.91(m, 1H), 3.27(d, J=15 Hz, 1H), 3.35(d, J=15 Hz, 1H), 3.73(s, 2H), 4.70(m, 1H), 4.80(m, 1H), 6.22(d, J=3.1 Hz, 1H), 6.30(m, 1H), 6.61(d, J=6.0 Hz, 1H), 6.91(d, J=9.0 Hz, 0.5H), 6.95(d, J=9.0 Hz, 0.5H), 7.11(m, 1H), 7.36(m, 1H), 7.83(m, 1H)

EXAMPLE 65

Preparation of (s)-1-furfurylthio-3-[(s)-4-methyl-2-(2, 3, 6-trifluorobenzoylamino)valerylamino]-2-heptanone (Compd. No. 128 in Table 1)

mp: 116°–117° C. IR(KBr, cm$^{-1}$): 3281 1734, 1647 NMR(CDCl$_3$, δ): 0.88(t, J=6.8 Hz, 3H), 0.99(d, J=4.9 Hz,

6H), 1.18–1.42(m, 4H), 1.50–1.82(m, 4H), 1.92(m, 1H), 3.27(d, J=15 Hz, 1H), 3.35(d, J=15 Hz, 1H), 3.73(s, 2H), 4.71(m, 1H), 4.81(m, 1H), 6.22(d, J=3.2 Hz, 1H), 6.30(m, 1H), 6.48(d, J=7.9 Hz, 1H), 6.64(d, J=7.3 Hz, 1H), 6.92(m, 1H), 7.25(m, 1H), 7.36(m, 1H)

EXAMPLE 66

Preparation of (s)-1-furfurylthio-3-[(s)-4-methyl-2-(3,4,5-trifluorobenzoylamino)valerylamino]-2-heptanone (Compd. No. 130 in Table 1)

IR(KBr, cm$^{-1}$): 3298, 1716, 1639 NMR(CDCl$_3$, δ): 0.83 (t, J=6.7 Hz, 3H), 0.98(d, J=6.7 Hz, 6H), 1.13–1.39(m, 4H), 1.47–1.80(m, 4H), 1.91(m, 1H), 3.27(d, J=15 Hz, 1H), 3.35(d, J=15 Hz, 1H), 3.73(s, 2H), 4.70(m, 1H), 4.78(m, 1H), 6.22(d, J=2.9 Hz, 1H), 6.30(m, 1H), 6.92(d, J=7.6 Hz, 1H), 7.35(m, 1H), 7.41–7.59(m, 3H)

EXAMPLE 67

Preparation of (s)-1-furfurylthio-3-[(s)-4-methyl-2-(2,3,4,5-tetrafluorobenzoylamino)valerylamino]-2-heptanone (Compd. No. 132 in Table 1)

mp: 107°–108° C. IR(KBr, cm$^{-1}$): 3277, 1705, 1641 NMR(CDCl$_3$, δ): 0.84(t, J=7.0 Hz, 3H), 0.98(d, J=5.9 Hz, 6H), 1.15–1.38(m, 4H), 1.43–1.80(m, 4H), 1.90(m, 1H), 3.27(d, J=15 Hz, 1H), 3.35(d, J=15 Hz, 1H), 3.73(s, 2H), 4.67(m, 1H), 4.81(m, 1H), 6.22(d, J=3.3 Hz, 1H), 6.30(m, 1H), 6.57(d, J=7.6 Hz, 1H), 6.99(d, J=8.0 Hz, 0.5H), 7.03(d, J=8.0 Hz, 0.5H), 7.36(m, 1H), 7.70(m, 1H)

EXAMPLE 68

Preparation of (s)-1-furfurylthio-3-((s)-4-methyl-2-pentafluorobenzoylaminovalerylamino)-2-heptanone (Compd. No. 135 in Table 1)

IR(KBr, cm$^{-1}$): 3287, 1714, 1653 NMR(CDCl$_3$, δ): 0.87 (t, J=6.7 Hz, 3H), 0.98(d, J=5.4 Hz, 6H), 1.12–1.39(m, 4H), 1.45–1.79(m, 4H), 1.80–1.98(m, 1H), 3.31(s, 2H), 3.72(s, 1H), 4.63–4.84(m, 2H), 6.21(d, J=3.2 Hz, 1H), 6.30(m, 1H), 6.68(d, J=7.8 Hz, 1H), 6.88(d, J=8.3 Hz, 1H), 7.35(m, 1H)

EXAMPLE 69

Preparation of (s)-1-furfurylthio-3-[(s)-4-methyl-2-(2-toluoylamino)valerylamino]-2-heptanone (Compd. No. 140 in Table 1)

mp: 118°–119° C. IR(KBr, cm$^{-1}$): 3275, –1 1734, 1635 NMR(CDCl$_3$, δ): 0.86(t, J=6.9 Hz, 3H), 0.99(d, J=5.7 Hz, 6H), 1.17–1.40(m, 4H), 1.44–1.80(m, 4H), 1.91(m, 1H), 2.44(s, 3H), 3.72(d, J=15 Hz, 1H), 3.35(d, J=15 Hz, 1H), 3.74(s, 2H), 4.65(m, 1H), 4.80(m, 1H), 6.15(d, J=8.2 Hz, 1H), 6.22(d, J=3.3 Hz, 1H), 6.30(m, 1H), 6.73(d, J=8.3 Hz, 1H), 7.17–7.41(m, 5H)

EXAMPLE 70

Preparation of (s)-1-furfurylthio-3-[(s)-4-methyl-2-(3-toluoylamino)valerylamino]-2-heptanone (Compd. No. 141 in Table 1)

mp: 123°–126° C. IR(KBr, cm$^{-1}$): 3285, 1732, 1635 NMR(CDCl$_3$, δ): 0.82(t, J=6..8 Hz, 3H), 0.98(d, J=5.9 Hz, 6H), 1.15–1.38(m, 4H), 1.56(m, 1H), 1.62–1.99(m, 4H), 2.39(s, 3H), 3.27(d, J=15 Hz, 3H), 3.35(d, J=15 Hz, 3H), 3.73(s, 2H), 4.65–4.81(m, 2H), 6.22(d, J=3.0 Hz, 1H), 6.30(m, 1H), 6.56(d, J=8.3 Hz, 1H), 6.77(d, J=7.7 Hz, 1H), 7.28–7.34(m, 2H), 7.36(m, 1H), 7.55–7.62(m, 2H)

EXAMPLE 71

Preparation of (s)-1-furfurylthio-3-[(s)-4-methyl-2-(4-toluoylamino)valerylamino]-2-heptanone (Compd. No. 142 in Table 1)

mp: 122°–123° C. IR(KBr, cm$^{-1}$); 3292, 1732, 1657 NMR(CDCl$_3$, δ): 0.81(t, J=6.7 Hz, 3H), 0.97(d, J=5.6 Hz, 6H), 1.17–1.37(m, 4H), 1.43–1.98(m, 5H), 2.39(s, 3H), 3.27(d, J=15 Hz, 1H), 3.35(d, J=15 Hz, 1H), 3.73(s, 2H), 4.65–4.81(m, 2H), 6.22(d, J=3.2 Hz, 1H), 6.30(m, 1H), 6.52(d, J=8.0 Hz, 1H), 6.75(d, J=7.6 Hz, 1H), 7.24(d, J=8.1 Hz, 2H), 7.36(m, 1H), 7.67(d, J=8.1 Hz, 2H)

EXAMPLE 72

Preparation of (s)-1-furfurylthio-3-[(s)-4-methyl-2-(2-trifluoromethylbenzoylamino)valerylamino]-2-heptanone (Compd. No. 143 in Table 1)

mp: 102°–106° C. IR(KBr, cm$^{-1}$): 3283, 1734, 1641, 1604 NMR(CDCl$_3$, δ): 0.87(t, J=6.9 Hz, 3H), 0.98(d, J=5.8 Hz, 6H), 1.18–1.39(m, 4H), 1.43–2.0(m, 5H), 3.27(d, J=15 Hz, 1H), 3.35(d, J=15 Hz, 1H), 3.72(s, 2H), 4.62–4.81(m, 2H), 6.21(d, J=3.2 Hz, 1H), 6.29(m, 1H), 6.51(d, J=8.4 Hz, 1H), 6.89(d, J=7.6 Hz, 1H), 7.35(m, 1H), 7.43–7.62(m, 3H), 7.69(dd, J=9.0 Hz, 2.4 Hz, 1H)

EXAMPLE 73

Preparation of (s)-1-furfurylthio-3-[(s)-4-methyl-2-(4-trifluoromethylbenzoylamino)valerylamino]-2-heptanone (Compd. No. 145 in Table 1)

mp: 121°–123° C. IR(KBr, cm$^{-1}$): 3289, 1732, 1657, 1639 NMR(CDCl$_3$, δ): 0.83(t, J=6.8 Hz, 3H), 0.97(d, J=6.0 Hz, 6H), 1.17–1.39(m, 4H), 1.43–1.82(m, 4H), 1.87(m, 1H), 3.28(d, J=15 Hz, 1H), 3.35(d, J=15 Hz, 1H), 3.74(s, 2H), 4.63–4.84(m, 2H), 6.22(d, J=3.1 Hz, 1H), 6.30(m, 1H), 6.61(d, J=7.3 Hz, 1H), 6.75(d, J=7.9 Hz, 1H), 7.36(m, 1H), 7.69(d, J=8.4 Hz, 2H), 7.89(d, J=8.4 Hz, 2H)

EXAMPLE 74

Preparation of (s)-3-[(s)-2-(2-fluoro-6-trifluoromethylbenzoylamino)-4-methylvalerylamino]-1-furfurylthio-2-heptanone (Compd. No. 146 in Table 1)

mp: 106°–107° C. IR(KBr, cm$^{-1}$): 3266, 1720, 1641 NMR(CDCl$_3$, δ): 0.83(t, J=6.7 Hz, 3H), 0.99(d, J=5.0 Hz, 6H), 1.15–1.39(m, 4H), 1.47–2.02(m, 5H), 3.27(d, J=15 Hz, 1H), 3.35(d, J=15 Hz, 1H), 3.73(s, 2H), 4.60–4.80(m, 2H), 6.22(d, J=3.1 Hz, 1H), 6.30(m, 1H), 6.60(d, J=7.7 Hz, 1H), 7.13(dd, J=8.0 Hz, 7.7 Hz, 1H), 7.20–7.36(m, 1H), 7.37(m, 1H), 7.75(m, 1H), 8.38(dd, J=6.7 Hz, 1.9 Hz, 1H)

EXAMPLE 75

Preparation of (s)-3-[(s)-2-(2-fluoro-4-trifluoromethylbenzoylamino)-4-methylvalerylamino]-1-furfurylthio-2-heptanone (Compd. No. 148 in Table 1)

mp: 102°–106° C. IR(KBr, cm$^{-1}$); 3289, 1732, 1643 NMR(CDCl$_3$, δ): 0.83(t, J=6.8 Hz, 3H), 0.97(d, J=6.0 Hz, 6H), 1.17–1.39(m, 4H), 1.45–2.0(m, 5H), 3.28(d, J=15 Hz,

1H), 3.36(d, J=15 Hz, 1H), 3.73(s, 2H), 4.63–4.84(m, 2H), 6.22(m, 1H), 6.30(m, 1H), 6.71(d, J=7.7 Hz, 1H), 7.13(dd, J=11 Hz, 8.0 Hz, 1H), 7.36(m, 1H), 7.42(d, J=11 Hz, 1H), 7.53(dd, J=8.0 Hz, 0.8 Hz, 1H), 8.18(dd, J=7.9 Hz, 7.6 Hz, 1H)

EXAMPLE 76

Preparation of (s)-3-[(s)-2-(4-fluoro-3-trifluoromethylbenzoylamino)-4-methylvalerylamino]-1-furfurylthio-2-heptanone (Compd. No. 149 in Table 1)

mp: 112°–114° C. IR(KBr, cm$^{-1}$): 3297, 1715, 1642 NMR(CDCl$_3$, δ): 0.82(t, J=6.7 Hz, 3H), 0.98(d, J=5.2 Hz, 6H), 1.15–1.40(m, 4H), 1.45–1.81(m, 4H), 1.87(m, 1H), 3.28(d, J=15 Hz, 1H), 3.35(d, J=15 Hz, 1H), 3.74(s, 2H), 4.62–4.83(m, 2H), 6.22(d, J=3.3 Hz, 1H), 6.30(m, 1H), 6.64(d, J=7.1 Hz, 1H), 6.93(d, J=6.5 Hz, 1H), 7.27(m, 1H), 7.36(m, 1H), 7.99(m, 1H), 8.05(dd, J=6.7 Hz, 4.8 Hz, 1H)

EXAMPLE 77

Preparation of (s)-1-furfurylthio-3-[(s)-2-(2-methoxybenzoylamino)-4-methylvalerylamino]-2-heptanone (Compd. No. 151 in Table 1)

mp: 77°–78° C. IR(KBr, cm$^{-1}$): 3306, 2953, 1732, 1660, 1630, 1601 NMR(CDCl$_3$, δ): 0.77(t, J=6.8 Hz, 3H), 0.96(d, J=6.1 Hz, 3H), 0.98(d, J=6.1 Hz, 3H), 1.17–1.37(m, 4H), 1.45–1.99(m, 5H), 3.27(d, J=15 Hz, 1H), 3.35(d, J=15 Hz, 1H), 3.72(s, 2H), 3.97(s, 3H), 4.65–4.78(m, 2H), 6.22(d, J=3.2 Hz, 1H), 6.29(m, 1H), 6.95–7.04(m, 2H), 7.09(d, J=7.3 Hz, 0.5H), 7.13(d, J=7.3 Hz, 0.5H), 7.35(m, 1H), 7.46(d, J=7.3 Hz, 0.5H), 7.50(d, J=7.3 Hz, 0.5H), 8.17(dd, J=7.8 Hz, 1.9 Hz, 2H)

EXAMPLE 78

Preparation of (s)-1-furfurylthio-3-[(s)-2-(3-methoxyphenoxyacetylamino)-4-methylvalerylamino]-2-heptanone (Compd. No. 103 in Table 1)

IR(neat, cm$^{-1}$): 3288, 1730, 1651, 1602 NMR(CDCl$_3$, δ): 0.86(t, J=6.8 Hz, 3H), 0.93(d, J=5.9 Hz, 6H), 1.17–1.40(m, 4H), 1.47–1.80(m, 4H), 1.83(m, 1H), 3.27(d, J=15 Hz, 1H), 3.35(d, J=15 Hz, 1H), 3.73(s, 2H), 3.79(s, 3H), 4.47(d, J=10 Hz, 1H), 4.52(d, J=10 Hz, 1H), 4.63(m, 1H), 4.78(m, 1H), 6.22(d, J=3.2 Hz, 1H), 6.29(m, 1H), 6.50–6.65(m, 3H), 7.01(t, J=8.7 Hz, 2H), 7.20(t, J=8.7 Hz, 1H), 7.35(m, 1H)

EXAMPLE 79

Preparation of (s)-1-furfurylthio-3-[(s)-2-(4-methoxybenzoylamino)-4-methylvalerylamino]-2-heptanone (Compd. No. 153 in Table 1)

mp: 124° C. IR(KBr, cm$^{-1}$); 3291, 1732, 1655, 1624 NMR(CDCl$_3$, δ): 0.81(t, J=6.1 Hz, 3H), 0.98(d, J=5.0 Hz, 6H), 1.15–1.35(m, 4H), 1.45–1.95(m, 5H), 3.27(d, J=15 Hz, 1H), 3.36(d, J=15 Hz, 1H), 3.73(s, 2H), 3.85(s, 3H), 4.63–4.80(m, 2H), 6.23(m, 1H), 6.30(m, 1H), 6.46(d, J=8.7 Hz, 1H), 6.75(d, J=7.5 Hz, 1H), 6.92(d, J=8.8 Hz, 2H), 7.36(m, 1H), 7.75(d, J=8.8 Hz, 2H)

EXAMPLE 80

Preparation of (s)-3-[(s)-2-(3,5-dimethoxybenzoylamino)-4-methylvalerylamino]-1-furfurylthio-2-heptanone (Compd. No. 155 in Table 1)

IR(KBr, cm$^{-1}$): 3279, 1713, 1636 NMR(CDCl$_3$, δ): 0.82 (t, J=6.8 Hz, 3H), 0.97(d, J=5.7 Hz, 6H), 1.17–1.39(m, 4H), 1.45–1.81(m, 4H), 1.89(m, 1H), 3.27(d, J=15 Hz, 1H), 3.35(d, J=15 Hz, 1H), 3.73(s, 2H), 3.82(s, 6H), 4.62–4.82(m, 2H), 6.22(d, J=3.2 Hz, 1H), 6.30(m, 1H), 6.55(d, J=6.8 Hz, 1H), 6.57(m, 1H), 6.73(d, J=6.9 Hz, 1H), 6.89(m, 2H), 7.35(m, 1H)

EXAMPLE 81

Preparation of (s)-1-furfurylthio-3-[(s)-2-(4-methoxycarbonylbenzoylamino)-4-methylvalerylamino]-2-heptanone (Compd. No. 157 in Table 1)

mp: 100°–102° C. IR(KBr, cm$^{-1}$): 3279, 1726, 1662, 1637 NMR(CDCl$_3$, δ): 0.82(t, J=6.7 Hz, 3H), 0.98(d, J=5.8 Hz, 6H), 1.18–1.40(m, 4H), 1.50–1.64(m, 1H), 1.64–2.0(m, 4H), 3.27(d, J=15 Hz, 1H), 3.36(d, J=15 Hz, 1H), 3.74(s, 2H), 3.95(s, 3H), 4.67–4.83(m, 2H), 6.22(d, J=3.2 Hz, 1H), 6.30(m, 1H), 6.75(d, J=7.7 Hz, 1H), 6.81(d, J=8.3 Hz, 1H), 7.36(m, 1H), 7.84(d, J=8.3 Hz, 2H), 8.09(d, J=8.3 Hz, 2H)

EXAMPLE 82

Preparation of (s)-1-furfurylthio-3-[(s)-4-methyl-2-(2-naphtoylamino)valerylamino]-2-heptanone (Compd. No. 162 in Table 1)

mp: 97°–99° C. IR(KBr, cm$^{-1}$); 3270, 1700, 1650, 1620 NMR(CDCl$_3$, δ): 0.77(t, J=6.8 Hz, 3H), 1.0(d, J=4.8 Hz, 6H), 1.15–2.0(m, 9H), 3.23–3.40(m, 2H), 3.66(s, 0.7H), 3.73(s, 1.3H), 4.70–4.96(m, 2H), 6.21(d, J=3.0 Hz, 1H), 6.29(m, 1H), 6.87–7.17(m, 2H), 7.21–7.40(m, 1H), 7.47–7.63(m, 2H), 7.76–8.0(m, 4H), 8.29(s, 1H)

EXAMPLE 83

Preparation of (s)-1-furfurylthio-3-[(s)-4-methyl-2-(1-naphtoylamino)valerylamino]-2-heptanone (Compd. No. 161 in Table 1)

mp: 81°–83° C. IR(KBr, cm$^{-1}$): 3270, 1720, 1650, 1630 NMR(CDCl$_3$, δ): 0.87–0.95(m, 3H), 1.01(d, J=6.3 Hz, 3H), 1.04(d, J=6.3 Hz, 3H), 1.17–2.0(m, 9H), 3.25–3.39(m, 2H), 3.71(s, 0.7H), 3.74(s, 1.3H), 4.75–4.93(m, 2H), 6.19(d, J=3.3 Hz, 0.4H), 6.23(d, J=3.3 Hz, 0.6H), 6.27–6.31(m, 1H), 6.44(d, J=8 Hz, 1H), 6.85(d, J=7 Hz, 0.6H), 6.98(d, J=7 Hz, 0.4H), 7.30–7.40(m, 1H), 7.41–7.70(m, 4H), 7.92–8.0(m, 2H), 8.27–8.39(m, 1H)

EXAMPLE 84

Preparation of (s)-1-furfurylthio-3-[(s)-2-(4-methoxycinnamoylamino)-4-methylvalerylamino]-2-heptanone (Compd. No. 165 in Table 1)

IR(KBr, cm$^{-1}$): 3269, 1715, 1647, 1603 NMR(CDCl$_3$, δ): 0.81(t, J=6.7 Hz, 3H), 0.95(d, J=4.6 Hz, 6H), 1.17–1.38(m, 4H), 1.46–1.79(m, 4H), 1.87(m, 1H), 3.27(d, J=15 Hz, 1H), 3.35(d, J=15 Hz, 1H), 3.73(s, 2H), 3.80(s, 3H), 4.67–4.84(m, 2H), 6.21(d, J=3.1 Hz, 1H), 6.28(m, 1H), 6.36(d, J=16 Hz, 1H), 6.69(d, J=8.4 Hz, 1H), 6.83(d, J=8.7 Hz, 2H), 7.26(d, a=6.9 Hz, 1H), 7.35(m, 1H), 7.41(d, J=8.7 Hz, 2H), 7.57(d, J=16 Hz, 1H)

EXAMPLE 85

Preparation of (s)-3-[(s)-2-(2,4-dimethoxycinnamoylamino)-3-methylvalerylamino]-1-furfurylthio-2-heptanone (Compd. No. 166 in Table 1)

IR(KBr, cm$^{-1}$): 3270, 1718, 1645, 1604 NMR(CDCl$_3$, δ): 0.86(t, J=8.6 Hz, 3H), 0.96(d, J=5.6 Hz, 6H), 1.17–1.38(m,

4H), 1.45–1.79(m, 4H), 1.84(m, 1H), 3.27(d, J=15 Hz, 1H), 3.35(d, J=15 Hz, 1H), 3.73(s, 2H), 3.83(s, 3H), 3.84(s, 3H), 4.63–4.82(m, 2H), 6.18(d, J=6.8 Hz, 1H), 6.22(d, J=3.0 Hz, 1H), 6.29(m, 1H), 6.40–6.58(m, 3H), 7.01(d, J=6.4 Hz, 1H), 7.31–7.42(m, 2H), 7.79(d, J=16 Hz, 1H)

EXAMPLE 86

Preparation of (s)-3-[(s)-2-(1-acetyl-4-piperidylcarbonylamino)-4-methylvalerylamino]-1-furfurylthio-2-heptanone (Compd. No. 168 in Table 1)

mp: 110°–112° C. IR(KBr, cm$^{-1}$): 3300, 1715, 1640 NMR(CDCl$_3$, δ): 0.81–1.01(m, 9H), 1.19–1.39(m, 4H), 1.47–1.78(m, 6H), 1.78–1.97.(m, 3H), 2.09(s, 3H), 2.42(m, 1H), 2.67(m, 1H), 3.09(m, 1H), 3.29(d, J=15 Hz, 1H), 3.34(d, J=15 Hz, 1H), 3.72(s, 2H), 3.86(d, J=13 Hz, 1H), 4.45–4.62(m, 2H), 4.68(m, 1H), 6.22(d, J=3.0 Hz, 1H), 6.29(m, 1H), 6.71(d, J=6.2 Hz, 1H), 7.20(d, J=7.4 Hz, 1H), 7.35(m, 1H)

EXAMPLE 87

Preparation of (s)-3-[(s)-2-(1-tert-butoxycarbonyl-4-piperidylcarbonylamino)-4-methylvalerylamino]-1-furfurylthio-2-heptanone (Compd. No. 171 in Table 1)

IR(KBr, cm$^{-1}$): 3289, 1698, 1640 NMR(CDCl$_3$, δ): 0.78–1.02(m, 9H), 1.13–1.71(m, 10H), 1.45(s, 9H), 1.71–1.97(m, 3H), 2.30(m, 1H), 2.61–2.83(m, 2H), 3.28(d, J=15 Hz, 1H), 3.33(d, J=15 Hz, 1H), 3.72(s, 2H), 4.0–4.22(m, 2H), 4.52(m, 1H), 4.69(m, 1H), 6.22(m, 1H), 6.29(m, 1H), 6.43(d, J=8.3 Hz, 1H), 7.05(d, J=7.6 Hz, 1H), 7.35(m, 1H)

EXAMPLE 88

Preparation of (s)-1-furfurylthio-3-[(s)-4-methyl-2-(4-piperidylcarbonylamino)valerylamino]-2-heptanone Hydrochloride (Compd. No. 172 in Table 1)

IR(KBr, cm$^{-1}$): 3350, 3250, 1700, 1660, 1635 NMR (CD$_3$OD, δ): 0.81–1.05(m, 9H), 1.21–1.43(m, 4H), 1.50–1.78(m, 5H), 1.78–2.17(m, 4H), 2.64(m, 1H), 2.95–3.17(m, 2H), 3.24–3.57(m, 4H), 3.72(s, 2H), 4.39(dd, J=7.0 Hz, 7.0 Hz, 1H), 4.55(dd, J=9.4 Hz, 4.3 Hz, 1H), 6.22(d, J=2.7 Hz, 1H), 6.32(m, 1H), 7.41(m, 1H)

EXAMPLE 89

Preparation of (s)-1-furfurylthio-3-((s)-4-methyl-2-nicotinoylaminovalerylamino)-2-heptanone (Compd. No. 176 in Table 1)

IR(neat, cm$^{-1}$): 3280, 1715, 1660, 1630 NMR(CDCl$_3$, δ): 0.80(t, J=7.0 Hz, 3H), 0.94(d, J=6.7 Hz, 6H), 1.12–1.39(m, 4H), 1.51(m, 1H), 1.67–1.80(m, 3H), 1.84(m, 1H), 3.29(d, J=15 Hz, 1H), 3.35(d, J=15 Hz, 1H), 3.73(s, 2H), 4.70–4.84(m, 2H), 6.22(d, J=3.2 Hz, 1H), 6.30(m, 1H), 6.98(d, J=7.7 Hz, 1H), 7.17(d, J=8.0 Hz, 1H), 7.30–7.42(m, 2H), 8.11(dd, J=8.0 Hz, 1.9 Hz, 1H), 8.73(dd, J=4.8 Hz, 1.6 Hz, 1H), 9.04(d, J=1.9 Hz, 1H)

EXAMPLE 90

Preparation of (s)-3-((s)-2-isonicotinoylamino-4-methylvalerylamino)-1-furfurylthio-2-heptanone (Compd. No. 177 in Table 1)

IR(neat, cm$^{-1}$): 3280, 1715, 1630 NMR(CDCl$_3$, δ): 0.81 (t, J=6.7 Hz, 3H), 0.92(d, J=4.0 Hz, 6H), 1.15–1.39(m, 5H), 1.59(m, 1H), 1.64–1,98(m, 3H), 3.33(s, 2H), 3.73(s, 2H), 4.68–4.95(m, 2H), 6.22(d, J=3.2 Hz, 1H), 6.30(m, 1H), 7.35(d, J=1.9 Hz, 1H), 7.43(d, J=6.7 Hz, 1H), 7.58–7.71(m, 2H), 7.81(d, J=7.5 Hz, 1H), 8.65–8.69(m, 2H)

EXAMPLE 91

Preparation of (s)-3-[(s)-2-(2-benzofuranylcarbonylamino)-4-methylvalerylamino]-1-furfurylthio-2-heptanone (Compd. No. 180 in Table 1)

IR(neat, cm$^{-1}$): 3300, 1710, 1640 NMR(CDCl$_3$, δ): 0.81 (t, J=6.9 Hz, 2.2H), 0.89(t, J=6.9 Hz, 0.8H), 1.0(d, J=6.5 Hz, 6H),-1.10–1.99(m, 9H), 3.23–3.40(m, 2H), 3.70(d, J=5.4 Hz, 0.5H), 3.73(s, 1.5H), 4.76–4.93(m, 2H), 6, 18(m, 1H), 6, 30(m, 1H), 6.70(d, J=7 Hz, 0.75H), 6.76(d, J=7 Hz, 0.25H), 7.05(d, J=8 Hz, 1H), 7.25–7.59(m, 5H), 7.67(d, J=7.4 Hz, 1H)

EXAMPLE 92

Preparation of (s)-3-[(s)-2-(3-benzofuranylcarbonylamino)-4-methylvalerylamino]-1-furfurylthio-2-heptanone (Compd. No. 181 in Table 1)

mp: 113°–116° C. IR(KBr, cm$^{-1}$): 3300, 1710, 1630 NMR(CDCl$_3$, δ): 0.77(t, J=6.7 Hz, 3H), 0.83–1.02(m, 6H), 1.07–1.38(m, 5H), 1.41–1.63(m, 1H), 1.63–1.97(m, 3H), 3.30(d, J=15 Hz, 1H), 3.35(d, J=15 Hz, 1H), 3.72(s, 2H), 4.70(m, 1H), 4.80(dt, J=7.1 Hz, 7.0 Hz, 1H), 6.21(d, J=3.1 Hz, 1H), 6.28(m, 1H), 7.21–7.38(m, 4H), 7.38–7.57(m, 2H), 7.93(m, 1H), 8.23(d, J=1.4 Hz, 1H)

EXAMPLE 93

Preparation of (s)-3-[(s)-2-(7-fluoro-2-benzofuranylcarbonylamino)-4-methylvalerylamino]-1-furfurylthio-2-heptanone (Compd. No. 182 in Table 1)

mp: 102°–103° C. IR(KBr, cm$^{-1}$): 3270, 1700, 1650 NMR(CDCl$_3$, δ): 0.79(t, J=6.8 Hz, 3H), 0.98(d, J=4.9 Hz, 6H), 1.18–1.40(m, 4H), 1.60(m, 1H), 1.64–1.97(m, 4H), 3.32(d, J=15 Hz, 1H), 3.40(d, J=15 Hz, 1H), 3.75(s, 2H), 4.75–4.95(m, 2H), 6.23(d, J=3.1 Hz, 1H), 6.29(m, 1H), 7.08–7.35(m, 5H), 7.37(s, 1H), 7.42(dd, J=7.5 Hz, 1.1 Hz, 1H)

EXAMPLE 94

Preparation of (s)-1-furfurylthio-3-[(s)-4-methyl-2-(4-oxo-4H-1-benzopyranylcarbonylamino) valerylamino]-2-heptanone (Compd. No. 188 in Table 1)

mp: 114°–115° C. IR(KBr, cm$^{-1}$): 3350, 3250, 1705, 1660, 1625 NMR(CDCl$_3$, δ): 0.84(t, J=6.8 Hz, 3H), 1.0(d, J=9.2 Hz, 6H), 1.15–2.0(m, 9H), 3.30(d, J=15 Hz, 1H), 3.38(d, J=15 Hz, 1H), 3.75(s, 2H), 4.69(m, 1H), 4.82(m, 1H), 6.23(d, J=2.9 Hz, 1H), 6.31(m, 1H), 6.61(d, J=8 Hz, 1H), 7.16(s, 1H), 7.36–7.55(m, 3H), 7.57(d, J=14 Hz, 1H), 7.72–7.80(m, 1H), 8.22(dd, J=1.6 Hz, 7.9 Hz, 1H)

EXAMPLE 95

Preparation of (s)-3-((2s, 3s)-2-benzyloxycarbonylamino-3-methylvalerylamino)-1-furfurylthio-2-heptanone (Compd. No. 205 in Table 1)

mp: 101°–103° C. IR(KBr, cm$^{-1}$): 3300, 3250, 1705, 1680, 1640 NMR(CDCl$_3$, δ): 0.83–1.10(m, 9H), 1.07–1.39

(m, 3H), 1.42–1.78(m, 4H), 1.82–2.01(m, 2H), 3.26(d, J=15 Hz, 1H), 3.34(d, J=15 Hz, 1H), 3.71(s, 2H), 4.05(dt, J=8.0 Hz, 6.4 Hz, 1H), 4.80(m, 1H), 5.12(s, 2H), 5.30(d, J=7.7 Hz, 1H), 6.22(d, J=3.3 Hz, 1H), 6.30(m, 1H), 6.43(d, J=8.0 Hz, 1H), 7.30–7.41(m, 6H)

EXAMPLE 96

Preparation of (s)-3-((s)-2-benzyloxycarbonylaminohexanoylamino)-1-furfurylthio-2-heptanone (Compd. No. 206 in Table 1)

mp: 95°–97° C. IR(KBr, cm$^{-1}$): 3280, 1730, 1690, 1650 NMR(CDCl$_3$, δ): 0.82–0.99(m, 6H), 1.12–1.45(m, 8H), 1.49–1.65(m, 2H), 1.75–1.99(m, 2H), 3.27(d, J=15 Hz, 1H), 3.34(d, J=15 Hz, 1H), 3.71(s, 2H), 4.16(td, J=7.3 Hz, 6.4 Hz, 1H), 4.76(m, 1H), 5.12(s, 2H), 5.26(d, J=7.9 Hz, 1H), 6.21(d, J=3.1 Hz, 1H), 6.29(m, 1H), 6.56(d, J=6.4 Hz, 1H), 7.29–7.39(m, 6H)

EXAMPLE 97

Preparation of (s)-3-( (s)-2-benzyloxycarbonylamino-3-phenylpropionylamino)-1-furfurylthio-2-heptanone (Compd. No. 208 in Table 1)

mp: 123°–124° C. IR(KBr, cm$^{-1}$): 3300, 1720, 1710, 1680, 1640 NMR(CDCl$_3$, δ): 0.85(t, J=6.9 Hz, 3H), 1.0–1.38(m, 2H), 1.51(m, 1H), 1.61–1.69(m, 2H), 1.83(m, 1H), 3.03(dd, J=14 Hz, 7.0 Hz, 1H), 3.15(dd, J=14 Hz, 7.0 Hz, 1H), 3.15(d, J=15 Hz, 1H), 3.22(d, J=15 Hz, 1H), 3.67(s, 2H), 4.45(td, J=6.9 Hz, 6.9 Hz, 1H), 4.70(m, 1H), 5.09(s, 2H), 5.27(d, J=5.6 Hz, 1H), 6.21(d, J=3.0 Hz, 1H), 6.29(m, 1H), 6.40(d, J=6.9 Hz, 1H), 7.09–7.21(m, 2H), 7.21–7.42(m, 9H)

EXAMPLE 98

Preparation of (s)-3-((s)-2-benzyloxycarbonylamino-3-tert-butoxypropionylamino)-1-furfurylthio-2-heptanone (Compd. No. 210 in Table 1)

mp: 71°–73° C. IR(KBr, cm$^{-1}$): 3300, 1720, 1690, 1660, 1640 NMR(CDCl$_3$, δ): 0.88(t, J=6.8 Hz, 3H), 1.16(s, 9H), 1.24–1.41(m, 4H), 1.59(m, 1H), 1.91(m, 1H), 3.24(d, J=15 Hz, 1H), 3.30(d, J=15 Hz, 1H), 3.42(dd, J=7.2 Hz, 7.2 Hz, 1H), 3.71(s, 2H), 3.84(m, 1H), 4.26(m, 1H), 4.77(m, 1H), 5.10(d, J=12 Hz, 1H), 5.16(d, J=12 Hz, 1H), 5.71(d, J=5.1 Hz, 1H), 6.21(d, J=3.2 Hz, 1H), 6.29(m, 1H), 7.23(d, J=5.1 Hz, 1H), 7.35–7.41(m, 6H)

EXAMPLE 99

Preparation of (s)-3-((s)-2-benzyloxycarbonylamino-4-tert-butoxycarbonylpropionylamino)-1-furfurylthio-2-heptanone (Compd. No. 213 in Table 1)

mp: 77°–78° C. IR(KBr, cm$^{-1}$): 3300, 1720, 1690, 1650 NMR(CDCl$_3$, δ): 0.88(t, J=6.8 Hz, 3H), 1.18–1.38(m, 4H), 1.43(s, 9H), 1.58(m, 1H), 1.84(m, 1H), 2.62(dd, J=17 Hz, 6.5 Hz, 1H), 2.96(dd, J=17 Hz, 4.1 Hz, 1H), 3.24(d, J=15 Hz, 1H), 3.32(d, J=15 Hz, 1H), 3.71(s, 2H), 4.54(m, 1H), 4.72(m, 1H), 5.15(s, 2H), 5.98(d, J=8.5 Hz, 1H), 6.22(d, J=2.3 Hz, 1H), 6.30(m, 1H), 7.10(d, J=7.0 Hz, 1H), 7.30–7.43(m, 6H)

EXAMPLE 100

Preparation of (s)-3-((s)-2-benzyloxycarbonylamino-4-tert-butoxycarbonylbutyrylamino)-1-furfurylthio-2-heptanone (Compd. No. 216 in Table 1)

mp: 78°–79° C. IR(KBr, cm$^{-1}$): 3300, 1730, 1710, 1690, 1650 NMR(CDCl$_3$, δ): 0.88(t, J=6.8 Hz, 3H), 1.18–1.39(m, 4H), 1.44(s, 9H), 1.50–1.70(m, 1H), 1.81–2.17(m, 3H), 2.31–2.49(m, 2H), 3.26(d, J=15 Hz, 1H), 3.29(d, J=15 Hz, 1H), 3.72(s, 2H), 4.25(dt, J=7.4 Hz, 6.8 Hz, 1H), 4.75(m, 1H), 5.11(s, 2H), 5.73(d, J=6.8 Hz, 1H), 6.22(d, J=3.0 Hz, 1H), 6.29(m, 1H), 6.82(d, J=7.4 Hz, 1H), 7.27–7.39(m, 6H)

EXAMPLE 101

Preparation of (s)-3-((s)-2-benzyloxycarbonylamino-4-carboxybutyrylamino)-1-furfurylthio-2-heptanone (Compd. No. 217 in Table 1)

mp: 67°–71° C. IR(KBr, cm$^{-1}$): 3300, 1720, 1705, 1680, 1650 NMR(CDCl$_3$, δ): 0.81–0.98(m, 3H), 1.18–1.43(m, 4H), 1.60(m, 1H), 1.72–2.0(m, 2H), 2.10(m, 1H), 2.37(t, J=7.5 Hz, 2H), 3.23–3.37(m, 2H), 3.72(s, 2H), 4.15(dt, J=5.0 Hz, 3.9 Hz, 1H), 4.57(m, 1H), 5.08(s, 2H), 6.22(d, J=2.9 Hz, 1H), 6.31(m, 1H), 7.21–7.39(m, 5H), 7.40(m, 1H)

EXAMPLE 102

Preparation of (s)-3-((s)-2-benzyloxycarbonylamino-6-tert-butoxycarbonylaminohexanoylamino)-1-furfurylthio-2-heptanone (Compd. No. 220 in Table 1)

mp: 60°–63° C. IR(KBr, cm$^{-1}$): 3350, 1725, 1690, 1650 NMR(CDCl$_3$, δ): 0.87(t, J=6.7 Hz, 3H), 1.15–1.78(m, 10H), 1.41(s, 9H), 1.79–1.99(m, 2H), 2.97–3.18(m, 2H), 3.25(d, J=15 Hz, 1H), 3.35(d, J=15 Hz, 1H), 3.71(s, 2H), 4.18(m, 1H), 4.59–4.82(m, 2H), 5.10(s, 2H), 5.63(m, 1H), 6.22(d, J=2.9 Hz, 1H), 6.29(m, 1H), 6.78(d, J=7.8 Hz, 1H), 7.24–7.41(m, 6H)

EXAMPLE 103

Preparation of (s)-3-((s)-6-amino-2-benzyloxycarbonylaminoheptanoylamino)-1-furfurylthio-2-heptanone Hydrochloride (Compd. No. 221 in Table 1)

mp: 95° C.(dec.) IR(KBr, cm$^{-1}$): 3310, 1720, 1680, 1635 NMR(CDCl$_3$, δ): 0.85–1.05(m, 3H), 1.22–1.42(m, 4H), 1.42–2.0(m, 8H), 2.96(t, J=7.5 Hz, 2H), 3.44(s, 2H), 3.76(s, 2H), 4.18(dd, J=8.5 Hz, 5.8 Hz, 1H), 4.64(m, 1H), 5.14(s, 2H), 6.27(d, J=3.1 Hz, 1H), 6.37(m, 1H), 7.26–7.43(m, 5H), 7.46(m, 1H), 8.33(d, J=7.9 Hz, 1H)

EXAMPLE 104

Preparation of (s)-3-((s)-2-benzyloxycarbonylamino-2-phenylacetylamino)-1-furfurylthio-2-heptanone (Compd. No. 224 in Table 1)

mp: 144°–146° C. IR(KBr, cm$^{-1}$): 3300, 1710, 1640 NMR(CDCl$_3$, δ): 0.87(t, J=7.1 Hz, 3H), 1.07–1.39(m, 4H), 1.42–1.63(m, 1H), 1.81–1.99(m, 1H), 3.13(s, 2H), 3.54(d, J=15 Hz, 1H), 3.59(d, J=15 Hz, 1H), 4.71(m, 1H), 5.03(d, J=12 Hz, 1H), 5.11(d, J=12 Hz, 1H), 5.23(d, J=6.1 Hz, 1H), 6.07(d, J=6.3 Hz, 1H), 6.10(d, J=3.1 Hz, 1H), 6.21(m, 1H), 6.31(d, J=7.4 Hz, 1H), 7.24–7.43(m, 11H)

EXAMPLE 105

Preparation of (s)-3-((s)-2-benzyloxycarbonylamino-4-methylvalerylamino)-1-(2-pyridylmethylthio)-2-heptanone (Compd. No. 226 in Table 1)

IR(neat, cm$^{-1}$): 3304, 1711, 1658 NMR(CD$_3$OD, δ): 0.80–1.0(m, 9H), 1.16–1.40(m, 4H), 1.45–1.98(m, 5H), 3.25–3.40(m, 2H), 3.80(s, 2H), 4.15(m, 1H), 4.57(m, 1H), 5.07(s, 2H), 7.25–7.39(m, 6H), 7.42(d, J=7.8 Hz, 1H), 7.76(ddd, J=7.7 Hz, 7.7 Hz, 1.8 Hz, 1H), 8.44(m, 1H)

EXAMPLE 106

Preparation of (s)-3-((s)-2-benzyloxycarbonylamino-4-methylvalerylamino)-1-(3-pyridylmethylthio)-2-heptanone (Compd. No. 228 in Table 1)

IR(neat, cm$^{-1}$): 3409, 1717, 1653 NMR(CD$_3$OD, δ): 0.92–1.03(m, 9H), 1.18–1.43(m, 4H), 1.47–1.98(m, 5H), 3.36(d, J=15 Hz, 1H), 3.42(d, J=15 Hz, 1H), 3.94(s, 2H), 4.15(dd, J=7.6 Hz, 7.5 Hz, 1H), 4.48(dd, J=9.6 Hz, 4.4 Hz, 1H), 5.06(d, J=10 Hz, 1H), 5.11(d, J=10 Hz, 1H), 7.21–7.40 (m, 5H), 8.04(dd, J=8.0 Hz, 5.8 Hz, 1H), 8.62(d, J=8.0 Hz, 1H), 8.75(d, J=5.8 Hz, 1H), 8.83(s, 1H)

EXAMPLE 107

Preparation of (s)-3-((s)-2-benzyloxycarbonylamino-4-methylvalerylamino)-1-(4-pyridylmethylthio)-2-heptanone (Compd. No. 230 in Table 1)

IR(neat, cm$^{-1}$): 3300, 1720, 1705, 1660, 1600 NMR (CDCl$_3$, δ): 0.86(t, J=6.7 Hz, 3H), 0.91–0.95(m, 6H), 1.13–1.39(m, 5H), 1.41–1.78(m, 3H), 1.84(m, 1H), 3.11(d, J=15 Hz, 1H), 3.24(d, J=15 Hz, 1H), 3.63(s, 2H), 4.22(m, 1H), 4.75(m, 1H), 5.11(s, 2H), 5.38(d, J=8.0 Hz, 1H), 6.81(d, J=6.9 Hz, 1H), 7.15–7.31(m, 2H), 7.31–7.41(m, 5H), 8.45–8.60(m, 2H)

EXAMPLE 108

Preparation of (s)-3-((s)-2-benzyloxycarbonylamino-4-methylvalerylamino)-4-cyclohexyl-1-methylthio-2-butanone (Compd. No. 236 in Table 1)

mp: 83°–84° C. IR(KBr, cm$^{-1}$): 3320, 1684, 1648 NMR (CDCl$_3$, δ): 0.90–1.05(m, 8H), 1.05–1.88(m, 14H), 2.06(s, 3H), 3.20(d, J=14 Hz, 1H), 3.38(d, J=14 Hz, 1H), 4.18(m, 1H), 4.88(m, 1H), 5.12(s, 2H), 5.13(m, 1H), 6.43(d, J=7 Hz, 1H), 7.35(s, 5H)

EXAMPLE 109

Preparation of (s)-3-((s)-2-benzyloxycarbonylamino-4-methylvalerylamino)-4-cyclohexyl-1-furfurylthio-2-butanone (Compd. No. 238 in Table 1)

IR(neat, cm$^{-1}$): 3320, 1700, 1650 NMR(CDCl$_3$, δ): 0.78–1.0(m, 8H), 1.04–1.85(m, 14H), 3.24(d, J=13 Hz, 1H), 3.35(d, J=13 Hz, 1H), 3.71(s, 2H), 4.10(m, 1H), 4.78(m, 1H), 5.07(m, 1H), 5.12(s, 2H), 6.22(d, J=3.2 Hz, 1H), 6.30(m, 1H), 6.38(d, J=8 Hz, 1H), 7.35(s, 5H), 7.39(m, 1H)

EXAMPLE 110

Preparation of (s)-4-cyclohexyl-1-furfurylthio-3-((s)-4-methyl-2-phenoxyacetylaminovalerylamino)-2-butanone (Compd. No. 240 in Table 1)

IR(neat, cm$^{-1}$): 3310, 1710, 1650 NMR(CDCl$_3$, δ): 0.88–1.07(m, 8H), 1.07–1.88(m, 14H), 3.28(d, J=15 Hz, 1H), 3.36(d, J=15 Hz, 1H), 3.73(s, 2H), 4.53(s, 2H), 4.57(m, 1H), 4.80(m, 1H), 6.21(d, J=3.2 Hz, 1H), 6.32(m, 1H), 6.48(d, J=8 Hz, 1H), 6.87–6.99(m, 3H), 7.05(t, J=8 Hz, 1H), 7.30–7.40(m, 3H)

EXAMPLE 111

Preparation of (s)-3-((s)-2-benzyloxycarbonylamino-4-methylvalerylamino)-1-mercapto-4-phenyl-2-butanone (Compd. No. 242 in Table 1)

mp: 171° C. IR(KBr, cm$^{-1}$): 3320, 1720 1690 1655 NMR(CDCl$_3$, δ): 0.80–1.0(m, 6H), 1.30–1.70(m, 3H), 2.92 (dd, J=7.6 Hz, 14 Hz, 1H), 3.03–3.25(m, 2H), 3.38(d, J=15 Hz, 1H), 4.13(m, 1H), 4.85(m, 1H), 4.95–5.18(m, 2H), 5.25(m, 1H), 6.76(d, J=7 Hz, 1H), 7.05–7.45(m, 10H)

EXAMPLE 112

Preparation of (s)-3-((s)-2-tert-butoxycarbonylamino-4-methylvalerylamino)-1-methylthio-4-phenyl-2-butanone (Compd. No. 243 in Table 1)

mp: 117°–118° C. IR(KBr, cm$^{-1}$): 3360, 1705, 1660 NMR(CDCl$_3$, δ): 0.85–1.05(m, 6H), 1.25–1.70(m, 3H), 1.44(s, 9H), 1.98(s, 3H), 2.95–3.25(m, 4H), 4.04(m, 1H), 4.77(m, 1H), 5.06(m, 1H), 6.67(m, 1H), 7.15–7.38(m, 5H)

EXAMPLE 113

Preparation of (s)-3-((s)-2-benzyloxycarbonylamino-4-methylvalerylamino)-1-methylthio-4-phenyl-2-butanone (Compd. No. 244 in Table 1)

mp: 81°–91° C. IR(KBr, cm$^{-1}$): 3340, 3290, 1720, 1683, 1652 NMR(CDCl$_3$, δ): 0.89(d, J=5.8 Hz, 6H), 1.30–1.65(m, 3H), 1.99(s, 3H), 2.90–3.25(m, 4H), 4.10(m, 1H), 4.95–5.15 (m, 2H), 5.10(s, 2H), 6.55(m, 1H), 7.08–7.43(m, 10H)

EXAMPLE 114

Preparation of (s)-3-[(s)-N-methyl-2-(benzyloxycarbonylamino)-4-methylvalerylamino]-1-methylthio-4-phenyl-2-butanone (Compd. No. 245 in Table 1)

IR(neat, cm$^{-1}$): 3300, 1720, 1640 NMR(CDCl$_3$, δ): 0.85–1.0(m, 6H), 1.20–1.82(m, 3H), 2.0(s, 3H), 2.84(s, 3H), 2.97(d, J=14 Hz, 1H), 3.0(d, J=14 Hz, 1H), 3.26(d, J=14 Hz, 1H), 3.35(d, J=14 Hz, 1H), 4.54(m, 1H), 4.90(m, 1H), 5.07(s, 2H), 5.26(d, J=8 Hz, 1H), 7.15–7.35(m, 10H)

EXAMPLE 115

Preparation of (s)-3-((s)-2-benzyloxycarbonylamino-4-methylvalerylamino)-1-methylsulfinyl-4-phenyl-2-butanone (Compd. No. 248 in Table 1)

mp: 97°–102° C. IR(KBr, cm$^{-1}$): 3320, 1715, 1685, 1648 NMR(CDCl$_3$, δ): 0.70–0.95(m, 6H), 1.10–1.70(m, 3H), 2.84(s, 2.1H), 2.87(s, 0.9H), 2.80–3.03(m, 3H), 3.13–3.45 (m, 2H), 3.50–3.75(m, 1H), 4.0–4.20(m, 1H), 4.28–4.88(m, 2H), 4.95–5.10(m, 1H), 5.09(s, 1.4H), 5.13(s, 0.6H), 7.10–7.55(m, 10H)

EXAMPLE 116

Preparation of (s)-3-((s)-2-benzyloxycarbonylamino-4-methylvalerylamino)-1-methylsulfonyl-4-phenyl-2-butanone (Compd. No. 249 in Table 1)

mp: 142°–144° C. IR(KBr, cm$^{-1}$): 3400, 3200, 1718, 1652 NMR(DMSO-d$_6$, δ): 0.78(d, J=8.4 Hz, 3H), 0.82(d,

J=8.4 Hz, 3H), 1.15–1.65(m, 3H), 2.78(m, 1H), 3.06(s, 3H), 3.18(m, 1H), 3.34(s, 2H), 3.95(m, 1H), 4.40–4.60(m, 2H), 5.01(s, 2H), 7.13–7.58(m, 10H), 8.50(d, J=8 Hz, 1H)

EXAMPLE 117

Preparation of (s)-3-((s)-2-amino-4-methylvalerylamino)-1-methylthio-4-phenyl-2-butanone Hydrochloride (Compd. No. 250 in Table 1)

mp: 141° C. IR(KBr, cm$^{-1}$): 3400, 1698, 1658 NMR (DMSO-d$_6$, δ): 0.85(d, J=2.4 Hz, 3H), 0.87(d, J=2.3 Hz, 3H), 1.45–1.70(m, 3H), 1.97(s, 3H), 2.88(dd, J=8.8 Hz, 14 Hz, 1H), 3.16(dd, J=5.1 Hz, 14 Hz, 1H), 3.43(d, J=15 Hz, 1H), 3.53(d, J=15 Hz, 1H), 3.75(m, 1H), 4.77(m, 1H), 7.15–7.35(m, 5H), 8.28(s, 3H), 9.11(d, J=7.3 Hz, 1H)

EXAMPLE 118

Preparation of (s)-3-((s)-2-acetylamino-4-methylvalerylamino)-1-methylthio-4-phenyl-2-butanone (Compd. No. 251 in Table 1)

mp: 118°–120° C. IR(KBr, cm$^{-1}$): 3320, 1720, 1645 NMR(CDCl$_3$, δ): 0.89(d, J=4.0 Hz, 3H), 0.91(d, J=4.1 Hz, 3H), 1.35–1.70(m, 3H), 1.95(s, 3H), 1.99(s, 3H), 2.90–3.25 (m, 4H), 4.40(m, 1H), 5.06(q, J=6.8 Hz, 1H), 5.83(d, J=7 Hz, 1H), 6.77(d, J=7 Hz, 1H), 7.15–7.38(m, 5H)

EXAMPLE 119

Preparation of (s)-3-[(s)-4-methyl-2-(3-phenylpropionylamino)valerylamino]-1-methylthio-4-phenyl-2-butanone (Compd. No. 254 in Table 1)

mp: 104°–107° C. IR(KBr, cm$^{-1}$): 3320, 3275, 1715, 1640 NMR(CDCl$_3$, δ): 0.83(d, J=3.8 Hz, 3H), 0.85(d, J=3.9 Hz, 3H), 1.25–1.65(m, 3H), 1.99(s, 3H), 2.40–2.58(m, 2H), 2.85–3.22(m, 6H), 4.37(m, 1H), 5.07(q, J=7.2 Hz, 1H), 5.61(d, J=7.6 Hz, 1H), 6.64(d, J=7.6 Hz, 1H), 7.10–7.35(m, 10H)

EXAMPLE 120

Preparation of (s)-3-[(s)-4-methyl-2-(1-naphtylacetylamino)valerylamino]-1-methylthio-4-phenyl-2-butanone (Compd. No. 256 in Table 1)

mp: 126°–129° C. IR(KBr, cm$^{-1}$): 3300, 1720, 1650 NMR(CDCl$_3$, δ): 0.55–0.68(m, 6H), 0.98–1.45(m, 3H), 1.99(s, 3H), 2.84(m, 1H), 3.0–3.20(m, 3H), 3.90–4.10(m, 2H), 4.30(m, 1H), 4.94(m, 1H), 5.38(d, J=8 Hz, 0.7H), 5.50(d, J=8 Hz, 0.3H), 6.53(m, 1H), 7.03–7.54(m, 9H), 7.78–7.92(m, 3H)

EXAMPLE 121

Preparation of (s)-3-((s)-4-methyl-2-(2-naphtylacetylamino)valerylamino-1-methylthio-4-phenyl-2-butanone (Compd. No. 257 in Table 1)

mp: 112°–114° C. IR(KBr, cm$^{-1}$): 3300, 1730, 1645 NMR(CDCl$_3$, δ): 0.73–0.83(m, 6H), 1.20–1.60(m, 3H), 1.97(s, 0.9H), 1.98(s, 2.1H), 2.96(m, 1H), 3.04–3.20(m, 3H), 3.62–3.75(m, 2H), 4.37(m, 1H), 5.01(q, J=6.7 Hz, 1H), 5.62(d, J=8 Hz, 0.7H), 5.70(d, J=8 Hz, 0.3H), 6.61(m, 1H), 7.05–7.19(m, 2H), 7.22–7.35(m, 4H), 7.40–7.56(m, 2H), 7.63–7.72(m, 1H), 7.75–7.90(m, 3H)

EXAMPLE 122

Preparation of (s)-3-((s)-4-methyl-2-phenylsulfonylaminovalerylamino)-1-methylthio-4-phenyl-2-butanone (Compd. No. 262 in Table 1)

mp: 133°–136° C. IR(KBr, cm$^{-1}$): 3350, 3280, 1700, 1675, 1645 NMR(CDCl$_3$, δ): 0.50–0.90(m, 6H), 1.20–1.60 (m, 3H), 1.97(s, 1.8H), 1.98(s, 1.2H), 2.80–3.20(m, 4H), 3.63(m, 1H), 4.90–5.10(m, 2H), 6.41(d, J=7 Hz, 0.4H), 6.62(d, J=7 Hz, 0.6H), 7.09–7.35(m, 5H), 7.45–7.64(m, 3H), 7.73–7.95(m, 2H)

EXAMPLE 123

Preparation of (s)-3-((s)-2-benzyloxycarbonylamino-4-methylvalerylamino)-1-octylthio-4-phenyl-2-butanone (Compd. No. 268 in Table 1)

mp: 69° C. IR(KBr, cm$^{-1}$): 3340, 3305, 1715, 1690, 1650 NMR(CDCl$_3$, δ): 0.75–1.0(m, 9H), 1.15–1.70(m, 15H), 2.35(t, J=7.2 Hz, 2H), 2.90–3.25(m, 4H), 4.0–4.20(m, 1H), 4.88–5.20(m, 2H), 5.08(s, 2H), 6.56(m, 1H), 7.07–7.45(m, 10H)

EXAMPLE 129

Preparation of (s)-3-((s)-2-benzyloxycarbonylamino-4-methylvalerylamino)-1-(2-chloroethylthio)-4-phenyl-2-butanone (Compd. No. 271 in Table 1)

mp: 77°–80° C. IR(KBr, cm$^{-1}$): 3310, 3270, 1715, 1680, 1650 NMR(CDCl$_3$, δ): 0.83–1.0(m, 6H), 1.38–1.60(m, 3H), 2.65–2.85(m, 2H), 3.0–3.30(m, 4H), 3.45–3.65(m, 2H), 4.11 (m, 1H), 4.90–5.08(m, 2H), 5.10(s, 2H), 6.65(m, 1H), 7.10–7.35(m, 10H)

EXAMPLE 125

Preparation of (s)-3-((s)-2-benzyloxycarbonylamino-4-methylvalerylamino)-1-(2-methoxyethylthio)-4-phenyl-2-butanone (Compd. No. 272 in Table 1)

mp: 68°–69° C. IR(KBr, cm$^{-1}$): 3340, 3300, 1725, 1685, 1660 NMR(CDCl$_3$, δ): 0.90(d, J=5.9 Hz, 6H), 1.30–1.75(m, 3H), 2.61(t, J=6.2 Hz, 2H), 3.0(dd, J=6.8 Hz, 13 Hz, 1H), 3.16(dd, J=6.8 Hz, 13 Hz, 1H), 3.26(d, J=4.5 Hz, 2H), 3.32(s, 3H), 3.50(t, J=6.2 Hz, 2H), 4.12(m, 1H), 4.97(m, 1H), 5.07(d, J=7 Hz, 1H), 5.10(s, 2H), 6.59(d, J=7 Hz, 1H), 7.10–7.35(m, 10H)

EXAMPLE 126

Preparation of (s)-3-((s)-2-benzyloxycarbonylamino-4-methylvalerylamino)-1-(2-dimethylaminoethylthio)-4-phenyl-2-butanone (Compd. No. 275 in Table 1)

mp: 67°–69° C. IR(KBr, cm$^{-1}$): 3320, 1710, 1655 NMR (CDCl$_3$, δ): 0.90–1.0(m, 6H), 1.20–1.75(m, 3H), 2.28(s, 3H), 2.31(s, 3H), 2.50–2.75(m, 4H), 2.98(m, 1H), 3.08–3.32 (m, 2H), 3.44(m, 1H), 4.18(m, 1H), 4.97–5.35(m, 2H), 5.10(s, 2H), 6.85(m, 1H), 7.13–7.50(m, 10H)

EXAMPLE 127

Preparation of (s)-1-(2-acetylaminoethylthio)-3-((s)-2-benzyloxycarbonylamino-4-methylvalerylamino)-4-phenyl-2-butanone (Compd. No. 276 in Table 1)

mp: 122°–123° C. IR(KBr, cm$^{-1}$): 3320, 1725, 1690, 1642 NMR(CDCl$_3$, δ): 0.83–0.98(m, 6H), 1.30–1.70(m, 3H), 1.97(s, 3H), 2.45–2.68(m, 2H), 2.90–3.45(m, 6H), 4.12(m, 1H), 4.95–5.15(m, 2H), 5.09(s, 2H), 6.21(m, 1H), 6.68(d, J=7 Hz, 1H), 7.10–7.40(m, 10H)

EXAMPLE 128

Preparation of (s)-3-((s)-2-benzyloxycarbonylamino-4-methylvalerylamino)-1-benzylthio-4-phenyl-2-butanone (Compd. No. 277 in Table 1)

mp: 86°–87° C. IR(KBr, cm$^{-1}$): 3320, 1700, 1680, 1658 NMR(CDCl$_3$, δ): 0.87(d, J=6.0 Hz, 3H), 0.89(d, J=6.1 Hz, 3H), 1.35–1.70(m, 3H), 2.88–3.22(m, 4H), 3.69(s, 2H), 4.12(m, 1H), 4.95–5.18(m, 2H), 5.09(s, 2H), 6.53(m, 1H), 7.10–7.50(m, 15H)

EXAMPLE 129

Preparation of (s)-3-((s)-2-benzyloxycarbonylamino-4-methylvalerylamino)-4-phenyl-1-phenylthio-2-butanone (Compd. No. 279 in Table 1)

mp: 105°–106° C. IR(KBr, cm$^{-1}$): 3330, 3280, 1713, 1685, 1653 NMR(CDCl$_3$, δ): 0.87(d, J=6.2 Hz, 6H), 1.30–1.70(m, 3H), 2.88–3.18(m, 2H), 3.63(s, 2H), 4.13(m, 1H), 4.95–5.18(m, 2H), 5.09(s, 2H), 6.53(m, 1H), 7.05–7.15(m, 2H), 7.15–7.50(m, 13H)

EXAMPLE 130

Preparation of (s)-3-benzyloxycarbonylaminoacetylamino-1-furfurylthio-4-phenyl-2-butanone (Compd. No. 280 in Table 1)

IR(neat, cm$^{-1}$): 3320, 1720, 1670 NMR(CDCl$_3$, δ): 2.95–3.20(m, 2H), 3.16(s, 2H), 3.63(s, 2H), 3.83(d, J=5.7 Hz, 2H), 5.06(q, J=6.8 Hz, 1H), 5.12(s, 2H), 5.30(m, 1H), 6.18(m, 1H), 6.29(m, 1H), 6.53(d, J=7 Hz, 1H), 7.07–7.50(m, 11H)

EXAMPLE 131

Preparation of (s)-3-((s)-2-benzyloxycarbonylamino-3-methylbutyrylamino)-1-furfurylthio-4-phenyl-2-butanone (Compd. No. 282 in Table 1)

mp: 122°–125° C. IR(KBr, cm$^{-1}$): 3340, 3290, 1732, 1692, 1661 NMR(CDCl$_3$, δ): 0.81(d, J=6.8 Hz, 3H), 0.90(d, J=6.7 Hz, 3H), 2.07(m, 1H), 2.92–3.25(m, 4H), 3.62(s, 2H), 3.96(m, 1H), 4.98–5.28(m, 2H), 5.11(s, 2H), 6.18(d, J=3.0 Hz, 1H), 6.29(m, 1H), 6.44(d, J=8 Hz, 1H), 7.08–7.50(m, 11H)

EXAMPLE 132

Preparation of (s)-1-furfurylthio-3-((s)-2-isobutoxycarbonylamino-4-methylvalerylamino)-4-phenyl-2-butanone (Compd. No. 284 in Table 1)

mp: 89°–90° C. IR(KBr, cm$^{-1}$): 3340, 3290, 1730, 1690, 1655 NMR(CDCl$_3$, δ): 0.83–0.98(m, 12H), 1.30–1.70(m, 3H), 1.92(m, 1H), 2.98(dd, J=7.5 Hz, 14 Hz, 1H), 3.08–3.25(m, 3H), 3.63(s, 2H), 3.83(d, J=6.6 Hz, 2H), 4.13(m, 1H), 4.88(m, 1H), 5.02(d, J=7.5 Hz, 1H), 6.19(d, J=3.2 Hz, 1H), 6.29(m, 1H), 6.57(d, J=7 Hz, 1H), 7.15(d, J=7.7 Hz, 2H), 7.19–7.32(m, 3H), 7.35(m, 1H)

EXAMPLE 133

Preparation of (s)-3-((s)-2-tert-butoxycarbonylamino-4-methylvalerylamino)-1-furfurylthio-4-phenyl-2-butanone (Compd. No. 285 in Table 1)

IR(KBr, cm$^{-1}$): 3320, 1705, 1690, 1655 NMR(CDCl$_3$, δ): 0.89(d, J=6.1 Hz, 3H), 0.91(d, J=6.2 Hz, 3H), 1.30–1.75(m, 3H), 1.43(s, 9H), 3.01(dd, J=7.0 Hz, 14 Hz, 1H), 3.14(dd, J=6.8 Hz, 14 Hz, 1H), 3.16(s, 2H), 3.62(s, 2H), 4.08(m, 1H), 4.75(m, 1H), 5.02(m, 1H), 6.18(d, J=3.0 Hz, 1H), 6.29(m, 1H), 6.65(d, J=7 Hz, 1H), 7.10–7.20(m, 2H), 7.20–7.32(m, 3H), 7.35(m, 1H)

EXAMPLE 134

Preparation of (s)-3-((s)-2-cyclopentylmethoxycarbonylamino-3-methylvalerylamino)-1-furfurylthio-4-phenyl-2-butanone (Compd. No. 287 in Table 1)

mp: 77°–78° C. IR(KBr, cm$^{-1}$): 3340, 3290, 1715, 1692, 1660 NMR(CDCl$_3$, δ): 0.89(d, J=6.0 Hz, 3H), 0.91(d, J=6.1 Hz, 3H), 1.15–1.83(m, 11H), 2.16(m, 1H), 3.01(dd, J=6.5 Hz, 14 Hz, 1H), 3.07–3.25(m, 3H), 3.63(s, 2H), 3.93(d, J=7.1 Hz, 2H), 4.13(m, 1H), 4.87(m, 1H), 5.0(q, J=7.3 Hz, 1H), 6.18(d, J=3.2 Hz, 1H), 6.29(m, 1H), 6.62(d, J=7 Hz, 1H), 7.14(d, J=6.1 Hz, 2H), 7.16–7.35(m, 4H)

EXAMPLE 135

Preparation of (s)-3-((s)-2-cyclohexylmethoxycarbonylamino-3-methylvalerylamino)-1-furfurylthio-4-phenyl-2-butanone (Compd. No. 288 in Table 1)

IR(neat, cm$^{-1}$): 3330, 1735, 1692, 1660 NMR(CDCl$_3$, δ): 0.80–1.05(m, 8H), 1.10–1.80(m, 12H), 3.01(dd, J=6.8 Hz, 14 Hz, 1H), 3.07–3.25(m, 3H), 3.63(s, 2H), 3.83(d, J=7.5 Hz, 2H), 4.09(m, 1H), 4.90(m, 1H), 4.99(q, J=7.5 Hz, 1H), 6.21(d, J=2.8 Hz, 1H), 6.32(m, 1H), 6.58(d, J=7 Hz, 1H), 7.05–7.37(m, 6H)

EXAMPLE 136

Preparation of (s)-3-((s)-2-cycloheptylmethoxycarbonylamino-4-methylvalerylamino)-1-furfurylthio-4-phenyl-2-butanone (Compd. No. 289 in Table 1)

mp: 77°–79° C. IR(KBr, cm$^{-1}$): 3350, 3300, 1718, 1690, 1660 NMR(CDCl$_3$, δ): 0.89(d, J=6.0 Hz, 3H), 0.91(d, J=6.1 Hz, 3H), 1.10–1.90(m, 16H), 2.99(dd, J=6.7 Hz, 15 Hz, 1H), 3.08–3.25(m, 3H), 3.63(s, 2H), 3.87(d, J=5.8 Hz, 2H), 4.12(m, 1H), 4.88(m, 1H), 4.99(q, J=6.7 Hz, 1H), 6.18(d, J=3.1 Hz, 1H), 6.29(m, 1H), 6.61(d, J=7 Hz, 1H), 7.13(d, J=7.8 Hz, 2H), 7.18–7.38(m, 4H)

EXAMPLE 137

Preparation of (s)-3-[(s)-2-(3-cyclohexenyl)methoxycarbonylamino-4-methylvalerylamino]-1-furfurylthio-4-phenyl-2-butanone (Compd. No. 293 in Table 1)

mp: 85°–87° C. IR(KBr, cm$^{-1}$): 3340, 3310, 1738, 1688, 1660 NMR(CDCl$_3$, δ): 0.90(d, J=6.0 Hz, 3H), 0.91(d, J=6.2 Hz, 3H), 1.20–2.20(m, 10H), 3.01(dd, J=6.8 Hz, 14 Hz, 1H), 3.08–3.29(m, 3H), 3.63(s, 2H), 3.96(d, J=6.4 Hz, 2H), 4.13(m, 1H), 4.92(m, 1H), 5.03(q, J=6.8 Hz, 1H), 5.60–5.76(m, 2H), 6.19(d, J=2.9 Hz, 1H), 6.29(m, 1H), 6.58(d, J=7 Hz, 1H), 7.08–7.38(m, 6H)

EXAMPLE 138

Preparation of (s)-3-((s)-2-cyclohexyloxycarbonylamino-4-methylvalerylamino)-1-furfurylthio-4-phenyl-2-butanone (Compd. No. 296 in Table 1)

mp: 102°–103° C. IR(KBr, cm$^{-1}$): 3330, 3270, 1718, 1681, 1660 NMR(CDCl$_3$, δ): 0.89(d, J=6.1 Hz, 3H), 0.91(d,

J=6.3 Hz, 3H), 1.35–1.93(m, 13H), 3.01(dd, J=6.5 Hz, 14 Hz, 1H), 3.08–3.25(m, 3H), 3.63(s, 2H), 4.12(m, 1H), 4.62(m, 1H), 4.84(m, 1H), 5.01(q, J=6.5 Hz, 1H), 6.18(d, J=2.9 Hz, 1H), 6.29(m, 1H), 6.66(d, J=7 Hz, 1H), 7.14(d, J=6.1 Hz, 2H), 7.20–7.35(m, 4H)

EXAMPLE 139

Preparation of (s)-3-((s)-2-benzyloxycarbonylamino-4-methylvalerylamino)-1-furfurylthio-4-phenyl-2-butanone (Compd. No. 297 in Table 1)

mp: 103°–105° C. IR(KBr, cm⁻¹): 3350, 3300, 1725, 1690, 1658 NMR(CDCl₃, δ): 0.90(d, J=6.2 Hz, 6H), 1.30–1.65(m, 3H), 2.96(dd, J=7.0 Hz, 14 Hz, 1H), 3.07–3.28 (m, 3H), 3.63(s, 2H), 4.13(m, 1H), 4.85–5.10(m, 2H), 5.09 (s, 2H), 6.18(d, J=3.0 Hz, 1H), 6.29(d, J=3.0 Hz, 1H), 6.56(d, J=7 Hz, 1H), 7.05–7.22(m, 11H)

EXAMPLE 140

Preparation of (s)-3-((R)-2-benzyloxycarbonylamino-4-methylvalerylamino)-1-furfurylthio-4-phenyl-2-butanone (Compd. No. 297 in Table 1)

mp: 77°–78° C. IR(KBr, cm⁻¹): 3300, 1730, 1690, 1650 NMR(CDCl₃, δ): 0.80–0.95(m, 6H), 1.20–1.70(m, 3H), 3.0(m, 1H), 3.12–3.20(m, 3H), 3.63(d, J=4.2 Hz, 2H), 4.11(m, 1H), 4.95–5.10(m, 2H), 5.09(s, 2H), 6.19(d, J=2.9 Hz, 1H), 6.28(m, 1H), 6.50(m, 1H), 7.07–7.40(m, 11H)

EXAMPLE 141

Preparation of (s)-1-furfurylthio-3-[(s)-N-methyl-2-(benzyloxycarbonylamino)-4-methylvalerylamino]-4-phenyl-2-butanone (Compd. No. 298 in Table 1)

IR(neat, cm⁻¹): 3320, 1720, 1650 NMR(CDCl₃, δ): 0.85–0.98(m, 6H), 1.20–1.75(m, 3H), 2.80(s, 3H), 3.02(m, 1H), 3.08(d, J=15 Hz, 1H), 3.23(d, J=15 Hz, 1H), 3.30(m, 1H), 3.65(s, 3H), 4.50(m, 1H), 4.74(m, 1H), 5.06(s, 2H), 5.20(d, J=8.5 Hz, 1H), 6.18(d, J=3.1 Hz, 1H), 6.30(m, 1H), 7.14–7.35(m, 11H)

EXAMPLE 142

Preparation of (s)-1-furfurylthio-3-[(s)-4-methyl-2-(N-methylbenzyloxycarbonylamino)valerylamino]-4-phenyl-2-butanone (Compd. No. 299 in Table 1)

IR(neat, cm⁻¹): 3300, 1710, 1695, 1650 NMR(CDCl₃, δ): 0.85–0.95(m, 6H), 1.35–1.68(m, 3H), 2.54(s, 2H), 2.78(s, 1H), 2.80–2.98(m, 1H), 3.0–3.25(m, 3H), 3.64(s, 0.7H), 3.67(s, 1.3H), 4.50–4.75(m, 1H), 4.95(m, 1H), 5.13(s, 2H), 6.19(d, J=2.9 Hz, 1H), 6.28(m, 1H), 6.55(d, J=7 Hz, 0.7H), 6.95–7.40(m, 11.3H)

EXAMPLE 143

Preparation of (s)-3-[(s)-2-(2-chlorobenzyloxycarbonylamino)-4-methylvalerylamino]-1-furfurylthio-4-phenyl-2-butanone (Compd. No. 301 in Table 1)

mp: 80°–85° C. IR(KBr, cm⁻¹): 3340, 3290, 1735, 1698, 1660 NMR(CDCl₃, δ): 0.83–0.98(m, 6H), 1.35–1.70(m, 3H), 2.98(dd, J=7.2 Hz, 14 Hz, 1H), 3.05–3.23(m, 3H), 3.63(s, 2H), 4.15(m, 1H), 4.93–5.03(m, 2H), 5.21(s, 2H), 6.17(d, J=3.2 Hz, 1H), 6.29(m, 1H), 6.58(d, J=7 Hz, 1H), 7.05–7.45(m, 10H)

EXAMPLE 144

Preparation of (s)-3-[(s)-2-(4-chlorobenzyloxycarbonylamino)-4-methylvalerylamino]-1-furfurylthio-4-phenyl-2-butanone (Compd. No. 303 in Table 1)

mp: 123°–124° C. IR(KBr, cm⁻¹): 3350, 3310, 1732, 1698, 1663 NMR(CDCl₃, δ): 0.89(d, J=6.1 Hz, 6H), 1.33–1.70(m, 3H), 2.98(dd, J=6.8 Hz, 14 Hz, 1H), 3.05–3.25 (m, 3H), 3.63(s, 2H), 4.13(m, 1H), 4.90–5.12(m, 2H), 5.05 (s, 2H), 6.19(d, J=3.2 Hz, 1H), 6.27(m, 1H), 6.53(d, J=7 Hz, 1H), 7.11(d, J=6.7 Hz, 2H), 7.15–7.38(m, 8H)

EXAMPLE 145

Preparation of (s)-1-furfurylthio-3-[(s)-4-methyl-2-(1,2,3,4-tetrahydro-1-naphtoxycarbonylamino)valerylamino]-4-phenyl-2-butanone (Compd. No. 308 in Table 1)

IR(KBr, cm⁻¹): 3300, 1715, 1675, 1655 NMR(CDCl₃, δ): 0.85–1.0(m, 6H), 1.30–1.70(m, 3H), 1.70–2.10(m, 4H), 2.65–3.30(m, 6H), 3.64(s, 2H), 4.15(m, 1H), 4.89(d, J=7.6 Hz, 1H), 5.01(m, 1H), 5.87(m, 1H), 6.20(d, J=3.1 Hz, 1H), 6.30(m, 1H), 6.64(d, J=6.2 Hz, 1H), 7.10–7.36(m, 10H)

EXAMPLE 146

Preparation of (s)-3-[(s)-2-(9-fluorenylmethoxycarbonylamino)-4-methylvalerylamino]-1-furfurylthio-4-phenyl-2-butanone (Compd. No. 309 in Table 1)

IR(KBr, cm⁻¹): 3320, 3280, 1680, 1660 NMR(CDCl₃, δ): 0.83–0.98(m, 6H), 1.40–1.70(m, 3H), 2.98(m, 1H), 3.08–3.20(m, 3H), 3.62(s, 2H), 4.05–4.30(m, 2H), 4.30–4.50(m, 2H), 4.90–5.15(m, 2H), 6.18(m, 1H), 6.28(m, 1H), 6.52(m, 1H), 7.10–7.50(m, 10H), 7.58(d, J=7.3 Hz, 2H), 7.77(d, J=7.3 Hz, 2H)

EXAMPLE 147

Preparation of (s)-1-furfurylthio-3-((s)-4-methyl-2-tetrahydrofurfuryloxycarbonylaminovalerylamino)-4-phenyl-2-butanone (Compd. No. 310 in Table 1)

IR(neat, cm⁻¹): 3320, 1710, 1650 NMR(CDCl₃, δ): 0.80–1.0(m, 6H), 1.20–1.70(m, 5H), 1.84–2.04(m, 2H), 2.98 (dd, J=8.2 Hz, 15 Hz, 1H), 3.10–3.25(m, 3H), 3.63(s, 2H), 3.66–4.0(m, 3H), 4.0–4.22(m, 3H), 4.96–5.08(m, 2H), 6.19 (m, 1H), 6.29(m, 1H), 6.64(m, 1H), 7.15–7.40(m, 6H)

EXAMPLE 148

Preparation of (s)-1-furfurylthio-3-[(s)-4-methyl-2-(2-tetrahydropyranylmethoxycarbonylamino)valerylamino]-4-phenyl-2-butanone (Compd. No. 311 in Table 1)

IR(KBr, cm⁻¹): 3300, 1720, 1680, 1650 NMR(CDCl₃, δ): 0.80–1.0(m, 6H), 1.23–1.90(m, 9H), 2.97(dd, J=7.3 Hz, 14 Hz, 1H), 3.08–3.26(m, 3H), 3.38–3.70(m, 2H), 3.63(s, 2H), 3.90–4.17(m, 4H), 4.92–5.08(m, 2H), 6.19(m, 1H), 6.29(m, 1H), 6.62(d, J=7 Hz, 1H), 7.05–7.40(m, 6H)

EXAMPLE 149

Preparation of (s)-3-((s)-2-furfuryloxycarbonylamino-4-methylvalerylamino)-1-furfurylthio-4-phenyl-2-butanone (Compd. No. 312 in Table 1)

mp: 115°–118° C. IR(KBr, cm⁻¹): 3350, 3300, 1730, 1695, 1666 NMR(CDCl₃, δ): 0.89(d, J=6.2 Hz, 6H), 1.28–1.65(m, 3H), 3.01(dd, J=6.5 Hz, 15 Hz, 1H), 3.08–3.27 (m, 3H), 3.63(s, 2H), 4.12(m, 1H), 4.86–5.07(m, 2H), 5.05 (s, 2H), 6.19(d, J=2.9 Hz, 1H), 6.29(m, 1H), 6.36(m, 1H), 6.41(d, J=3.2 Hz, 1H), 6.54(m, 6H), 7.13(d, J=7.8 Hz, 2H), 7.1B–7.32(m, 3H), 7.35(m, 1H), 7.42(s, 1H)

EXAMPLE 150

Preparation of (s)-1-furfurylthio-3-[(s)-4-methyl-2-(2-pyridylmethoxycarbonylamino)valerylamino]-4-phenyl-2-butanone (Compd. No. 313 in Table 1)

mp: 93°–94° C. IR(KBr, cm$^{-1}$): 3350, 3300, 1733, 1698, 1658 NMR(CDCl$_3$, δ): 0.89(d, J=6.4 Hz, 3H), 0.91(d, J=6.1 Hz, 3H), 1.33–1.75(m, 3H), 2.98(dd, J=6.5 Hz, 14 Hz, 1H), 3.08–3.27(m, 3H), 3.62(s, 2H), 4.14(m, 1H), 4.98(q, J=6.5 Hz, 1H), 5.10–5.30(m, 1H), 5.21(s, 2H), 6.17(d, J=3.2 Hz, 1H), 6.29(m, 1H), 6.65(d, J=7 Hz, 1H), 7.07–7.38(m, 8H), 7.72(t, J=8.3 Hz, 1H), 8.57(d, J=5.0 Hz, 1H)

EXAMPLE 151

Preparation of (s)-1-furfurylthio-3-[(s)-4-methyl-2-(3-pyridylmethoxycarbonylamino)valerylamino]-4-phenyl-2-butanone (Compd. No. 315 in Table 1)

IR(neat, cm$^{-1}$): 3320, 1720, 1698, 1600 NMR(CDCl$_3$, δ): 0.90(d, J=6.2 Hz, 6H), 1.33–1.72(m, 3H), 2.98(dd, J=6.7 Hz, 14 Hz, 1H), 3.08–3.27(m, 3H), 3.63(s, 2H), 4.12(m, 1H), 5.01(q, J=7.5 Hz, 1H), 5.0–5.20(m, 1H), 5.11(s, 2H), 6.19(d, J=3.0 Hz, 1H), 6.29(m, 1H), 6.53(m, 1H), 7.13(d, J=7.7 Hz, 2H), 7.1B–7.37(m, 5H), 7.68(d, J=8 Hz, 1H), 8.52–8.63(m, 2H)

EXAMPLE 152

Preparation of (s)-1-furfurylthio-3-[(s)-4-methyl-2-(4-pyridylmethoxycarbonylamino)valerylamino]-4-phenyl-2-butanone (Compd. No. 317 in Table 1)

IR(neat, cm$^{-1}$): 3320, 1718, 1663 NMR(CDCl$_3$, δ): 0.90–1.02(m, 6H), 1.36–1.75(m, 3H), 3.04(dd, J=6.7 Hz, 14 Hz, 1H), 3.07–3.24(m, 3H), 3.63(s, 2H), 4.13(m, 1H), 5.03(q, J=6.7 Hz, 1H), 5.10(s, 2H), 5.30(d, J=7 Hz, 1H), 6.19(d, J=2.9 Hz, 1H), 6.29(m, 1H), 6.67(d, J=7 Hz, 1H), 7.08–7.33(m, 7H), 7.35(m, 1H), 8.59(d, J=7.5 Hz, 2H)

EXAMPLE 153

Preparation of (s)-3-((s)-2-amino-4-methylvalerylamino)-1-furfurylthio-4-phenyl-2-butanone hydrochloride (Compd. No. 323 in Table 1)

IR(KBr, cm$^{-1}$): 3400, 1700, 1655 NMR(D$_2$O, δ): 0.65–0.85(m, 6H), 1.30–1.50(m, 3H), 2.73(dd, J=9.2 Hz, 14 Hz, 1H), 3.02(dd, J=7.5 Hz, 14 Hz, 1H), 3.28(d, J=15 Hz, 1H), 3.42(d, J=15 Hz, 1H), 3.55(s, 2H), 3.73(m, 1H), 4.67(m, 1H), 6.08(d, J=2.8 Hz, 1H), 6.20(m, 1H), 6.95–7.30 (m, 5H), 7.28(m, 1H)

EXAMPLE 154

Preparation of (s)-1-furfurylthio-3-((s)-2-isovalerylamino-4-methylvalerylamino)-4-phenyl-2-butanone (Compd. No. 325 in Table 1)

mp: 108°–115° C. IR(KBr, cm$^{-1}$): 3310, 1715, 1640 NMR(CDCl$_3$, δ): 0.93–1.06(m, 12H), 1.40–1.75(m, 4H), 1.95–2.20(m, 2H), 2.98(dd, J=7.2 Hz, 14 Hz, 1H), 3.16(dd, J=6.7 Hz, 14 Hz, 1H), 3.16(s, 2H), 3.65(s, 2H), 4.43(m, 1H), 4.98(m, 1H), 5.70(d, J=7 Hz, 1H), 6.18(d, J=2.6 Hz, 1H), 6.29(m, 1H), 6.70(d, J=7 Hz, 1H), 7.08–7.38(m, 6H)

EXAMPLE 155

Preparation of (s)-3-[(s)-2-(3-cyclohexylpropionylamino)-4-methylvalerylamino]-1-furfurylthio-4-phenyl-2-butanone (Compd. No. 328 in Table 1)

mp: 116°–118° C. IR(KBr, cm$^{-1}$): 3300, 1722, 1710, 1638 NMR(CDCl$_3$, δ): 0.80–1.0(m, 8H), 1.08–1.80(m, 14H), 2.15(t, J=7.8 Hz, 2H), 2.98(dd, J=7.3 Hz, 14 Hz, 1H), 3.15(dd, J=5.3 Hz, 14 Hz, 1H), 3.16(s, 2H), 3.64(s, 2H), 4.40(m, 1H), 4.97(q, J=7.2 Hz, 1H), 5.66(d, J=7 Hz, 1H), 6.19(d, J=3.1 Hz, 1H), 6.29(m, 1H), 6.66(d, J=7 Hz, 1H), 7.13–7.38(m, 6H)

EXAMPLE 156

Preparation of (s)-3-[(s)-2-(4-cyclohexylbutyrylamino)-4-methylvalerylamino]-1-furfurylthio-4-phenyl-2-butanone (Compd. No. 329 in Table 1)

IR(KBr, cm$^{-1}$): 3270, 1730, 1650, 1640 NMR(CDCl$_3$, δ): 0.75–1.03(m, 8H), 1.03–1.75(m, 16H), 2.11(t, J=7.8 Hz, 2H), 2.98(dd, J=7.2 Hz, 14 Hz, 1H), 3.11(dd, J=6.5 Hz, 14 Hz, 1H), 3.16(s, 2H), 3.64(s, 2H), 4.41(m, 1H), 4.98(m, 1H), 5.67(d, J=8 Hz, 1H), 6.19(d, J=3.0 Hz, 1H), 6.29(m, 1H), 6.69(d, J=7 Hz, 1H), 7.10–7.37(m, 11H)

EXAMPLE 157

Preparation of (s)-1-furfurylthio-3-[4-methyl-2-(3-phenylpropionylamino)valerylamino]-4-phenyl-2-butanone (Compd. No. 331 in Table 1)

mp: 117°–119° C. IR(KBr, cm$^{-1}$): 3320, 1730, 1710, 1643 NMR(CDCl$_3$, δ): 0.83(d, J=6.2 Hz, 3H), 0.85(d, J=6.2 Hz, 3H), 1.25–1.65(m, 3H), 2.33–2.53(m, 2H), 2.85–3.03(m, 3H), 3.05–3.18(m, 1H), 3.15(s, 2H), 3.64(s, 2H), 4.35(m, 1H), 4.96(q, J=6.7 Hz, 1H), 5.53(d, J=7 Hz, 1H), 6.19(d, J=3.3 Hz, 1H), 6.30(m, 1H), 6.58(d, J=7 Hz, 1H), 7.10–7.40 (m, 11H)

EXAMPLE 158

Preparation of (s)-1-furfurylthio-3-[(s)-4-methyl-2-(4-phenylbutyrylamino)valerylamino]-4-phenyl-2-butanone (Compd. No. 332 in Table 1)

mp: 106°–108° C. IR(KBr, cm$^{-1}$): 3300, 1728, 1708, 1638 NMR(CDCl$_3$, δ): 0.89(d, J=5.9 Hz, 3H), 0.91(d, J=6.1 Hz, 3H), 1.40–1.65(m, 3H), 1.85–2.05(m, 2H), 2.14(t, J=7.4 Hz, 2H), 2.63(t, J=7.3 Hz, 2H), 2.96(dd, J=7.4 Hz, 14 Hz, 1H), 3.15(dd, J=7.5 Hz, 14 Hz, 1H), 3.16(s, 2H), 3.63(s, 2H), 4.40(m, 1H), 4.98(d, J=6.6 Hz, 1H), 5.64(d, J=7 Hz, 1H), 6.18(d, J=3.2 Hz, 1H), 6.29(m, 1H), 6.63(d, J=7 Hz, 1H), 7.10–7.40(m, 11H)

EXAMPLE 159

Preparation of (s)-1-furfurylthio-3-[(s)-4-methyl-2-(l-naphtylacetylamino)valerylamino]-4-phenyl-2-butanone (Compd. No. 333 in Table 1)

mp: 143°–146° C. IR(KBr, cm$^{-1}$): 3300, 1715, 1650 NMR(CDCl$_3$, δ): 0.64(d, J=6.8 Hz, 3H), 0.66(d, J=6.8 Hz,

3H), 0.98–1.15(m, 2H), 1.25–1.45(m, 1H), 2.78(dd, J=7.9 Hz, 14 Hz, 1H), 3.07(dd, J=6.5 Hz, 14 Hz, 1H), 3.14(d, J=1.7 Hz, 2H), 3.64(s, 2H), 3.93(d, J=16 Hz, 1H), 4.04(d, J=16 Hz, 1H), 4.29(m, 1H), 4.86(m, 1H), 5.37(d, J=7 Hz, 1H), 6.19(d, J=2.9 Hz, 1H), 6.29(m, 1H), 6.53(d, J=8 Hz, 1H), 6.95–7.10(m, 2H), 7.20–7.30(m, 5H), 7.30–7.40(m, 2H), 7.45–7.60(m, 3H), 7.87(m, 1H)

EXAMPLE 160

Preparation of (s)-1-furfurylthio-3-[(s)-4-methyl-2-(2-naphtylacetylamino)valerylamino]-4-phenyl-2-butanone (Compd. No. 334 in Table 1)

mp: 123°–125° C. IR(KBr, cm$^{-1}$): 3320, 3300, 1715, 1640 NMR(CDCl$_3$, δ): 0.73–0.90(m, 6H), 1.20–1.70(m, 3H), 2.91(dd, J=7.7 Hz, 14 Hz, 1H), 3.09(dd, J=7.7 Hz, 14 Hz, 1H), 3.14(s, 2H), 3.63(s, 2H), 3.69(d, J=3.1 Hz, 2H), 4.37(m, 1H), 4.93(m, 1H), 5.60(d, J=8.3 Hz, 1H), 6.18(d, J=3.1 Hz, 1H), 6.28(m, 1H), 6.62(d, J=7.5 Hz, 1H), 7.05–7.16(m, 2H), 7.20–7.35(m, 5H), 7.45–7.55(m, 2H), 7.67(s, 1H), 7.74–7.90(m, 3H)

EXAMPLE 161

Preparation of (s)-3-((s)-2-cinnamoylamino-4-methylvalerylamino)-1-furfurylthio-4-phenyl-2-butanone (Compd. No. 335 in Table 1)

mp: 141°–143° C. IR(KBr, cm$^{-1}$): 3300, 1730, 1710, 1650, 1623 NMR(CDCl$_3$, δ): 0.93(d, J=4.3 Hz, 6H), 1.43–1.78(m, 3H), 2.95(dd, J=7.5 Hz, 15 Hz, 1H), 3.15(dd, J=7.5 Hz, 15 Hz, 1H), 3.19(s, 2H), 3.65(s, 2H), 4.59(m, 1H), 5.0(q, J=6.6 Hz, 1H), 5.94(d, J=8 Hz, 1H), 6.19(d, J=3.3 Hz, 1H), 6.29(m, 1H), 6.35(d, J=16 Hz, 1H), 6.82(d, J=8 Hz, 1H), 7.10–7.30(m, 5H), 7.30–7.45(m, 4H), 7.45–7.55(m, 2H), 7.63(d, J=16 Hz, 1H)

EXAMPLE 162

Preparation of (s)-3-[(s)-2-(3-benzothienylacetylamino)-4-methylvalerylamino]-1-furfurylthio-4-phenyl-2-butanone (Compd. No. 345 in Table 1)

mp: 150°–153° C. IR(KBr, cm$^{-1}$): 3300, 1710, 1640 NMR(CDCl$_3$, δ): 0.65–0.80(m, 6H), 1.13–1.28(m, 2H), 1.35–1.55(m, 1H), 2.83(dd, J=7.7 Hz, 18 Hz, 1H), 3.07(dd, J=7.7 Hz, 18 Hz, 1H), 3.14(s, 2H), 3.63(s, 2H), 3.78(s, 2H), 4.30–4.45(m, 1H), 4.59(q, J=6.7 Hz, 1H), 5.68(d, J=8 Hz, 1H), 6.18(d, J=3.2 Hz, 1H), 6.27–6.34(m, 1H), 6.63(d, J=8 Hz, 1H), 7.05–7.15(m, 2H), 7.20–7.48(m, 7H), 7.65–7.78 (m, 1H), 7.85–7.97(m, 1H)

EXAMPLE 163

Preparation of (s)-3-((s)-2-cyclohexyloxyacetylamino-4-methylvalerylamino)-1-furfurylthio-4-phenyl-2-butanone (Compd. No. 347 in Table 1)

IR(neat, cm$^{-1}$): 3300, 1700, 1650 NMR(CDCl$_3$, δ): 0.87–0.92(m, 6H), 1.18–1.90(m, 13H), 2.97(dd, J=7.6 Hz, 14 Hz, 1H), 3.14(dd, J=6.3 Hz, 14 Hz, 1H), 3.14(d, J=15 Hz, 1H), 3.21(d, J=15 Hz, 1H), 3.28(m, 1H), 3.64(s, 2H), 3.86(d, J=16 Hz, 1H), 3.95(d, J=16 Hz, 1H), 4.39(m, 1H), 4.97(q, J=7.5 Hz, 1H), 6.19(d, J=2.9 Hz, 1H), 6.29(m, 1H), 6.76(d, J=8 Hz, 1H), 6.80(d, J=8 Hz, 1H), 7.13–7.36(m, 6H)

EXAMPLE 164

Preparation of (s)-1-furfurylthio-3-((s)-4-methyl-2-phenoxyacetylaminovalerylamino)-4-phenyl-2-butanone (Compd. No. 348 in Table 1)

mp: 91°–95° C. IR(KBr, cm$^{-1}$): 3300, 3270, 1735, 1650 NMR(CDCl$_3$, δ): 0.80–0.95(m, 6H), 1.30–1.75(m, 3H), 2.95(dd, J=7.7 Hz, 14 Hz, 1H), 3.14(dd, J=6.4 Hz, 14 Hz, 1H), 3.19(d, J=1.9 Hz, 2H), 3.66(s, 2H), 4.39(d, J=15 Hz, 1H), 4.47(m, 1H), 4.49(d, J=15 Hz, 1H), 5.0(q, J=7.4 Hz, 1H), 6.20(d, J=2.9 Hz, 1H), 6.29(m, 1H), 6.60(d, J=7 Hz, 1H), 6.73(d, J=8 Hz, 1H), 6.91(d, J=8.8 Hz, 2H), 7.0–7.36 (m, 9H)

EXAMPLE 165

Preparation of (s)-1-furfurylthio-3-[(s)-4-methyl-2-(2-phenoxypropionylamino)valerylamino]-4-phenyl-2-butanone (Compd. No. 349 in Table 1)

IR(KBr, cm$^{-1}$); 3280, 1710, 1640 NMR(CDCl$_3$, δ): 0.75 (d, J=6.5 Hz, 3H), 0.89(d, J=6.6 Hz, 1.5H), 0.91(d, J=6.6 Hz, 1.5H), 1.05–1.70(m, 6H), 2.76(dd, J=7.9 Hz, 14 Hz, 0.5H), 2.93–3.20(m, 3.5H), 3.64(s, 2H), 4.37(m, 1H), 4.67(m, 1H), 4.87(q, J=7.3 Hz, 0.5H), 4.99(q, J=7.3 Hz, 0.5H), 6.19(m, 1H), 6.29(m, 1H), 6.42(d, J=8 Hz, 0.5H), 6.62–6.67(m, 1.5H), 6.86–6.93(m, 2H), 6.99–7.06(m, 2H), 7.13–7.36(m, 7H)

EXAMPLE 166

Preparation of (s)-1-furfurylthio-3-[(s)-4-methyl-2-(2-phenoxybutyrylamino)valerylamino]-4-phenyl-2-butanone (Compd. No. 350 in Table 1)

IR(KBr, cm$^{-1}$): 3260, 1720, 1705, 1640 NMR(CDCl$_3$, δ): 0.73(d, J=6.5 Hz, 3H), 0.80–0.96(m, 3H), 0.96–1.10(m, 3H), 1.20–1.65(m, 3H), 1.75–2.05(m, 2H), 2.73(dd, J=8.1 Hz, 14 Hz, 0.5H), 2.86–3.20(m, 1.5H), 3.14(s, 2H), 3.63(s, 2H), 4.37(m, 1H), 4.53(m, 1H), 4.85(q, J=5.0 Hz, 0.5H), 4.99(q, J=5.0 Hz, 0.5H), 6.19(m, 1H), 6.29(m, 1H), 6.43(d, J=8 Hz, 0.5H), 6.52(d, J=8 Hz, 0.5H), 6.55(d, J=8 Hz, 0.5H), 6.64(d, J=8 Hz, 0.5H), 6.84–6.96(m, 2H), 6.96–7.05(m, 2H), 7.05–7.40(m, 7H)

EXAMPLE 167

Preparation of (s)-3-[(s)-2-(2-chlorophenoxyacetylamino)-4-methylvalerylamino]-1-furfurylthio-4-phenyl-2-butanone (Compd. No. 354 in Table 1)

mp: 99°–102° C. IR(KBr, cm$^{-1}$): 3300, 1710, 1670, 1640 NMR(CDCl$_3$, δ): 0.85–0.95(m, 6H), 1.42–1.75(m, 3H), 2.97(dd, J=7.5 Hz, 14 Hz, 1H), 3.16(dd, J=5.3 Hz, 14 Hz, 1H), 3.16(d, J=15 Hz, 1H), 3.23(d, J=15 Hz, 1H), 3.65(s, 2H), 4.24(m, 1H), 4.43(d, J=15 Hz, 1H), 4.51(d, J=15 Hz, 1H), 5.02(q, J=7.5 Hz, 1H), 6.19(d, J=2.9 Hz, 1H), 6.29(m, 1H), 6.67(d, J=8 Hz, 1H), 6.88(d, J=8 Hz, 1H), 6.95–7.45(m, 10H)

EXAMPLE 168

Preparation of (s)-3-[(s)-2-(4-chlorophenoxyacetylamino)-4-methylvalerylamino]-1-furfurylthio-4-phenyl-2-butanone (Compd. No. 356 in Table 1)

mp: 116°–117° C. IR(KBr, cm$^{-1}$): 3300, 3250, 1730, 1670, 1650 NMR(CDCl$_3$, δ): 0.83–0.96(m, 6H), 1.45–1.70 (m, 3H), 2.96(dd, J=7.6 Hz, 14 Hz, 1H), 3.11(dd, J=6.4 Hz, 14 Hz, 1H), 3.19(s, 2H), 3.66(s, 2H), 4.35(d, J=15 Hz, 1H), 4.46(d, J=15 Hz, 1H), 4.44(m, 1H), 5.01(dd, J=7.5 Hz, 14 Hz, 1H), 6.20(m, 1H), 6.30(m, 1H), 6.58(d, J=8 Hz, 1H), 6.71(d, J=9 Hz, 1H), 6.80–6.86(m, 2H), 7.11–7.36(m, 8H)

EXAMPLE 169

Preparation of (s)-1-furfurylthio-3-[(s)-2-(2-methoxyphenoxyacetylamino)-4-methylvalerylamino]-4-phenyl-2-butanone (Compd. No. 361 in Table 1)

IR(KBr, cm$^{-1}$): 3280, 1705, 1665, 1645 NMR(CDCl$_3$, δ): 0.87(d, J=6.7 Hz, 3H), 0.89(d, J=6.7 Hz, 3H), 1.39–1.71(m,

3H), 2.91(dd, J=7.7 Hz, 14 Hz, 1H), 3.10(dd, J=7.7 Hz, 14 Hz, 1H), 3.13(d, J=17 Hz, 1H), 3.21(d, J=17 Hz, 1H), 3.64(s, 2H), 3.86(s, 2H), 4.42(m, 1H), 4.45(d, J=15 Hz, 1H), 4.55(d, J=15 Hz, 1H), 4.95(q, J=6.4 Hz, 1H), 4.85–5.05(m, 1H), 6.20(m, 1H), 6.29(m, 1H), 6.70(d, J=7.1 Hz, 1H), 6.90–7.0 (m, 3H), 7.0–7.40(m, 7H)

EXAMPLE 170

Preparation of (s)-1-furfurylthio-3-[(s)-4-methyl-2-(1-naphtoxyacetylamino)valerylamino]-4-phenyl-2-butanone (Compd. No. 364 in Table 1)

mp: 118°–120° C. IR(KBr, cm$^{-1}$): 3300, 1730, 1670, 1650 NMR(CDCl$_3$, δ): 0.75–1.03(m, 6H), 1.38–1.65(m, 3H), 2.95(dd, J=7.8 Hz, 14 Hz, 1H), 3.15(dd, J=6.4 Hz, 14 Hz, 1H), 3.19(s, 2H), 3.66(s, 2H), 4.50(m, 1H), 4.61(d, J=15 Hz, 1H), 4.69(d, J=15 Hz, 1H), 5.04(q, J=7.0 Hz, 1H), 6.20(d, J=3.1 Hz, 1H), 6.29(m, 1H), 6.62(d, J=7.1 Hz, 1H), 6.70–6.90(m, 2H), 7.0–7.65(m, 10H), 7.84(m, 1H), 8.18(m, 1H)

EXAMPLE 171

Preparation of (s)-1-furfurylthio-3-[(s)-4-methyl-2-(2-naphtoxyacetylamino)valerylamino]-4-phenyl-2-butanone (Compd. No. 365 in Table 1)

IR(Kbr, cm$^{-1}$): 3300, 1710, 1675, 1650 NMR(CDCl$_3$, δ): 0.86(d, J=6.1 Hz, 6H), 1.45–1.70(m, 3H), 2.95(dd, J=7.6 Hz, 14 Hz, 1H), 3.12(dd, J=6.5 Hz, 14 Hz, 1H), 3.18(d, J=1.8 Hz, 2H), 3.66(s, 2H), 4.50(m, 1H), 4.52(d, J=15 Hz, 1H), 4.61(d, J=15 Hz, 1H), 5.0(q, J=6.5 Hz, 1H), 6.20(m, 1H), 6.29(m, 1H), 6.62(d, J=8 Hz, 1H), 6.79(d, J=8.5 Hz, 1H), 7.10–7.30(m, 7H), 7.30–7.52(m, 3H), 7.70–7.90(m, 3H)

EXAMPLE 172

Preparation of (s)-3-((s)-2-benzyloxyacetylamino-4-methylvalerylamino)-1-furfurylthio-4-phenyl-2-butanone (Compd. No. 366 in Table 1)

IR(Kbr, cm$^{-1}$): 3350, 3310, 1690, 1640 NMR(CDCl$_3$, δ): 0.89(d, J=5.7 Hz, 3H), 0.91(d, J=5.7 Hz, 3H), 1.46–1.70(m, 3H), 2.96(dd, J=7.7 Hz, 14 Hz, 1H), 3.14(dd, J=6.4 Hz, 14 Hz, 1H), 3.17(d, J=2.7 Hz, 2H), 3.64(s, 2H), 3.88(d, J=14 Hz, 1H), 3.96(d, J=14 Hz, 1H), 4.41(m, 1H), 4.55(s, 2H), 4.98(q, J=6.6 Hz, 1H), 6.19(m, 1H), 6.29(m, 1H), 6.69(d, J=8 Hz, 1H), 6.78(d, J=8 Hz, 1H), 7.10–7.42(m, 11H)

EXAMPLE 173

Preparation of (s)-1-furfurylthio-3-[(s)-4-methyl-2-(2-tetrahydropyranyloxyacetylamino)valerylamino]-4-phenyl-2-butanone (Compd. No. 370 in Table 1)

IR(neat, cm$^{-1}$): 3300, 1710, 1660 NMR(CDCl$_3$, δ): 0.85–0.95(m, 6H), 1.40–1.88(m, 9H), 2.97(m, 1H), 3.13(m, 1H), 3.19(m, 2H), 3.50(m, 1H), 3.64(s, 2H), 3.78(m, 1H), 3.91–4.20(m, 2H), 4.42(m, 1H), 4.55(m, 1H), 4.97(m, 1H), 6.19(m, 1H), 6.29(m, 1H), 6.30–6.85(m, 2H), 7.10–7.36(m, 6H)

EXAMPLE 174

Preparation of (s)-3-[(s)-2-(2-benzofuranylcarbonylamino)-4-methylvalerylamino]-1-furfurylthio-4-phenyl-2-butanone (Compd. No. 382 in Table 1)

IR(KBr, cm$^{-1}$): 3300, 1720, 1640 NMR(CDCl$_3$, δ): 0.90–1–0(m, 6H), 1.55–1.80(m, 3H), 2.97(dd, J=7.6 Hz, 14 Hz, 1H), 3.13(dd, J=6.4 Hz, 14 Hz, 1H), 3.20(s, 2H), 3.66(s, 2H), 4.63(m, 1H), 5.04(q, J=7.4 Hz, 1H), 6.20(m, 1H), 6.29(m, 1H), 6.68(d, J=8 Hz, 1H), 6.82(d, J=8 Hz, 1H), 7.02–7.20(m, 5H), 7.27–7.36(m, 2H), 7.40–7.55(m, 3H), 7.70(d, J=7.9 Hz, 1H)

EXAMPLE 175

Preparation of (s)-3-[(s)-2-(2-chromanylcarbonylamino)-4-methylvalerylamino]-1-furfurylthio-4-phenyl-2-butanone (Compd. No. 384 in Table 1)

IR(KBr, cm$^{-1}$): 3300, 1730, 1650 NMR(CDCl$_3$, δ): 0.78–0.85(m, 3H), 0.93(d, J=6.3 Hz, 1.5H), 0.95(d, J=6.3 Hz, 1.5H), 1.22–1.78(m, 3H), 1.78–2.15(m, 1H), 2.28–2.45 (m, 1H), 2.66–3.13(m, 4H), 3.13–3.20(m, 2H), 3.63(s, 1H), 3.65(s, 1H), 4.35–4.54(m, 2H), 4.90–5.08(m, 1H), 6.18–6.22(m, 1H), 6.30–6.34(m, 1H), 6.51(d, J=8 Hz, 0.5H), 6.70(d, J=8 Hz, 0.5H), 6.76(d, J=9 Hz, 0.5H), 6.83(d, J=8 Hz, 0.5H), 6.87–6.94(m, 2H), 7.04–7.36(m, 8H)

EXAMPLE 176

Preparation of (s)-1-furfurylthio-3-[(s)-4-methyl-2-(4-oxo-4H-1-benzopyran-2-ylcarbonylamino) valerylamino]-4-phenyl-2-butanone (Compd. No. 386 in Table 1)

IR(neat, cm$^{-1}$): 3320, 1710, 1650 NMR(CDCl$_3$, δ): 0.95–0.98(m, 6H), 1.62–1.80(m, 3H), 2.98(dd, J=7.5 Hz, 14 Hz, 1H), 3.16(dd, J=6.4 Hz, 14 Hz, 1H), 3.21(s, 2H), 3.64(s, 1H), 4.62(m, 1H), 5.08(q, J=6.6 Hz, 1H), 6.20(m, 1H), 6.30(m, 1H), 6.56(d, J=8 Hz, 1H), 7.06–7.26(m, 7H), 7.36 (m, 1H), 7.44–7.60(m, 2H), 7.70–7.82(m, 1H), 8.24(dd, J=1.7 Hz, 7.9 Hz, 1H)

EXAMPLE 177

Preparation of (s)-3-[(s)-2-(3-benzylureido)-4-methylvalerylamino]-1-furfurylthio-4-phenyl-2-butanone (Compd. No. 388 in Table 1)

mp: 95°–97° C. IR(KBr, cm$^{-1}$): 3310, 1708, 1650, 1628 NMR(CDCl$_3$, δ): 0.87(d, J=4.9 Hz, 6H), 1.30–1.70(m, 3H), 2.93(dd, J=6.5 Hz, 14 Hz, 1H), 2.98–3.19(m, 3H), 3.58(s, 2H), 4.17–4.45(m, 3H), 4.87(q, J=6.5 Hz, 1H), 5.17–5.35(m, 2H), 6.16(d, J=3.1 Hz, 1H), 6.28(m, 1H), 6.95–7.38(m, 12H)

EXAMPLE 178

Preparation of (s)-3-((s)-2-benzyloxycarbonylamino-3-cyclohexylpropionylamino)-1-furfurylthio-4-phenyl-2-butanone (Compd. No. 400 in Table 1)

mp: 124°–125° C. IR(KBr, cm$^{-1}$): 3350, 3310, 1735, 1690, 1655 NMR(CDCl$_3$, δ): 0.78–1.0(m, 2H), 1.0–1.45(m, 6H), 1.45–1.80(m, 5H), 2.83–3.24(m, 4H), 3.62(s, 2H), 4.16(m, 1H), 4.99(q, J=6.8 Hz, 1H), 5.10(s, 2H), 4.95–5.07 (m, 1H), 6.18(d, J=2.8 Hz, 1H), 6.29(m, 1H), 6.58(m, 1H), 7.03–7.42(m, 11H)

EXAMPLE 179

Preparation of (s)-3-((s)-2-benzyloxycarbonylamino-3-phenylpropionylamino)-1-furfurylthio-4-phenyl-2-butanone (Compd. No. 401 in Table 1)

IR(KBr, cm$^{-1}$): 3300, 3260, 1725, 1685, 1650 NMR (CDCl$_3$, δ): 2.91(dd, J=7.1 Hz, 14 Hz, 1H), 2.95–3.10(m,

5H), 3.56(s, 2H), 4.37(m, 1H), 4.95(q, J=7.4 Hz, 1H), 5.08(s, 2H), 5.13(m, 1H), 6.17(d, J=2.5 Hz, 1H), 6.29(m, 1H), 6.32(d, J=7 Hz, 1H), 7.0–7.04(m, 2H), 7.10–7.35(m, 14H)

EXAMPLE 180

Preparation of (s)-3-(2-benzoylamino-2-methoxyacetylamino)-1-furfurylthio-4-phenyl-2-butanone (Compd. No. 404 in Table 1)

IR(KBr, cm$^{-1}$): 3300, 1730, 1670, 1640 NMR(CDCl$_3$, δ): 3.04(dd, J=7.0 Hz, 14 Hz, 1H), 3.11–3.22(m, 3H), 3.45(s, 0.9H), 3.49(s, 2.1H), 3.65(s, 0.6H), 3.68(s, 1.4H), 5.09(m, 1H), 5.66(d, J=8 Hz, 0.7H), 5.67(d, J=8 Hz, 0.3H), 6.20(m, 1H), 6.30(m, 1H), 6.87(d, J=8 Hz, 0.3H), 7.03(d, J=8 Hz, 0.7H), 7.08–7.28(m, 7H), 7.41–7.60(m, 3H), 7.78–7.86(m, 2H)

EXAMPLE 181

Preparation of (s)-3-(2-benzyloxycarbonylamino-2-isopropoxyacetylamino)-1-furfurylthio-4-phenyl-2-butanone (Compd. No. 405 in Table 1)

IR(KBr, cm$^{-1}$): 3300, 1720, 1695, 1655 NMR(CDCl$_3$, δ): 1.05–1.24(m, 6H), 2.98–3.20(m, 2H), 3.13(s, 1H), 3.21(s, 1H), 3.63(s, 1H), 3.65(s, 1H), 3.96(m, 1H), 4.99(m, 1H), 5.13(s, 2H), 5.35(m, 1H), 5.40(d, J=7 Hz, 0.5H), 5.57(d, J=7 Hz, 0.5H), 6.19(m, 1H), 6.29(m, 1H), 7.07–7.40(m, 12H)

EXAMPLE 182

Preparation of (s)-3-((s)-2-benzyloxycarbonylamino-4-methylvalerylamino)-1-(5-methoxycarbonylfurfurylthio)-4-phenyl-2-butanone (Compd. No. 413 in Table 1)

mp: 85°–93° C. IR(KBr, cm$^{-1}$): 3300, 1740, 1680, 1658 NMR(CDCl$_3$, δ): 0.89(d, J=6.3 Hz, 6H), 1.25–1.65(m, 3H), 2.86–3.03(m, 1H), 3.05–3.38(m, 2H), 3.42(d, J=14 Hz, 1H), 3.65(s, 2H), 3.87(s, 3H), 4.08–4.23(m, 1H), 4.95–5.15(m, 4H), 6.31(d, J=3.5 Hz, 1H), 6.85–6.95(m, 1H), 7.09(d, J=3.5 Hz, 1H), 7.13–7.45(m, 10H)

EXAMPLE 183

Preparation of (s)-3-((s)-2-benzyloxycarbonylamino-4-methylvalerylamino)-1-(5-chloro-2-thienylmethylthio)-4-phenyl-2-butanone (Compd. No. 423 in Table 1)

mp: 105°–107° C. IR(KBr, cm$^{-1}$): 3340, 3310, 1728, 1692, 1650 NMR(CDCl$_3$, δ): 0.90–1.0(m, 6H), 1.30–1.65 (m, 3H), 2.90–3.23(m, 4H), 3.70(s, 2H), 4.13(m, 1H), 4.85–5.0(m, 2H), 5.09(s, 2H), 6.53(m, 1H), 6.60–6.73(m, 2H), 7.12(d, J=6.0 Hz, 2H), 7.15–7.40(m, 8H)

EXAMPLE 184

Preparation of (s)-3-((s)-2-benzyloxycarbonylamino-4-methylvalerylamino)-4-phenyl-1-(2-pyridylmethylthio)-2-butanone (Compd. No. 428 in Table 1)

mp: 82°–87° C. IR(KBr, cm$^{-1}$): 3330, 3280, 1718, 1680, 1655 NMR(CDCl$_3$, δ): 0.89(d, J=6..2 Hz, 6H), 1.30–1.70(m, 3H), 2.98(dd, J=4.8 Hz, 14 Hz, 1H), 3.14(dd, J=4.8 Hz, 14 Hz, 1H), 3.16(d, J=15 Hz, 1H), 3.31(d, J=15 Hz, 1H), 3.75(s, 2H), 4.13(m, 1H), 5.0(q, J=7.4 Hz, 1H), 5.08(s, 2H), 4.93–5.15(m, 1H), 6.74(d, J=7 Hz, 1H), 7.10–7.42(m, 12H), 7.65(dt, J=1.8 Hz, 7.7 Hz, 1H), 8.52(d, J=4.9 Hz, 1H)

EXAMPLE 185

Preparation of (s)-1-(2-benzimidazorylmethylthio)-3-((s)-2-benzyloxycarbonylamino-4-methylvalerylamino)-4-phenyl-2-butanone (Compd. No. 434 in Table 1)

mp: 125°–129° C. IR(KBr, cm$^{-1}$): 3300, 1710, 1690, 1653 NMR(CDCl$_3$, δ): 0.80–1.0(m, 6H), 1.30–1.70(m, 3H), 2.75–2.95(m, 1H), 2.95–3.25(m, 2H), 3.25–3.55(m, 1H), 3.73–4.08(m, 2H), 4.10–4.25(m, 1H), 4.90–5.25(m, 2H), 5.07(s, 2H), 7.0–7.15(m, 2H), 7.15–7.40(m, 12H), 7.40–7.70(m, 2H)

EXAMPLE 186

Preparation of (s)-3-((s)-2-benzyloxycarbonylamino-4-methylvalerylamino)-1-(3-5-dimethyl-4-isooxazorylmethylthio)-4-phenyl-2-butanone (Compd. No. 438 in Table 1)

IR(neat, cm$^{-1}$): 3320, 1720, 1705, 1655 NMR(CDCl$_3$, δ): 0.90(d, J=5.8 Hz, 6H), 1.30–1.65(m, 3H), 2.24(s, 3H), 2.34(s, 3H), 2.90–3.10(m, 4H), 3.35(s, 2H), 4.12(m, 1H), 4.93–5.13(m, 2H), 5.09(s, 2H), 6.63(d, J=8 Hz, 1H), 7.10–7.45(m, 10H)

EXAMPLE 187

Preparation of (s)-3-((s)-2-benzyloxycarbonylamino-4-methylvalerylamino)-1-(2-methyl-4-thiazolylmethylthio)-4-phenyl-2-butanone (Compd. No. 443 in Table 1)

IR(neat, cm$^{-1}$): 3330, 1725, 1705, 1660 NMR(CDCl$_3$, δ): 0.89(d, J=5.9 Hz, 6H), 1.30–1.70(m, 3H), 2.68(s, 3H), 2.95–3.07(m, 1H), 3.07–3.30(m, 3H), 3.69(s, 2H), 4.05–4.20(m, 1H), 4.93–5.20(m, 2H), 5.09(s, 2H), 6.58–6.78(m, 1H), 6.94(s, 1H), 7.08–7.50(m, 10H)

EXAMPLE 188

Preparation of (s)-3-((s)-2-benzyloxycarbonylamino-4-methylvalerylamino)-1-(2-oxo-4-oxazolidinylmethylthio)-4-phenyl-2-butanone (Compd. No. 445 in Table 1)

IR(neat, cm$^{-1}$); 3330, 1705, 1695, 1655 NMR(CDCl$_3$, δ): 0.78–0.95(m, 6H), 1.20–1.75(m, 3H), 2.40–2.62(m, 2H), 2.93(m, 1H), 3.01–3.22(m, 2H), 3.37(m, 1H), 3.84(m, 1H), 3.99(m, 1H), 4.12(m, 1H), 4.38(m, 1H), 4.92(m, 1H), 5.09(s, 2H), 5.56(d, J=7 Hz, 1H), 6.42(s, 1H), 6.95–7.22(m, 11H)

EXAMPLE 189

Preparation of (s)-3-((s)-2-benzyloxycarbonylamino-4-methylvalerylamino)-1-methoxy-4-phenyl-2-butanone (Compd. No. 447 in Table 1)

mp: 87°–92° C. IR(KBr, cm$^{-1}$); 3340, 3285, 1739, 1688, 1657 NMR(CDCl$_3$, δ): 0.90(d, J=6.2 Hz, 6H), 1.30–1.75(m, 3H), 2.90–3.10(m, 2H), 3.35(s, 3H), 3.87(d, J=18 Hz, 1H), 4.08(d, J=18 Hz, 1H), 4.13(m, 1H), 4.96(m, 1H), 5.06(m, 1H), 5.09(s, 2H), 6.57(m, 1H), 7.11(d, J=7.4 Hz, 2H), 7.10–7.33(m, 3H), 7.35(s, 5H)

EXAMPLE 190

Preparation of (s)-3-((s)-2-benzyloxycarbonylamino-4-methylvalerylamino)-1-dimethylamino-4-phenyl-2-butanone (Compd. No. 465 in Table 1)

mp: 81°–82° C. IR(KBr, cm$^{-1}$): 3330, 3295, 1730, 1683, 1653 NMR(CDCl$_3$, δ): 0.75–1.0(m, 6H), 1.30–1.70(m, 3H), 2.18(s, 3H), 2.21(s, 3H), 2.80–3.15(m, 3H), 3.25(t, J=19 Hz, 1H), 4.14(m, 1H), 4.91(m, 1H), 5.08(s, 2H), 5.15–5.35(m, 1H), 6.70–6.90(m, 1H), 7.05–7.18(m, 2H), 7.18–7.30(m, 3H), 7.30–7.40(m, 5H)

EXAMPLE 191

Preparation of (s)-3-((s)-2-benzyloxycarbonylamino-4-methylvalerylamino)-1-(N-methylfurfurylamino)-4-phenyl-2-butanone (Compd. No. 479 in Table 1)

IR(KBr, cm$^{-1}$): 3320, 1728, 1685, 1550 NMR(CDCl$_3$, δ): 0.85–1.0(m, 6H), 1.25–1.80(m, 3H), 2.25(s, 3H), 2.75–2.95 (m, 1H), 2.95–3.15(m, 2H), 3.28–3.45(m, 1H), 3.45–3.70 (m, 2H), 4.15(m, 1H), 4.87–5.15(m, 2H), 5.09(s, 2H), 6.18 (d, J=2.8 Hz, 1H), 6.29(dd, J=3.1 Hz, 1.9 Hz, 1H), 6.55–6.75 (m, 1H), 7.03–7.15(m, 2H), 7.15–7.25(m, 3H), 7.25–7.40 (m, 6H)

EXAMPLE 192

Preparation of (s)-3-((s)-2-benzyloxycarbonylamino-4-methylvalerylamino)-1-(4-methyl-1-piperazyl)-4-phenyl-2-butanone (Compd. No. 488 in Table 1)

mp: 99°–100° C. IR(KBr, cm$^{-1}$): 3320, 1733, 1696, 1655 NMR(CDCl$_3$, δ): 0.87–1.0(m, 6H), 1.30–1.70(m, 3H), 2.27 (s, 3H), 2.30–2.50(m, 8H), 2.85–3.10(m, 3H), 3.10–3.33(m, 1H), 4.10(m, 1H), 4.99(q, J=7.4 Hz, 1H), 5.09(s, 2H), 5.0–5.20(m, 1H), 6.60–6.90(m, 1H), 7.15(d, J=7.0 Hz, 2H), 7.18–7.30(m, 3H), 7.30–7.40(m, 5H)

EXAMPLE 193

3-((s)-2-benzyloxycarbonylamino-4-methylvalerylamino)-4-(4-fluorophenyl)-1-furfurylthio-2-butanone (Compd. No. 496 in Table 1)

mp: 101° C. IR(KBr, cm$^{-1}$): 3300, 1720, 1680, 1650 NMR(CDCl$_3$, δ): 0.82–0.99(m, 6H), 1.23–1.75(m, 3H), 2.82–3.02(m, 1H), 3.05–3.25(m, 3H), 3.65(s, 2H), 4.05–4.18(m, 1H), 4.90–5.02(m, 2H), 5.07(s, 2H), 6.21(d, J=3.0 Hz, 1H), 6.28(m, 1H), 6.50–6.55(m, 1H), 6.87–7.0(m, 2H), 7.03–7.15(m, 2H), 7.25–7.40(m, 6H)

EXAMPLE 194

Preparation of (s)-3-((s)-2-benzyloxycarbonylamino-4-methylvalerylamino)-4-(2-chlorophenyl)-1-furfurylthio-2-butanone (Compd. No. 503 in Table 1)

mp: 110° C. IR(KBr, cm$^{-1}$); 3300, 1735, 1690, 1660 NMR(CDCl$_3$, δ): 0.86(d, J=6.0 Hz, 3H), 0.88(d, J=6.0 Hz, 3H), 1.21–1.80(m, 3H), 2.97–3.12(m, 1H), 3.19–3.38(m, 1H), 3.28(s, 2H), 3.67(s, 2H), 4.10(m, 1H), 4.90–5.07(m, 2H), 5.09(d, J=3.9 Hz, 2H), 6.21(d, J=2.8 Hz, 1H), 6.30(m, 1H), 6.63(m, 1H), 7.08–7.20(m, 5H), 7.30–7.51(m, 5H)

EXAMPLE 195

Preparation of (s)-3-((s)-2-benzyloxycarbonylamino-4-methylvalerylamino)-4-(4-chlorophenyl)-1-methylthio-2-butanone (Compd. No. 506 in Table 1)

mp: 119°–121° C. IR(KBr, cm$^{-1}$): 3320, 3280,.1703, 1685, 1658 NMR(CDCl$_3$, δ): 0.80–1.0(m, 6H), 1.30–1.65 (m, 3H), 1.99(s, 3H), 2.93(dd, J=7.0 Hz, 15 Hz, 1H), 3.05–3.35(m, 3H), 4.15(m, 1H), 4.90–5.22(m, 2H), 5.10(s, 2H), 5.62(d, J=7 Hz, 1H), 7.07(d, J=8.2 Hz, 2H), 7.23(d, J=8.2 Hz, 2H), 7.36(s, 5H)

EXAMPLE 196

Preparation of (s)-3-((s)-2-benzyloxycarbonylamino-4-methylvalerylamino)-4-(4-chlorophenyl)-1-furfurylthio-4-butanone (Compd. No. 508 in Table 1)

IR(KBr, cm$^{-1}$): 3300, 3270, 1705, 1685, 1645 NMR (CDCl$_3$, δ): 0.82–0.95(m, 6H), 1.30–1.66(m, 3H), 2.93(m, 1H), 3.05–3.15(m, 3H), 3.64(s, 2H), 4.10(m, 1H), 4.90–5.05 (m, 2H), 5.10(s, 2H), 6.19(m, 1H), 6.30(m, 1H), 6.57(m, 1H), 7.06(d, J=8.2 Hz, 2H), 7.18–7.30(m, 3H), 7.30–7.40(m, 5H)

EXAMPLE 197

Preparation of (s)-4-(4-chlorophenyl)-1-furfurylthio-3-((s)-4-methyl-2-phenoxyacetylaminovalerylamino)-2-butanone (Compd. No. 511 in Table 1)

IR(KBr, cm$^{-1}$): 3280, 1720, 1645 NMR(CDCl$_3$, δ): 0.80–0.95(m, 6H), 1.38–1.70(m, 3H), 2.90(dd, J=7.3 Hz, 14 Hz, 1H), 3.10–3.23(m, 3H), 3.66(s, 2H), 4.35–4.53(m, 3H), 4.97(m, 1H), 6.20(m, 1H), 6.30(m, 1H), 6.63(d, J=7 Hz, 1H), 6.73(d, J=8 Hz, 1H), 7.88–7.95(m, 2H), 7.0–7.15(m, 3H), 7.20–7.40(m, 5H)

EXAMPLE 198

Preparation of (s)-3-((s)-2-benzyloxycarbonylamino-4-methylvalerylamino)-4-(4-methoxyphenyl)-1-methylthio-2-butanone (Compd. No. 516 in Table 1)

mp: 100°–101° C. IR(KBr, cm$^{-1}$): 3340, 1730, 1705, 1683, 1662 NMR(CDCl$_3$, δ): 0.89(d, J=6.0 Hz, 6H), 1.30–1.75(m, 3H), 1.99(s, 3H), 2.85–3.25(m, 4H), 3.75(s, 3H), 4.12(m, 1H), 4.95–5.20(m, 2H), 5.10(s, 2H), 6.54(d, J=7 Hz, 1H), 6.78(d, J=8.6 Hz, 2H), 7.06(d, J=8.6 Hz, 2H), 7.35(s, 5H)

EXAMPLE 199

Preparation of (s)-3-((s)-2-benzyloxycarbonylamino-4-methylvalerylamino)-4-(4-hydroxyphenyl)-1-methylthio-2-butanone (Compd. No. 520 in Table 1)

mp: 108°–111° C. IR(KBr, cm$^{-1}$): 3440, 3340, 1725, 1683, 1658 NMR(CDCl$_3$, δ): 0.89(d, J=5.9 Hz, 6H), 1.30–1.75(m, 3H), 1.99(s, 3H), 2.89(m, 1H), 2.99–3.30(m, 3H), 4.14(m, 1H), 4.95–5.10(m, 2H), 5.10(s, 2H), 5.72(s, 1H), 6.58–6.80(m, 1H), 6.70(d, J=8.2 Hz, 2H), 6.98(d, J=8.2 Hz, 2H), 7.35(s, 5H)

EXAMPLE 200

Preparation of (s)-3-((s)-2-benzyloxycarbonylamino-4-methylvalerylamino)-1-methylthio-4-(2-thienyl)-2-butanone (Compd. No. 527 in Table 1)

mp: 93°–97° C. IR(KBr, cm$^{-1}$): 3340, 3290, 1728, 1688, 1655 NMR(CDCl$_3$, δ): 0.92(d, J=6.2 Hz, 6H), 1.35–1.75(m, 3H), 2.0(s, 3H), 3.14(d, J=15 Hz, 1H), 3.23–3.50(m, 3H), 4.18(m, 1H), 4.93–5.13(m, 2H), 5.11(s, 2H), 6.70–6.85(m, 2H), 6.90(m, 1H), 7.14(d, J=5.1 Hz, 1H), 7.35(s, 5H)

EXAMPLE 201

Preparation of (s)-3-((s)-2-benzyloxycarbonylamino-4-methylvalerylamino)-1-furfurylthio-4-(2-thienyl)-2-butanone (Compd. No. 529 in Table 1)

mp: 106°–107° C. IR(KBr, cm$^{-1}$): 3350, 3300, 1730, 1692, 1662 NMR(CDCl$_3$, δ): 0.92(d, J=6.0 Hz, 6H), 1.38–1.75(m, 3H), 3.12–3.43(m, 4H), 3.64(s, 2H), 4.18(m, 1H), 4.90–5.15(m, 2H), 5.11(s, 2H), 6.16(d, J=3.1 Hz, 1H), 6.30(m, 1H), 6.67–6.88(m, 2H), 6.89(m, 1H), 7.13(d, J=5.1 Hz, 1H), 7.30–7.40(m, 6H)

EXAMPLE 202

Preparation of (s)-3-((s)-2-benzyloxycarbonylamino-4-methylvalerylamino)-1-methylthio-5-phenyl-2-pentanone (Compd. No. 534 in Table 1)

mp: 119°–120° C. IR(KBr, cm$^{-1}$): 3320, 1715, 1685, 1645 NMR(CDCl$_3$, δ): 0.95(d, J=6.2 Hz, 6H), 1.40–1.75(m, 3H), 1.95(m, 1H), 2.05(s, 3H), 2.28(m, 1H), 2.63(t, J=7.8 Hz, 2H), 3.17(d, J=15 Hz, 1H), 3.33(d, J=15 Hz, 1H), 4.18(m, 1H), 4.86(m, 1H), 4.99(d, J=7 Hz, 1H), 5.12(s, 2H), 6.58(d, J=7 Hz, 1H), 7.10–7.40(m, 10H)

EXAMPLE 203

Preparation of (s)-3-((s)-4-methyl-2-phenoxyacetylaminovalerylamino)-1-methylthio-5-phenyl-2-pentanone (Compd. No. 536 in Table 1)

IR(KBr, cm$^{-1}$): 3260, 1720, 1650 NMR(CDCl$_3$, δ): 0.85–1.02(m, 6H), 1.50–1.80(m, 3H), 1.93(m, 1H), 2.06(s, 3H), 2.30(m, 1H), 2.62(t, J=7.6 Hz, 2H), 3.17(d, J=14 Hz, 1H), 3.32(d, J=14 Hz, 1H), 4.50(m, 1H), 4.54(s, 2H), 4.88(m, 1H), 6.63(d, J=7 Hz, 1H), 6.82–7.10(m, 4H), 7.10–7.40(m, 7H)

EXAMPLE 204

Preparation of (s)-3-((s)-2-benzyloxycarbonylamino-4-methylvalerylamino)-1-furfurylthio-5-phenyl-2-pentanone (Compd. No. 540 in Table 1)

mp: 73°–77° C. IR(KBr, cm$^{-1}$): 3340, 1704, 1680, 1658 NMR(CDCl$_3$, δ): 0.94(d, J=5.9 Hz, 6H), 1.40–1.75(m, 3H), 1.91(m, 1H), 2.21(m, 1H), 2.61(t, J=7.5 Hz, 2H), 3.15–3.35 (m, 2H), 3.70(s, 2H), 4.16(m, 1H), 4.78(m, 1H), 5.02(d, J=7.5 Hz, 1H), 5.12(s, 2H), 6.20(d, J=2.9 Hz, 1H), 6.28(m, 1H), 6.59(d, J=7 Hz, 1H), 7.08–7.45(m, 11H)

EXAMPLE 205

Preparation of (s)-3-((R)-2-benzyloxycarbonylamino-4-methylvalerylamino)-1-furfurylthio-5-phenyl-2-pentanone (Compd. No. 540 in Table 1)

mp: 107° C. IR(KBr, cm$^{-1}$): 3320, 1725, 1690, 1645 NMR(CDCl$_3$, δ): 0.95(d, J=6.1 Hz, 6H), 1.35–2.0(m, 4H), 2.25(m, 1H), 2.50–2.65(m, 2H), 3.20(d, J=15 Hz, 2H), 3.28(d, J=15 Hz, 1H), 3.70(s, 2H), 4.17(m, 1H), 4.78(m, 1H), 5.10(m, 1H), 5.12(d, J=1.8 Hz, 2H), 6.20(d, J=2.1 Hz, 1H), 6.27(m, 1H), 6.63(m, 1H), 7.10–7.40(m, 11H)

EXAMPLE 206

Preparation of (s)-1-furfurylthio-3-((s)-4-methyl-2-phenoxyacetylaminovalerylamino)-5-phenyl-2-pentanone (Compd. No. 543 in Table 1)

IR(KBr, cm$^{-1}$): 3270, 1720, 1655 NMR(CDCl$_3$, δ): 0.90–0.95(m, 6H), 1.48–1.80(m, 3H), 1.90(m, 1H), 2.22(m, 1H), 2.60(t, J=7.8 Hz, 2H), 3.22(d, J=15 Hz, 1H), 3.30(d, J=15 Hz, 1H), 3.71(s, 2H), 4.50(m, 1H), 4.54(s, 2H), 4.78 (m, 1H), 6.21(m, 1H), 6.28(m, 1H), 6.62(d, J=8 Hz, 1H), 6.86(d, J=8 Hz, 1H), 6.90–6.98(m, 1H), 7.03(t, J=7.3 Hz, 1H), 7.06–7.36(m, 9H)

EXAMPLE 207

Preparation of 3-((s)-2-benzyloxycarbonylamino-4-methylvalerylamino)-1-methylthio-4-(1-naphtyl)-2-butanone (Compd. No. 547 in Table 1)

mp: 77°–80° C. IR(KBr, cm$^{-1}$): 3340, 1700, 1685, 1665 NMR(CDCl$_3$, δ): 0.78–0.90(m, 6H), 1.20–1.65(m, 3H), 1.92(s, 1.5H), 1.95(s, 1.5H), 2.93(t, J=14 Hz, 2H), 3.52(d, J=7.1 Hz, 2H), 4.07(m, 1H), 4.92(m, 1H), 5.09(s, 2H), 5.18(m, 1H), 6.55–6.65(m, 1H), 7.20–7.45(m, 7H), 7.50–7.62(m, 2H), 7.76(dd, J=2.7 Hz, 7.8 Hz, 1H), 7.86(d, J=8.0 Hz, 1H), 8.20(d, J=7.8 Hz, 1H)

EXAMPLE 208

Preparation of 3-((s)-2-benzyloxycarbonylamino-4-methylvalerylamino)-1-furfurylthio-4-(1-naphtyl)-2-butanone (Compd. No. 550 in Table 1)

mp: 71°–74° C. IR(KBr, cm$^{-1}$): 3330, 1730, 1690, 1650 NMR(CDCl$_3$, δ): 0.78–0.90(m, 6H), 1.25–1.60(m, 3H), 2.90–3.05(m, 2H), 3.49(d, J=7.1 Hz, 2H), 3.57(d, J=6.3 Hz, 2H), 4.08(m, 1H), 4.88(m, 1H), 5.08(s, 2H), 5.11(m, 1H), 6.12(m, 1H), 6.25(m, 1H), 6.57(d, J=7 Hz, 0.5H), 6.66(d, J=7 Hz, 0.5H), 7.20–7.40(m, 8H), 7.42–7.62(m, 2H), 7.75 (dd, J=3.1 Hz, 8.2 Hz, 1H), 7.85(d, J=8.0 Hz, 1H), 8.17(d, J=8.0 Hz, 1H)

EXAMPLE 209

Preparation of 1-furfurylthio-3-((s)-4-methyl-2-phenoxyacetylaminovalerylamino)-4-(1-naphtyl)-2-butanone (Compd. No. 555 in Table 1)

IR(KBr, cm$^{-1}$): 3280, 1650 NMR(CDCl$_3$, δ): 0.72–0.92 (m, 6H), 1.20–1.70(m, 3H), 2.90–3.05(m, 2H), 3.40–3.60 (m, 2H), 3.60(s, 2H), 4.41(m, 1H), 4.45(s, 2H), 5.11(m, 1H), 6.14(m, 1H), 6.25(m, 1H), 6.65–7.12(m, 5H), 7.20–7.42(m, 5H), 7.42–7.65(m, 2H), 7.70–7.90(m, 2H), 8.13(t, J=8.3 Hz, 1H)

EXAMPLE 210

Preparation of (s)-3-((s)-2-benzyloxycarbonylamino-4-methylvalerylamino)-1-methylthio-4-(2-naphtyl)-2-butanone (Compd. No. 559 in Table 1)

mp: 101°–103° C. IR(KBr, cm$^{-1}$): 3340, 1730, 1690, 1650 NMR(CDCl$_3$, δ): 0.65–0.76(m, 2.4H), 0.83(d, J=5.7 Hz, 3.6H), 1.25–1.63(m, 3H), 1.97(s, 1.8H), 1.99(s, 1.2H), 3.05–3.40(m, 4H), 4.08(m, 1H), 4.94–5.07(m, 3H), 5.16(q, J=7.0 Hz, 1H), 6.52(d, J=7 Hz, 0.4H), 6.68(d, J=7 Hz, 0.6H), 7.25–7.40(m, 6H), 7.40–7.50(m, 2H), 7.60(s, 1H), 7.70–7.85(m, 3H)

EXAMPLE 211

Preparation of (s)-3-((s)-2-benzyloxycarbonylamino-4-methylvalerylamino)-1-furfurylthio-4-(2-naphtyl)-2-butanone (Compd. No. 563 in Table 1)

mp: 103°–104° C. IR(KBr, cm$^{-1}$): 3330, 3300, 1710, 1690, 1650 NMR(CDCl$_3$, δ): 0.70–0.80(m, 1.8H), 0.84(d, J=5.7 Hz, 4.2H), 1.20–1.60(m, 3H), 3.10–3.40(m, 4H), 3.61(s, 1.4H), 3.64(s, 0.6H), 4.10(m, 1H), 4.90–5.15(m, 4H), 6.14(m, 1H), 6.26(m, 1H), 6.52(d, J=7 Hz, 0.3H), 6.64(d, J=7 Hz, 0.7H), 7.26–7.40(m, 7H), 7.40–7.50(m, 2H), 7.59(m, 1H), 7.76–7.84(m, 3H)

EXAMPLE 212

Preparation of (s)-1-((s)-2-benzyloxycarbonylamino-4-methylvalerylamino)-3-methylthio-1-phenyl-2-propanone (Compd. No. 565 in Table 1)

IR(neat, cm$^{-1}$): 3330, 1710, 1650 NMR(CDCl$_3$, δ): 0.80–1.0(m, 6H), 1.20–1.75(m, 3H), 2.00(s, 3H), 3.08(dd, J=3.4 Hz, 14 Hz, 1H), 3.25(dd, J=3.8 Hz, 14 Hz, 1H), 4.25(m, 1H), 5.09(s, 1H), 5.13(s, 1H), 5.92(d, J=6.3 Hz, 1H), 7.17(m, 1H), 7.25–7.45(m, 10H)

EXAMPLE 213

Preparation of (s)-4-benzyloxy-3-((s)-2-benzyloxycarbonylamino-4-methylvalerylamino)-1-methylthio-2-butanone (Compd. No. 571 in Table 1)

mp: 58°–70° C. IR(KBr, cm$^{-1}$): 3340, 1723, 1688, 1650 NMR(CDCl$_3$, δ): 0.85–1.05(m, 6H), 1.40–1.80(m, 3H), 2.02(s, 3H), 3.22(d, J=15 Hz, 1H), 3.35(d, J=15 Hz, 1H), 3.65(m, 1H), 3.93(m, 1H), 4.23(m, 1H), 4.43(d, J=13 Hz, 1H), 4.53(d, J=13 Hz, 1H), 5.0(m, 1H), 5.11(s, 2H), 5.15(m, 1H), 6.90(m, 1H), 7.20–7.45(m, 10H)

EXAMPLE 214

Preparation of (s)-3-((s)-2-benzyloxycarbonylamino-4-methylvalerylamino)-1-5-bis(methylthio)-2-pentanone (Compd. No. 584 in Table 1)

mp: 61°–67° C. IR(KBr, cm$^{-1}$): 3320, 1715, 1682, 1642 NMR(CDCl$_3$, δ): 0.93(d, J=5.4 Hz, 6H), 1.45–2.35(m, 5H), 2.06(s, 3H), 2.07(s, 3H), 2.49(t, J=6.9 Hz, 2H), 3.24(d, J=14 Hz, 1H), 3.36(d, J=14 Hz, 1H), 4.23(m, 1H), 4.93(m, 1H), 5.11(s, 2H), 5.35(m, 1H), 6.98(m, 1H), 7.34(s, 5H)

EXAMPLE 215

Preparation of 3-((s)-2-benzyloxycarbonylamino-4-methylvalerylamino)-5-furfurylthio-1-methylthio-2-pentanone (Compd. No. 588 in Table 1)

IR(neat, cm$^{-1}$): 3350, 3310, 1715, 1690, 1660, 1643 NMR(CDCl$_3$, δ): 0.93(d, J=5.5 Hz, 3H), 0.95(d, J=5.5 Hz, 3H), 1.45–1.93(m, 4H), 2.05(s, 3H), 2.13(m, 1H), 2.50(t, J=6.7 Hz, 2H), 3.14–3.42(m, 2H), 3.70(s, 2H), 4.21(m, 1H), 4.89(m, 1H), 5.12(s, 2H), 5.13(m, 1H), 6.19(d, J=2.9 Hz, 1H), 6.32(m, 1H), 6.77(m, 1H), 7.30–7.40(m, 5H)

EXAMPLE 216

Preparation of (s)-4-((s)-2-benzyloxycarbonylamino-4-methylvalerylamino)-6-furfurylthio-5-oxohexanoic Acid Methyl Ester (Compd. No. 598 in Table 1)

IR(neat, cm$^{-1}$): 3330, 1735, 1715, 1660 NMR(CDCl$_3$, δ): 0.93(d, J=5.9 Hz, 6H), 1.42–2.50(m, 7H), 3.29(d, J=15 Hz, 1H), 3.36(d, J=15 Hz, 1H), 3.65(s, 3H), 3.70(s, 2H), 4.19(m, 1H), 4.77(m, 1H), 5.11(s, 2H), 5.16(m, 1H), 6.22(d, J=2.4 Hz, 1H), 6.28(m, 1H), 6.90(m, 1H), 7.25–7.40(m, 6H)

EXAMPLE 217

Preparation of (s)-4-((s)-2-benzyloxycarbonylamino-4-methylvalerylamino)-6-furfurylthio-5-oxohexanoic Acid (Compd. No. 600 in Table 1)

IR(neat, cm$^{-1}$): 3420, 1710, 1650 NMR(CDCl$_3$, δ): 0.91 (d, J=5.0 Hz, 6H), 1.40–2.75(m, 7H), 3.31(s, 2H), 3.68(s, 2H), 4.22(m, 1H), 4.78(m, 1H), 5.09(s, 2H), 5.43(m, 1H), 6.19(d, J=2.1 Hz, 1H), 6.26(m, 1H), 6.91(m, 1H), 7.13–7.35 (m, 7H)

EXAMPLE 218

Preparation of 1-((s)-2-benzyloxycarbonylamino-4-methylvalerylamino)-3-furfurylthio-1-propoxy-2-propanone (Compd. No. 604 in Table 1)

IR(neat, cm$^{-1}$): 3300, 1710, 1660 NMR(CDCl$_3$, δ): 0.89 (t, J=7.5 Hz, 3H), 0.95(d, J=5.9 Hz, 6H), 1.40–1.80(m, 5H), 3.37(d, J=15 Hz, 1H), 3.50(d, J=15 Hz, 1H), 3.50–3.67(m, 2H), 3.68(s, 2H), 4.25(m, 1H), 5.12(s, 2H), 5.14(m, 1H), 5.76(m, 1H), 6.20(d, J=2.5 Hz, 1H), 6.28(m, 1H), 6.88(d, J=9 Hz, 0.7H), 6.97(d, J=9 Hz, 0.3H), 7.30–7.40(m, 6H)

EXAMPLE 219

Preparation of 3-((s)-2-benzyloxycarbonylamino-4-methylvalerylamino)-4-phenyl-1-phenylthio-3-buten-2-one (Compd. No. 610 in Table 1)

mp: 142°–143° C. IR(Kbr, cm$^{-1}$): 3385, 1692, 1650 NMR(CDCl$_3$, δ): 0.93(d, J=5.2 Hz, 3H), 0.96(d, J=6.1 Hz, 3H), 1.52(m, 1H), 1.70(m, 2H), 3.98(s, 2H), 4.38(m, 1H), 5.05(d, J=6.5 Hz, 1H), 5.13(s, 2H), 7.09(s, 1H), 7.20–7.48 (m, 15H), 7.88(s, 1H)

EXAMPLE 220

Preparation of (s)-1-furfurylthio-3-[(s)-2-{3-(2-furyl)acryloylamino}-4-methylvalerylamino]-2-heptane (Compd. No. 645 in Table 1)

IR(KBr, cm$^{-1}$): 3272, 1715, 1651, 1618 NMR(CDCl$_3$, δ): 0.81(t, J=6.7 Hz, 3H), 0.92(d, J=5.6 Hz, 6H), 1.13–1.41(m, 4H), 1.45–1.79(m, 4H), 1.85(m, 1H), 3.27(d, J=15 Hz, 1H), 3.36(d, J=15 Hz, 1H), 3.72(s, 2H), 4.62–4.83(m, 2H), 6.18–6.60(m, 6H), 7.06(d, J=7.7 Hz, 1H), 7.28–7.51(m, 3H)

EXAMPLE 221

Preparation of (s)-3-((s)-1-benzyloxycarbonyl-2-pyrrolidinylamino)-1-furfurylthio-2-heptanone (Compd. No. 669 in Table 1)

IR(neat, cm$^{-1}$): 3320, 1720, 1680 NMR(CDCl$_3$, δ): 0.86 (t, J=6.7 Hz, 3H), 1.10–1.39(m, 4H), 1.55(m, 1H), 1.75–2.10 (m, 4H), 2.21(m, 1H), 3.03–3.38(m, 2H), 3.38–3.63(m, 2H), 3.63–3.78(m, 2H), 4.36(m, 1H), 4.67(m, 1H), 5.18(s, 2H), 6.22(m, 1H), 6.29(m, 1H), 6.58(m, 1H), 7.22–7.45(m, 6H)

EXAMPLE 222

Preparation of (s)-3-((s)-1-benzyloxycarbonyl-2-pyrrolidinylcarbonylamino)-1-methylthio-4-phenyl-2-butanone (Compd. No. 673 in Table 1)

IR(neat, cm$^{-1}$): 3330, 1705, 1680 NMR(CDCl$_3$, δ): 1.40–2.05(m, 4H), 1.97(s, 3H), 2.85–3.60(m, 6H), 4.31(m, 1H), 5.02(m, 1H), 5.15(s, 2H), 7.12(d, J=7.5 Hz, 2H), 7.15–7.45(m, 8H)

EXAMPLE 223

Preparation of (s)-3-((s)-2-benzyloxycarbonyl-3-perhydroisoquinolylcarbonylamino)-1-furfurylthio-4-phenyl-2-butanone (Compd. No. 683 in Table 1)

IR(neat, cm$^{-1}$): 3350, 1690 NMR(CDCl$_3$, δ): 1.15–1.90 (m, 12H), 2.80–3.25(m, 6H), 3.60–3.70(m, 2H), 4.70–5.25 (m, 4H), 6.20(m, 1H), 6.29(m, 1H), 6.52(m, 1H), 7.0–7.45 (m, 11H)

EXAMPLE 224

Preparation of (s)-3-[(s)-2-((s)-2-cyclohexylmethoxycarbonylamino-4-methylvalerylamino)-4-methylvalerylamino]-1-furfurylthio-2-heptanone (Compd. No. 699 in Table 2)

IR(neat, cm$^{-1}$): 3300, 1700, 1670, 1640 NMR(CDCl$_3$, δ): 0.85–1.70(m, 15H), 1.15–2.0(m, 23H), 3.26(d, J=15 Hz, 1H), 3.32(d, J=15 Hz, 1H), 3.71(s, 2H), 3.87(d, J=6.4 Hz, 2H), 4.12(m, 1H), 4.42(m, 1H), 4.69(m, 1H), 5.03(d, J=5.8 Hz, 1H), 6.22(d, J=3.3 Hz, 1H), 6.28(dd, J=3.3 Hz, 2.1 Hz, 1H), 6.47(d, J=7.5 Hz, 1H), 6.76(m, 1H), 7.35(d, J=2.1 Hz, 1H)

REFERENCE EXAMPLE 3

Preparation of (s)-1-((s)-2-benzyloxycarbonylamino-4-methylvaleryl)-2-furfurylthioacetylpyrrolidine IR(neat, cm$^{-1}$): 3300, 1710, 1640 NMR(CDCl$_3$, δ): 0.93 (d, J=5.9 Hz, 3H), 0.98(d, J=6.5 Hz, 3H), 1.48(dd, J=6.9 Hz, 6.9 Hz, 2H), 1.64–1.80(m, 2H), 1.84–2.28(m, 3H), 3.30(d, J=15 Hz, 1H), 3.42(d, J=15 Hz, 1H), 3.59(m, 1H), 3.70(s, 2H), 3.82(m, 1H), 4.57(m, 1H), 4.74(dd, J=7.9 Hz, 5.9 Hz, 1H), 5.03–5.12(m, 2H), 5.39(d, J=6.8 Hz, 1H), 6.23(m, 1H), 6.29(m, 1H), 7.24–7.39(m, 6H)

The following experiments were conducted to evaluate the biological activity of compound (I) prepared in the above Examples.

EXPERIMENT 1

Assay of Thiol Protease Inhibitory Activity

Inhibitory activity against papain (P-3125, Sigma) and cathepsin B (C-6286, Sigma) was assayed according to the method described in a literature [Biochemical Journal, 201, 189 (1982)]. Cathepsin L was purified from rat kidney according to the method in a literature [Journal of Biochemistry, 100, 35 (1986)], and the inhibitory activity against it was assayed in the same manner as described in the above literature for cathepsin B. Furthermore, m-calpain was purified from rat brain according to a known method [Journal of Biological Chemistry, 254, p. 3210 (1984)] and the inhibitory activity against it was assayed by a method described in a literature [Journal of Biological Chemistry, 259, 12489 (1984)]. The results are shown in Tables 3 and 4. It is evident from Tables 3 and 4 that the compounds of the present invention have a potent inhibitory activity against thiol proteases such as papain, cathepsin B, cathepsin L or m-calpain.

TABLE 3

(Inhibitory activity against thiol protease)

| Compd. of Ex. No. (Compd. No. in Table 1) | IC$_{50}$ (μM) papain | cathepsin B | cathepsin L | m-calpain |
|---|---|---|---|---|
| 3 (No. 82) | 0.26 | 0.71 | 0.016 | 3.3 |
| 4 (No. 83) | 0.21 | 0.044 | 0.045 | 12 |
| 21 (No. 46) | 0.13 | 0.14 | — | 4.7 |
| 22 (No. 48) | 1.1 | 0.98 | 1.3 | 11 |
| 23 (No. 49) | 22 | 3.7 | 1.1 | 6.4 |
| 28 (No. 59) | 3.4 | 2.1 | 15 | 11 |
| 30 (No. 66) | 0.15 | 0.59 | — | 5.1 |
| 31 (No. 69) | 1.4 | 0.55 | 0.63 | 22 |
| 33 (No. 76) | 0.70 | 1.2 | 0.27 | 6.4 |
| 34 (No. 79) | 0.36 | 0.41 | 0.51 | 5.5 |
| 35 (No. 81) | 0.21 | 0.70 | 1.1 | 8.6 |
| 36 (No. 85) | 26 | 4.9 | 1.3 | 25 |
| 37 (No. 86) | 1.3 | 0.70 | 0.45 | 15 |
| 38 (No. 87) | 0.42 | 0.62 | 0.72 | 5.0 |
| 39 (No. 88) | 0.25 | 0.29 | — | 2.2 |
| 40 (No. 90) | 2.1 | 0.27 | 0.85 | 8.4 |
| 41 (No. 91) | 21 | 5.7 | 1.1 | 14 |
| 42 (No. 92) | 4.5 | 1.9 | 0.74 | 23 |
| 43 (No. 94) | 0.37 | 0.057 | 0.038 | 5.8 |
| 44 (No. 96) | 0.88 | 0.17 | 0.060 | 22 |
| 45 (No. 97) | 0.51 | 0.38 | 0.19 | 11 |
| 46 (No. 100) | 0.39 | 0.40 | 0.10 | 16 |
| 49 (No. 107) | 0.040 | 0.59 | 0.67 | 11 |
| 52 (No. 114) | 0.34 | 0.82 | — | 2.5 |
| 53 (No. 115) | 9.2 | 11 | 1.5 | 6.2 |
| 54 (No. 116) | 0.38 | 0.88 | 0.25 | 14 |
| 82 (No. 162) | 34 | 2.7 | 0.32 | 20 |
| 83 (No. 161) | 47 | 5.0 | 0.40 | 12 |
| 91 (No. 180) | 0.16 | 0.050 | 0.069 | 14 |
| 94 (No. 188) | 0.77 | 1.1 | 0.024 | 9.2 |
| 109 (No. 238) | 4.2 | 1.1 | 1.2 | 13 |
| 110 (No. 240) | 21 | 3.3 | 0.98 | 6.0 |
| 120 (No. 256) | 56 | 3.9 | 0.49 | 26 |
| 135 (No. 288) | 59 | 0.31 | 0.054 | 3.2 |
| 150 (No. 313) | 91 | 1.1 | 0.27 | 5.4 |
| 159 (No. 333) | 0.38 | 0.75 | 1.1 | 1.9 |
| 160 (No. 334) | 35 | 3.3 | 6.6 | 28 |
| 162 (No. 345) | 0.95 | 5.3 | — | 3.7 |
| 164 (No. 348) | 35 | 64 | 3.2 | 1.7 |
| 165 (No. 349) | 9.2 | 7.0 | 1.9 | 13 |
| 167 (No. 354) | >100 | 30 | 1.4 | 20 |
| 170 (No. 364) | 9.2 | 6.5 | 8.6 | 19 |
| 174 (No. 382) | 12 | 23 | 1.6 | 16 |
| 190 (No. 465) | 40 | 1.6 | 2.8 | 7.3 |
| 191 (No. 479) | >100 | 3.5 | 9.3 | 24 |
| 197 (No. 511) | 13 | 6.0 | 1.7 | 7.8 |
| 202 (No. 534) | >100 | 0.25 | 0.39 | 13 |
| 203 (No. 536) | 4.4 | 0.34 | 0.38 | 9.1 |
| 206 (No. 543) | 6.0 | 0.82 | 0.62 | 15 |
| 209 (No. 555) | 9.0 | 6.5 | 1.5 | 19 |
| 217 (No. 600) | 26 | 2.5 | 11 | 19 |

TABLE 4

(Inhibitory activity against m-calpain)

| Compd. of Ex. No. (Compd. No. in Table 1) | IC$_{50}$ (μM) m-calpain | Compd. of Ex. No. (Compd. No. in Table 1) | IC$_{50}$ (μM) m-calpain |
|---|---|---|---|
| 26 (No. 57) | 2.8 | 67 (No. 132) | 2.1 |
| 29 (No. 65) | 3.6 | 68 (No. 135) | 2.1 |
| 32 (No. 73) | 6.2 | 69 (No. 140) | 5.0 |
| 47 (No. 102) | 1.3 | 71 (No. 142) | 4.2 |
| 48 (No. 104) | 1.0 | 77 (No. 151) | 1.2 |
| 55 (No. 117) | 1.5 | 78 (No. 103) | 6.0 |

TABLE 4-continued (Inhibitory activity against m-calpain)

| Compd. of Ex. No. (Compd. No. in Table 1) | IC$_{50}$ (μM) m-calpain | Compd. of Ex. No. (Compd. No. in Table 1) | IC$_{50}$ (μM) m-calpain |
|---|---|---|---|
| 56 (No. 118) | 5.2 | 79 (No. 153) | 1.9 |
| 57 (No. 119) | 5.3 | 80 (No. 155) | 4.2 |
| 58 (No. 120) | 1.6 | 81 (No. 157) | 3.4 |
| 59 (No. 121) | 4.2 | 84 (No. 165) | 2.1 |
| 60 (No. 122) | 1.3 | 85 (No. 166) | 1.3 |
| 61 (No. 123) | 1.9 | 93 (No. 182) | 7.8 |
| 62 (No. 124) | 4.3 | 105 (No. 226) | 1.3 |
| 63 (No. 125) | 5.5 | 106 (No. 228) | 3.1 |
| 64 (No. 126) | 4.3 | 107 (No. 230) | 4.2 |
| 65 (No. 128) | 5.0 | 139 (No. 297) | 4.5 |
| 66 (No. 130) | 1.4 | 183 (No. 423) | 9.6 |
|  |  | compd. of Ref. Ex. No. 3 | >100 |

EXPERIMENT 2

Confirmation of Reversible Inhibitory

According to the assay for inhibitory activity against calpain in Experiment 1, reversible inhibitory activity of the present compounds was confirmed as follows.

To an imidazole buffer (54 μl) were added 500 mM CaCl$_2$ solution (1 μl), 5 mM solution of the synthetic substrate described in the literature (4 μl), 10 μM–150 μM inhibitor solution (1 μl) and m-calpain solution (40 μl), and the mixture was incubated for 0 to 20 minutes at a temperature of 10° C. Then, 100 mM EDTA solution (5 μl) was added to inactivate the enzymatic activity. To the mixture was then added imidazole buffer (900 μl) followed by an addition of 5 mM synthetic substrate solution (40 μl) and 500 mM CaCl$_2$ solution (10 μl), and the decomposition rate of the synthetic substrate was measured for 10 minutes at a temperature of 30° C. to determine the remaining activity of the enzyme.

Figure 2:
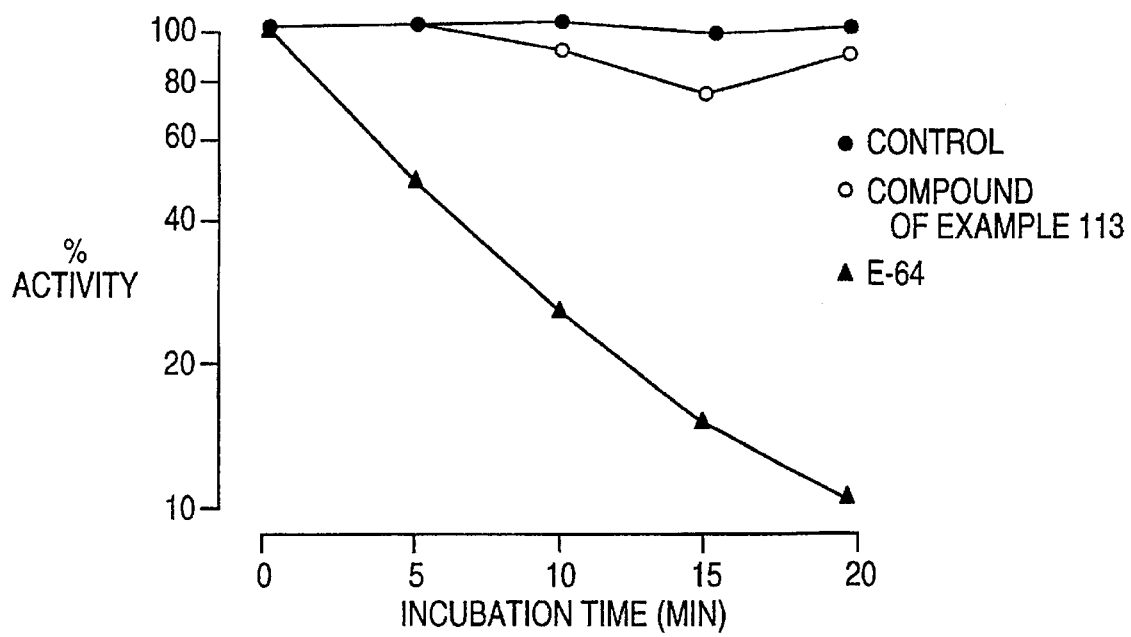
Figure 3:
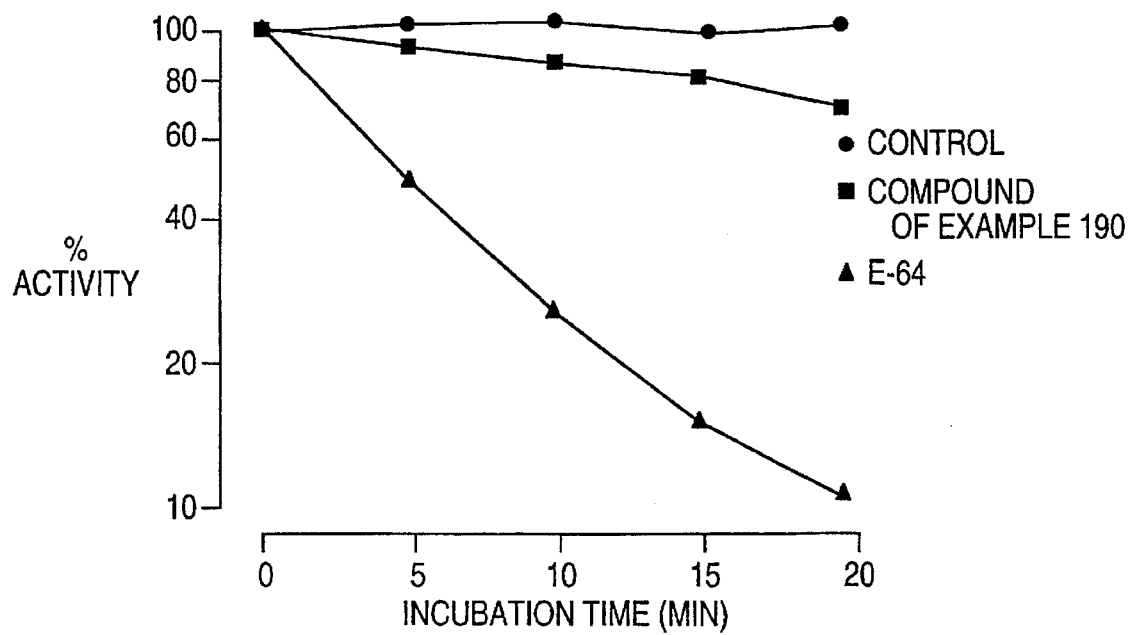

The compounds of Examples 3, 113 and 190 were used as the inhibitor, and E-64 which is an irreversible inhibitor was also used for comparison. The results are shown in FIGS. 1 to 3. As is clear from FIGS. 1 to 3, enzymatic activity rapidly disappeared in proportion to the incubation period when used irreversible inhibitor E-64, while the activity nearly equal to that of a control remained when used the compounds of the present invention, indicating that the present compounds are a reversible inhibitor.

EXPERIMENT 3

Acute toxicity

A suspension of the present compound in 0.5% CMC-Na aqueous solution was orally administered to SD female and male rats, and the rats were observed for 7 days. The LD$_{50}$ value of the compound prepared in Example 94 was: >2,000 mg/kg.

The following formulation examples are illustrative only.

FORMULATION 1

(1) Tablet

The following ingredients were admixed in a conventional manner and compressed on a customary tablet machine.

| Compound in Example 94 | 30 mg |
|---|---|
| Crystalline cellulose | 60 mg |
| Corn starch | 100 mg |
| Lactose | 200 mg |
| Magnesium stearate | 4 mg |

(2) Soft gelatin capsule

The following ingredients were admixed in a conventional manner and filled in soft capsules.

| Compound in Example 94 | 30 mg |
|---|---|
| Olive oil | 300 mg |
| Lecithin | 20 mg |

(3) Injection

The following ingredients were admixed in a conventional manner and filled in an ampoule in a volume of 1 ml.

| Compound in Example 106 | 2.5 mg |
|---|---|
| Sodium chloride | 3.5 mg |
| Distilled water for injection | 1 ml |

What we claim is:

1. A ketone derivative of the formula (I):

$$R^1 - \left[ \begin{array}{c} R^3 \\ | \\ N-CH-C \\ | \quad \quad \| \\ R^2 \quad \quad O \end{array} \right]_n - N-CH-C-N-C-C-CH_2-A-R^9$$

wherein $R^1$ is $R^{10}$—CO— (where $R^{10}$ is chromon-2-yl);

$R^2$, $R^4$ and $R^6$ each are independently hydrogen or $C_1$–$C_5$ alkyl;

$R^3$ and $R^5$ each are independently $C_1$–$C_6$ alkyl;

$R^7$ is $C_1$–$C_6$ alkyl group optionally substituted by a phenyl group;

$R^8$ is hydrogen or $C_1$–$C_5$ alkyl;

A is —S—, —SO— or —SO$_2$—;

$R^9$ is —(CH$_2$)$_m$—X in which X is furanyl; and m is 0 or an integer of 1 to 15; and n is 0;

or a pharmaceutically acceptable salt thereof.

2. The ketone derivative according to claim 1 wherein $R^6$ and $R^8$ are hydrogen, A is —S—, n is 0 and m is 1.

3. The ketone derivative according to claim 2 wherein $R^5$ is —CH$_2$CH(CH$_3$)$_2$ and $R^7$ is —CH$_2$CH$_2$CH$_2$CH$_3$.

4. The ketone derivative according to claim 2 wherein $R^5$ is —CH$_2$CH(CH$_3$)$_2$ and $R^7$ is —CH$_2$ phenyl.

5. A pharmaceutical composition which comprises, as an active ingredient, a compound of claim 1 together with pharmaceutically acceptable carriers.

* * * * *